United States Patent
Moran et al.

(10) Patent No.: US 9,815,838 B2
(45) Date of Patent: *Nov. 14, 2017

(54) METHODS AND COMPOSITIONS FOR TREATING PAIN

(71) Applicant: HYDRA BIOSCIENCES, INC., Cambridge, MA (US)

(72) Inventors: Magdalene M. Moran, Brookline, MA (US); Christopher Fanger, Bolton, MA (US); Jayhong A. Chong, Brookline, MA (US); Colleen Mcnamara, Brookline, MA (US); Xiaoguang Zhen, Newton, MA (US); Josh Mandel-Brehm, Ann Arbor, MI (US)

(73) Assignee: Hydra Biosciences, Inc., Cambridge, MA (US)

( * ) Notice: Subject to any disclaimer, the term of this patent is extended or adjusted under 35 U.S.C. 154(b) by 336 days.

This patent is subject to a terminal disclaimer.

(21) Appl. No.: 13/966,546

(22) Filed: Aug. 14, 2013

(65) Prior Publication Data

US 2014/0221401 A1  Aug. 7, 2014

Related U.S. Application Data

(60) Continuation of application No. 13/444,213, filed on Apr. 11, 2012, now Pat. No. 8,541,423, which is a continuation of application No. 12/688,241, filed on Jan. 15, 2010, now Pat. No. 8,178,542, which is a division of application No. 11/645,307, filed on Dec. 22, 2006, now Pat. No. 7,671,061.

(60) Provisional application No. 60/753,665, filed on Dec. 22, 2005, provisional application No. 60/817,892, filed on Jun. 29, 2006.

(51) Int. Cl.

| | |
|---|---|
| *A61K 31/522* | (2006.01) |
| *A61K 31/513* | (2006.01) |
| *C07D 473/08* | (2006.01) |
| *A61K 31/505* | (2006.01) |
| *A61K 31/555* | (2006.01) |
| *C07K 14/705* | (2006.01) |
| *C07D 239/22* | (2006.01) |

(52) U.S. Cl.
CPC .......... *C07D 473/08* (2013.01); *A61K 31/505* (2013.01); *A61K 31/513* (2013.01); *A61K 31/522* (2013.01); *A61K 31/555* (2013.01); *C07D 239/22* (2013.01); *C07K 14/705* (2013.01)

(58) Field of Classification Search
CPC .......................... A61K 31/522; A61K 31/513
See application file for complete search history.

(56) References Cited

U.S. PATENT DOCUMENTS

| | | | |
|---|---|---|---|
| 7,018,617 | B1 | 3/2006 | Tracey, Jr. et al. |
| 7,176,242 | B2 | 2/2007 | John et al. |
| 2005/0147825 | A1 | 7/2005 | Arnaud et al. |
| 2005/0266515 | A1 | 12/2005 | O'Brien et al. |
| 2006/0142309 | A1 | 6/2006 | Baraldi et al. |
| 2006/0142547 | A1 | 6/2006 | Bevan et al. |

FOREIGN PATENT DOCUMENTS

| | | |
|---|---|---|
| EP | 1 736 465 A1 | 12/2006 |
| JP | 03196037 A | 8/1991 |
| WO | 89/10744 A1 | 11/1989 |
| WO | 02/28820 A1 | 4/2002 |
| WO | 03/087158 A2 | 10/2003 |
| WO | 2004/055054 A1 | 7/2004 |
| WO | 2004/065576 A2 | 8/2004 |
| WO | 2004/094449 A1 | 11/2004 |
| WO | 2005/089206 A2 | 9/2005 |
| WO | 2005/095327 A1 | 10/2005 |
| WO | 2005/103018 A1 | 11/2005 |

OTHER PUBLICATIONS

Roushdi, Pharmazie, "7-substituted theophyllines 7-acetamido and 7-malondiamidotheophylline", 1973, 28(5), 300-303.
Schenker et al., "Down-Regulated Proteins of Mesenchymal Tumor Cells," Experimental Cell Research, 239:161-168 (1998).
Shaoyong Yu, et al. "TRPA 1 in bradykinin-induced mechano-hypersensitivity of vagal C fibers in guinea pig esophagus", American Journal of Physiological SOCiety, Nov. 25, 2008.
Sharma, "Synthesis of phthalimido/succinimido [2-substituted aryl-3-(N7-theophyllinylacetamidyl)-4-oxo-1 ,3-thiazolidin-5-yl]ethanolic acids", Indian Journal of Heterocyclic Chemistry, 2005, 15(1), pp. 35-38.
Sotomayor et al., "In Search of the Hair-Cell Gating Spring: Elastic Properties of Ankyrin and Cadherin Repeats" Structure Current BioloQY Ltd. 13(4):669-682 (2005).
STN Registry File History II.
STN Registry File History I.
Stokes et al., "TRPA 1 is a substrate for de-ubiquitination by the tumor suppressor CYLD", Cellular Signaling, 18:1584-1594 (2006).
Story et al., "ANKTM1, a TRP-like Channel Expressed in Nociceptive Neurons, Is Activated by Cold Temperatures," Cell, 112:819-829 (2003).
Supplementary European Search Report from corresponding European Patent Application No. 06848704.0, dated Feb. 26, 2009.
Taylor-Clark, et al. "Nitrooleic acid, an endogenous product of nitrative stress, activates nociceptive sensory nerves via the direct activation of TRPA 1", Molecular Pharmacology Fast Forward, Published on Jan. 26, 2009, MOL #54445.
Taylor-Clark, et al. "Prostaglandin-induced activation of nociceptive neurons via direct interaction with transient receptor potential A 1 (TRPA 1)", Molecular Pharmacology, vol. 73, No. 2; 274-281.
Trevisani, et al. al. "4-Hydroxynonenal, an endogenous aldehyde, causes pain and neurogenic inflammation through activation of the irritant receptorTRPA1", PNAS, Aug. 14, 2007, vol. 104, No. 33, p. 13519-13524.

(Continued)

*Primary Examiner* — Sahar Javanmard
(74) *Attorney, Agent, or Firm* — Goodwin Procter LLP

(57) ABSTRACT

The present application relates to compounds and methods for treating pain, incontinence and other conditions.

8 Claims, 4 Drawing Sheets

(56) References Cited

OTHER PUBLICATIONS

Figure 1:
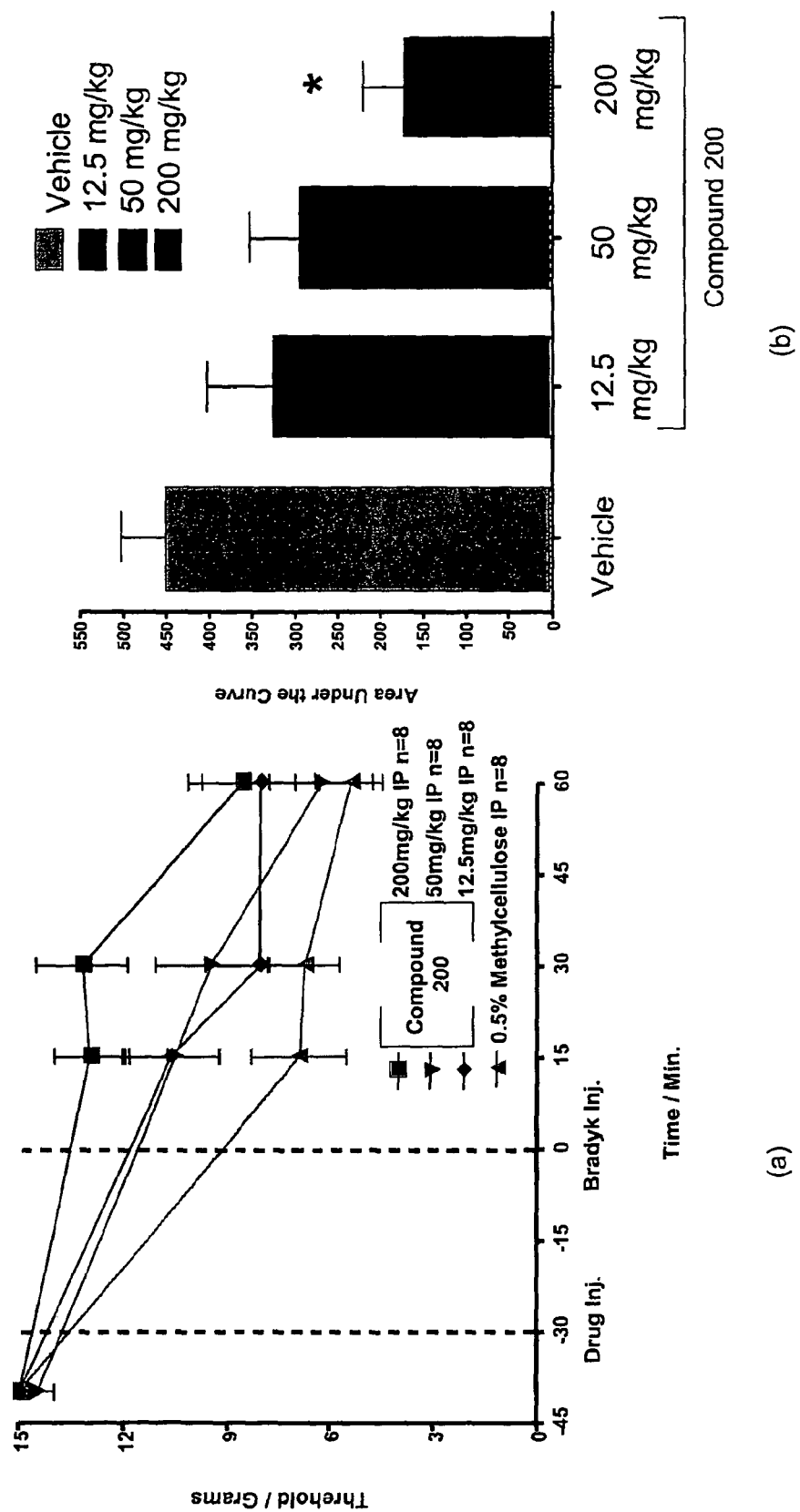

Ugawa et al., "Amiloride-blockable acid-sensing ion channels are leading acid sensors expressed in human nociceptors," Journal of Clinical Investigation, 110((3): 1185-1190 (2002).
Viswanath et al., "Opposite thermosensor in fruitfly and mouse," Nature, 423:822-823 (2003).
Wang, et al., "Extracellular ATP Shows Synergistic Enhancement of DNA SyntheSiS When Combined With Agents That Are Active in Wound Healing or as Neurotransmitters," Biochemical and Biophysical Research Communications, 166(1):251-258 (1990).
Wayne E. Childers, et al. "Advances in the development of novel analgesics" Expert Opinion (2008) 18(9) pp. 1027-1067.
Written Opinion of the International Searching Authority for PCT/US2006/049244, dated Jun. 22 2008.
Xu et al., "Camphor Activates and Strongly Desensitizes the Transient Receptor Potential Vanilloid Subtype 1 Channel in a Vanilloid-Independent Mechanism," Journal of Neuroscience, 25(39):8924-8937(2005).
Xu et al., "Oregano, thyme and clove-derived flavors and skin sensitizers activate specific TRP channels," Nature Neuroscience, 9(5):628-635 (2006).
Lu et al. "TRPV1b, a Functional Human Vanilloid Receptor Splice Variant" Molecular Pharmacology (2005) vol. 67, pp. 1119-1127.
Anderson et al., "Transient Receptor Potential A 1 Is a Sensory Receptor for Multiple Products of Oxidative Stress" The Journal of Neuroscience, Mar. 5, 2008, 28(10):2485-2494.
Andrade, et al., "Contractile mechanisms coupled to TRPA 1 receptor activation in rat urinary bladder," Biochemical Pharmacology, 72: 104-114 (2006).
Andre et al., "Cigarette Smoke-induced neurogenic inflammation is mediated by alpha, beta-unsaturated aldehydes and the TRPA 1 receptor in rodents" The Journal of Clinical Investigation, 2008 pp. 1-9.
Bandell et al., "Noxious Cold Ion Channel TRPA 1 Is Activated by Pungent Compounds and Bradykinin," Neuron, 41:849-857 (2004).
Barrick et al., "Expression and function of the cold channels in urinary bladder urothelium: TRPM8 and TRPA 1," Journal of Pain, Saunders, Philadelphia, PA, US, 6(3):S 10 (2005).
Bautista et al., "Pungent products from garlic activate the sensory ion channel TRPA 1," PNAS, 102(34):12248-12252 (2005).
Bautista et al., "TRPA 1 Mediates the Inflammatory Actions of Environmental Irritants and Proalgesic Agents," Cell, 124: 1269-1282 (2006).
Bessac et al., "TRPA 1 is a major oxidant sensor in murine ail'Nay sensory neurons" The Journal of Clinical Investigation, 2008 pp. 1-12.
Brone, et al. "Tear gasses CN, CR and CS are potent activators of the human TRPA1 receptor" Toxicology and Applied Pharmacology, 231 (2008) 150-156.
Burnstock, "Pathophysiology and Therapeutic Potential of Purinergic Signaling," Pharmacological Reviews, 58 (1):58-86 (2006).
Burnstock, et al., "P2 purinergic Receptors: Modulation of Cell Function and Therapeutic Potential," The Journal of Pharmacology and Experimental Therapeutics, 295(3):862-869 (2000).
Callsen-Cencic et al., "Abolition of Cystitis-Induced Bladder Instability by Local Spinal Cord Cooling," The Journal of Urology, 160:236-241 (1998).
Chen et al., "Runx1 Determines NOCiceptive Sensory Neuron Phenotype and Is Required for Thermal and Neuropathic Pain," Neuron, 49:365-377 (2006).
Corey et al., "TRPA 1 is a candidate for the mechanosensitive transduction channel of vertebrate hair cells," Nature, 432:723-730 (2004).
Database Registry "349085-38-7," XP002442765 Abstract.
Early, et al. "Endothelium-Dependent Cerebral Artery Dilation Mediated by TRPA1 and Ca2+-activated k+ channels" Mar. 2009 downloaded from circres.ahajournals.org.
Eid, et al. "HC-030031, a TRPA 1 selective antagonist, attenuates inflammatory-and neuropathy-induced mechanical hypersensitivity" Department of Pain Research.
Elitt et al., "Artemin Overexpression in Skin Enhances Expression of TRPV1 and TRPA 1 in Cutaneous Sensory Neurons and Leads to Behavioral Sensitivity to Heat and Cold," The Journal of Neuroscience, 26(33):8578-8587 (2006).
Fajardo, et al. "TRPA1 Channels Mediate Cold Temperature Sensing in Mammalian Vagal Sensory Neurons: Pharmacological and Genetic Evidence", The Journal of Neuroscience, Jul. 2008,28(31): 7863-7875.
Foresta, et al., "Extracellular ATP is a trigger for the Acrosome Reaction in Human Spermatozoa," The Journal of Biological Chemistry, 267(27):19443-19447 (1992).
GenBank Accession No. NM 007332.
GenBank Accession No. NM 177781.
Ghelardini et al., "Caffeine induces central cholinergic analgesia," Naunyn-Schmiedeberg's Archives of Pharmacology, 356(5):590-595 (1997).
Heppelmann et al., "Inhibitory effect of amiloride and gadolinium on fine afferent nerves in the rat knee: evidence of mechanogated ion channels in joints," Experimantal Brain Research, 167 (1):114-118 (2005).
Hinman, et al. "TRP channel activation by reversible covalent modification", PNAS: Dec. 19, 2006, vol. 103, p. 19564-19568.
International Preliminary Report on Patentability for PCT/US2006/049244, dated Jun. 24, 2008.
Japanese Office Action for 2008-547657 dated Apr. 23, 2012.
Jaquemar, et al., "An ankyrin-like protein with transmembrane domains is specifically lost after oncogenic transformation of human fibroblasts", Journal od J. Biol. Chem. 1999, vol. 274, No. 11, p. 7325-7333.
Jordt et al., "Mustard oils and cannabinoids excite sensory nerve fibres through the TRP channel ANKTM1 ," Nature, 427:260-265 (2004).
Katsura et al., "Antisense knock down of TRPA 1, but not TRPM8, alleviates cold hyperalgesia after spinal nerve liqation in rats," Experimental Neuroloqv, 200: 112-123 (2006).
Keiichi, "Nociceptor and hair cell transducer properties of TRPA1, a channel for pain and hearing." The Journal of Neuroscience, Apr. 20, 2005, V25 N16, P4052-4061.
Klosa, "Synthesis in the theophylline series. I. Derivatives of 7-theophyllinacetic acid", Archiv der Pharmazie und Berichte der Deutchen Pharmazeutischen Gesellschaft, 1955,288, 114-119.(abstract submitted only).
Krause et al., "Transient receptor potential ion channels as targets for the discovery of pain therapeutics," Current Opinion in Investigational Drugs, 6(1):48-57 (2005).
Kwan et al., "TRPA1 Contibutes to Cold, Mechanical, and Chemical Nociception but Is Not Essential for Hair-Cell Transduction," Neuron, 50:277-289 (2006).
Luger et al., "The Effect of Ciprofloxacin and Gentamicin on Spinal Morphine-Induced Antinociception in Rats," Basic & Clinical Pharmacology & Toxicology, 96(5):366-374 (2005).
Macpherson, et al. "Noxious compounds activate TRPA 1 ion channels through covalent modification of cysteines", Nature,2007, The Nature Publishing Group: 1-5.
Materazzi, et al. "Cox-dependent fatty acid metabolites cause pain through activation of the irritant receptor TRPA1", PNAS, Aug. 19, 2008, vol. 105, No. 33, p. 12045-12050.
McKemy, "How cold is it? TRPM8 and TRPA 1 in the molecular logic of cold sensation," Molecular Pain, 1(16):1-7 (2005).
McNamara, et al. "TRPA1 mediates forlmalin-induced pain", PNAS; Aug. 14, 2007, vol. 104, No. 33; p. 13525-13530.
Milletti, "Derivatives of 1 ,3-dimethylxanthine-7-acetic acetic acid", Sperimentale, Sezione di Chimica Biologica 1954, 5, pp. 53-59.
Montell, "The TRP Superfamily of Cation Channels," Science's Stke: Signal Transduction Knowledge Environment, 2005(272):1-24 (2005).
Myers et al., "Hypoalgesic Effect of Caffenine n Experimental Ischemic Muscle Contraction Pain," 37(10):654-658 (1997).

(56) References Cited

OTHER PUBLICATIONS

N Jaquemar et al., "An Ankyrin-like Protein with Transmembrane Domains Is Specifically Lost after Oncogenic Transformation of Human Fibroblasts," The Journnal of Biological Chemistry, 274(11):7325-7333 (1999).

Nagata et al., "Nociceptor and Hair Cell Transducer Properties ofTRPA1, a Channel for Pain and Hearinq," The Journal of Neuroscience., 25(16):4052-4061 (2005).

Obata et al., "TRPA 1 induced in sensory neurons contributes to cold hyperalgesia after inflammation and nerve iniury," The Journal of Clinical Investigation, 115(9):2393-2401 (2005).

Omar, et al., "Steroidal Derivatives Part 3: Synthesis of Some Novel Steroidal Hydrazones Containinq Theophylline and Ouinazolone Moieties," Pharmazie, 33(H11 ):747-748 (1979).

Park et al., "Functional Expression of Thermo-transient Receptor Potential Channels in Dental Primary Afferent Neurons," The Journal of Biological Chemistry, 281 (25): 17304-17311 (2006).

Partial International Search Report for PCT/US2006/049244 dated Sep. 28, 2007.

Petrus, et al. "A role ofTRPA1 in mechanical hyperalgesia is revealed by pharmacological inhibition", Molecular Pain, Dec. 17, 2007, 1-8.

Ramsey, et al., "An Introduction to TRP Channels," Annu. Rev. Physiol. 68:619-64i(2006).

SEQUENCE LISTING

<160> NUMBER OF SEQ ID NOS: 6

<210> SEQ ID NO 1
<211> LENGTH: 1119
<212> TYPE: PRT
<213> ORGANISM: Homo sapiens

<400> SEQUENCE: 1

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

Asn Phe Asn Lys Gln Lys Lys Leu Lys Arg Cys Asp Asp Met Asp Thr
    50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

```
Phe Asn Met Met Ala Pro Leu His Ile Ala Val Gln Gly Met Asn Asn
130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Asn Lys Gly Ala Lys Pro Cys
            180                 185                 190

Lys Ser Asn Lys Trp Gly Cys Phe Pro Ile His Gln Ala Ala Phe Ser
        195                 200                 205

Gly Ser Lys Glu Cys Met Glu Ile Ile Leu Arg Phe Gly Glu Glu His
210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
            260                 265                 270

Cys Thr Ala Ile His Phe Ala Ala Thr Gln Gly Ala Thr Glu Ile Val
        275                 280                 285

Lys Leu Met Ile Ser Ser Tyr Ser Gly Ser Val Asp Ile Val Asn Thr
290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                325                 330                 335

Lys Ile Asp Ser Glu Gly Arg Ser Pro Leu Ile Leu Ala Thr Ala Ser
            340                 345                 350

Ala Ser Trp Asn Ile Val Asn Leu Leu Leu Ser Lys Gly Ala Gln Val
        355                 360                 365

Asp Ile Lys Asp Asn Phe Gly Arg Asn Phe Leu His Leu Thr Val Gln
370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Gly Ser Val Asn Asn Leu
            420                 425                 430

Leu Gly Phe Asn Val Ser Ile His Ser Lys Ser Lys Asp Lys Lys Ser
        435                 440                 445

Pro Leu His Phe Ala Ala Ser Tyr Gly Arg Ile Asn Thr Cys Gln Arg
450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
            500                 505                 510

Asn Gly Trp Thr Ala Leu His His Ala Ser Met Gly Gly Tyr Thr Gln
        515                 520                 525

Thr Met Lys Val Ile Leu Asp Thr Asn Leu Lys Cys Thr Asp Arg Leu
530                 535                 540

Asp Glu Asp Gly Asn Thr Ala Leu His Phe Ala Ala Arg Glu Gly His
```

```
                         545                 550                 555                 560

Ala Lys Ala Val Ala Leu Leu Ser His Asn Ala Asp Ile Val Leu
                         565                 570                 575

Asn Lys Gln Gln Ala Ser Phe Leu His Leu Ala Leu His Asn Lys Arg
                         580                 585                 590

Lys Glu Val Val Leu Thr Ile Ile Arg Ser Lys Arg Trp Asp Glu Cys
                         595                 600                 605

Leu Lys Ile Phe Ser His Asn Ser Pro Gly Asn Lys Cys Pro Ile Thr
                         610                 615                 620

Glu Met Ile Glu Tyr Leu Pro Glu Cys Met Lys Val Leu Leu Asp Phe
        625                 630                 635                 640

Cys Met Leu His Ser Thr Glu Asp Lys Ser Cys Arg Asp Tyr Tyr Ile
                         645                 650                 655

Glu Tyr Asn Phe Lys Tyr Leu Gln Cys Pro Leu Glu Phe Thr Lys Lys
                         660                 665                 670

Thr Pro Thr Gln Asp Val Ile Tyr Glu Pro Leu Thr Ala Leu Asn Ala
                         675                 680                 685

Met Val Gln Asn Asn Arg Ile Glu Leu Leu Asn His Pro Val Cys Lys
                         690                 695                 700

Glu Tyr Leu Leu Met Lys Trp Leu Ala Tyr Gly Phe Arg Ala His Met
        705                 710                 715                 720

Met Asn Leu Gly Ser Tyr Cys Leu Gly Leu Ile Pro Met Thr Ile Leu
                         725                 730                 735

Val Val Asn Ile Lys Pro Gly Met Ala Phe Asn Ser Thr Gly Ile Ile
                         740                 745                 750

Asn Glu Thr Ser Asp His Ser Glu Ile Leu Asp Thr Thr Asn Ser Tyr
                         755                 760                 765

Leu Ile Lys Thr Cys Met Ile Leu Val Phe Leu Ser Ile Phe Gly
                         770                 775                 780

Tyr Cys Lys Glu Ala Gly Gln Ile Phe Gln Gln Lys Arg Asn Tyr Phe
        785                 790                 795                 800

Met Asp Ile Ser Asn Val Leu Glu Trp Ile Ile Tyr Thr Thr Gly Ile
                         805                 810                 815

Ile Phe Val Leu Pro Leu Phe Val Glu Ile Pro Ala His Leu Gln Trp
                         820                 825                 830

Gln Cys Gly Ala Ile Ala Val Tyr Phe Tyr Trp Met Asn Phe Leu Leu
                         835                 840                 845

Tyr Leu Gln Arg Phe Glu Asn Cys Gly Ile Phe Ile Val Met Leu Glu
                         850                 855                 860

Val Ile Leu Lys Thr Leu Leu Arg Ser Thr Val Val Phe Ile Phe Leu
        865                 870                 875                 880

Leu Leu Ala Phe Gly Leu Ser Phe Tyr Ile Leu Leu Asn Leu Gln Asp
                         885                 890                 895

Pro Phe Ser Ser Pro Leu Leu Ser Ile Ile Gln Thr Phe Ser Met Met
                         900                 905                 910

Leu Gly Asp Ile Asn Tyr Arg Glu Ser Phe Leu Glu Pro Tyr Leu Arg
                         915                 920                 925

Asn Glu Leu Ala His Pro Val Leu Ser Phe Ala Gln Leu Val Ser Phe
                         930                 935                 940

Thr Ile Phe Val Pro Ile Val Leu Met Asn Leu Leu Ile Gly Leu Ala
        945                 950                 955                 960

Val Gly Asp Ile Ala Glu Val Gln Lys His Ala Ser Leu Lys Arg Ile
                         965                 970                 975
```

```
Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
        995                1000                1005

Lys Pro Arg Ser Gly Gly Met Leu Phe His Ile Phe Cys Phe Leu Phe
    1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
            1045                1050                1055

Leu Leu Glu Lys Gln His Glu Leu Ile Lys Leu Ile Ile Gln Lys Met
                1060                1065                1070

Glu Ile Ile Ser Glu Thr Glu Asp Asp Ser His Cys Ser Phe Gln
            1075                1080                1085

Asp Arg Phe Lys Lys Glu Gln Met Glu Gln Arg Asn Ser Arg Trp Asn
        1090                1095                1100

Thr Val Leu Arg Ala Val Lys Ala Lys Thr His His Leu Glu Pro
1105                1110                1115
```

<210> SEQ ID NO 2
<211> LENGTH: 3360
<212> TYPE: DNA
<213> ORGANISM: Homo sapiens
<400> SEQUENCE: 2

```
atgaagcgca gcctgaggaa gatgtggcgc cctggagaaa agaaggagcc ccagggcgtt      60
gtctatgagg atgtgccgga cgacacggag gatttcaagg aatcgcttaa ggtggttttt     120
gaaggaagtg catatggatt acaaaacttt aataagcaaa agaaattaaa agatgtgac     180
gatatggaca ccttcttctt gcattatgct gcagcagaag gccaaattga gctaatggag     240
aagatcacca gagattcctc tttggaagtg ctgcatgaaa tggatgatta tggaaatacc     300
cctctgcatt gtgctgtaga aaaaaaccaa attgaaagcg ttaagtttct tctcagcaga     360
ggagcaaacc caaaccctccg aaacttcaac atgatggctc ctctccacat agctgtgcag     420
ggcatgaata atgaggtgat gaaggtcttg cttgagcata gaactattga tgttaatttg     480
gaaggagaaa atgaaacac agctgtgatc attgcgtgca ccacaaataa tagcgaagca     540
ttgcagattt tgcttaacaa aggagctaag ccatgtaaat caaataaatg gggatgtttc     600
cctattcacc aagctgcatt ttcaggttcc aaagaatgca tggaaataat actaaggttt     660
ggtgaagagc atgggtacag tagacagttg cacattaact ttatgaataa tgggaaagcc     720
accctctcc acctggctgt gcaaaatggt gacttggaaa tgatcaaaat gtgcctggac     780
aatggtgcac aaatagaccc agtggagaag ggaaggtgca cagccattca ttttgctgcc     840
acccagggag ccactgagat tgttaaactg atgatatcgt cctattctgg tagcgtggat     900
attgttaaca caaccgatgg atgtcatgag accatgcttc acagagcttc attgtttgat     960
caccatgagc tagcagacta tttaatttca gtgggagcag atattaataa gatcgattct    1020
gaaggacgct ctccacttat attagcaact gcttctgcat cttggaatat tgtaaatttg    1080
ctactctcta aggtgcccca agtagacata aaagataatt ttggacgtaa ttttctgcat    1140
ttaactgtac agcaacctta tggattaaaa aatctgcgac ctgaattat gcagatgcaa    1200
cagatcaaag agctggtaat ggatgaagac aacgatgggt gtactcctct acattatgca    1260
tgtagacagg ggggccctgg ttctgtaaat aacctacttg gctttaatgt gtccattcat    1320
```

```
tccaaaagca aagataagaa atcacctctg cattttgcag ccagttatgg gcgtatcaat    1380
acctgtcaga ggctcctaca agacataagt gatacgaggc ttctgaatga aggtgaccct    1440
catggaatga ctcctctcca tctggcagca aagaatggac atgataaagt agttcagctt    1500
cttctgaaaa aaggtgcatt gtttctcagt gaccacaatg gctggacagc tttgcatcat    1560
gcgtccatgg gcgggtacac tcagaccatg aaggtcattc ttgatactaa tttgaagtgc    1620
acagatcgct tggatgaaga cgggaacact gcacttcact ttgctgcaag ggaaggccat    1680
gccaaagccg ttgcgcttct tctgagccac aatgctgaca tagtcctgaa caagcagcag    1740
gcctcctttt tgcaccttgc acttcacaat aagaggaagg aggttgttct tacgatcatc    1800
aggagcaaaa gatgggatga atgtcttaag attttcagtc ataattctcc aggcaataaa    1860
tgtccaatta cagaaatgat agaataccta cctgaatgca tgaaggtact tttagatttc    1920
tgcatgttgc attccacaga agacaagtcc tgccgagact attatatcga gtataatttc    1980
aaatatcttc aatgtccatt agaattcacc aaaaaaacac ctacacagga tgttatatat    2040
gaaccgctta cagccctcaa cgcaatggta caaaataacc gcatagagct tctcaatcat    2100
cctgtgtgta aagaatattt actcatgaaa tggttggctt atggatttag agctcatatg    2160
atgaatttag gatcttactg tcttggtctc ataccctatga ccattctcgt tgtcaatata    2220
aaaccaggaa tggctttcaa ctcaactggc atcatcaatg aaactagtga tcattcagaa    2280
atactagata ccacgaattc atatctaata aaaacttgta tgattttagt gttttatca    2340
agtatatttg ggtattgcaa agaagcgggg caaattttcc aacagaaaag gaattattt    2400
atggatataa gcaatgttct tgaatggatt atctacacga cgggcatcat ttttgtgctg    2460
cccttgtttg ttgaaatacc agctcatctg cagtggcaat gtggagcaat tgctgtttac    2520
ttctattgga tgaatttctt attgtatctt caaagatttg aaaattgtgg aatttttatt    2580
gttatgttgg aggtaatttt gaaaactttg ttgaggtcta cagttgtatt tatcttcctt    2640
cttctggctt ttggactcag cttttacatc ctcctgaatt tacaggatcc cttcagctct    2700
ccattgcttt ctataatcca gaccttcagc atgatgctag gagatatcaa ttatcgagag    2760
tccttcctag aaccatatct gagaaatgaa ttggcacatc cagttctgtc ctttgcacaa    2820
cttgtttcct tcacaatatt tgtcccaatt gtcctcatga atttacttat tggtttggca    2880
gttggcgaca ttgctgaggt ccagaaacat gcatcattga gaggatagc tatgcaggtg    2940
gaacttcata ccagcttaga gaagaagctg ccactttggt ttctacgcaa agtggatcag    3000
aaatccacca tcgtgtatcc caacaaaccc agatctggtg ggatgttatt ccatatattc    3060
tgtttttttat tttgcactgg ggaaataaga caagaaatac caaatgctga taaatcttta    3120
gaaatggaaa tattaaagca gaaataccgg ctgaaggatc ttacttttct cctggaaaaa    3180
cagcatgagc tcattaaact gatcattcag aagatggaga tcatctctga gacagaggat    3240
gatgatagcc attgttcttt tcaagacagg tttaagaaag agcagatgga acaaaggaat    3300
agcagatgga atactgtgtt gagagcagtc aaggcaaaaa cacaccatct tgagccttag    3360
```

<210> SEQ ID NO 3
<211> LENGTH: 1119
<212> TYPE: PRT
<213> ORGANISM: Homo sapiens

<400> SEQUENCE: 3

Met Lys Cys Ser Leu Arg Lys Met Trp Arg Pro Gly Glu Lys Lys Glu
1               5                   10                  15

-continued

```
Pro Gln Gly Val Val Tyr Glu Asp Val Pro Asp Asp Thr Glu Asp Phe
             20                  25                  30
Lys Glu Ser Leu Lys Val Val Phe Glu Gly Ser Ala Tyr Gly Leu Gln
         35                  40                  45
Asn Phe Asn Lys Gln Lys Lys Leu Lys Thr Cys Asp Asp Met Asp Thr
 50                  55                  60
Phe Phe Leu His Tyr Ala Ala Ala Glu Gly Gln Ile Glu Leu Met Glu
 65                  70                  75                  80
Lys Ile Thr Arg Asp Ser Ser Leu Glu Val Leu His Glu Met Asp Asp
                 85                  90                  95
Tyr Gly Asn Thr Pro Leu His Cys Ala Val Glu Lys Asn Gln Ile Glu
                100                 105                 110
Ser Val Lys Phe Leu Leu Ser Arg Gly Ala Asn Pro Asn Leu Arg Asn
            115                 120                 125
Phe Asn Met Met Ala Pro Leu His Ile Ala Val Gln Gly Met Asn Asn
130                 135                 140
Glu Val Met Lys Val Leu Leu Glu His Arg Thr Ile Asp Val Asn Leu
145                 150                 155                 160
Glu Gly Glu Asn Gly Asn Thr Ala Val Ile Ile Ala Cys Thr Thr Asn
                165                 170                 175
Asn Ser Glu Ala Leu Gln Ile Leu Leu Asn Lys Gly Ala Lys Pro Cys
            180                 185                 190
Lys Ser Asn Lys Trp Gly Cys Phe Pro Ile His Gln Ala Ala Phe Ser
            195                 200                 205
Gly Ser Lys Glu Cys Met Glu Ile Ile Leu Arg Phe Gly Glu Glu His
        210                 215                 220
Gly Tyr Ser Arg Gln Leu His Ile Asn Phe Met Asn Asn Gly Lys Ala
225                 230                 235                 240
Thr Pro Leu His Leu Ala Val Gln Asn Gly Asp Leu Glu Met Ile Lys
                245                 250                 255
Met Cys Leu Asp Asn Gly Ala Gln Ile Asp Pro Val Glu Lys Gly Arg
            260                 265                 270
Cys Thr Ala Ile His Phe Ala Ala Thr Gln Gly Ala Thr Glu Ile Val
        275                 280                 285
Lys Leu Met Ile Ser Ser Tyr Ser Gly Ser Val Asp Ile Val Asn Thr
    290                 295                 300
Thr Asp Gly Cys His Glu Thr Met Leu His Arg Ala Ser Leu Phe Asp
305                 310                 315                 320
His His Glu Leu Ala Asp Tyr Leu Ile Ser Val Gly Ala Asp Ile Asn
                325                 330                 335
Lys Ile Asp Ser Glu Gly Arg Ser Pro Leu Ile Leu Ala Thr Ala Ser
            340                 345                 350
Ala Ser Trp Asn Ile Val Asn Leu Leu Leu Ser Lys Gly Ala Gln Val
        355                 360                 365
Asp Ile Lys Asp Asn Phe Gly Arg Asn Phe Leu His Leu Thr Val Gln
    370                 375                 380
Gln Pro Tyr Gly Leu Lys Asn Leu Arg Pro Glu Phe Met Gln Met Gln
385                 390                 395                 400
Gln Ile Lys Glu Leu Val Met Asp Glu Asp Asn Asp Gly Cys Thr Pro
                405                 410                 415
Leu His Tyr Ala Cys Arg Gln Gly Gly Pro Gly Ser Val Asn Asn Leu
            420                 425                 430
```

-continued

```
Leu Gly Phe Asn Val Ser Ile His Ser Lys Ser Lys Asp Lys Lys Ser
            435                 440                 445

Pro Leu His Phe Ala Ala Ser Tyr Gly Arg Ile Asn Thr Cys Gln Arg
    450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Lys Lys Gly Ala Leu Phe Leu Ser Asp His
            500                 505                 510

Asn Gly Trp Thr Ala Leu His His Ala Ser Met Gly Tyr Thr Gln
        515                 520                 525

Thr Met Lys Val Ile Leu Asp Thr Asn Leu Lys Cys Thr Asp Arg Leu
    530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
        595                 600                 605

Leu Lys Ile Phe Ser His Asn Ser Pro Gly Asn Lys Cys Pro Ile Thr
    610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
        675                 680                 685

Met Val Gln Asn Asn Arg Ile Glu Leu Leu Asn His Pro Val Cys Lys
    690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
        755                 760                 765

Leu Ile Lys Thr Cys Met Ile Leu Val Phe Leu Ser Ser Ile Phe Gly
    770                 775                 780

Tyr Cys Lys Glu Ala Gly Gln Ile Phe Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
        835                 840                 845

Tyr Leu Gln Arg Phe Glu Asn Cys Gly Ile Phe Ile Val Met Leu Glu
```

```
            850                 855                 860
Val Ile Leu Lys Thr Leu Leu Arg Ser Thr Val Phe Ile Phe Leu
865                 870                 875                 880

Leu Leu Ala Phe Gly Leu Ser Phe Tyr Ile Leu Asn Leu Gln Asp
                885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
            915                 920                 925

Asn Glu Leu Ala His Pro Val Leu Ser Phe Ala Gln Leu Val Ser Phe
            930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
            965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
            995                 1000                1005

Lys Pro Arg Ser Gly Gly Met Leu Phe His Ile Phe Cys Phe Leu Phe
            1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
            1045                1050                1055

Leu Leu Glu Lys Gln His Glu Leu Ile Lys Leu Ile Ile Gln Lys Met
            1060                1065                1070

Glu Ile Ile Ser Glu Thr Glu Asp Asp Ser His Cys Ser Phe Gln
            1075                1080                1085

Asp Arg Phe Lys Lys Glu Gln Met Glu Gln Arg Asn Ser Arg Trp Asn
            1090                1095                1100

Thr Val Leu Arg Ala Val Lys Ala Lys Thr His His Leu Glu Pro
1105                1110                1115

<210> SEQ ID NO 4
<211> LENGTH: 3360
<212> TYPE: DNA
<213> ORGANISM: Homo sapiens

<400> SEQUENCE: 4
atgaagtgca gcctgaggaa gatgtggcgc cctggagaaa agaaggagcc ccagggcgtt      60
gtctatgagg atgtgccgga cgacacggag gatttcaagg aatcgcttaa ggtggttttt     120
gaaggaagtg catatggatt acaaaacttt aataagcaaa agaaattaaa acatgtgac     180 gatatggaca ccttcttctt gcattatgct gcagcagaag gccaaattga gctaatggag     240
aagatcacca gagattcctc tttggaagtg ctgcatgaaa tggatgatta tggaaatacc     300
cctctgcatt gtgctgtaga aaaaaaccaa attgaaagcg ttaagtttct tctcagcaga     360
ggagcaaacc caaaccctccg aaacttcaac atgatggctc ctctccacat agctgtgcag     420
ggcatgaata atgaggtgat gaaggtcttg cttgagcata gaactattga tgttaatttg     480
gaaggagaaa atggaaacac agctgtgatc attgcgtgca ccacaaataa tagcgaagca     540
ttgcagattt tgcttaacaa aggagctaag ccatgtaaat caaataaatg gggatgtttc     600
cctattcacc aagctgcatt ttcaggttcc aaagaatgca tggaaataat actaaggttt     660
```

```
ggtgaagagc atgggtacag tagacagttg cacattaact ttatgaataa tgggaaagcc    720
accctctcc  acctggctgt gcaaaatggt gacttggaaa tgatcaaaat gtgcctggac    780
aatggtgcac aaatagaccc agtggagaag ggaaggtgca cagccattca ttttgctgcc    840
acccagggag ccactgagat tgttaaactg atgatatcgt cctattctgg tagcgtggat    900
attgttaaca caaccgatgg atgtcatgag accatgcttc acagagcttc attgtttgat    960
caccatgagc tagcagacta tttaatttca gtgggagcag atattaataa gatcgattct   1020
gaaggacgct ctccacttat attagcaact gcttctgcat cttggaatat tgtaaatttg   1080
ctactctcta aaggtgccca gtagacata  aaagataatt ttggacgtaa ttttctgcat   1140
ttaactgtac agcaaccta  tggattaaaa atctgcgac  ctgaatttat gcagatgcaa   1200
cagatcaaag agctggtaat ggatgaagac aacgatgggt gtactcctct acattatgca   1260
tgtagacagg ggggccctgg ttctgtaaat aacctacttg gctttaatgt gtccattcat   1320
tccaaaagca aagataagaa atcacctctg cattttgcag ccagttatgg gcgtatcaat   1380
acctgtcaga ggctcctaca agacataagt gatacgaggc ttctgaatga aggtgacctt   1440
catgaatga  ctcctctcca tctggcagca aagaatggac atgataaagt agttcagctt   1500
cttctgaaaa aaggtgcatt gtttctcagt gaccacaatg gctggacagc tttgcatcat   1560
gcgtccatgg gcgggtacac tcagaccatg aaggtcattc ttgatactaa tttgaagtgc   1620
acagatcgct tggatgaaga cgggaacact gcacttcact ttgctgcaag ggaaggccac   1680
gccaaagccg ttgcgcttct tctgagccac aatgctgaca tagtcctgaa caagcagcag   1740
gcctcctttt tgcaccttgc acttcacaat aagaggaagg aggttgttct tacgatcatc   1800
aggagcaaaa gatgggatga atgtcttaag attttcagtc ataattctcc aggcaataaa   1860
tgtccaatta cagaaatgat agaataccta cctgaatgca tgaaggtact tttagatttc   1920
tgcatgttgc attccacaga agacaagtcc tgccgagact attatatcga gtataatttc   1980
aaatatcttc aatgtccatt agaattcacc aaaaaaacac ctacacagga tgttatatat   2040
gaaccgctta cagccctcaa cgcaatggta caaaataacc gcatagagct tctcaatcat   2100
cctgtgtgta agaatatttt actcatgaaa tggttggctt atggatttag agctcatatg   2160
atgaatttag gatcttactg tcttggtctc ataccatatga ccattctcgt tgtcaatata   2220
aaaccaggaa tggcttttcaa ctcaactggc atcatcaatg aaactagtga tcattcagaa   2280
atactagata ccacgaattc atatctaata aaaacttgta tgattttagt gtttttatca   2340
agtatatttg ggtattgcaa agaagcgggg caaattttcc aacagaaaag gaattatttt   2400
atggatataa gcaatgttct tgaatggatt atctacacga cgggcatcat ttttgtgctg   2460
cccttgtttg ttgaaatacc agctcatctg cagtggcaat gtggagcaat tgctgtttac   2520
ttctattgga tgaatttctt attgtatctt caaagatttg aaaattgtgg aatttttatt   2580
gttatgttgg aggtaatttt gaaactttg  ttgaggtcta cagttgtatt tatcttcctt   2640
cttctggctt ttggactcag cttttacatc ctcctgaatt tacaggatcc cttcagctct   2700
ccattgcttt ctataatcca gaccttcagc atgatgctag gagatatcaa ttatcgagag   2760
tccttcctag aaccatatct gagaaatgaa ttggcacatc cagttctgtc ctttgcacaa   2820
cttgttttcct tcacaatatt tgtcccaatt gtcctcatga atttacttat tggtttggca   2880
gttggcgaca ttgctgaggt ccagaaacat gcatcattga agaggatagc tatgcaggtg   2940
gaacttcata ccagcttaga gaagaagctg ccactttggt ttctacgcaa agtggatcag   3000
```

-continued

```
aaatccacca tcgtgtatcc caacaaaccc agatctggtg ggatgttatt ccatatattc   3060
tgttttttat tttgcactgg ggaaataaga caagaaatac caaatgctga taaatcttta   3120
gaaatggaaa tattaaagca gaaataccgg ctgaaggatc ttacttttct cctggaaaaa   3180
cagcatgagc tcattaaact gatcattcag aagatggaga tcatctctga dacagaggat   3240
gatgatagcc attgttcttt tcaagacagg tttaagaaag agcagatgga acaaaggaat   3300
agcagatgga atactgtgtt gagagcagtc aaggcaaaaa cacaccatct tgagccttag   3360
```

<210> SEQ ID NO 5
<211> LENGTH: 1125
<212> TYPE: PRT
<213> ORGANISM: mus musculus

<400> SEQUENCE: 5

```
Met Lys Arg Gly Leu Arg Arg Ile Leu Leu Pro Glu Glu Arg Lys Glu
 1               5                  10                  15

Val Gln Gly Val Val Tyr Arg Gly Val Gly Glu Asp Met Asp Cys Ser
            20                  25                  30

Lys Glu Ser Phe Lys Val Asp Ile Glu Gly Asp Met Cys Arg Leu Glu
        35                  40                  45

Asp Phe Ile Lys Asn Arg Arg Lys Leu Ser Lys Tyr Glu Asp Glu Asn
    50                  55                  60

Leu Cys Pro Leu His His Ala Ala Ala Glu Gly Gln Val Glu Leu Met
65                  70                  75                  80

Glu Leu Ile Ile Asn Gly Ser Ser Cys Glu Val Leu Asn Ile Met Asp
                85                  90                  95

Gly Tyr Gly Asn Thr Pro Leu His Cys Ala Ala Glu Lys Asn Gln Val
            100                 105                 110

Glu Ser Val Lys Phe Leu Leu Ser Gln Gly Ala Asn Pro Asn Leu Arg
        115                 120                 125

Asn Arg Asn Met Met Ser Pro Leu His Ile Ala Val His Gly Met Tyr
    130                 135                 140

Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                165                 170                 175

Asp Asn Ser Glu Ala Leu Gln Ile Leu Leu Glu Lys Gly Ala Lys Leu
            180                 185                 190

Cys Lys Ser Asn Lys Trp Gly Asp Tyr Pro Val His Gln Ala Ala Phe
        195                 200                 205

Ser Gly Ala Lys Lys Cys Met Glu Leu Ile Leu Ala Tyr Gly Glu Lys
    210                 215                 220

Asn Gly Tyr Ser Arg Glu Thr His Ile Asn Phe Val Asn His Lys Lys
225                 230                 235                 240

Ala Ser Pro Leu His Leu Ala Val Gln Ser Gly Asp Leu Asp Met Ile
                245                 250                 255

Lys Met Cys Leu Asp Asn Gly Ala His Ile Asp Met Met Glu Asn Ala
            260                 265                 270

Lys Cys Met Ala Leu His Phe Ala Thr Gln Gly Ala Thr Asp Ile
        275                 280                 285

Val Lys Leu Met Ile Ser Ser Tyr Thr Gly Ser Ser Asp Ile Val Asn
    290                 295                 300

Ala Val Asp Gly Asn Gln Glu Thr Leu Leu His Arg Ala Ser Leu Phe
305                 310                 315                 320
```

-continued

```
Asp His His Asp Leu Ala Glu Tyr Leu Ile Ser Val Gly Ala Asp Ile
            325                 330                 335

Asn Ser Thr Asp Ser Glu Gly Arg Ser Pro Leu Ile Leu Ala Thr Ala
            340                 345                 350

Ser Ala Ser Trp Asn Ile Val Asn Leu Leu Cys Lys Gly Ala Lys
            355                 360                 365

Val Asp Ile Lys Asp His Leu Gly Arg Asn Phe Leu His Leu Thr Val
    370                 375                 380

Gln Gln Pro Tyr Gly Leu Arg Asn Leu Arg Pro Glu Phe Met Gln Met
385                 390                 395                 400

Gln His Ile Lys Glu Leu Val Met Asp Glu Asp Asn Asp Gly Cys Thr
            405                 410                 415

Pro Leu His Tyr Ala Cys Arg Gln Gly Val Pro Val Ser Val Asn Asn
            420                 425                 430

Leu Leu Gly Phe Asn Val Ser Ile His Ser Lys Ser Lys Asp Lys Lys
            435                 440                 445

Ser Pro Leu His Phe Ala Ala Ser Tyr Gly Arg Ile Asn Thr Cys Gln
    450                 455                 460

Arg Leu Leu Gln Asp Ile Ser Asp Thr Arg Leu Leu Asn Glu Gly Asp
465                 470                 475                 480

Leu His Gly Met Thr Pro Leu His Leu Ala Ala Lys Asn Gly His Asp
            485                 490                 495

Lys Val Val Gln Leu Leu Leu Lys Lys Gly Ala Leu Phe Leu Ser Asp
            500                 505                 510

His Asn Gly Trp Thr Ala Leu His His Ala Ser Met Gly Gly Tyr Thr
    515                 520                 525

Gln Thr Met Lys Val Ile Leu Asp Thr Asn Leu Lys Cys Thr Asp Arg
    530                 535                 540

Leu Asp Glu Glu Gly Asn Thr Ala Leu His Phe Ala Ala Arg Glu Gly
545                 550                 555                 560

His Ala Lys Ala Val Ala Met Leu Leu Ser Tyr Asn Ala Asp Ile Leu
            565                 570                 575

Leu Asn Lys Lys Gln Ala Ser Phe Leu His Ile Ala Leu His Asn Lys
            580                 585                 590

Arg Lys Glu Val Val Leu Thr Thr Ile Arg Asn Lys Arg Trp Asp Glu
    595                 600                 605

Cys Leu Gln Val Phe Thr His Asn Ser Pro Ser Asn Arg Cys Pro Ile
    610                 615                 620

Met Glu Met Val Glu Tyr Leu Pro Glu Cys Met Lys Val Leu Leu Asp
625                 630                 635                 640

Phe Cys Met Ile Pro Ser Thr Glu Asp Lys Ser Cys Gln Asp Tyr His
            645                 650                 655

Ile Glu Tyr Asn Phe Lys Tyr Leu Gln Cys Pro Leu Ser Met Thr Lys
            660                 665                 670

Lys Val Ala Pro Thr Gln Asp Val Val Tyr Glu Pro Leu Thr Ile Leu
            675                 680                 685

Asn Val Met Val Gln His Asn Arg Ile Glu Leu Leu Asn His Pro Val
    690                 695                 700

Cys Arg Glu Tyr Leu Leu Met Lys Trp Cys Ala Tyr Gly Phe Arg Ala
705                 710                 715                 720

His Met Met Asn Leu Gly Ser Tyr Cys Leu Gly Leu Ile Pro Met Thr
            725                 730                 735
```

```
Leu Leu Val Val Lys Ile Gln Pro Gly Met Ala Phe Asn Ser Thr Gly
            740                 745                 750

Ile Ile Asn Gly Thr Ser Ser Thr His Glu Glu Arg Ile Asp Thr Leu
        755                 760                 765

Asn Ser Phe Pro Ile Lys Ile Cys Met Ile Leu Val Phe Leu Ser Ser
770                 775                 780

Ile Phe Gly Tyr Cys Lys Glu Val Ile Gln Ile Phe Gln Gln Lys Arg
785                 790                 795                 800

Asn Tyr Phe Leu Asp Tyr Asn Asn Ala Leu Glu Trp Val Ile Tyr Thr
            805                 810                 815

Thr Ser Ile Ile Phe Val Leu Pro Leu Phe Leu Asn Ile Pro Ala Tyr
        820                 825                 830

Met Gln Trp Gln Cys Gly Ala Ile Ala Ile Phe Phe Tyr Trp Met Asn
    835                 840                 845

Phe Leu Leu Tyr Leu Gln Arg Phe Glu Asn Cys Gly Ile Phe Ile Val
850                 855                 860

Met Leu Glu Val Ile Phe Lys Thr Leu Leu Arg Ser Thr Gly Val Phe
865                 870                 875                 880

Ile Phe Leu Leu Leu Ala Phe Gly Leu Ser Phe Tyr Val Leu Leu Asn
            885                 890                 895

Phe Gln Asp Ala Phe Ser Thr Pro Leu Leu Ser Leu Ile Gln Thr Phe
        900                 905                 910

Ser Met Met Leu Gly Asp Ile Asn Tyr Arg Asp Ala Phe Leu Glu Pro
    915                 920                 925

Leu Phe Arg Asn Glu Leu Ala Tyr Pro Val Leu Thr Phe Gly Gln Leu
930                 935                 940

Ile Ala Phe Thr Met Phe Val Pro Ile Val Leu Met Asn Leu Leu Ile
945                 950                 955                 960

Gly Leu Ala Val Gly Asp Ile Ala Glu Val Gln Lys His Ala Ser Leu
            965                 970                 975

Lys Arg Ile Ala Met Gln Val Glu Leu His Thr Asn Leu Glu Lys Lys
        980                 985                 990

Leu Pro Leu Trp Tyr Leu Arg Lys Val Asp Gln Arg Ser Thr Ile Val
    995                 1000                1005

Tyr Pro Asn Arg Pro Arg His Gly Arg Met Leu Arg Phe Phe His Tyr
1010                1015                1020

Phe Leu Asn Met Gln Glu Thr Arg Gln Glu Val Pro Asn Ile Asp Thr
1025                1030                1035                1040

Cys Leu Glu Met Glu Ile Leu Lys Gln Lys Tyr Arg Leu Lys Asp Leu
                1045                1050                1055

Thr Ser Leu Leu Glu Lys Gln His Glu Leu Ile Lys Leu Ile Ile Gln
            1060                1065                1070

Lys Met Glu Ile Ile Ser Glu Thr Glu Asp Glu Asp Asn His Cys Ser
        1075                1080                1085

Phe Gln Asp Arg Phe Lys Lys Glu Arg Leu Glu Gln Met His Ser Lys
    1090                1095                1100

Trp Asn Phe Val Leu Asn Ala Val Lys Thr Lys Thr His Cys Ser Ile
1105                1110                1115                1120

Ser His Pro Asp Phe
            1125

<210> SEQ ID NO 6
<211> LENGTH: 3378
<212> TYPE: DNA
```

<213> ORGANISM: mus musculus

<400> SEQUENCE: 6

| | |
|---|---|
| atgaagcgcg gcttgaggag gattctgctc ccggaggaaa ggaaggaggt ccagggcgtt | 60 |
| gtctatcgcg gcgtcgggga agacatggac tgctccaagg aatcctttaa ggtggacatt | 120 |
| gaaggagata tgtgtagatt agaagacttc atcaagaacc gaagaaaact aagcaaatat | 180 |
| gaggatgaaa atctctgtcc tctgcatcac gcagcagcag aaggtcaagt tgaactgatg | 240 |
| gaactgatca tcaatggttc ttcgtgtgaa gtgctgaata taatggatgg ttatggaaat | 300 |
| accccactgc attgtgctgc agaaaaaaat caagttgaaa gtgtaaagtt tcttctcagc | 360 |
| caaggagcaa atccaaacct ccgaaataga aacatgatgt caccccttca catagctgtg | 420 |
| catggcatgt acaacgaagt gatcaaggtg ttgactgagc acaaggccac taacatcaat | 480 |
| ttagaaggag agaatgggaa cacggctttg atgtccacgt gtgccaaaga caacagtgaa | 540 |
| gctttgcaaa ttttgttaga aaaggagct aagctgtgta atcaaataa gtggggagac | 600 |
| taccctgtgc accaggcagc attttcaggt gccaaaaaat gcatggaatt aatcttagca | 660 |
| tatggtgaaa agaacggcta cagcaggag actcacatta attttgtgaa tcacaagaaa | 720 |
| gccagccctc tccacctagc agttcaaagc ggagacttgg acatgattaa gatgtgcctg | 780 |
| gacaacggtg cacacatcga catgatggag aatgccaaat gcatggccct ccatttgct | 840 |
| gcaacccagg gagccactga catcgttaag ctcatgatct catcctatac cggaagtagt | 900 |
| gatattgtga atgcagttga tggcaatcag gagaccctgc ttcacagagc ctcgttattt | 960 |
| gatcaccatg acctggcaga ataccctata tcagtgggag cagacatcaa cagcactgat | 1020 |
| tctgaaggac gctctccact tatttttagca acagcttctg catcctggaa cattgtgaat | 1080 |
| ttgctcctct gtaaaggtgc caagtagac ataaagatc atcttggacg taacttttttg | 1140 |
| catttgactg tgcagcagcc ttatggacta agaaatttgc ggcctgagtt tatgcagatg | 1200 |
| caacacatca aagagctggt gatggatgaa acaatgacg gatgcacacc tctccattat | 1260 |
| gcctgtaggc aggggggttcc tgtctctgta aataacctcc ttggcttcaa tgtgtccatt | 1320 |
| catagcaaaa gtaaagataa gaagtcgccc ctgcattttg cagccagtta tgggcgcatc | 1380 |
| aatacatgtc agagacttct gcaagacata agtgatacga ggcttttgaa tgaaggggat | 1440 |
| ctccatggga tgaccctct ccacctggca gcaaaaaatg gcatgataa agtcgttcaa | 1500 |
| ctccttctga gaaaggggc cttatttctc agtgaccaca atggctggac tgcttttgcat | 1560 |
| cacgcctcca tgggtgggta cactcagacc atgaaggtca ttcttgatac taacttgaaa | 1620 |
| tgcacagacc gactagatga agaagggaac acagcactcc actttgcagc acgggaaggc | 1680 |
| catgccaagg ctgttgcaat gcttttgagc tacaatgctg acatcctcct gaacaagaag | 1740 |
| caagcttcct ttctgcatat tgccctgcac aataagcgca aggaagtggt tctcacaacc | 1800 |
| atcagaaata aagatgggga tgagtgtctt caagttttca ctcataattc tccaagcaat | 1860 |
| cgatgtccaa tcatggagat ggtagaatac ctccccgagt gcatgaaagt tcttttagat | 1920 |
| ttctgcatga taccttccac agaagacaag tcctgtcaag actaccatat tgagtataat | 1980 |
| ttcaagtatc tccaatgccc attatccatg accaaaaaag tagcacctac ccaggatgtg | 2040 |
| gtatatgagc tcttacaat cctcaatgtc atggtccaac ataaccgcat agaactcctc | 2100 |
| aaccaccctg tgtgtaggga gtacttactg atgaaatggt gtgcctatgg attcagggcc | 2160 |
| catatgatga acctaggatc ttattgtctt ggtctcatac ccatgaccct tcttgttgtc | 2220 |
| aaaatacagc ctggaatggc cttcaattct actggaataa tcaatggaac tagtagtact | 2280 |

```
catgaggaaa gaatagacac tctgaattca tttccaataa aaatatgtat gattctagtt    2340
tttttatcaa gtatatttgg atattgcaaa gaagtgatcc aaattttcca acagaaaagg    2400
aattacttcc tggattacaa caatgctctg gaatgggtta tctatacaac tagtatcatc    2460
ttcgtgttgc ccttgttcct caacatccca gcgtatatgc agtggcaatg tggagcaata    2520
gcgatattct tctactggat gaacttccta ctgtatcttc aaaggtttga gaactgtgga    2580
attttcattg ttatgttgga ggtgatttt aaaacattgc tgagatcgac cggagtgttt     2640
atcttcctcc tactggcttt tggcctcagc ttttatgttc tcctgaattt ccaagatgcc    2700
ttcagcaccc cattgctttc cttaatccag acattcagta tgatgctagg agacatcaat    2760
tatcgagatg ccttcctaga accattgttt agaaatgagt tggcatascc agtcctgacc    2820
tttgggcagc ttattgcctt cacaatgttt gtcccaattg ttctcatgaa cttactgatt    2880
ggcttggcgg ttggggacat tgctgaggtc cagaagcatg cgtcattgaa gaggattgct    2940
atgcaggtgg aacttcatac caacttagaa aaaaagctgc cactctggta cttacgcaaa    3000
gtggatcaga ggtccaccat cgtgtatcca aatagaccca ggcacggcag gatgctacgg    3060
ttttttcatt actttcttaa tatgcaagaa acacgacaag aagtaccaaa cattgacaca    3120
tgcttggaaa tggaaatatt gaaacagaaa tatcggctga aggacctcac ttccctcttg    3180
gaaaagcagc atgagctcat caaactcatc atccagaaga tggagatcat ctcagagaca    3240
gaagatgaag ataaccattg ctctttccaa gacaggttca agaaggagag gctggaacag    3300
atgcacagca agtggaattt tgtcttaaac gcagttaaga ctaaaacaca ttgttctatt    3360
agccacccgg acttttag                                                 3378
```

METHODS AND COMPOSITIONS FOR TREATING PAIN

RELATED APPLICATIONS

This application is a continuation of and claims priority under 35 U.S.C. §121 to U.S. patent application Ser. No. 13/444,213, now U.S. Pat. No. 8,541,423, filed on Apr. 11, 2012, which is a continuation of U.S. patent application Ser. No. 12/688,241, now U.S. Pat. No. 8,178,542, filed on Jan. 15, 2010, which is a divisional of U.S. patent application Ser. No. 11/645,307, now U.S. Pat. No. 7,671,061, filed on Dec. 22, 2006, which is a non-provisional application of and which claims priority under 35 U.S.C. §119 to U.S. Patent Application No. 60/753,665, filed on Dec. 22, 2005, and U.S. Patent Application No. 60/817,892, filed on Jun. 29, 2006. The specifications of each of the foregoing applications are hereby incorporated by reference in their entirety.

BACKGROUND

A variety of ion channel proteins exist to mediate ion flux across cellular membranes. The proper expression and function of ion channel proteins is essential for the maintenance of cell function, intracellular communication, and the like. Numerous diseases are the result of misregulation of membrane potential or aberrant calcium handling. Given the central importance of ion channels in modulating membrane potential and ion flux in cells, identification of agents that can promote or inhibit particular ion channels are of great interest as research tools and as possible therapeutic agents.

One such channel is the Transient Receptor Potential A1 (TRPA1) channel (ANKTM1). TRPA1 is a calcium permeable channel, specifically a non-selective calcium permeable cation channel. In addition to calcium ions, TRPA1 channels are permeable to other cations, for example sodium. Thus, TRPA1 channels modulate membrane potential by modulating the flux of cations such as calcium and sodium ions. Although non-selective cation channels such as TRPA1 modulate, among other things, calcium ion flux, they are mechanistically distinct from voltage-gated calcium channels. Generally, voltage-gated calcium channels respond to depolarization of the potential difference across the membrane and can open to permit an influx of calcium from the extracellular medium and a rapid increase in intracellular calcium levels or concentrations. In contrast, non-selective cation channels are generally signal transduction gated, long lasting, and produce less rapid changes in ion concentration. These mechanistic differences are accompanied by structural differences among voltage-gated and cation permeable channels. Thus, although many diverse channels act to regulate ion flux and membrane potential in various cell types and in response to numerous stimuli, it is important to recognize the significant structural, functional, and mechanistic differences among different classes of ion channels.

Since the mis-regulation of ion channels is often associated with pathological conditions, it would be desirable to identify and make compounds that can modulate one or more functions of ion channels including TRPA1. Such compounds have a variety of in vitro and in vivo uses.

SUMMARY

An important aspect of achieving cellular homeostasis is the maintenance of appropriate ion concentrations in various cell types during development and in response to numerous stimuli. Large numbers of diverse types of ion channels act to maintain cellular homeostasis by moving ions into and out of cells across the plasma membrane, and within cells by moving ions across membranes of intracellular organelles including, for example, the endoplasmic reticulum, sarcoplasmic reticulum, mitochondria and endocytic organelles including endosomes and lysosomes. One such ion channel is the non-selective cation channel TRPA1. TRPA1 is cation permeable and belongs to the larger family of TRP ion channels.

TRP channels have been classified into at least six groups: TRPC (short), TRPV (vanilloid), TRPM (long, melastatin), TRPP (polycystins), TRPML (mucolipins), and TRPA (ANKTM1). The TRPC group can be divided into 4 subfamilies (TRPC1, TRPC4,5, TRPC3,6,7 and TRPC2) based on sequence homology and functional similarities. Currently the TRPV family has 6 members. TRPV5 and TRPV6 are more closely related to each other than to TRPV1, TRPV2, TRPV3, or TRPV4. TRPA1 is most closely related to TRPV3, and is more closely related to TRPV1 and TRPV2 than to TRPV5 and TRPV6. The TRPM family has 8 members. Constituents include the following: the founding member TRPM1 (Melastatin or LTRPC1), TRPM3 (KIAA1616 or LTRPC3), TRPM7 (TRP-PLIK, ChaK(1), LTRPC7), TRPM6 (ChaK2), TRPM2 (TRPC7 or LTRPC2), TRPM8 (Trp-p8 or CMR1), TRPM5 (Mtr 1 or LTRPC5), and TRPM4 (F1120041 or LTRPC4). The sole mammalian member of the TRPA family is ANKTM1. The TRPML family consists of the mucolipins, which include TRPML1 (mucolipins 1), TRPML2 (mucolipins 2), and TRPML3 (mucolipin3). The TRPP family consists of two groups of channels: those predicted to have six transmembrane domains and those that have 11. TRPP2 (PKD2), TRPP3 (PKD2L1), TRPP5 (PKD2L2) are all predicted to have six transmembrane domains. TRPP1 (PKD1, PC1), PKD-REJ and PKD-1L1 are all thought to have 11 transmembrane domains.

The TRP channels constitute a large and important class of channels involved in modulating cellular homeostasis. The present invention provides methods and compositions that modulate at least one TRP family member. Specifically, the present invention provides methods and compositions for antagonizing a function of TRPA1. Modulating a function of TRPA1 provides a means for modulating calcium homeostasis, sodium homeostasis, intracellular calcium levels, membrane polarization (resting membrane potential), and/or cation levels in a cell. Compounds that can modulate one or more TRPA1 functions are useful in many aspects including, but not limited to, maintaining calcium homeostasis; maintaining sodium homeostasis; modulating intracellular calcium levels; modulating membrane polarization (membrane potential); modulating cation levels; and/or treating or preventing diseases, disorders, or conditions associated with calcium homeostasis, sodium homeostasis, calcium or sodium dyshomeostasis, or membrane polarization/hyperpolarization (including hypo and hyperexcitability), and/or treating or preventing diseases, disorders, or conditions associated with regulation or misregulation of TRPA1 expression or function. Additionally, the present invention provides, in certain embodiments, methods and compositions that antagonize both a function of TRPA1 and a function of one or more additional TRP channels.

The present application provides compounds that can modulate TRPA1 function. Methods employing these compounds are also provided. Certain embodiments provide a method of modulating a TRPA1 function in a cell or animal comprising administering an effective amount of a compound that inhibits a TRPA1 function, wherein the compound inhibits a TRPA1-mediated ion flux. Certain embodiments provide a method of modulating a TRPA1 function in a cell comprising administering to the cell an effective amount of a compound that inhibits TRPA1 function, wherein the compound inhibits outward current mediated by TRPA1. Certain embodiments provide a method of modulating a TRPA1 function in a cell comprising administering to the cell an effective amount of a compound that inhibits TRPA1 function, wherein the compound inhibits inward current mediated by TRPA1. Certain embodiments provide a method of modulating a TRPA1 function in a cell comprising administering to the cell an effective amount of a compound that inhibits TRPA1 function, wherein the compound inhibits both the inward and outward currents mediated by TRPA1. Certain embodiments also provide a method of preventing or treating a disease or condition related to TRPA1 function in a subject comprising administering to the subject a therapeutically effective amount of a compound that inhibits TRPA1 function, wherein the compound inhibits the inward current mediated by TRPA1. Certain embodiments provide a method of preventing or treating a disease or condition related to TRPA1 function in a subject comprising administering to the subject a therapeutically effective amount of a compound that inhibits TRPA1 function, wherein the compound inhibits the outward current mediated by TRPA1. Certain embodiments also provide a method of preventing or treating a disease or condition related to TRPA1 function in a subject comprising administering to the subject a therapeutically effective amount of a compound that inhibits TRPA1 function, wherein the compound inhibits both the inward and outward current mediated by TRPA1. Certain embodiments provide a method of preventing or treating a disease or condition related to TRPA1 function in a subject comprising administering to the subject a therapeutically effective amount of a compound that inhibits TRPA1 function, wherein the compound inhibits the ion flux mediated by TRPA1. Note that inhibition of a particular current refers to the ability of a compound to inhibit that current (e.g., inward and/or outward) in either an in vitro or an in vivo assay. Inhibition of a particular current in either an in vivo or an in vitro assay serves as a proxy for the particular functional activity of the particular compound.

The following articles are exemplary of the state of the art regarding the structure and function of TRPA1 (Jordt et al. (2004) Nature 427:260-265; Bautista et al., (2005) PNAS: 102(34):12248-12252). The foregoing articles are incorporated by reference in their entirety.

One aspect of the present invention relates to a method for treating or preventing a condition involving activation of TRPA1 or for which reduced TRPA1 activity can reduce the severity by administering a TRPA1 antagonist that inhibits TRPA1-mediated current and/or TRPA1-mediated ion flux. Described in greater detail below are TRPA1 antagonists that have measured $IC_{50}$'s for inhibition of TRPA1 of 10 micromolar or less, 5 micromolar or less, 2 micromolar or less, 1 micromolar or less, 500 nanomolar or less, 200 nanomolar or less, 100 nanomolar or less, and even 10 nanomolar or less. In certain embodiments, the TRPA1 antagonist inhibit one or both of inward and outward TRPA1-mediated current with an $IC_{50}$ of 1 micromolar or less, and more preferably with an $IC_{50}$ of 500 nanomolar or less, 200 nanomolar or less, 100 nanomolar or less, 25 nanomolar or less and even 10 nanomolar or less. In certain embodiments, the TRPA1 antagonist inhibits at least 95% of TRPA1-mediated current or TRPA1-mediated ion flux when administered at 5 micromolar or less, and even more preferably at 1 micromolar or less.

In certain embodiments, the subject TRPA1 antagonists inhibit TRPA1 with an $IC_{50}$ at least one order of magnitude lower than its $IC_{50}$ for inhibition of one or more of TRPV5, TRPV6, NaV 1.2, TRPV1, mitochondrial uniporter and hERG channel activities, and even more preferably two or even three orders of magnitude lower.

In certain embodiments, the subject TRPA1 antagonists are at least 10, 20, 30, 40, or 50 fold selective for inhibiting TRPA1 activity over that of one or more of TRPV5, TRPV6, NaV 1.2, TRPV1, mitochondrial uniporter, or hERG channel activities. In other words, the antagonist inhibits TRPA1 activity (one or more functions of TRPA1) 10, 20, 30, 40, or 50 times more potently than that of one or more of the foregoing channels.

In certain embodiments, the subject TRPA1 antagonists inhibit TRPA1 with an $IC_{50}$ at least one order of magnitude more potent than its Ki for the AMPA receptor. In certain other embodiments, the subject TRPA1 antagonists inhibit TRPA1 with an $IC_{50}$ at least two orders of magnitude, or even three orders of magnitude, or four orders of magnitude more potent than its Ki for the AMPA receptor. In certain embodiments, the subject TRPA1 antagonists do not appreciably bind the AMPA receptor. In other words, the subject antagonists inhibit TRPA1 with a particular $IC_{50}$ and, when administered at that concentration, the antagonist does not appreciably bind AMPA receptor (e.g., does specifically and appreciably bind the AMPA receptor). In certain embodiments, compounds of the invention inhibit a TRPA1-mediated current with an $IC_{50}$ that is more potent than its Ki for the AMPA receptor. In such embodiments, the ability of the subject TRPA1 inhibitors to decrease pain would thus be independent of binding to and modulation of the alpha-amino-3-hydroxy-5-methyl-4-isoxazolepropionic acid (AMPA) receptor which has been implicated in neuropathic pain reception.

In certain embodiments, the TRPA1 antagonists inhibit TRPA1 with an $IC_{50}$ at least one order of magnitude lower than its $IC_{50}$ for inhibition of TRPV1, and even more preferably two or even three orders of magnitude lower. In certain embodiments, the subject TRPA1 antagonists can be selected for selectivity for TRPA1 versus TRPV1 on the basis of having $IC_{50}$ for TRPV1 inhibition greater than 10 micromolar.

In certain embodiments, the TRPA1 antagonists inhibit one or more of TRPV2, TRPV4, TRPV3 and/or TRPM8 with an $IC_{50}$ of 10 micromolar or less.

In certain embodiments, the TRPA1 antagonist has a therapeutic index (T.I.) for treating the condition with the compound of 10 or greater, and even more preferably has a T.I. of at least 25, 50 or even 100.

In preferred embodiments, the TRPA1 inhibitor has an $IC_{50}$ for TRPA1 inhibition that, at that concentration, does not cause QT interval elongation in the patient nor alter temperature regulation in the patient.

In certain embodiments, the TRPA1 inhibitor is used to treat or ameliorate pain. Exemplary classes of pain that can be treated using a TRPA1 inhibitor include, but are not limited to nociceptive pain, inflammatory pain, and neuropathic pain. Pain that can be treated with a TRPA1 inhibitor can be chronic or acute.

In certain embodiments, the TRPA1 inhibitor is used to treat or ameliorate the symptoms of incontinence.

In certain embodiments, the TRPA1 inhibitor is non-narcotic and has little or no narcotic side-effects. In certain other embodiments, the TRPA1 inhibitor can be used to treat or ameliorate pain with fewer side-effects than narcotic pain relievers. Exemplary side-effects that may be substantially absent at effective dosages of TRPV3 inhibitors include one or more of exopthalmos, catalepsy, disruption of gut motility, and inhibition of sensation in non-injured areas of the body.

In certain embodiments, a TRPA1 inhibitor used in the treatment of any of the diseases or indications disclosed herein has one or more of the structural or functional characteristics disclosed herein.

In certain embodiments, the present invention provides a method for treating or preventing a condition involving activation of TRPA1 or for which reduced TRPA1 activity can reduce the severity, comprising administering an effective amount of a compound of Formula I or a salt thereof, or a solvate, hydrate, oxidative metabolite or prodrug of the compound or its salt:

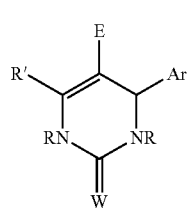

(I)

wherein
W represents O or S, preferably S;
R, independently for each occurrence, represents H or lower alkyl, preferably H;
R' represents substituted or unsubstituted alkyl or substituted or unsubstituted aryl;
E represents carboxylic acid ($CO_2H$), ester or amide; and
Ar represents a substituted or unsubstituted aryl ring; and
wherein said compound inhibits TRPA1 with an with an $IC_{50}$ of 10 micromolar or less.

In certain embodiments, the present invention provides a method for treating or preventing a condition involving activation of TRPA1 or for which reduced TRPA1 activity can reduce the severity, comprising administering an effective amount of a compound of Formula II or a salt thereof, or a solvate, hydrate, oxidative metabolite or prodrug of the compound or its salt:

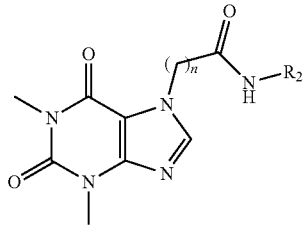

(II)

wherein
n is an integer from 1 to 3; and
$R_2$ represents a substituent; and
wherein said compound inhibits TRPA1 with an with an $IC_{50}$ of 10 micromolar or less.

In certain embodiments, $R_2$ represents optionally substituted alkyl, optionally substituted aryl, optionally substituted heteroaryl, optionally substituted aralkyl, optionally substituted cycloalkyl, optionally substituted heterocyclyl, or optionally substituted heteroaralkyl.

In certain embodiments, $R_2$ is not

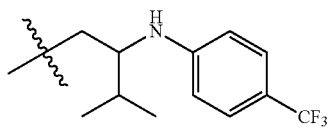

when n=1.

In certain embodiments, the present invention provides a method for treating or preventing a condition involving activation of TRPA1 or for which reduced TRPA1 activity can reduce the severity, comprising administering an effective amount of a compound of Formula III or a salt thereof, or a solvate, hydrate, oxidative metabolite or prodrug of the compound or its salt:

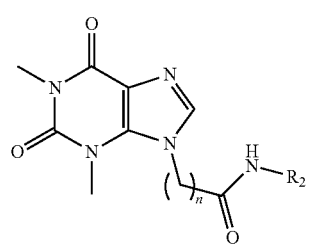

(III)

wherein
n is an integer from 1 to 3; and
$R_2$ represents a substituent; and
wherein said compound inhibits TRPA1 with an with an $IC_{50}$ of 10 micromolar or less.

In certain embodiments, $R_2$ represents optionally substituted alkyl, optionally substituted aryl, optionally substituted heteroaryl, optionally substituted aralkyl, optionally substituted cycloalkyl, optionally substituted heterocyclyl, or optionally substituted heteroaralkyl.

In certain embodiments, the present invention provides a method for treating or preventing a condition involving activation of TRPA1 or for which reduced TRPA1 activity can reduce the severity, comprising administering an effective amount of a compound of Formula IV or a salt thereof, or a solvate, hydrate, oxidative metabolite or prodrug of the compound or its salt:

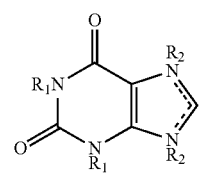

(IV)

wherein
$R_1$, independently for each occurrence, represents H or lower alkyl;
one occurrence of $R_2$ is absent and one occurrence of $R_2$ is $M_mR_3$;
$R_3$ represents substituted or unsubstituted aryl;
M, independently for each occurrence, represents a substituted or unsubstituted methylene group (e.g., substituted with lower alkyl, oxo, hydroxyl, etc.), NR$_1$, O, S, S(O), or S(O$_2$), preferably selected such that no two heteroatoms are adjacent to each other; and m is an integer from 0-10; and wherein said compound inhibits TRPA1 with an with an IC$_{50}$ of 10 micromolar or less.

In certain embodiments, M$_m$R$_3$ represents

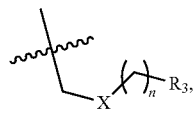

wherein n is an integer between 0 and 4; and

X is —C(═O)O— or —C(═O)NR$_4$— wherein R$_4$ is H or lower alkyl, preferably —C(═O)NH—.

One aspect of the present invention provides a pharmaceutical preparation suitable for use in a human patient, or for veterinary use, comprising an effective amount of any of the compounds shown above (e.g., a compound of Formula I, Formula II, Formula III, or Formula IV, or a salt thereof, or a solvate, hydrate, oxidative metabolite or prodrug of the compound or its salt), and one or more pharmaceutically acceptable excipients. In certain embodiments, the pharmaceutical preparations may be for use in treating or preventing a condition involving activation of TRPA1 or for which reduced TRPA1 activity can reduce the severity. In certain embodiments, the pharmaceutical preparations have a low enough pyrogen activity to be suitable for use in a human patient, or for veterinary use. In certain embodiments, the pharmaceutical preparation comprises an effective amount of any of the compounds shown above, wherein the compound inhibits TRPA1 (e.g., a TRPA1-mediated current and/or TRPA1-mediated ion flux) with an IC$_{50}$ of 10 micromolar or less. In certain embodiments, the pharmaceutical preparation comprises a compound which inhibits TRPA1 with an IC$_{50}$ of 5 micromolar or less, 2 micromolar or less, 1 micromolar or less, or even with an IC$_{50}$ of 500 nM or less, 250 nM or less, 200 nM or less, or even 100 nM or less.

In certain embodiments, the TRPA1 inhibitor for use in methods or pharmaceutical preparations of the present invention is selected from a compound depicted in Tables 1-2. In certain embodiments, the present invention contemplates the use of any compound as depicted in Tables 1-2 in any of the methods or pharmaceutical preparations of the present invention.

TRPA1 antagonists of the subject invention can be used as part of a prophylaxis or treatment for a variety of disorders and conditions, including, but not limited to, acute and/or chronic pain, touch sensitivity, burns, inflammation, diabetic neuropathy, psoriasis, eczema, dermatitis, post-herpetic neuralgia (shingles), migraine, incontinence, fever, hot flashes, osteoarthritis, oral mucositis, cancer pain, bladder cystits, pain associated with Crohn's disease and Irritable Bowel Syndrome (IBS), rheumatoid arthritis, Grierson-Gopalan syndrome (better known as burning feet syndrome), burning mouth syndrome (BMS) and cough, or is used as a depilatory to promote loss of or inhibit the growth of hair on a patient. Other exemplary diseases or conditions that can be treated using a TRPA1 antagonist of the present invention are detailed throughout the specification. The invention contemplates the use of compounds having any of the structures provided in the specification in the treatment of or to reduce the symptoms of any of the diseases or conditions disclosed in the application. The invention further contemplates the use of compounds having any of the structures provided in the specification in the manufacture of a medicament or pharmaceutical preparation to treat or reduce the symptoms of any of the diseases or conditions provided in the specification. Compounds for use in treating a particular disease or condition can be formulated for administration via a route appropriate for the particular disease or condition.

TRPA1 antagonists can be administered alone or in combination with other therapeutic agents. For instance, the TRPA1 antagonists is administered conjointly with one or more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor.

TRPA1 antagonists can be administered topically, orally, transdermally, rectally, vaginally, parentally, intranasally, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

In certain preferred embodiments, a TRPA1 antagonist is administered topically.

In certain preferred embodiments, a TRPA1 antagonist is administered orally.

In certain preferred embodiments, a TRPA1 antagonist is administered parentally.

In certain preferred embodiments, a TRPA1 antagonist is administered to prevent, treat or alleviate signs and symptoms of acute pain, chronic pain, touch sensitivity, itching sensitivity, or as part of treating a burn, such as, for example, post-surgical pain, cancer pain, or neuropathic pain.

In certain preferred embodiments, a TRPA1 antagonist is administered to prevent, treat or alleviate signs and symptoms of migraine.

In certain preferred embodiments, a TRPA1 antagonist is administered to prevent, treat or alleviate signs and symptoms of a disorder or condition selected from the group consisting of diabetic neuropathy, inflammation, psoriasis, eczema, dermatitis, post-herpetic neuralgia (shingles), incontinence, bladder incontinence, fever, hot flashes, pancreatitis, chronic regional pain syndrome, Fabray's disease, and cough.

In certain preferred embodiments, a TRPA1 antagonist is administered to prevent, treat or alleviate signs and symptoms of osteoarthritis.

In certain preferred embodiments, a TRPA1 antagonist is administered to prevent, treat or alleviate signs and symptoms of rheumatoid arthritis.

In certain preferred embodiments, a TRPA1 antagonist is administered to prevent, treat or alleviate signs and symptoms of oral mucositis.

In certain preferred embodiments, a TRPA1 antagonist is administered to promote loss of or inhibit the growth of hair on a patient.

Still another aspect of the present invention relates to the use of a TRPA1 antagonist, e.g., a small molecule agent that inhibits inward TRPA1-mediated current with an IC$_{50}$ of 1 micromolar or less, in the manufacture of a medicament to prevent, treat or alleviate symptoms of a disease, disorder or condition involving activation of TRPA1, or for which reduced TRPA1 activity can reduce the severity, in a patient.

Yet another aspect of the present invention relates to a pharmaceutical preparation comprising an agent that inhibits inward TRPA1-mediated current with an IC$_{50}$ of 1 micromolar or less; and a pharmaceutically acceptable excipient or solvent wherein the agent is provided in a dosage form providing an amount effective to prevent, treat or alleviate symptoms of a disease, disorder or condition involving activation of TRPA1, or for which reduced TRPA1 activity can reduce the severity, in a patient. In certain preferred embodiments, the pharmaceutical preparation does not cause QT interval elongation in the patient.

In certain illustrative embodiments, the pharmaceutical preparation comprises an agent that inhibits TRPA1-mediated current with an $IC_{50}$ of at least one order of magnitude lower than its $IC_{50}$ for inhibition of NaV 1.2 function, TRPV1 function, TRPV5 function, TRPV6 function, mitochondrial uniporter function and HERG function; and a pharmaceutically acceptable excipient or solvent, wherein the agent is provided in a dosage form providing an amount effective to prevent, treat or alleviate symptoms of a disease, disorder or condition involving activation of TRPA1, or for which reduced TRPA1 activity can reduce the severity, in a patient, but which does not cause QT interval elongation.

In another illustrative embodiment, the pharmaceutical preparation comprises an agent that inhibits a TRPA1-mediated current with an $IC_{50}$ of 1 micromolar or less; and a pharmaceutically acceptable excipient or solvent, wherein the agent is provided in a dosage form providing an amount effective to prevent, treat or alleviate symptoms of a disease, disorder or condition involving activation of TRPA1, or for which reduced TRPA1 activity can reduce the severity, in a patient, but which does not cause QT interval elongation.

One preferred preparation is a topical formulation for reducing TRPA1 activity in skin or mucosa, comprising an agent that inhibits a TRPA1-mediated current with an $IC_{50}$ of 1 micromolar or less.

Another preferred preparation is a removable patch or bandage, comprising: (i) a polymeric base; and (ii) an agent that inhibits a TRPA1-mediated current with an $IC_{50}$ of 1 micromolar or less.

Still another illustrative formulation is a skin exfoliant composition for topical application to an animal subject comprising a topical vehicle; one or more skin exfoliant ingredients selected from the group consisting of carboxylic acids, keto acids, α-hydroxy acids, β-hydroxy acids, retinoids, peroxides, and organic alcohols, said one or more skin exfoliant ingredients contained in a total amount of at least about 12% by weight and capable of inducing skin irritation and effecting exfoliation of the skin of said subject; and an agent that inhibits a TRPA1-mediated current with an $IC_{50}$ of 1 micromolar or less, which agent is provided in an amount effective for analgesic, anti-irritant and/or anti-inflammatory effects when applied to skin.

Yet another embodiment is an antitussive composition for peroral administration comprising an agent that inhibits both a TRPA1-mediated current with an $IC_{50}$ of 1 micromolar or less, and an orally-acceptable pharmaceutical carrier in the form of an aqueous-based liquid, or solid dissolvable in the mouth, selected from the group consisting of syrup, elixer, suspension, spray, lozenge, chewable lozenge, powder, and chewable tablet. Such antitussive compositions can include one or more additional agents for treating cough, allergy or asthma symptom selected from the group consisting of: antihistamines, 5-lipoxygenase inhibitors, leukotriene inhibitors, H3 inhibitors, β-adrenergic receptor agonists, xanthine derivatives, α-adrenergic receptor agonists, mast cell stabilizers, expectorants, NK1, NK2 and NK3 tachykinin receptor antagonists, and $GABA_B$ agonists.

Still another embodiment is a metered dose aerosol dispenser containing an aerosol pharmaceutical composition for pulmonary or nasal delivery comprising an agent that inhibits a TRPA1-mediated current with an $IC_{50}$ of 1 micromolar or less. For instance, it can be a metered dose inhaler, a dry powder inhaler or an air-jet nebulizer.

Still another embodiment is an eye ointment or eyedrops for ocular administration. Such ocular compositions may be useful for the treatment or alleviation of ocular pain including pain resulting from eye abrasion or post-surgical pain.

In another aspect, the invention contemplates that any of the TRPA1 inhibitors of the present invention, including inhibitors having one or more of the characteristics disclosed herein, can be used to inhibit a function of TRPA1, for example a TRPA1-mediated current and/or a TRPA1-mediated ion flux. In some embodiments, the compounds can be used to inhibit a TRPA1 mediated current in vitro, for example in cells in culture. In some embodiments, the compounds can be used to inhibit a TRPA1 mediated current in vivo. In certain embodiments, the compounds inhibit both an inward and an outward TRPA1-mediated current. In certain embodiments, the compounds inhibit a TRPA1 mediated ion flux in vitro, for example in cells in culture. In certain other embodiments, the compounds inhibit a TRPA1 mediated in flux in vivo.

The invention contemplates pharmaceutical preparations and uses of TRPA1 antagonists having any combination of the foregoing or following characteristics, as well as any combination of the structural or functional characteristics of the TRPA1 antagonists described herein. Any such antagonists or preparations can be used in the treatment of any of the diseases or conditions described herein. Any such antagonists or preparations can be used to inhibit a function of TRPA1, for example a TRPA1-mediated current and/or a TRPA1-mediated ion flux.

DETAILED DESCRIPTION OF THE DRAWINGS

FIGS. 1a and 1b summarize experiments showing the efficacy of a TRPA1 antagonist in decreasing a symptom of pain in the bradykinin pain model.

Figure 2:
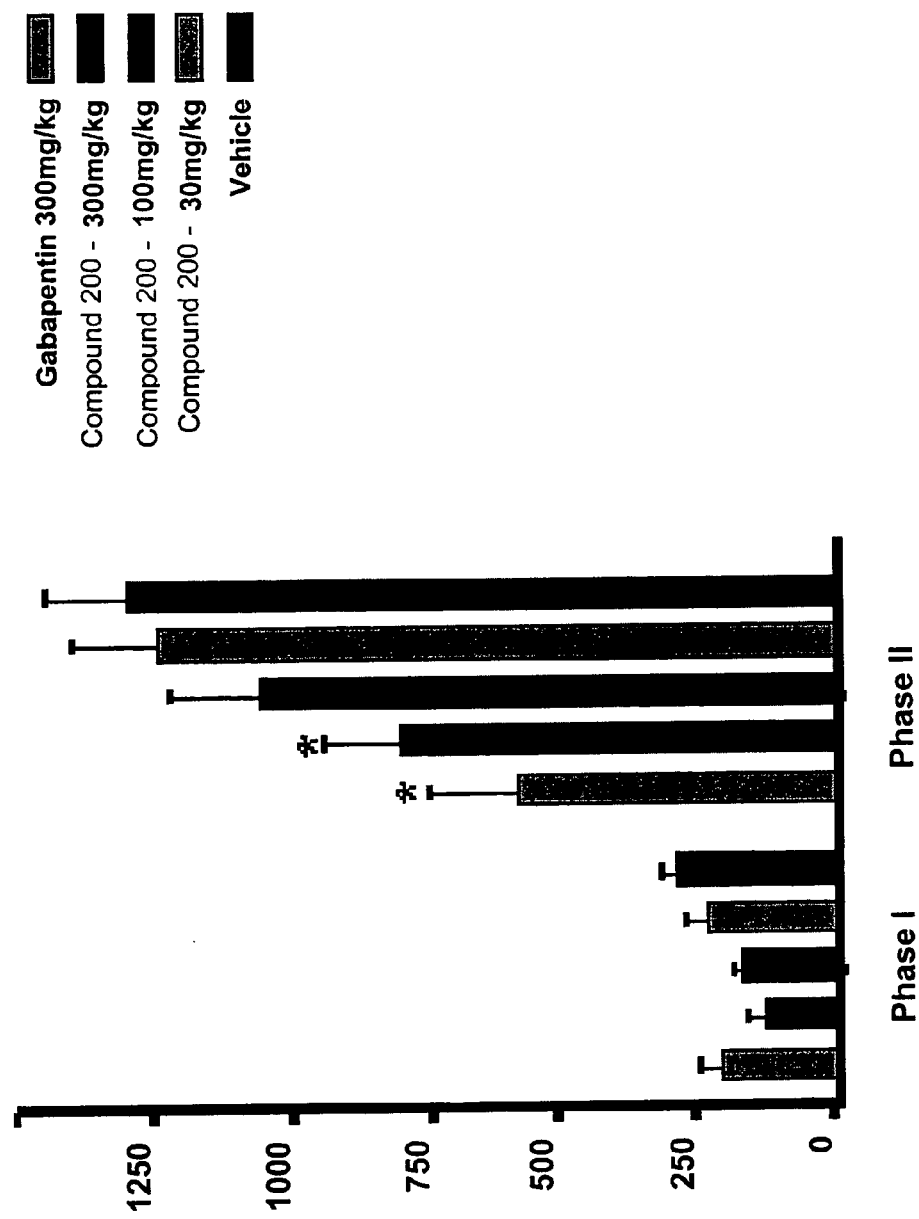

FIG. 2 summarizes experiments showing the efficacy of a TRPA1 antagonist in decreasing pain in the formalin pain model.

FIGS. 3a and 3b summarize experiments showing the efficacy of a TRPA1 antagonist in decreasing carrageenan-induced inflammation.

Figure 4:
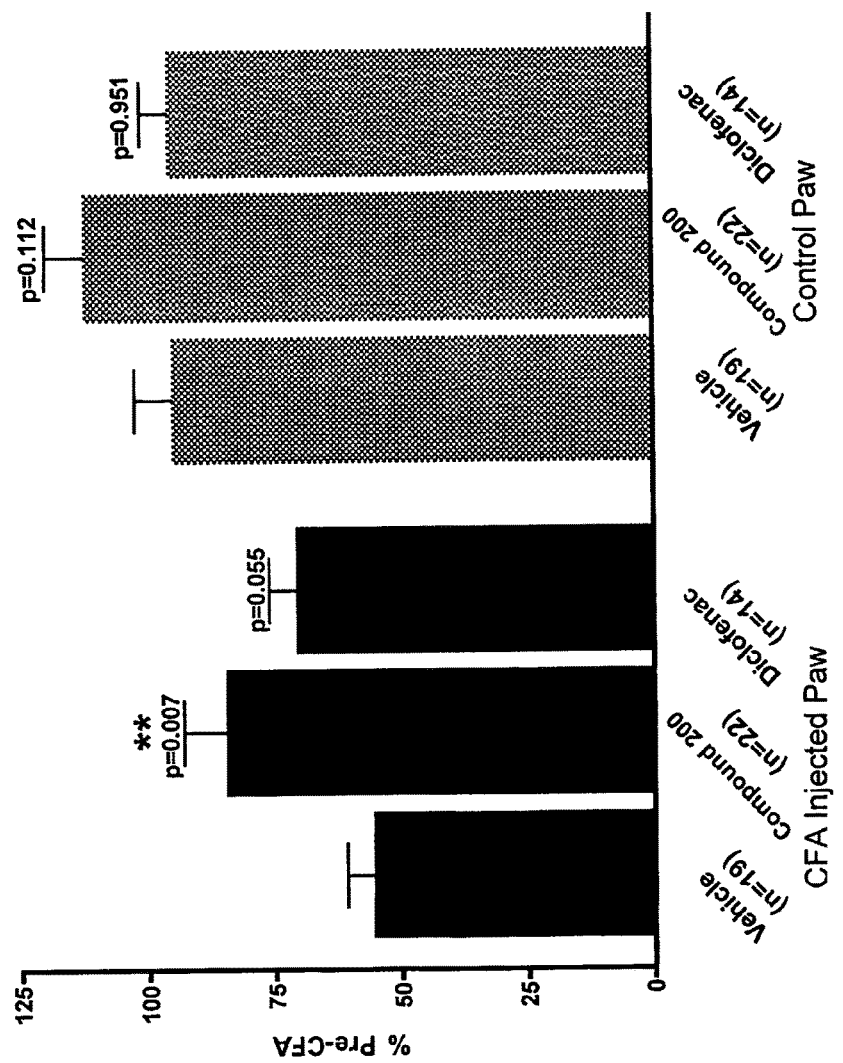

FIG. 4 summarizes experiments showing the efficacy of a TRPA1 antagonist in decreasing pain in the CFA pain model. The results depicted in FIG. 4 additionally show that the effects of the TRPA1 antagonist are specific to the injured paw.

DETAILED DESCRIPTION OF THE TABLES

Table 1 provides exemplary compounds of Formula I with their corresponding in vitro activity as assessed in patch-clamp experiments. The table also includes data indicative of the specificity of various tested compounds for inhibiting TRPA1 activity in comparison to that of other ion channels. Comparative data against other ion channels was assessed in patch-clamp.

Table 2 provides exemplary compounds of Formula II with their corresponding in vitro activity as assessed in patch-clamp experiments. The table also includes data indicative of the specificity of various tested compounds for inhibiting TRPA1 activity in comparison to that of other ion channels. Comparative data against other ion channels was assessed in patch-clamp. At least two of the compounds indicated as inhibiting a TRPA1 mediated current with an $IC_{50}$ of less that 500 nM inhibit a TRPA1 mediated current with an $IC_{50}$ of less than 200 nM. At least one of the compounds indicated as inhibiting a TRPA1 mediated current with an $IC_{50}$ of less than 500 nM inhibits a TRPA1 mediated current with an $IC_{50}$ of less than 100 nM.

DETAILED DESCRIPTION OF THE INVENTION

Cellular homeostasis is a result of the summation of regulatory systems involved in, amongst other things, the regulation of ion flux and membrane potential. Cellular homeostasis is achieved, at least in part, by movement of ions into and out of cells across the plasma membrane and within cells by movement of ions across membranes of intracellular organelles including, for example, the endoplasmic reticulum, sarcoplasmic reticulum, mitochondria and endocytic organelles including endosomes and lysosomes.

Movement of ions across cellular membranes is carried out by specialized proteins. TRP channels are one large family of non-selective cation channels that function to help regulate ion flux and membrane potential. TRP channels are subdivided into 6 sub-families including the TRPA (ANKTM1) family. TRPA1 is a member of the TRPA class of TRP channels.

Non-selective cation channels such as TRPA1 modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPA1 also alters the intracellular free calcium concentration. Calcium is a ubiquitous second messenger molecule within the cell. Thus alterations in intracellular calcium levels have profound effects on signal transduction and gene expression. Thus, activation of non-selective cation channels such as TRPA1 can lead to changes in gene expression and cellular phenotype. Gene expression events include, but are not limited to, production of mRNAs encoding cell surface receptors, ion channels, and kinases. These changes in gene expression can lead to hyperexcitability in that cell. Blockers of TRPA1 therefore also have the potential to decrease or prevent pain and/or to decrease overactive bladder.

TRPA1 proteins are receptor operated channels expressed in sensory neurons (see, e.g., Jordt et al. (2004) Nature 427:260-265) including those with cell bodies residing in the dorsal root ganglion, trigeminal ganglion, and nodose ganglia (see Jordt et al. (2004) Nature 427:260-265, Nagata et al. (2005) J. Neurosci 25(16) 4052-61). In addition, low levels of TRPA1 message can be found in some types of fibroblasts (see Jaquemar et al. (1999) JBC 274(11): 7325-33). TRPA1 has also been reported to be expressed in the bladder. Stimulation of a number of extracellular receptors, including, but not limited to, G-protein coupled receptors or receptor tyrosine kinases are sufficient to activate TRPA1.

TRPA1 proteins suitable for use in accordance with the methods provided herein include, for example: human (SEQ ID NO: 1 and SEQ ID NO: 3 amino acid sequences, encoded by SEQ ID NO: 2 and SEQ ID NO: 4 nucleotide sequences respectively) and murine (SEQ ID NO: 5 amino acid sequence, encoded by SEQ ID NO: 6 nucleotide sequence). Particular TRPA1 proteins also include proteins encoded by cDNAs that would hybridize to the TRPA1 sequence (see SEQ ID NO: 2) under stringent conditions.

TRPA1 is the ion channel that responds to mustard oil. The active ingredients in mustard oil (allyl isothiocyanate) and the active ingredient in garlic (allicin) are both capable of activating TRPA1. Other stimuli may also be able to activate TRPA1. It has been reported that severe cold temperatures between 4 and 15° C. activate TRPA1 (see Story et al., (2003) Cell 112(6): 819-829). However, this finding has been controversial (see Jordt et al. (2004) Nature 427:260-265; Nagata et al. (2005) J. Neurosci 25(16): 4052-61). In addition, TRPA1 shares many structural similarities with TRP channels (i.e., TRPN1, Drosophila TRPA1) in lower animals that respond to mechanical stimulation.

TRPA1 is expressed in, among other tissues, the hair cell epithelia of the inner ear, and disruption of this channel in zebrafish and mouse inhibits hair cell transduction. Therefore, TRPA1 has been proposed in the art as a candidate for the mechanosensitive vertebrate hearing transduction channel (see Corey et al., (2004) Nature 432(7018): 723-730). If this were the case, it would suggest that blockers of TRPA1 might lead to hearing loss, and thus would not have any practical use as a therapeutic agent. However, the observation that the startle response is not substantially impaired in the TRPA1 knockout mouse has led us to conclude that TRPA1 antagonists may not impair hearing, and would thus be suitable drug candidates.

Modulating the function of TRPA1 proteins provides a means of modulating calcium homeostasis, sodium homeostasis, membrane polarization, and/or intracellular calcium levels, and compounds that can modulate TRPA1 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

In certain aspects, the present invention provides methods for treating or ameliorating the effects of diseases and conditions using small molecules that inhibit a TRPA1-mediated current and/or a TRPA1-mediated ion flux with an $IC_{50}$ of less than 10 micromolar. Exemplary suitable compounds for use in any of the methods of the invention (e.g., to treat any of the diseases or conditions disclosed herein) include compounds having one or more of the structural or functional characteristics disclosed herein (e.g., structure, specificity, potency, solubility, etc.). The present invention contemplates the use of any TRPA1 antagonist possessing one or more of the functional or structural attributes described herein. Additionally, the present invention contemplates the use of TRPA1 antagonists of Formula I, II, III, or IV, as well as the use of any of the particular antagonists provided in Tables 1 and 2. Throughout the application, when particular functional attributes are attributed to TRPA1 antagonists, it is understood that such attributes may characterize TRPA1 inhibitors structurally related to or differing from compound of Formulas I, II, III, or IV.

In certain embodiments, a suitable compound inhibits an inward and/or outward TRPA1 mediated current with an $IC_{50}$ of less than 10 micromolar. In certain embodiments, a suitable compound additionally or alternatively inhibits TRPA1 mediated ion flux with an $IC_{50}$ of less than 10 micromolar. $IC_{50}$ can be calculated, for example, in an in vitro assay. For example, IC50 can be calculated using electrophysiological determinations of current, such as standard patch clamp analysis. $IC_{50}$ can also be evaluated using changes in concentration or flux of ion indicators, such as the calcium flux methods described herein.

In certain embodiments, the invention provides a method for treating or preventing a condition involving activation of TRPA1 or for which reduced TRPA1 activity can reduce the severity, comprising administering an effective amount of a compound of Formula I or a salt thereof, or a solvate, hydrate, oxidative metabolite or prodrug of the compound or its salt:

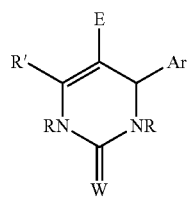
(I)

wherein
W represents O or S, preferably S;
R, independently for each occurrence, represents H or lower alkyl, preferably H;
R' represents substituted or unsubstituted alkyl or substituted or unsubstituted aryl;
E represents carboxylic acid ($CO_2H$), ester or amide; and
Ar represents a substituted or unsubstituted aryl ring; and
wherein said compound inhibits TRPA1 with an with an $IC_{50}$ of 10 micromolar or less.

Examples of compounds within the above formula include:

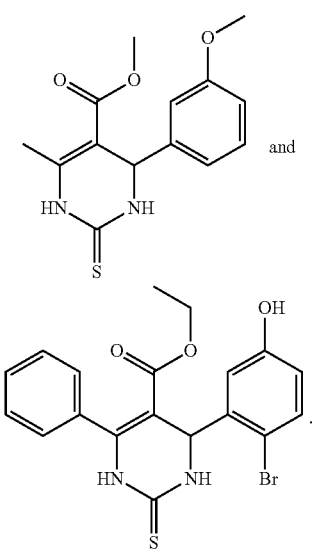

and

Further examples of compounds within formula I are shown in Table 1 along with their corresponding in vitro data.

In certain embodiments, the invention provides a method for treating or preventing a condition involving activation of TRPA1 or for which reduced TRPA1 activity can reduce the severity, comprising administering an effective amount of a compound of Formula II or a salt thereof, or a solvate, hydrate, oxidative metabolite or prodrug of the compound or its salt:

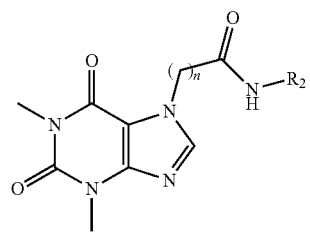
(II)

wherein
n is an integer from 1 to 3; and
$R_2$ represents a substituent; and
wherein said compound inhibits TRPA1 with an with an $IC_{50}$ of 10 micromolar or less.

In certain embodiments, $R_2$ represents optionally substituted alkyl, optionally substituted aryl, optionally substituted heteroaryl, optionally substituted aralkyl, optionally substituted cycloalkyl, optionally substituted heterocyclyl, or optionally substituted heteroaralkyl.

In certain embodiments, $R_2$ is not

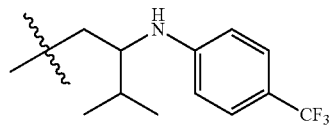 [SMILES: *CC(Nc1ccc(C(F)(F)F)cc1)C(C)C]

when n=1.

In certain embodiments, a compound of Formula II is 10-fold more selective for its TRPA1 activity than for its kininogenase inhibitory activity.

Examples of compounds of formula II include, but are not limited to, compounds 200-204, 206-243, 245-255, 257-282, 284-287, 289-290, 294-295, 298, 304-306, 308-310, 312-313, 316-317, 319, 321, 323, 325-326, 330, 332-333, 335, 337-341, 343-386, 389-390, 395-398, and 400-409, as are depicted in Table 2 along with their in vitro data.

In certain embodiments, the invention provides a method for treating or preventing a condition involving activation of TRPA1 or for which reduced TRPA1 activity can reduce the severity, comprising administering an effective amount of a compound of Formula III or a salt thereof, or a solvate, hydrate, oxidative metabolite or prodrug of the compound or its salt:

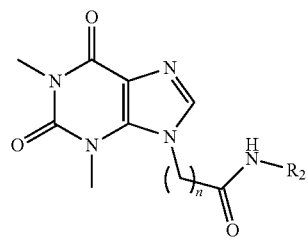
(III)

wherein
n is an integer from 1 to 3; and $R_2$ represents a substituent; and
wherein said compound inhibits TRPA1 with an with an $IC_{50}$ of 10 micromolar or less.

In certain embodiments, $R_2$ represents optionally substituted alkyl, optionally substituted aryl, optionally substituted heteroaryl, optionally substituted aralkyl, optionally substituted cycloalkyl, optionally substituted heterocyclyl, or optionally substituted heteroaralkyl.

In certain embodiments, the invention provides a method for treating or preventing a condition involving activation of TRPA1 or for which reduced TRPA1 activity can reduce the severity, comprising administering an effective amount of a compound of Formula IV or a salt thereof, or a solvate, hydrate, oxidative metabolite or prodrug of the compound or its salt:

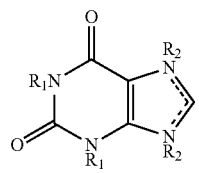

(IV)

wherein
$R_1$, independently for each occurrence, represents H or lower alkyl;
one occurrence of $R_2$ is absent and one occurrence of $R_2$ is $M_mR_3$;
$R_3$ represents substituted or unsubstituted aryl;
M, independently for each occurrence, represents a substituted or unsubstituted methylene group (e.g., substituted with lower alkyl, oxo, hydroxyl, etc.), $NR_1$, O, S, S(O), or $S(O_2)$, preferably selected such that no two heteroatoms are adjacent to each other; and
m is an integer from 0-10; and
wherein said compound inhibits TRPA1 with an with an $IC_{50}$ of 10 micromolar or less.

In certain embodiments, $M_mR_3$ represents

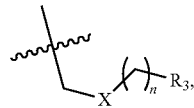

wherein
n is an integer between 0 and 4; and
X is —C(=O)O— or —C(=O)$NR_4$— wherein $R_4$ is H or lower alkyl, preferably —C(=O)NH—.

In certain embodiments, a compound of Formula IV is 10-fold more selective for its TRPA1 activity than for its kininogenase inhibitory activity.

Examples of compounds of formula IV include, but are not limited to, compounds 200-202, 204, 207-210, 212-215, 217, 219-224, 226-229, 231, 236-238, 240, 245-254, 256-268, 273, 275-277, 280-286, 288, 290-306, 309-311, 313-316, 318-320, 322, 324-331, 333-334, 336-338, 342, 344-347, 350-351, 353-355, 358-366, 371, 373-375, 377, 379-380, and 383-409, as are depicted in Table 2 along with their in vitro data.

One aspect of the present invention provides a pharmaceutical preparation suitable for use in a human patient, or for veterinary use, comprising an effective amount of any of the compounds shown above (e.g., a compound of Formula I, Formula II, Formula III, or Formula IV, or a salt thereof, or a solvate, hydrate, oxidative metabolite or prodrug of the compound or its salt), and one or more pharmaceutically acceptable excipients. In certain embodiments, the pharmaceutical preparations may be for use in treating or preventing a condition involving activation of TRPA1 or for which reduced TRPA1 activity can reduce the severity. In certain embodiments, the pharmaceutical preparations have a low enough pyrogen activity to be suitable for use in a human patient, or for veterinary use. In certain embodiments, the pharmaceutical preparation comprises an effective amount of any of the compounds shown above, wherein the compound inhibits TRPA1 with an $IC_{50}$ of 10 micromolar or less. In certain embodiments, the pharmaceutical preparation comprises a compound which inhibits TRPA1 with an $IC_{50}$ of 1 micromolar or less, or even with an $IC_{50}$ of 500 nM or less, 250 nM or less, 200 nM or less, or even 100 nM or less.

In certain embodiments, the TRPA1 inhibitor for use in methods or pharmaceutical preparations of the present invention is selected from a compound depicted in Tables 1-2. In certain embodiments, the present invention contemplates the use of any compound as depicted in optionally substituted in any of the methods or pharmaceutical preparations of the present invention.

One aspect of the current invention provides use of a TRPA1 inhibitor in the manufacture of a medicament for treating or preventing a condition involving activation of TRPA1 or for which reduced TRPA1 activity can reduce the severity, wherein the TRPA1 inhibitor is represented by any of the compounds shown above (e.g., a compound of Formula I, Formula II, Formula III, or Formula IV, or a salt thereof, or a solvate, hydrate, oxidative metabolite or prodrug of the compound or its salt). In certain embodiments, the compound inhibits a TRPA1 mediated current with an $IC_{50}$ of less than 10 micromolar.

In certain embodiments of the above formula, substituted substituents may be substituted with one or more of: alkyl, alkenyl, alkynyl, cycloalkyl, heterocyclyl, aryl, heteroaryl, cycloalkylalkyl, heterocyclylalkyl, aralkyl, or heteroaralkyl, any of which may itself be further substituted, or halogen, hydroxyl, carbonyl (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, and phosphoryl.

Exemplary compounds of are provided in Tables 1 and 2. Table 1 summarizes data collected for the various tested compounds. Table 1 provides $IC_{50}$ data for inhibiting a TRPA1 mediated current. Table 1 also provides selectivity data, where currently available, indicating the degree to which certain compounds also inhibit other ion channels. Additionally, note that compounds represented in Table 1 have various degrees of selectivity for inhibiting TRPA1. Table 2 provides $IC_{50}$ data for inhibiting a TRPA1 mediated current. Table 2 also provides selectivity data, where currently available, indicating the degree to which certain compounds also inhibit other ion channels. Note that at least two of the compounds represented in Table 2 as inhibiting a TRPA1 mediated current with an $IC_{50}$ of 500 nM or less inhibit a TRPA1 mediated current with an $IC_{50}$ of 200 nM or less. Furthermore, at least one compound represented in Table 2 as inhibiting a TRPA1 mediated current with an $IC_{50}$ less than 500 nM or less inhibits a TRPA1 mediated current with an $IC_{50}$ of 100 nM or less. Additionally, note that compounds represented in Table 2 have various degrees of selectivity for inhibiting TRPA1.

In certain embodiments, the invention contemplates that any of the particular compounds depicted in Tables 1 or 2 can be administered to treat any of the diseases or conditions disclosed herein. In some embodiments, the compound is formulated as a pharmaceutical preparation prior to administration. In certain embodiments, the TRPA1 inhibitor for use in methods or pharmaceutical preparations of the present invention is selected from a compound depicted in Tables 1 or 2. In certain embodiments, the present invention contemplates the use of any compound as depicted in Tables 1 or 2 in any of the methods or pharmaceutical preparations of the present invention.

The particular compounds and structural formulas disclosed herein are merely exemplary. The use of small molecule TRPA1 inhibitors having one or more of the functional or structural characteristics described herein are similarly contemplated, Compounds of any of the above structures may be used in the manufacture of medicaments for the treatment of any diseases disclosed herein.

Compounds of any of the above structures may be used to inhibit a function of a TRPA1 channel in vitro or in vivo.

In certain embodiments, compounds that include all or a functional portion of any of the foregoing structures may be used in the manufacture of medicaments for the treatment of any of the diseases disclosed herein. Additionally or alternatively, such compounds may be used in in vitro or in vivo methods of inhibiting TRPA1 function, such as a TRPA1-mediated current.

In certain embodiments, the TRPA1 antagonist for use in the methods of the present invention is a small molecule that is not an aminoglycoside.

In particular embodiments, a small molecule TRPA1 antagonist is chosen for use because it is more selective for one TRP isoform than others, e.g., 10-fold, and more preferably at least 20, 40, 50, 60, 70, 80, or at least 100- or even 1000-fold more selective for TRPA1 over one or more of TRPC6, TRPV5, TRPV6, TRPM8, TRPV1, TRPV2, TRPV4, and/or TRPV3. In other embodiments, the differential is smaller, e.g., it more strongly inhibits TRPA1 than TRPM8, TRPV1, TRPV2, TRPV3, and/or TRPV4, preferably at least twice, three times, five times, or even ten times more strongly. Such comparisons may be made, for example, by comparing $IC_{50}$ values.

In particular embodiments, a small molecule TRPA1 antagonist is chosen for use because it is more selective for one TRPA1 than for other non-TRP ion channels, e.g., 10-fold, and more preferably at least 20, 40, 50, 60, 70, 80, or at least 100- or even 1000-fold more selective for TRPA1 over one or more of NaV1.2, Cav1.2, Cav3.1, HERG, and/or mitochondrial uniporter. In other embodiments, the differential is smaller, e.g., it more strongly inhibits TRPA1 than NaV1.2, Cav1.2, Cav3.1, HERG, and/or mitochondrial uniporter, preferably at least twice, three times, five times, or even ten times more strongly. Such comparisons may be made, for example, by comparing $IC_{50}$ values.

In certain embodiments, a compound which is an antagonist of TRPA1 is chosen to selectively antagonize TRPA1 over other ion channels, e.g., the compound modulates the activity of TRPA1 at least an order of magnitude more strongly than it modulates the activity of one or more of NaV1.2, Cav1.2, Cav3.1, HERG, and/or mitochondrial uniporter, preferably at least two orders of magnitude more strongly, even more preferably at least three orders of magnitude more strongly. In certain embodiments, the compound modulates the activity of TRPA1 at least 1.5 orders of magnitude more strongly than the activity of one or more of NaV1.2, Cav1.2, Cav3.1, HERG, or mitochondrial uniporter. Such comparisons may be made, for example, by comparing $IC_{50}$ values.

Similarly, in particular embodiments, a small molecule is chosen for use because it lacks significant activity against one or more targets other than TRPA1. For example, the compound may have an $IC_{50}$ above 500 nM, above 1 μM, or even above 10 μM or 100 μM for inhibiting one or more of TRPC6, TRPV5, TRPV6, Cav1.2, Cav3.1, NaV1.2, HERG, and the mitochondrial uniporter.

In particular embodiments, the small molecule is chosen for use because it is more selective for one TRP isoform than others, e.g., 10-fold, and more preferably at least 100- or even 1000-fold more selective for TRPA1 over one or more of TRPC6, TRPV5, TRPV6, TRPM8, TRPV1, HERG, NaV1.2, mitochondrial uniporter, TRPV3 and/or TRPV4. In other embodiments, the differential is smaller, e.g., it more strongly inhibits TRPA1 than TRPM8, TRPV1 and/or TRPV4, preferably at least twice, three times, five times, or even ten times more strongly. Such comparisons may be made, for example, by comparing $IC_{50}$ values.

In certain embodiment, a small molecule is chosen because it antagonizes the function of both TRPA1 and TRPM8, TRPV1 and/or TRPV3. Although such compounds selectively antagonize the function of both ion channels, the $IC_{50}$ values need not be identical.

In certain embodiments of any of the foregoing, the small molecule may be chosen because it is capable of inhibiting receptor-mediated (or cold/stress mediated) activation of TRPA1. In certain embodiments, the TRPA1 antagonist inhibits receptor mediated activation of TRPA1 and mustard oil induced activation of TRPA1. In certain other embodiments, the TRPA1 antagonist inhibits receptor operated activation of TRPA1 but does not inhibit mustard oil induced activation of TRPA1. In certain other embodiments, the TRPA1 antagonist inhibits mustard oil induced activation of TRPA1 but does not inhibit cold mediated activation of TRPA1.

In certain embodiments of any of the foregoing, the small molecule may be chosen because it inhibits a TRPA1 function with an $IC_{50}$ less than or equal to 1 uM, or even less than or equal to 700, 600, 500, 400, 300, 250, 200, or 100 nM. In other embodiments, the small molecule is chosen because it inhibits a TRPA1 function with an $IC_{50}$ less than or equal to 75 nM, less than or equal to 50 nM, or even less than or equal to 25, 10, 5, or 1 nM. In certain other embodiments of any of the foregoing, the small molecule inhibits TRPA1 function with an $IC_{50}$ less than or equal to 10 micromolar or less than or equal to 5 micromolar or less than or equal to 2.5 micromolar or less than or equal to 1.5 micromolar.

In certain embodiments of any of the foregoing, the compound may be chosen based on the rate of inhibition of a TRPA1 function. In one embodiment, the compound inhibits a TRPA1 function in less than 5 minutes, preferably less than 4, 3, or 2 minutes. In another embodiment, the compound inhibits a TRPA1 function in less than about 1 minute. In yet another embodiment, the compound inhibits a TRPA1 function in less than about 30 seconds.

In any of the foregoing embodiments, the small molecule antagonist of TRPA1 function may inhibit the outward current, the inward current, or any combination of one or more of these currents. Compounds that inhibit more than one of the foregoing currents may do so with the same or with differing $IC_{50}$ values. In any of the foregoing, the ability of a compound to inhibit a particular current can be assessed either in vitro or in vivo. Compounds that inhibit any of the foregoing currents in an in vitro or in vivo assay are characterized as compounds that inhibit a function of TRPA1. Stated another way, an exemplary function of TRPA1 that may be inhibited by the present compounds is a TRPA1-mediated current. Additionally or alternatively, a further exemplary function of TRPA1 that may be inhibited by the present compounds is ion flux mediated by TRPA1.

In any of the foregoing or following embodiments, the small molecule is characterized by some level of activity versus other ion channels (e.g., certain compounds are selective for inhibiting TRPA1 and other compounds exhibit a level of cross reactivity against one or more other ion channel). When a small molecule is characterized by its activity against another ion channel, inhibition of a function or activity of the other ion channel is defined analogously to the way in which a function of a TRPA1 channel is defined. Thus, inhibiting the function of another ion channel means, for example, inhibiting ion flux mediated by that other ion channel or inhibiting the current mediated by that other ion channel.

In certain embodiments of any of the foregoing, inhibition of a TRPA1 function means that a function, for example a TRPA1 mediated current, is decreased by greater than 50% in the presence of an effective amount of a compound in comparison to in the absence of the compound or in comparison to an ineffective amount of a compound. In certain other embodiments, the inhibition of a TRPA1 function means that a function, for example a TRPA1 mediated current or TRPA1 mediated ion flux, is decreased by at least 50%, 60%, 70%, 75%, 80%, 85%, or 90% in the presence of an effective amount of a compound in comparison to in the absence of the compound. In still other embodiments, the inhibition of a TRPA1 function means that a function, for example a TRPA1 mediated current, is decreased by at least 92%, 95%, 97%, 98%, 99%, or 100% in the presence of an effective amount of a compound in comparison to in the absence of the compound.

In any of the foregoing embodiments, $IC_{50}$ values are measured in vitro using, for example, patch clamp analysis or standard measurements of calcium flux. Exemplary in vitro methods for calcium flux-based $IC_{50}$ estimation are described in Example 1. Methods used to obtain more definitive $IC_{50}$ measurements are described in Example 2. Alternatively, estimates of % inhibition of current or ion flux can also be calculated and used to assess efficacy of a compound as an inhibitor.

Without being bound by theory, a compound may inhibit a function of TRPA1 by binding covalently or non-covalently to a portion of TRPA1. Alternatively, a compound may inhibit a function of TRPA1 indirectly, for example, by associating with a protein or non-protein cofactor necessary for a function of TRPA1. One of skill in the art will readily appreciate that an inhibitory compound may associate reversibly or irreversibly with TRPA1 or a cofactor thereof. Compounds that reversibly associate with TRPA1 or a cofactor thereof may continue to inhibit a function of TRPA1 even after dissociation.

In certain embodiments of any of the foregoing, the compound that inhibits a function of TRPA1 is a small organic molecule or a small inorganic molecule. Exemplary small molecules include, but are not limited to, small molecules that bind to a TRPA1 channel and inhibit one or more function of a TRPA1 channel.

In certain embodiments of any of the foregoing, the TRPA1 inhibitor is used to treat or ameliorate pain. Exemplary classes of pain that can treated using a TRPA1 inhibitor include, but are not limited to nociceptive pain, inflammatory pain, and neuropathic pain. Pain that can be treated with a TRPA1 inhibitor can be chronic or acute. Throughout the specification, a variety of conditions and diseases characterized, at least in part, by pain are discussed in detail. The invention contemplates that the pain associated with any of these diseases or conditions can be treated using any of the TRPA1 inhibitors described herein. The inhibitor can be formulated in a pharmaceutical preparation appropriate for the intended route of administration.

In certain embodiments, the TRPA1 inhibitor is non-narcotic and has little or no narcotic side-effects. In certain other embodiments, the TRPA1 inhibitor can be used to treat or ameliorate pain with fewer side-effects than narcotic pain relievers. Exemplary side-effects that may be substantially absent at effective dosages of TRPA1 inhibitors include one or more of exopthalmos, catalepsy, disruption of gut motility, and inhibition of sensation in non-injured areas of the body.

In certain embodiments, the TRPA1 inhibitor can be used to treat incontinence. In certain embodiments, the TRPA1 inhibitor is used to reduce bladder hyperactivity by decreasing the activity of the neurons that innervate the bladder. In certain embodiments, incontinence is accompanied by pain. For example, incontinence incident to bladder cystitis or incontinence incident to an injury may be accompanied by pain. When incontinence is accompanied by pain, a TRPA1 inhibitor may be administered to treat both incontinence and to reduce pain.

The subject TRPA1 inhibitors can be used alone or in combination with other pharmaceutically active agents. Examples of such other pharmaceutically active agents include, but are not limited to, anti-inflammatory agents (e.g., NSAIDS, bradykinin receptor antagonists, hormones and autacoids such as corticosteroids), anti-acne agents (e.g., retinoids), anti-wrinkle agents, anti-scarring agents, anti-incontinence agents (such as M1-receptor antagonists) anti-emetics (such as NK1 antagonists), anti-psoriatic agents, antacids, anti-proliferative agents (e.g., anti-eczema agents, anti-cancer), anti-fungal agents, anti-viral agents, anti-septic agents (e.g., antibacterials), local anaesthetics, anti-migraine agents, keratolytic agents, hair growth stimulants, hair growth inhibitors, and other agents used for the treatment of skin diseases or conditions. Certain active agents belong to more than one category.

For any of the foregoing, a TRPA1 inhibitor can be formulated for administration by a route appropriate for the disease or injury being treated. For example, the TRPA1 inhibitor can be formulated, for example, for oral, transdermal, topical, intraperitoneal, intravenous, intravascular, intrathecal, intrapericardial, intramyocardial, subcutaneous, rectal, vaginal, or urethral delivery. Furthermore, the TRPA1 inhibitor can be formulated for delivery via a device. Exemplary devices include, but are not limited to, a catheter, wire, stent, or other intraluminal device. Further exemplary delivery devices also include a patch, bandage, mouthguard, or dental apparatus.

The invention contemplates pharmaceutical compositions of any of the foregoing TRPA1 inhibitors. Exemplary pharmaceutical compositions are formulated in a pharmaceutically acceptable carrier.

The subject TRPA1 inhibitors can be used alone or as part of a therapeutic regimen combined with other treatments, therapies, or interventions appropriate for the particular disease, condition, injury or disorder being treated. When used as part of a therapeutic regimen, the invention contemplates use of TRPA1 inhibitors in combination with one or more of the following treatment modalities: administration of non-TRPA1 inhibitor pharmaceuticals, chemotherapy, radiotherapy, homeopathic therapy, diet, stress management, and surgery.

When administered alone or as part of a therapeutic regimen, in certain embodiments, the invention contemplates administration of TRPA1 inhibitors to treat a particular primary disease, injury, disorder, or condition. Additionally or alternatively, the invention contemplates administration of TRPA1 inhibitors to treat pain associated with a disease, injury, disorder, or condition. In still other embodiments, the invention contemplates administration of TRPA1 inhibitors to treat symptoms secondary to the primary disease, injury, disorder, or conditions.

The invention contemplates pharmaceutical preparations and uses of TRPA1 antagonists having any combination of the foregoing or following characteristics, as well as any combination of the structural or functional characteristics of the TRPA1 antagonists described herein. Any such antagonists or preparations can be used in the treatment of any of the diseases or conditions described herein. Additionally, the invention contemplates the use of any such antagonists or preparations for inhibiting a TRPA1 mediated current in vitro. Combinations of any of the foregoing or following aspects and embodiments of the invention are also contemplated. For example, the invention contemplates that TRPA1 antagonists having any of the particular potencies and specificities outlined herein can be formulated for the appropriate route of administration and can be used in treating any of the conditions or diseases detailed herein. In certain embodiments, the invention contemplates pharmaceutical preparations and uses of any of the TRPA1 antagonists presented in Tables 1 or 2.

In certain embodiments of any of the foregoing, TRPA1 antagonist compounds for use in the methods of the present invention have one or more of any of the foregoing properties (e.g., $IC_{50}$, specificity, selectivity, activity, formulation, etc.). Compounds and uses of antagonist compounds having any combination of the foregoing properties are specifically contemplated.

Definitions

The terms "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

An "effective amount" of, e.g., a TRPA1 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPA1 antagonist for use in the methods of the present invention, includes an amount of a TRPA1 antagonist effective to decrease one or more in vitro or in vivo function of a TRPA1 channel. Exemplary functions include, but are not limited to, membrane polarization (e.g., an antagonist may promote hyperpolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPA1 mediated ion flux.

The TRPA1 inhibitors for use in the methods of the present invention may be characterized according to their activity, or lack of activity, against one or more other ion channels. When other ion channels are referred to, inhibition of a function of such other ion channels is defined similarly. For example, inhibition of an ion channel or an activity of an ion channel means the antagonist inhibits one or more functional activities of the other ion channel. Such functions include the current mediated by the particular ion channel, ion flux, or membrane polarization.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "small molecule" refers to a compound having a molecular weight less than about 2500 amu, preferably less than about 2000 amu, even more preferably less than about 1500 amu, still more preferably less than about 1000 amu, or most preferably less than about 750 amu.

The terms "stringent conditions" or "stringent hybridization conditions" refer to conditions which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of the a polynucleotide sequence hybridizes to a perfectly matched complementary strand. In certain cases it may be desirable to increase the stringency of the hybridization conditions to be about equal to the Tm for a particular duplex. In certain embodiments, stringent hybridization conditions include a wash step of 0.2×SSC at 65° C.

The terms "TRPA1", "TRPA1 protein", and "TRPA1 channel" are used interchangeably throughout the application. These terms refer to an ion channel (e.g., a polypeptide) comprising the amino acid sequence set forth in SEQ ID NO: 1, SEQ ID NO:3, or SEQ ID NO: 5, or an equivalent polypeptide, or a functional bioactive fragment thereof. In certain embodiments, the term refers to a polypeptide comprising, consisting of, or consisting essentially of, the amino acid sequence set forth in SEQ ID NO: 1, SEQ ID NO:3, or SEQ ID NO: 5. TRPA1 includes polypeptides that retain a function of TRPA1 and comprise (i) all or a portion of the amino acid sequence set forth in SEQ ID NO: 1, SEQ ID NO:3 or SEQ ID NO: 5; (ii) the amino acid sequence set forth in SEQ ID NO: 1, SEQ ID NO:3 or SEQ ID NO: 5 with 1 to about 2, 3, 5, 7, 10, 15, 20, 30, 50, 75 or more conservative amino acid substitutions; (iii) an amino acid sequence that is at least 70%, 75%, 80%, 90%, 95%, 96%, 97%, 98%, or 99% identical to SEQ ID NO: 1, SEQ ID NO:3 or SEQ ID NO: 5; and (iv) functional fragments thereof. Polypeptides of the invention also include homologs, e.g., orthologs and paralogs, of SEQ ID NO: 1, SEQ ID NO: 3 or SEQ ID NO: 5.

The term "TRPA1" further refers to a nucleic acid encoding a polypeptide of the invention, e.g., a nucleic acid comprising a sequence consisting of, or consisting essentially of, the polynucleotide sequence set forth in SEQ ID NO: 2, SEQ ID NO: 4 or SEQ ID NO: 6. A nucleic acid of the invention may comprise all, or a portion of: the nucleotide sequence of SEQ ID NO: 2, SEQ ID NO: 4 or SEQ ID NO: 6; a nucleotide sequence at least 70%, 75%, 80%, 90%, 95%, 96%, 97%, 98% or 99% identical to SEQ ID NO: 2, SEQ ID NO: 4 or SEQ ID NO: 6; a nucleotide sequence that hybridizes under stringent conditions to SEQ ID NO: 2, SEQ ID NO: 4 or SEQ ID NO: 6; nucleotide sequences encoding polypeptides that are functionally equivalent to polypeptides of the invention; nucleotide sequences encoding polypeptides at least about 70%, 75%, 80%, 85%, 90%, 95%, 98%, 99% homologous or identical with an amino acid sequence of SEQ ID NO: 1, SEQ ID NO:3 or SEQ ID NO: 5; nucleotide sequences encoding polypeptides having an activity of a polypeptide of the invention and having at least about 70%, 75%, 80%, 85%, 90%, 95%, 98%, 99% or more homology or identity with SEQ ID NO: 1, SEQ ID NO:3 or SEQ ID NO: 5; nucleotide sequences that differ by 1 to about 2, 3, 5, 7, 10, 15, 20, 30, 50, 75 or more nucleotide substitutions, additions or deletions, such as allelic variants, of SEQ ID NO: 2, SEQ ID NO: 4 or SEQ ID NO: 6; nucleic acids derived from and evolutionarily related to SEQ ID NO: 2, SEQ ID NO: 4 or SEQ ID NO: 6; and complements of, and nucleotide sequences resulting from the degeneracy of the genetic code, for all of the foregoing and other nucleic acids of the invention. Nucleic acids of the invention also include homologs, e.g., orthologs and paralogs, of SEQ ID NO: 2, SEQ ID NO: 4 or SEQ ID NO: 6 and also variants of SEQ ID NO: 2, SEQ ID NO: 4 or SEQ ID NO: 6 which have been codon optimized for expression in a particular organism (e.g., host cell). Where not explicitly stated, one of skill in the art can readily assess whether TRPA1 refers to a nucleic acid or a protein.

The term "oxidative metabolite" is intended to encompass compounds that are produced by metabolism of the parent compound under normal physiological conditions. Specifically, an oxidative metabolite is formed by oxidation of the parent compound during metabolism. For example, a thioether group may be oxidized to the corresponding sulfoxide or sulfone.

The term "solvate" as used herein, refers to a compound formed by solvation (e.g., a compound formed by the combination of solvent molecules with molecules or ions of the solute).

The term "hydrate" as used herein, refers to a compound formed by the union of water with the parent compound.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The terms "compound" and "agent" are used interchangeably to refer to the inhibitors/antagonists of the invention. In certain embodiments, the compounds are small organic or inorganic molecules, e.g., with molecular weights less than 7500 amu, preferably less than 5000 amu, and even more preferably less than 2000, 1500, 1000, or 500 amu. One class of small organic or inorganic molecules are non-peptidyl, e.g., containing 2, 1, or no peptide and/or saccharide linkages. In certain other embodiments, the compounds are peptidyl agents such as polypeptides or antibodies. In certain other embodiments, the compounds are proteins, for example, antibodies or aptamers. Such compounds can bind to and inhibit a function of TRPA1. In certain other embodiments, the compounds are nucleic acids, for example, TRPA1 antisense oligonucleotides or TRPA1 RNAi constructs. Such compounds can inhibit the expression of TRPA1, thereby inhibiting the activity of TRPA1. Other exemplary compounds that may act as inhibitors include ribozymes and peptide fragments.

The term "acyl" is art-recognized and refers to a group represented by the general formula hydrocarbylC(O)—, preferably alkylC(O)—.

The term "acylamino" is art-recognized and refers to a moiety that can be represented by the general formula:

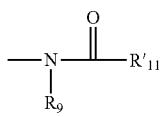

wherein $R_9$ is as defined above, and $R'_{11}$ represents a hydrogen, an alkyl, an alkenyl or —(CH2)m-R8, where m and R8 are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH2)m-R8, where m and R8 are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C1-C30 for straight chains, C3-C30 for branched chains), and more preferably 20 or fewer, and most preferably 10 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

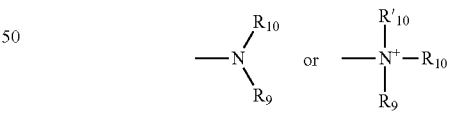

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In certain such embodiments, neither $R_9$ and $R_{10}$ is attached to N by a carbonyl, e.g., the amine is not an amide or imide, and the amine is preferably basic, e.g., its conjugate acid has a $pK_a$ above 7. In even more preferred embodiments, $R_9$ and $R_{10}$ (and optionally R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group.

The term "amido" is art-recognized as an amino-substituted carbonyl and includes a moiety that can be represented by the general formula:

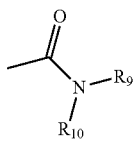

wherein R$_9$, R$_{10}$ are as defined above. Preferred embodiments of the amide will not include imides that may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

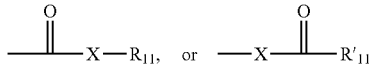

wherein X is a bond or represents an oxygen or a sulfur, and R$_{11}$ represents a hydrogen, an alkyl, an alkenyl, —(CH$_2$)$_m$ —R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiocarbonyl" group. Where X is a sulfur and R$_{11}$ or R'$_{11}$ is not hydrogen, the formula represents a "thioester." Where X is a sulfur and R$_{11}$ is hydrogen, the formula represents a "thiocarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The term "electron withdrawing group" refers to chemical groups which withdraw electron density from the atom or group of atoms to which electron withdrawing group is attached. The withdrawal of electron density includes withdrawal both by inductive and by delocalization/resonance effects. Examples of electron withdrawing groups attached to aromatic rings include perhaloalkyl groups, such as trifluoromethyl, halogens, azides, carbonyl containing groups such as acyl groups, cyano groups, and imine containing groups.

The term "ester", as used herein, refers to a group —C(O)OR$^9$ wherein R$^9$ represents a hydrocarbyl group.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —SO2-.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

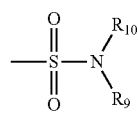

in which R9 and R10 are as defined above.

The term "sulfate" is art recognized and includes a moiety that can be represented by the general formula:

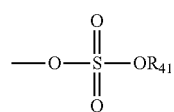

in which R41 is as defined above.

The term "sulfonamido" is art recognized and includes a moiety that can be represented by the general formula:

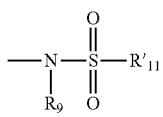

in which R9 and R'11 are as defined above.

The term "sulfonate" is art-recognized and includes a moiety that can be represented by the general formula:

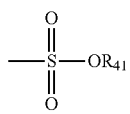

in which R41 is an electron pair, hydrogen, alkyl, cycloalkyl, or aryl.

The terms "sulfoxido" or "sulfinyl", as used herein, refers to a moiety that can be represented by the general formula:

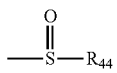

in which R44 is selected from the group consisting of hydrogen, alkyl, alkenyl, alkynyl, cycloalkyl, heterocyclyl, aralkyl, or aryl.

The term "thioester", as used herein, refers to a group —C(O)SR$^9$ or —SC(O)R$^9$ wherein R$^9$ represents a hydrocarbyl.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Methods of preparing substantially isomerically pure compounds are known in the art. If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers. Alternatively, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Techniques for inverting or leaving unchanged a particular stereocenter, and those for resolving mixtures of stereoisomers are well known in the art, and it is well within the ability of one of skill in the art to choose an appropriate method for a particular situation. See, generally, Furniss et al. (eds.), *Vogel's Encyclopedia of Practical Organic Chemistry* 5$^{th}$ Ed., a Longman Scientific and Technical Ltd., Essex, 1991, pp. 809-816; and Heller, *Acc. Chem. Res.* 23: 128 (1990).

Contemplated equivalents of the compounds described above include compounds which otherwise correspond thereto, and which have the same general properties thereof (e.g., the ability to inhibit TRPA1 activity), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The symbol ~~~, whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Wherein substituent groups are specified by their conventional chemical formulae, written from left to right, they equally encompass the chemically identical substituents, which would result from writing the structure from right to left, e.g., —CH$_2$O— is intended to also recite —OCH$_2$—; —NHS(O)$_2$— is also intended to represent —S(O)$_2$HN—; etc.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, trifluoroacetic, propionic, isobutyric, maleic, malonic, benzoic, succinic, suberic, fumaric, lactic, mandelic, phthalic, benzensulfonic, p-tolylsulfonic, citric, tartaric, methanesulfonic, and the like. Also included are the salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs form the various salt forms in certain physical properties, such as solubility in polar solvents, but otherwise the salts are equivalent to the parent form of the compound for the purposes of the present invention.

The term "low enough pyrogen activity", with reference to a pharmaceutical preparation, refers to a preparation that does not contain a pyrogen in an amount that would lead to an adverse effect (e.g., irritation, fever, inflammation, diarrhea, respiratory distress, endotoxic shock, etc.) in a subject to which the preparation has been administered. For example, the term is meant to encompass preparations that are free of, or substantially free of, an endotoxin such as, for example, a lipopolysaccharide (LPS).

Diseases, Disorders, or Conditions Related to TRPA1 Function

In certain embodiments, the invention provides methods and compositions for inhibiting a function of a TRPA1 channel in vitro or in vivo. Exemplary functions include, but are not limited to, TRPA1-mediated current. In certain embodiments, the invention provides methods for preventing or treating a disease or disorder or condition by administering an agent that modulates the level and/or activity of a TRPA1 protein. In other embodiments, the compound selectively inhibits the expression level and/or activity of a TRPA1 protein. In other words, in certain embodiment, the compound inhibits the activity of a TRPA1 protein preferentially in comparison to the activity of one or more other ion channels.

In particular embodiments of the methods for preventing or treating diseases and disorders provided herein, the disease or disorder can be, for example, a pain or sensitivity to touch such as pain related to a disease or disorder, e.g., cancer pain, a dermatological disease or disorder, e.g., psoriasis and basal cell and squamous cell cariconomas, a neurodegenerative disease or disorder, e.g., Alzheimer's disease (AD), Parkinson's disease, Huntington's disease, amyotrophic lateral sclerosis (ALS), and other brain disorders caused by trauma or other insults including aging, an inflammatory disease (e.g., asthma, chronic obstructive pulmonary disease, rheumatoid arthritis, osteoarthritis, inflammatory bowel disease, glomerulonephritis, neuroinflammatory diseases, multiple sclerosis, and disorders of the immune system), cancer (e.g. liposarcoma) or other proliferative disease, kidney disease and liver disease, a metabolic disorder such as diabetes. Further diseases and conditions include post-surgical pain, post herpetic neuraligia, incontinence, and shingles.

Because of the important role that calcium regulation plays in many cellular processes including cellular activation, gene expression, cellular trafficking and apoptotic cell death, calcium dyshomeostasis is implicated in the many diseases and disorders involving such cellular activities. These diseases and disorders include dermatological diseases and disorders; neurological and neurodegenerative diseases and disorders; fever associated with various diseases, disorders or conditions; incontinence; inflammatory diseases and disorders such as inflammatory bowel disease and Crohn's disease; respiratory diseases and disorders such as chronic cough, asthma and chronic obstructive pulmonary disease (COPD); digestive disorders such as ulcers and acid reflux; metabolic diseases and disorders including obesity and diabetes; liver and kidney diseases and disorders; malignancies including cancers; aging-related disorders; and sensitivity to pain and touch.

Additional diseases or conditions that can be treated include ATP-related diseases or disorders including epilepsy, cognition, emesis, pain (e.g., migraine), asthma, peripheral vascular disease, hypertension, immune and inflammatory conditions, irritable bowel syndrome, cystitis, depression, aging-associated degenerative diseases, urinary incontinence, premature ejaculation, cystic fibrosis, diabetes, contraception and sterility, and wound healing (see, for example, Foresta et al. (1992) J. Biol. Chem. 257:19443-19447; Wang et al. (1990) Biochim. Biophys. Res. Commun. 166:251-258; Burnstock and Williams, (2000) J. Pharmacol. Exp. Ther. 295: 862-869; and Burnstock, Pharmacol Rev (2006) 58:58-86).

TRPA1 inhibitors described herein can be used in the treatment of any of the foregoing or following diseases or conditions, including in the treatment of pain associated with any of the foregoing or following diseases or conditions. When used in a method of treatment, an inhibitor can be selected and formulated based on the intended route of administration. Inhibitors can be used to treat the underlying disease or condition, or to relieve a symptom of the disease or condition. Exemplary symptoms include pain associated with a disease or condition.

a. Sensitivity to Pain and Touch, or Pain-Related Diseases or Disorders

Compositions and methods provided herein may be used in connection with prevention or treatment of pain or sensitivity to pain and touch. Pain or sensitivity to pain and touch may be indicated in a variety of diseases, disorders or conditions, including, but not limited to, diabetic neuropathy, breast pain, psoriasis, eczema, dermatitis, burn, postherpetic neuralgia (shingles), nociceptive pain, peripheral neuropathic and central neuropathic pain, chronic pain, cancer and tumor pain, spinal cord injury, crush injury and trauma induced pain, migraine, cerebrovascular and vascular pain, sickle cell disease pain, rheumatoid arthritis pain, musculoskeletal pain including treating signs and symptoms of osteoarthritis and rheumatoid arthritis, orofacial and facial pain, including dental, temperomandibular disorder, and cancer related, lower back or pelvic pain, surgical incision related pain, inflammatory and non-inflammatory pain, visceral pain, psychogenic pain and soft tissue inflammatory pain, fibromyalgia-related pain, and reflex sympathetic dystrophy, and pain resulting from kidney stones or urinary tract infection. The compounds and methods of the invention may be used in the treatment of chronic, as well as acute pain. Chronic or acute pain may be the result of injury, age, or disease.

Other ion channels have been implicated in reception or transmission of pain. For example, the involvement of N-type calcium channels in the synaptic transmissions that convey pain signals from sensory afferent nerve cells to the central nervous system has been recognized. Certain naturally occurring peptide neurotoxins that specifically block N-type calcium channel have been shown to act as extremely potent and efficient analgesics in a wide range of animal pain models, including models of inflammatory and neuropathic pain. The available evidence suggests that N-type calcium channel blockers are at least as efficacious as opiates, are devoid of a number of the typical opiate side effects (e.g. respiratory depression) and that the analgesic effect is not subject to tolerance development.

It has also been shown that potent peripheral analgesia induced by 5-alpha-reduced neurosteroid is mediated in part by effects on T-type $Ca^{2+}$ channels (Pathirathna et al., Pain. 2005 April; 114(3):429-43).

Ethosuximide, an anti-epileptic and relatively selective T-type calcium channel blocker, has also been shown as being highly effective in reversing neuropathic pain caused by the commonly employed cytotoxics paclitaxel or vincristine (Flatters and Bennett, Pain. 2004 May; 109(1-2):150-61).

Pregabalin, a new drug that interacts with the alpha(2)-delta protein subunit of the voltage-gated calcium channel, is an efficacious and safe treatment for the pain of diabetic neuropathy (Richter et al., J Pain. 2005 April; 6(4):253-60).

The foregoing demonstrate the involvement of various non-TRP channels in the reception or transmission of pain. Specifically, the foregoing demonstrate the involvement of various calcium channels in pain.

The present invention provides methods for treating pain that include administration of (i) antagonists of a TRPA1 function; (ii) combinations of selective antagonists of a TRPA1 function and selective antagonists of TRPV1 and/or TRPV3 function; or (iii) a pan-TRP inhibitor that inhibits a function of two or more of TRPA1, TRPV1, and TRPV3.

In addition to TRPV family members, other TRP channels have been implicated in pain reception and/or sensation. For example, certain TRPM channels including TRPM8 have been implicated in the reception and/or sensation of pain. Accordingly, in certain embodiments, the methods of the present invention include treating pain by administering (i) a combination of a selective TRPA1 antagonist and a selective TRPM8 antagonist; (ii) a combination of a selective TRPA1 antagonist, a selective TRPM8 antagonist, and one or more of a selective TRPV1 and/or TRPV3 antagonist; (iii) a cross-TRP inhibitor that antagonizes a function of TRPA1 and TRPM8; or (iv) a pan inhibitor that antagonizes a function of TRPA1, TRPM8, and one or more of TRPV1 and TRPV3.

Without being bound by theory, we propose one possible mechanism for how a TRPA1 antagonist may help reduce pain. TRPA1 antagonists can lead to hyperpolarization of the cell.

This may lead to a reduction in the firing of neurons and/or a decrease in action potential frequency. In addition, TRPA1 inhibitors may reduce calcium influx into injured cells and could prevent the calcium dependent changes in gene expression that sometimes accompany injury.

b. Dermatological Diseases or Disorders

Influx of calcium across plasma membrane of skin cells is a critical signaling element involved in cellular differentiation in the skin epidermis (Dotto, 1999 Crit. Rev Oral Biol Med 10:442-457). Regulating or modulating the calcium entry pathway, and thus a critical control point for skin cell growth, can treat or prevent skin diseases or disorders that are characterized by epidermal hyperplasia, a condition in which skin cells both proliferate too rapidly and differentiate poorly. Such diseases include psoriasis, and basal and squamous cell carcinomas. Psoriasis, estimated to affect up to 7 million Americans, afflicts sufferers with mild to extreme discomfort, enhanced susceptibility to secondary infections, and psychological impact due to disfigurement of the affected areas (Lebwohl and Ali, 2001 J Am Acad Dermatol 45:487-498). Basal cell carcinomas (BCC) and squamous cell carcinomas (SCC) of the skin represent at least one-third of all cancers diagnosed in the United States each year. More than 1 million new cases are reported annually and incidence is increasing. Despite being relatively non-aggressive, slow-growing cancers, BCCs are capable of significant local tissue destruction and disfigurement. SCCs are more aggressive and thus present even greater complications. Further, given that 80% of lesions are on the head and neck with another 15% on shoulders, back or chest, BCCs and SCCs of the skin can have a significant impact on the appearance and quality of life of the afflicted patient.

Many dermatological disorders are accompanied by itch (pruritus). Pruritus and pain share many mechanistic similarities. Both are associated with activation of C-fibers, both are potentiated by increases in temperature and inflammatory mediators and both can be quelled with opiates. Decreasing neuronal excitability, particularly C-fiber excitability may alleviate pruritus associated with dialysis, dermatitis, pregnancy, poison ivy, allergy, dry skin, chemotherapy and eczema.

c. Neurological or Neurodegenerative Diseases and Disorders

Neurodegenerative diseases and disorders include but are not limited to Alzheimer's disease (AD), Parkinson's disease, Huntington's disease, amyotrophic lateral sclerosis (ALS), and other brain disorders caused by trauma or other insults including aging.

Mechanisms associated with calcium signaling may be altered in many neurodegenerative diseases and in disorders resulting from brain injury. For example, fibroblasts or T-lymphocytes from patients with AD have consistently displayed an increase in $Ca^{2+}$ release from intracellular stores compared to controls (Ito et al. (1994) Proc. Natl. Acad. Sci. U.S.A. 91:534-538; Gibson et al. (1996) Biochem. Biophys. ACTA 1316:71-77; Etchenberrigaray et al. (1998) Neurobiology of Disease, 5:37-45). Consistent with these observations, mutations in presenilin genes (PS1 or PS2) associated with familial AD (FAD) have been shown to increase InsP3-mediated $Ca^{2+}$ release from internal stores (Guo et al. (1996) Neuro Report, 8:379-383; Leissring et al. (1999) J. Neurochemistry, 72:1061-1068; Leissring et al. (1999) J. Biol. Chem. 274(46):32535-32538; Leissring et al. (2000) J. Cell Biol. 149(4):793-797; Leissring et al. (2000) Proc. Natl. Acad. Sci. U.S.A. 97(15):8590-8593). Furthermore, mutations in PS1 or PS2 associated with an increase in amyloidogenic amyloid 13 peptide generation in AD are reported to be associated with a decrease in intracellular calcium level (Yoo et al. (2000) Neuron, 27(3):561-572).

Experimental traumatic brain injury has been shown to initiate massive disturbances in $Ca^{2+}$ concentrations in the brain that may contribute to further neuronal damage. Intracellular $Ca^{2+}$ may be elevated by many different ion channels. It has been further shown that channel blockers may be beneficial in the treatment of neurological motor dysfunction when administered in the acute posttraumatic period (Cheney et al. (2000) J. Neurotrauma, 17(1):83-91).

d. Inflammatory Diseases and Disorders

Compositions and methods provided herein may also be used in connection with treatment of inflammatory diseases. These diseases include but are not limited to asthma, chronic obstructive pulmonary disease, rheumatoid arthritis, osteoarthritis, inflammatory bowel disease, glomerulonephritis, neuroinflammatory diseases such as multiple sclerosis, and disorders of the immune system.

The activation of neutrophils (PMN) by inflammatory mediators is partly achieved by increasing cytosolic calcium concentration ($[Ca^{2+}]_i$). Certain calcium channel-mediated calcium influx in particular is thought to play an important role in PMN activation. It has been shown that trauma increases PMN store-operated calcium influx (Hauser et al. (2000) J. Trauma Injury Infection and Critical Care 48 (4):592-598) and that prolonged elevations of $[Ca^{2+}]_i$ due to enhanced store-operated calcium influx may alter stimulus-response coupling to chemotaxins and contribute to PMN dysfunction after injury. Modulation of PMN $[Ca^{2+}]_i$ through store-operated calcium channels might therefore be useful in regulating PMN-mediated inflammation and spare cardiovascular function after injury, shock or sepsis (Hauser et al. (2001) J. Leukocyte Biology 69 (1):63-68).

Peripheral neuropathy, for example diabetic neuropathy, is a particular condition that involves both a neuronal and an inflammatory component. Without being bound by a mechanistic theory, the TRPA1 antagonists of the invention may be useful in treating peripheral neuropathies including, but not limited to, diabetic neuropathy. In addition to their use in the treatment of peripheral neuropathies (e.g., reducing inflammation), the subject inhibitors may also be useful in reducing the pain associated with peripheral neuropathy.

Neurogenic inflammation often occurs when neuronal hyperexcitability leads to the release of peptides that trigger inflammation. These peptides include substance P and CGRP. Blocking TRPA1 would reduce neuronal activity and thus could block neurogenic inflammation.

e. Cancer and Other Proliferative Diseases

Compositions and methods provided herein may also be used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer, in addition to skin cancers described above. Intracellular calcium level may play an important role in cell proliferation in cancer cells (Weiss et al. (2001) International Journal of Cancer 92 (6):877-882).

In addition, pain associated with cancer or with cancer treatment is a significant cause of chronic pain. Cancers of the bone, for example, osteosarcoma, are considered exceptionally painful, and patients with advanced bone cancer may require sedation to tolerate the intense and persistent pain. Accordingly, TRPA1 antagonists of the invention represent a significant possible therapeutic for the treatment of pain, for example, the pain associated with cancer or with cancer treatment.

Given that TRPA1 is differentially expressed in transformed cells, TRPA1 blockers may also affect the proliferation of transformed cells and thus be a useful way to slow the disease (see Jaquemar et al. (1999) JBC 274(11): 7325-33). Thus TRPA1 antagonists could alleviate both the cause and symptoms of cancer pain.

Cancer treatments are not only painful, but they may even be toxic to healthy tissue. Some chemotherapeutic agents can cause painful neuropathy. Accordingly, TRPA1 antagonists of the invention represent a significant possible therapeutic for the treatment of the pain and/or inflammation associated with cancer treatments that cause neuropathy.

A major function of prostaglandins is to protect the gastric mucosa. Included in this function is the modulation of intracellular calcium level in human gastric cells which plays a critical role in cell proliferation. Consequently, inhibition of prostaglandins by nonsteroidal anti-inflammatory drugs (NSAIDs) can inhibit calcium influx in gastric cells (Kokoska et al. (1998) Surgery (St Louis) 124 (2):429-437). The NSAIDs that relieve inflammation most effectively also produce the greatest gastrointestinal damage (Canadian Family Physician, January 1998, p. 101). Thus, the ability to independently modulate calcium channels in specific cell types may help to alleviate such side effect of anti-inflammatory therapy. Additionally or alternatively, administration of TRPA1 inhibitory compounds of the present invention may be used in combination with NSAIDs, thus promoting pain relief using reduced dosage of NSAIDs.

f. Incontinence

Incontinence is a significant social and medical problem affecting both men and women. Incontinence has many causes including, but not limited to, age, pregnancy, radiation exposure, surgery, injury, cancer, enlargement of the prostatic, prostatic hyperplasia, and diseases of the bladder or musculature that supports the urethra. The invention contemplates methods for treating incontinence due to any of the foregoing, as well as incontinence of unknown cause or continence due to anxiety, stress, or depression.

Compositions and methods provided herein may be useful in connection with the treatment of incontinence. Animal models of incontinence are often associated with an increase in the frequency of spontaneous action potentials and a chronic depolarization of the smooth muscle cells. Evidence suggests that a non-selective cation current could lead to this depolarization. Since TRPA1 mRNA is expressed in neurons that innervate bladder, blocking TRPA1 might be an effective treatment for incontinence. In addition, TRPA1 is activated by stimulation of the muscarinic type 1 acetylcholine receptor (M1, see Jordt et al. (2004) Nature 427:260-265). Antimuscarininc agents are well known drugs for the treatment of condition such as overactive bladder. Thus blocking TRPA1, a downstream target of the M1 receptor might alleviate such conditions without the side effects that are associated with muscarinic antagonists.

Incontinence can be caused by any of a number of injuries, diseases, and conditions. Some of these may cause significant discomfort and pain, in addition to the inconvenience and embarrassment of the incontinence itself. For example, bladder cystitis is a painful condition that can also lead to incontinence. For injuries or conditions resulting in both incontinence and pain, TRPA1 inhibitors can be used to treat the incontinence, as well as to relieve the accompanying pain.

For embodiments in which a TRPA1 inhibitor is used to treat incontinence, the invention contemplates additional possible routes of administration. For example, in certain embodiments, the TRPA1 inhibitor can be administered directly to the urethra or bladder via a catheter or other intraluminal device. However, in other embodiments, the TRPA1 inhibitor can be administered orally, intravenously, subcutaneously, etc.

g. Temperature Regulation

Because of the effects of ion flux on arterial tension and relaxation, the subject compounds can also be used to affect thermal sensitivity. Furthermore, given that TRPA1 channels are thermal responsive channels involved in the reception and sensation of cold stimuli, TRPA1 antagonists can be used to modulate the sensation of cool, cold and decreased temperatures that often accompany pain.

h. Hypertension

Blockers of voltage-gated calcium channels belong to a class of medications originally developed to treat hypertension. Such blockers inhibit the movement of calcium into the muscle cells of the heart and arteries. Because calcium is needed for these muscles to contract, such blockers lower blood pressure by decreasing the force of cardiac contractile response and relaxing the muscle walls of the arteries. Although TRPA1 is not a voltage-gated calcium channel, it is still instrumental in regulating calcium homeostasis, as well as the balance of other ions, in cells and tissues. Accordingly, TRPA1 antagonists of the invention may be used to treat hypertension. Additional uses of the subject compounds include other conditions that may be ameliorated, in whole or in part, by relaxing the muscle walls of blood vessels. Exemplary conditions include headaches and migraine attacks.

As outlined above, compounds that antagonize a function of TRPA1 can be used in the treatment of many diseases, injuries, disorders, and conditions. In certain embodiments, TRPA1 inhibitors can be used in the treatment of pain. As outlined above, TRPA1 inhibitors can be used in the treatment of pain resulting from injury or disease, as well as pain experienced as a consequence of treatment. Exemplary classes of pain include nociceptive pain, inflammatory pain, and neuropathic pain. Such pain can be chronic or acute. TRPA1 inhibitors can be used in the treatment of one or more of any of the foregoing classes of pain. In certain embodiments, TRPA1 inhibitors can be used in the treatment of nociceptive pain. In certain other embodiments, TRPA1 inhibitors can be used in the treatment of inflammatory pain. In certain other embodiments, TRPA1 inhibitors can be used in the treatment of neuropathic pain.

As outlined above, TRPA1 inhibitors may be particularly useful in the treatment of pain associated with cancer, osteoarthritis, rheumatoid arthritis, post-herpetic neuralgia, burns, and other indications detailed above. To further illustrate, additional exemplary indications for which compounds of the present invention can be used include oral pain, Fabry's disease, complex regional pain syndrome, pancreatitis, and fibromyalgia syndrome. Fabry's disease Vague complaints of pain in hands and feet may be a presenting feature. These symptoms are called acroparesthesias, as they reflect the peripheral neuropathy that is a frequent manifestation of the disease. This pain may be both episodic and chronic. Acute episodes may be triggered by exposure to extremes of temperature, stress, emotion, and/or fatigue.

Fibromyalgia

Fibromyalgia (FMS; fibromyalgia syndrome) is a widespread musculoskeletal pain and fatigue disorder. Fibromyalgia is characterized by pain in the muscles, ligaments, and tendons. The condition affects more women than men, and occurs in people of all ages. Overall, FMS is estimated to afflict 3-6% of the population.

Patients have described the pain associated with fibromyalagia as deep muscular aching, throbbing, shooting, and stabbing. The pain sometimes includes an intense burning sensation. The pain and stiffness are often worse in the morning or after repetitive use of a particular muscle group.

Additionally, varying levels of fatigue ranging from mild to incapacitating are often associated with fibromyalagia. Other symptoms of fibromyalagia include gastrointestinal symptoms. Irritable bowel syndrome and IBS-like symptoms such as constipation, diarrhea, frequent abdominal pain, abdominal gas, and nausea occur in roughly 40 to 70% of FMS patients. Acid reflux or gastroesophogeal reflux disease (GERD) occurs at a similar frequency.

Another frequent and debilitating symptom of FMS is chronic headaches, including migraine and tension-type headaches. Such headaches are experienced by approximately 70% of FMS patients. Additionally, FMS patients often experience temporomandibular joint dysfunction syndrome (also known as TMJ) which produces pain in the jaw, teeth, and mouth. TMJ may also exacerbate headaches.

Other common symptoms of FMS include, but are not limited to, premenstrual syndrome and painful periods; chest pain; morning stiffness; cognitive or memory impairment; numbness and tingling sensations; muscle twitching; irritable bladder; the feeling of swollen extremities; skin sensitivities; dry eyes and mouth; dizziness; and impaired coordination. Additionally, patients are often sensitive to odors, loud noises, and bright lights.

The cause of FMS remains unknown. However, the onset of the disorder has been linked to infections (viral or bacterial), rheumatoid arthritis, lupus, and hypothyroidism. The link between these and other possible triggers is unclear.

The impact of FMS on the patient is directly correlated with the level of pain and fatigue. Pain may be so severe as to interfere with normal work or family functioning. There is currently no cure for FMS, and current therapies focus primarily on improving sleep (to decrease fatigue) and treating pain. Compounds of the present invention could be used to help manage the pain associated with FMS. Such pain includes, but is not limited to, oral pain in the jaw, teeth, and mouth. Such pain also includes non-oral musco-skeletal pain, pain due to headaches, and pain due to gastrointestinal symptoms.

Complex Regional Pain Syndrome (CRPS; also known as chronic regional pain syndrome) is a chronic pain condition.

CRPS was formerly known as reflex sympathetic dystrophy (RSD). CRPS is a chronic, painful, and progressive neurological condition that affects skin, muscles, joints, and bones. The syndrome usually develops in an injured limb, such as a broken leg or following surgery. However, many cases involve only a minor injury, such as a sprain, and sometimes no precipitating injurious event can be identified. CRPS involves continuous, intense pain that is disproportionate to the severity of the injury. The pain worsens, rather than improves, over time.

Although CRPS can affect a variety of regions of the body, it most often affects the arms, legs, hands, or feet. Often the pain begins in one portion of a limb, but spreads over time to include the entire limb or even to include a different limb. Typical features include dramatic changes in the color and temperature of the skin over the affected limb or body part, accompanied by intense burning pain, skin sensitivity, sweating, and swelling.

Generally, CRPS is characterized into two categories. Type I occurs in the absence of a precipitating nerve injury—although there may have been some other type of precipitating injury. Type II (formerly called causalgia) occurs following a nerve injury. These categories are merely descriptive, and do not correlate with symptomology or prognosis.

The National Institute of Neurological Disorders and Strokes (NINDS) reports that 2% to 5% of peripheral nerve injury patients and 12% to 21% of patients with paralysis on one side of the body (hemiplegia) develop reflex sympathetic dystrophy as a complication. The Reflex Sympathetic Dystrophy Syndrome Association of America (RSDSA) reports that the condition occurs following 1-2% of bone fractures.

Precipitating events associated with the onset of CRPS include the following: cerebral lesions, heart disease, heart attack, infection, paralysis on one side of the body (hemiplegia), radiation therapy, repetitive motion disorder (e.g., carpal tunnel syndrome), spinal cord disorders, surgery, and trauma (e.g., bone fracture, gunshot, car accident). However, in 10-20% of cases, no precipitating event can be found. Note that the injury that precedes the onset of CRPS may or may not be significant.

The symptoms of CRPS may progress in three stages. An acute stage occurs during the first 1-3 months and may include burning pain, swelling, increased sensitivity to touch, increased hair and nail growth in the affected region, joint pain, and color and temperature changes. A dystrophic stage may involve constant pain and swelling. The effected limb often feels cool to the touch and looks bluish. There is typically muscle stiffness and wasting (atrophy), as well as early bone loss (osteoporosis). These symptoms usually occur 3-6 months after development of the disorder. During an atrophic stage, the skin becomes cool and shiny, increased muscle stiffness and weakness occur, and symptoms may spread to another limb.

Other symptoms include: burning pain, extreme sensitivity to touch, skin color changes (red or bluish), skin temperature changes (hot or cold), joint pain, swelling (edema), frequent infections, muscle stiffness, muscle spasm, tremor, weakness, dermatitis, eczema, excessive sweating, and migraine headache. A TRPA1 inhibitor can be useful not only in treating the pain associated with CRPS, but also in relieving many of these other symptoms including dermatitis, eczema, and migraines.

Patients with CRPS often suffer from depression and anxiety due to the impact of the disease of their quality of life.

There is currently no cure for CRPS, and thus treatment typically aims to relieve painful symptoms. Doctors may prescribe topical analgesics, antidepressants, corticosteroids, and opioids to relieve pain. However, to this point, no single drug or combination of drugs has produced consistent long-lasting improvement in symptoms. Other treatments may include physical therapy, sympathetic nerve block, spinal cord stimulation, and intrathecal drug pumps to deliver opioids and local anesthetic agents via the spinal cord.

The goals of treatment are to control pain and to maintain as much mobilization of the affected limb as possible. An individualized treatment plan is designed, which often combines treatment modalities. Currently, physical therapy, medications, nerve blocks, and psychosocial support are used. TRPA1 inhibitors according to the present invention can be used instead of or in addition to one or more of the current treatment modalities. For example, a TRPA1 inhibitor can be used as an alternative to current medications, but combined with physical therapy.

TRPA1 inhibitors provide an alternative for managing pain in CRPS patients. TRPA1 inhibitors may be used in combination with any of the current medications used to treat CRPS patients. Alternatively, TRPA1 inhibitors may be used as an alternative medication.

In addition to drug therapy, CRPS patients often receive physical therapy. TRPA1 inhibitors can be used in addition to physical therapy. Physical therapy may be important for helping retain range of motion and function in the affected limb. Appropriate pain management, for example using a TRPA1 inhibitor, not only increases patient comfort, but also facilitates involvement in physical therapy.

Regardless of the particular combination of therapies used to manage pain in CRPS patients, psychological support is often critical. TRPA1 inhibitors can be used in combination with psychological support.

TRPA1 inhibitors of the present invention may be used in the treatment of CRPS. For example, TRPA1 inhibitors of the present invention may be used to help relieve the pain associated with CRPS. TRPA1 inhibitors can be used alone or as part of an overall treatment regimen to help manage the pain and other symptoms associated with CRPS. Pain management for CRPS sufferers is critical for maintaining a meaningful quality of life. Furthermore, effective pain management may allow sufferers to participate in physical therapy to help retain mobility and use of the effected limbs.

Pancreatitis is an inflammation of the pancreas. The pancreas is a large gland behind the stomach and close to the duodenum. Normally, digestive enzymes do not become active until they reach the small intestine, where they begin digesting food. But if these enzymes become active inside the pancreas, they start "digesting" the pancreas itself.

Acute pancreatitis occurs suddenly, lasts for a short period of time, and usually resolves. Chronic pancreatitis does not resolve itself and results in a slow destruction of the pancreas. Either form can cause serious complications including bleeding, tissue damage, and infection.

Acute pancreatitis can be a severe, life-threatening illness with many complications. About 80,000 cases occur in the United States each year, and approximately 20 percent of these cases are characterized as severe.

Acute pancreatitis is usually, although not exclusively, caused by gallstones or by alcohol abuse. Acute pancreatitis usually begins with pain in the upper abdomen that may last for a few days. The pain may be severe and may become constant. The pain may be isolated to the abdomen or it may reach to the back and other areas. Sometimes, and for some patients, the pain is sudden and intense. Other times, or for other patients, the pain begins as a mild pain that worsens after eating. Someone with acute pancreatitis often looks and feels very sick. Other symptoms may include swollen and tender abdomen, nausea, vomiting, fever, and rapid pulse. Severe cases of acute pancreatitis may cause dehydration and low blood pressure, and may even lead to organ failure, internal bleeding, or death.

During acute pancreatitis attacks, the blood levels of amylase and lipase are often increased by at least 3-fold. Changes may also occur in blood levels of glucose, calcium, magnesium, sodium, potassium, and bicarbonate.

The current treatment depends on the severity of the attack. Treatment, in general, is designed to support vital bodily functions, manage pain, and prevent complications. Although acute pancreatitis typically resolved in a few days, pain management during an attack is often required. TPRV3 inhibitors can be used to relieve the pain associated with acute pancreatitis.

Chronic pancreatitis—If injury to the pancreas continues, chronic pancreatitis may develop. Chronic pancreatitis occurs when digestive enzymes attack and destroy the pancreas and nearby tissues, causing scarring and pain. Chronic pancreatitis may be caused by alcoholism, or by blocked, damaged, or narrowed pancreatic ducts. Additionally, hereditary factors appear to influence the disease, and in certain cases, there is no identifiable cause (so called idiopathic pancreatitis).

Most people with chronic pancreatitis have abdominal pain. The pain may get worse when eating or drinking, spread to the back, or become constant and disabling. Other symptoms include nausea, vomiting, weight loss, and fatty stools.

Relieving pain is the first step in treating chronic pancreatitis. Once the pain has been managed, a high carbohydrate and low fat dietary plan is put in place. Pancreatic enzymes may be used to help compensate for decrease enzyme production from the injured pancreas. Sometimes insulin or other drugs are needed to control blood glucose.

Although pain is typically managed using drug therapy, surgery may be necessary to relieve pain. Surgery may be necessary to drain an enlarged pancreatic duct or even to removing a portion of a seriously injured pancreas.

Pain is frequently present with chronic pancreatitis. For example, pain is present for approximately 75% of patients with alcoholic chronic pancreatitis, 50% of patients with late-onset idiopathic chronic pancreatitis, and 100% of patients with early-onset idiopathic chronic pancreatitis (DiMagno, 1999, Gastroenterology 116(5): 1252-1257).

A minority of patients with pain have readily identifiable lesions which are relatively easy to treat surgically or endoscopically. In other patients, pain is often thought to result from a variety of causes, including elevated intrapancreatic pressure, ischemia, and fibrosis. Without being bound by theory, however, these phenomena are not likely the underlying cause of the pain. Rather, pain may result from a background of neuronal sensitization induced by damage to the perineurium and subsequent exposure of the nerves to mediators and products of inflammation.

Given the importance of effective pain management in patients with chronic pancreatitis, additional therapies for treating painful symptoms are important and useful. TRPA1 inhibitors can be used to manage the pain associated with chronic pancreatitis. TRPA1 inhibitors can be used alone or as part of an overall therapeutic treatment plan to manage patients with chronic pancreatits. For example, TRPA1 inhibitors can be administered with pancreatic enzymes and/or insulin as part of a therapeutic regimen designed to manage patients with chronic pancreatitis.

Oral pain is a particular category of pain that may be treated using the TRPA1 inhibitors of the present invention. The term "oral pain" refers to any pain in the mouth, throat, lips, gums, teeth, tongue, or jaw. The term is used regardless of the cause of the pain and regardless of whether the oral pain is a primary or secondary symptom of a particular disease, injury, or condition.

Oral pain has a large number of possible causes. In certain embodiments, oral pain is caused by an injury or disease of the mouth, jaw, teeth, gums, throat, lips, or tongue. In certain other embodiments, oral pain is a consequence of an injury or disease that primarily affects another part of the body. In still other embodiments, oral pain is a side effect of a therapy used to treat an injury or disease of the mouth or another part of the body. TRPA1 inhibitors are useful in treating oral pain regardless of its cause.

All pain has a serious negative impact on the health and well being of the sufferer. However, oral pain may have a particularly deleterious impact on patient health and quality of life. In particular, oral pain can interfere with appropriate eating and drinking. Thus, individuals with oral pain are susceptible to weight loss, malnutrition, and dehydration. In some instances, oral pain may interfere with hydration and nutrition so significantly as to require intravenous, nasogastric, or other artificial support (e.g., tube feeding and/or hydration). Additionally, oral pain can interfere with proper oral hygiene. Poor oral hygiene may further exacerbate many of the causes of oral pain, for example, oral pain due to infection or abscess.

In certain embodiments, oral pain is caused by ulcers, sores, or other lesions in the mouth. For example, oral pain may be caused by ulcers, sores, or other lesions on the tongue, gums, lips, throat, or other tissues of the mouth. Alternatively or additionally, oral pain may be caused by inflammation of the throat, tongue, gums, lips, or other tissues of the mouth. Inflammation may accompany ulcers or other lesions, or inflammation may occur prior to or in the absence of formation of ulcers or other lesions.

The invention contemplates treatment of oral pain by administering a TRPA1 inhibitor by any route of administration described herein. In certain embodiments, TRPA1 inhibitors for use in the treatment of oral pain are administered orally. Preferred preparations for oral administration of TRPA1 inhibitors for use in treating oral pain are as a mouthwash, a gel, a tooth paste or other paste, a liquid, a lozenge, via a swab, or in association with a mouth guard or dental apparatus. The preparation and particular method of administration will depend on the cause of the oral pain, the overall health and underlying medical conditions of the patient, the severity of the pain, and other medications or therapies the patient is concurrently receiving. A medical practitioner can readily determine the optimal formulation for use in a particular patient.

The conditions provided below are intended to illustrate the range of injuries and diseases of diverse etiology that may lead to oral pain. The invention contemplates administration of a TRPA1 inhibitor, according to the present invention, to treat or prevent oral pain. In certain embodiments, compounds of the invention can be orally administered, for example as a gel, paste, mouth wash, or other oral preparation, to help treat or prevent oral pain associated with any injury, disease, or condition. Regardless of the particular formulation, the invention contemplates administration by, for example, direct application to the affected area of the mouth, rinsing of the entire mouth, via a swab, via a syringe, or on a mouth guard or other dental apparatus.

For any of these conditions, the invention contemplates administration of a TRPA1 inhibitor alone, or in combination with one or more other compounds or treatment regimens appropriate for the particular injury or condition.

Oral Mucositis

Oral mucositis, also known as stomatitis, is a common complication of many cancer treatments. Patients receiving systemic chemotherapy and/or local radiotherapy often develop extremely painful ulcers of the oral mucosa. This side effect is not limited to patients suffering from cancers of the head and neck, but rather is a debilitating side effect afflicting approximately 40% of all chemotherapy patients (Prevention and Treatment of Oral Mucositis in Cancer Patients, 1998, *Best Practice:* 2, pages 1-6.)

Oral mucositis is extremely painful. Additionally, oral mucositis interferes with proper nutrition and hydration of cancer patients. Given the already compromised status of patients undergoing chemotherapy and/or radiotherapy, further interference with nutrition and hydration may seriously undermine patient health. Furthermore, these ulcers present an increased risk of infection. This risk is particularly acute in patients with compromised immune systems. Examples of patients at particular risk of developing an opportunistic infection are patients whose treatment included removal of one or more lymph nodes, patients who previously received high-dose chemotherapy in preparation for a bone marrow or stem cell transplant, and patients with an underlying immunosuppressive disorder (e.g., HIV or hepatitis).

Canker Sores

Canker sores, also known as aphthous ulcers (aphthae), may be relatively small and out-of-sight. However, they are often painful, persistent and annoying. Canker sores are shallow ulcers in the mouth that can make eating and talking uncomfortable. They may occur on the tongue, soft palate, inside the cheek or lip, or at the base of the gums. Canker sores differ from cold sores in that they occur on the internal soft tissues of the mouth and aren't contagious. Conversely, cold sores almost always start out on the lips and don't often spread to the soft tissues of the mouth. In addition, cold sores are caused by a form of the herpes virus, making them extremely contagious.

Researchers generally believe that stress or tissue injury may cause the eruption of canker sores. In some cases a minor injury, for example biting the inside of the mouth or eating rough foods, may trigger a canker sore. Other causes may include: (i) faulty immune system function; (ii) nutritional problems, such as a deficiency of vitamin B-12, zinc, folic acid or iron; (iii) diseases of the gastrointestinal tract; (iv) food allergies; or (v) the menstrual cycle.

Canker sores can occur at any age, but often they first appear between the ages of 10 and 40 years. Although canker sores typically resolve on their own, they can be very uncomfortable.

Dental/Tooth Abscess

Infection or decay can lead to an abscess. An abscess may have serious dental and medical consequences. For example, a severe infection caused by a dental abscess may lead to a sinus or systemic infection. Furthermore, an abscess may lead to the need to extract one or more teeth. Extraction may be necessary due to significant tooth decay, or because the infection is too severe to fully treat in the presence of the offending tooth.

Regardless of the ultimate outcome, a dental abscess may be extremely painful. Not only is the pain uncomfortable, but it may interfere with proper nutrition and hydration. Methods and compositions for reducing the pain associated with dental abscess would provide significant benefits for their management.

Gastroesophageal Reflux Disease

Gastroesophageal reflux disease, or GERD, occurs when the lower esophageal sphincter (LES) does not close properly and stomach contents leak back into the esophagus. The LES is a ring of muscle at the bottom of the esophagus that acts like a valve between the esophagus and stomach. When refluxed stomach acid touches the lining of the esophagus, it causes a burning sensation in the chest or throat. This is often experienced as heartburn. The refluxed fluid may even be tasted in the back of the mouth, a sensation commonly referred to as acid indigestion.

Although occasional heartburn is uncommon and not necessarily indicative of GERD, heartburn that occurs more than twice a week may be a sign of GERD. In addition to the discomfort of heartburn and indigestion, GERD may lead to other serious health problems. For example, over time, acid refluxed to the back of the throat can lead to oral sores, lesions, or ulcers in the mouth, gums, tongue, throat, or lips. The lesions can cause significant pain, can interfere with nutrition and hydration, and can leave a person vulnerable to infection.

Administration of TRPA1 inhibitors, according to the present invention, may be useful in treating oral pain from lesions caused by GERD. TRPA1 inhibitors may be used as part of a treatment regimen where the TRPA1 inhibitor is administered to help manage the discomfort of the oral lesion, while other agents or therapeutics interventions are used to manage the GERD.

Gingivostomatitis

Gingivostomatitis is a disorder involving sores on the mouth and gums that result from a viral infection. Gingivostomatitis is characterized by inflammation of the gums and mucosa and multiple oral ulcers. The inflammation and ulcers are caused by viral infections, particularly those that cause common childhood illness such as herpes virus (cold sores and acute herpetic stomatitis), and Coxsackie viruses (hand, foot and mouth disease and herpangina). These viruses cause shallow ulcers with a grayish or yellowish base and a slightly red margin, on the tissues of the gums (gingiva), the lining of the cheeks (buccal mucosa), or other soft tissues of the mouth. Although this condition can occur in patients of any age, it is particularly common in children.

The oral ulcers caused by these viruses can be very painful. The ulcers are often accompanied by a fever. Overall, the condition can take several weeks to resolve. The recognized treatments for gingivostomatitis focus on reducing the pain caused by the oral ulcers. This is particularly important for children who may refuse food or liquids because of their discomfort, thus making them especially susceptible to dehydration. Compounds of the present invention can be used to treat the pain associated with these oral ulcers.

Oral Thrush

Oral thrush is a fungal infection generally caused by the yeast fungus, *Candida albicans*, in the mucous membranes of the mouth. Strictly speaking, thrush is only a temporary *Candida* infection in the oral cavity of babies. However, the term is used generally to refer to fungal infections in the mouths and throats of children and adults.

*Candida* is present in the oral cavity of almost half of the population. For example, everyone who wears dentures has *Candida*, without necessarily suffering any ill effects. Generally, *Candida* does not create problems until there is a change in the chemistry of the oral cavity such that the growth of *Candida* is favored over the other microorganisms that typically inhabit the mouth and throat. Changes in oral chemistry sufficient to permit the growth of *Candida* may occur as a side effect to taking antibiotics or chemotherapeutics. Overall patient health may also influence the chemistry of the mouth. HIV infection, diabetes, malnutrition, age, and immunodeficiency are exemplary conditions that can shift oral chemistry enough to permit the overgrowth of *Candida* in the mouth and throat.

In addition to shifts in oral chemistry, people whose dentures don't fit well can sustain breaks in the mucous membranes in their mouth. These breaks provide an opportunity for *Candida* infection in the mouth and lips.

Thrush causes white, cream-colored, or yellow spots in the mouth. The spots are slightly raised. If these spots are scraped they tend to bleed. Thrush can be very uncomfortable, and may cause a burning sensation in the mouth and throat. The discomfort may interfere with hydration and nutrition. Furthermore, the discomfort may interfere with proper oral hygiene such as brushing and flossing.

Standard treatment of thrush is by administration of anti-fungal agents. These agents can be administered directly to the mouth, for example, in the form of pastilles that are sucked or oral suspensions that are held in the mouth before swallowing. Examples include nystatin (e.g., Nystan oral suspension), amphotericin (e.g., Fungilin lozenges) or miconazole (e.g., Daktarin oral gel). In addition to standard anti-fungal therapy, compounds of the present invention can be administered to manage the pain and discomfort associated with thrush.

Glossitis

Glossitis is an abnormality of the tongue that results from inflammation. Glossitis occurs when there is acute or chronic inflammation of the tongue. It causes the tongue to swell and change color. Finger-like projections on the surface of the tongue (papillae) are lost, causing the tongue to appear smooth. Glossitis has a number of causes including, but not limited to, the following: bacterial infections; viral infections (including oral herpes simplex); injury or trauma; exposure to irritants (e.g., tobacco, alcohol, hot foods, spices); allergic reactions; vitamin or mineral deficiencies (e.g., iron deficiency anemia, pernicious anemia and other B-vitamin deficiencies); or as a side effect of other diseases or disorders.

The symptoms of glossitis include swelling, soreness, and tenderness of the tongue. Additionally, the tongue often changes appearance, becoming smooth and dark red in color. As a consequence of the swelling and discomfort, glossitis often makes chewing, swallowing, and speaking difficult.

The typical treatment for glossitis depends on the underlying cause of the inflammation. Regardless of the particular antibiotics, anti-inflammatories, or anti-viral agents that may be administered to combat the underlying cause of glossitis, compounds according to the present invention may be administered to decrease the pain and discomfort associated with glossitis. Decreasing the pain associated with glossitis is especially important when it interferes with proper nutrition and hydration, or when it interferes with or prevents proper oral hygiene.

Cutaneous Diseases

Oral ulcers may result from any of a number of cutaneous diseases. For example, lichen planus, pemphigus, pemphigoid, and erythema multiforme may lead to oral ulcers. Such oral ulcers may cause significant pain that can be treated using the compounds of the present invention.

Reduction of pain may help facilitate healing. This is especially important for patients with pemphigus and pemphigoid who develop oral ulcers. Such patients are already immunosuppressed, and may thus be more susceptible to opportunistic infections from lesions in the mouth.

Gastrointestinal Diseases

Oral ulcers may result from any of a number of gastrointestinal diseases. Conditions which interfere with proper digestion, management and flow of stomach and other digestive acids, motility, and elimination may lead to oral ulcers and other lesions. In some instances, the oral ulcers are the results of acids or partially digested food refluxing into the esophagus. In other instances, the oral ulcers result from frequent vomiting. In still other instances, oral ulcers occur due to vitamin deficiency, mineral deficiency or other nutritional deficiency secondary to the gastrointestinal disease. In still other instances, oral ulcers are part of the complex etiology that characterizes the gastrointestinal disease.

Oral ulcers resulting from or experienced as part of a gastrointestinal disease may be extremely painful. They may undermine proper nutrition and hydration for a patient whose underlying gastrointestinal disease may already impose multiple limitations on diet. Accordingly, methods and compositions for decreasing the discomfort and pain associated with these oral ulcers offer substantial benefits for patients with an underlying gastrointestinal condition.

Exemplary gastrointestinal conditions which may lead to oral inflammation, lesions, or ulcers include, but are not limited to, Crohn's disease, ulcerative colitis, irritable bowel syndrome, celiac sprue, and dermatitis herpetiformis. The primary symptoms of these conditions may be managed with diet, stress management, and medications. The TRPA1 inhibitors of the present invention may be used to help manage the pain and discomfort of oral inflammation, lesions, or ulcers caused by any of these gastrointestinal conditions.

Rheumatoid Diseases

A consequence of several rheumatoid diseases is oral ulcers. For example, lupus, Behcet's syndrome, Sweet's syndrome, and Reiter's disease may all lead to oral ulcers. Such oral ulcers may cause significant mouth pain that can be treated using the compounds of the present invention.

Sjogren's Syndrome

Dry mouth is a common symptom associated with Sjögren's syndrome. Dry mouth is caused by a decrease in the production of saliva. Saliva is an essential body fluid for protection and preservation of the oral cavity and oral functions. Although saliva is mostly water, it also contains over 60 substances which serve the following important functions: protect, lubricate and cleanse the oral mucosa; aid chewing, swallowing and talking; protect the teeth against decay; protect the mouth, teeth, and throat from infection by bacteria, yeasts, and viruses; support and facilitate our sense of taste.

Given the important functions of saliva, decreased salivation can lead to many problems. If the condition persists for months or years, a patient may develop oral complications such as difficulty swallowing, severe and progressive tooth decay, oral infections (particularly fungal), or combinations of these. Many of the conditions can cause discomfort, in their own right, and may also lead to oral lesions or ulcers.

Several medications are available to help increase salivary secretion in patients with dry mouth. Pilocarpine (Salagen®) and cevimeline (Evoxac®) reduce symptoms of dry mouth and increase salivary secretion. However, these drugs don't prevent tooth decay or treat the oral pain associated with the symptoms or effects of dry mouth. Compounds of the present invention can be used to treat the pain associated with dry mouth.

Vitamin or Mineral Deficiencies

In some instances, vitamin or mineral deficiencies may lead to ulcers or other sores in the mouth. For example, deficiency in vitamin C may lead to the oral lesions characteristic of scurvy. Deficiencies in vitamins B1, B2, B6, or B12 may also lead to oral lesions. Additionally, deficiencies in zinc, folic acid, iron, selenium, or calcium may lead to oral lesions.

In certain embodiments, a vitamin or mineral deficiency is a precipitating factor leading to a canker sore. However, a vitamin or mineral deficiency may also lead to other types of oral ulcers and lesions. Regardless of the nature of the lesion, compounds of the present invention can be used to help manage the associated pain.

Allergies

Allergies can sometimes lead to canker sores and other oral lesions. Oral lesions due to an allergy may be more likely when a person's oral tissues come into contact with the causative allergen. However, contact between the allergen and oral tissue is not necessarily required to produce an oral lesion. Exemplary allergens that can lead to oral lesions include food allergens such as fruits and vegetables (e.g., strawberries, lemons, oranges, pineapples, apples, figs, tomatoes); shellfish; chocolate; nuts; dairy (e.g., milk and cheese); cereal grains (e.g., buckwheat, wheat, oats, rye, barley, gluten protein found in grains); additives (e.g., cinnamonaldehyde (a flavoring agent), benzoic acid (a preservative); toothpastes (e.g., some people have a sensitivity to sodium laurel sulfate found in certain toothpastes and mouthwashes); nonsteroidal anti-inflammatory drugs (NSAIDs; some people have a sensitivity leading to canker sores in response to this class of drug).

Other Exemplary Conditions and Injuries

The foregoing are merely exemplary of diseases and conditions that cause or lead to inflammation, lesions, ulcers, or other sources of oral pain. In other embodiments, the oral pain is due to an injury to the mouth, jaw, lips, gums, or teeth. In other embodiments, the oral pain is due to oral surgery, for example, surgery for cancer, tooth extraction, or jaw remodeling. Other conditions that may lead to oral ulcers, and thus oral pain, include, but are not limited to chickpox, herpes zoster, infectious mononucleosis, syphilis, tuberculosis, acute necrotizing gingivitis, and burning mouth syndrome. Additionally, conditions that lead to a compromised immune system put patients at risk for, among other complications, oral inflammation, lesions, or ulcers. HIV infection, AIDS, and hepatitis are all conditions that undermine the immune system and may lead to oral lesions or ulcers. Additionally, individuals taking immunosuppressants (e.g., organ transplant recipients, bone marrow recipients, stem cells recipients, patients with an autoimmune disease) are at increased risk of developing painful oral lesions.

The invention contemplates the use of TRPA1 inhibitors, according to the present invention, in the treatment of oral pain regardless of the underlying cause. In certain embodiments, TRPA1 inhibitors for treating oral pain can be administered orally, for example, as a paste, mouth wash, gel, or other liquid preparation. In certain embodiments, the paste, mouth wash, gel, or other liquid preparation is administered via a swab, mouth guard, or other dental apparatus. In certain embodiments, the preparation is applied locally to the mouth, but is not otherwise ingested. For example, a mouth wash formulation that is not swallowed may be used.

Regardless of the formulation and route of administration, the invention contemplates administration of the subject TRPA1 inhibitors as part of an overall treatment strategy that also includes therapies appropriate for the particular disease or condition that caused the oral inflammation, lesion, or ulcer.

TRPA1 inhibitors may be used to treat oral pain resulting from any of the foregoing injuries, diseases, or conditions. Additionally, Applicants note that the subject TRPA1 inhibitors may also be useful in the treatment of the underlying aforementioned diseases and conditions themselves. Specifically, TRPA1 inhibitors may be useful in the treatment of inflammation, and thus diseases or conditions with an inflammatory component, whether the symptoms manifest themselves in the mouth or in other parts of the body, may themselves be treatable with the subject TRPA1 inhibitors. Accordingly, the invention contemplates and recognizes that for some conditions the therapeutic affects of administering a TRPA1 inhibitor may be two-fold: (i) decreasing pain associated with one or more symptoms of a disease or condition and (ii) treating the underlying symptoms or disease.

Disease and Injury Models

Compounds that antagonize TRPA1 function may be useful in the prophylaxis and treatment of any of the foregoing injuries, diseases, disorders, or conditions. In addition to in vitro assays of the activity of these compounds, their efficacy can be readily tested in one or more animal models. By way of example, numerous well known animal models exist. One or more suitable animal models (e.g., suitable in light of the particular indication) can be selected.

Pain can be generally categorized as chronic pain and acute pain. The two categories of pain differ in duration, as well as underlying mechanism. Chronic pain is not only persistent, but also does not generally respond well to treatment with currently available analgesics, non-steroidal anti-inflammatory drugs, and opioids.

Two broad sub-categories of chronic pain are neuropathic pain and cancer pain. Wang and Wang (2003) Advanced Drug Delivery Reviews 55: 949-965. Neuropathic pain refers to pain resulting from damage (e.g., from disease, injury, age) to the nervous system (e.g., nerves, spinal cord, CNS, PNS). Cancer-related pain may be caused by tumor infiltration, nerve compression, substances secreted by tumors, or the particular treatment regimen (e.g., radiation, chemotherapeutics, surgery).

Pain is also often classified mechanistically as nociceptive, inflammatory, or neuropathic. Nociceptive pain is pain experienced following, for example, changes or extremes in temperature, exposure to acids, exposure to chemical agents, exposure to force, and exposure to pressure. Reception of painful stimuli sends impulses to the dorsal root ganglia. The response is typically a combination of a reflexive response (e.g., withdrawal from the stimuli) and an emotional reaction. Inflammation is the immune system's response to injury or disease. In response to injury or disease, macrophages, mast cells, neutrophils, and other cells of the immune system are recruited. This infiltration of cells, along with the release of cytokines and other factors (e.g., histamine, serotonin, bradykinin, prostaglandins, ATP, H+, nerve growth factor, TNFα, endothelins, interleukins), can cause fever, swelling, and pain. Current treatments for the pain of inflammation include Cox2 inhibitors and opioids. Neuropathic pain refers to pain resulting from damage (e.g., from disease, injury, age) to the nervous system (e.g., nerves, spinal cord, CNS, PNS). Current treatment for neuropathic pain includes tricyclic antidepressants, anticonvulsants, Na+ channel blockers, NMDA receptor antagonists, and opioids.

There are numerous animal models for studying pain. The various models use various agents or procedures to simulate pain resulting from injuries, diseases, or other conditions. Blackburn-Munro (2004) Trends in Pharmacological Sciences 25: 299-305 (see, for example, Table 1). Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. Id. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the Chung model, the carageenan induced hyperalgesia model, the Freund's complete adjuvant induced hyperalgesia model, the thermal injury model, the formalin model and the Bennett Model. The Chung model of neuropathic pain (without inflammation) involves ligating one or more spinal nerves. Chung et al. (2004) Methods Mol Med 99: 35-45; Kim and Chung (1992) Pain 50: 355-363. Ligation of the spinal nerves results in a variety of behavioral changes in the animals including heat hyperalgesia, cold allodynia, and ongoing pain. Compounds that antagonize TRPA1 can be administered to ligated animals to assess whether they diminish these ligation-induced behavioral changes in comparison to that observed in the absence of compound.

Carageenan induced hyperalgesia and Freund's complete adjuvant (FCA) induced hyperalgesia are models of inflammatory pain. Walker et al. (2003) Journal of Pharmacol Exp Ther 304: 56-62; McGaraughty et al. (2003) Br J Pharmacol 140: 1381-1388; Honore et al. (2005) J Pharmacol Exp Ther. Compounds that antagonize TRPA1 can be administered to carrageenan or FCA challenged animals to assess whether they diminish thermal hyperalgesia in comparison to that observed in the absence of compound. In addition, the ability of compounds that antagonize TRPA1 function to diminish cold and/or mechanical hypersensitivity can also be assessed in these models. Typically, the carrageenan induced hyperalgesia model is believed to mimic acute inflammatory pain and the CFA model is believed to mimic chronic pain and chronic inflammatory pain.

The Bennett model uses prolonged ischemia of the paw to mirror chronic pain. Xanthos et al. (2004) J Pain 5: S1. This provides an animal model for chronic pain including postoperative pain, complex regional pain syndrome, and reflex sympathetic dystrophy. Prolonged ischemia induces behavioral changes in the animals including hyperalgesia to mechanical stimuli, sensitivity to cold, pain behaviors (e.g., paw shaking, licking, and/or favoring), and hyperpathia. Compounds that antagonize TRPA1 can be administered to challenged animals to assess whether they diminish any or all of these behaviors in comparison to that observed in the absence of compound. Similar experiments can be conducted in a thermal injury or UV-burn model which can be used to mimic post-operative pain.

Migraines are associated with significant pain and inability to complete normal tasks. Several models of migraine exist including the rat neurogenic inflammation model, (see Buzzi et al (1990) Br J Pharmacol; 99:202-206), and the Burstein Model (see Strassman et al., (1996) Nature 384: 560-564).

Additional models of neuropathic pain include central pain models based on spinal cord injury. Chronic pain is generated by inducing a spinal cord injury, for example, by dropping a weight on a surgically exposed area of spinal cord (e.g., weight-drop model). Spinal cord injury can additionally be induced by crushing or compressing the spinal cord, by delivering neurotoxin, using photochemicals, or by hemisecting the spinal cord. Wang and Wang (2003).

Additional models of neuropathic pain include peripheral nerve injury models. The term peripheral neuropathy encompasses a variety of diseases, conditions, and injuries. One of skill in the art can readily select an appropriate model in light of the particular condition or disease under investigation. Exemplary models include, but are not limited to, the neuroma model, the Bennett model, the Seltzer model, the Chung model (ligation at either L5 or L5/L6), the sciatic cryoneurolysis model, the inferior caudal trunk resection model, and the sciatic inflammatory neuritis model. Id.

Exemplary models of inflammatory pain include the rat model of intraplantar bradykinin injection. Briefly, the baseline thermal sensitivity of the animals is assessed on a Hargreave's apparatus. TRPA1 blockers are then administered systemically. Bradykinin is subsequently injected into the paw and a hyperalgesia is allowed to develop. Thermal escape latency is then measured at multiple time points over the next few hours (Chuang et al., 2001; Vale et al., 2004).

Exemplary models of neuropathic pain associated with particular diseases are also available. Diabetes and shingles are two diseases often accompanied by neuropathic pain. Even following an acute shingles episodes, some patients continue to suffer from postherpetic neuralgia and experience persistent pain lasting years. Neuropathic pain caused by shingles and/or postherpetic neuralgia can be studied in the postherpetic neuralgia model (PHN). Diabetic neuropathy can be studied in diabetic mouse models, as well as chemically induced models of diabetic neuropathy. Wang and Wang (2003).

As outlined above, cancer pain may have any of a number of causes, and numerous animal models exist to examine cancer pain related to, for example, chemotherapeutics or tumor infiltration. Exemplary models of toxin-related cancer pain include the vincristine-induced peripheral neuropathy model, the taxol-induced peripheral neuropathy model, and the cisplatin-induced peripheral neuropathy model. Wang and Wang (2003). An exemplary model of cancer pain caused by tumor infiltration is the cancer invasion pain model (CIP). Id.

Primary and metastatic bone cancers are associated with tremendous pain. Several models of bone cancer pain exist including the mouse femur bone cancer pain model (FBC), the mouse calcaneus bone cancer pain model (CBC), and the rat tibia bone cancer model (TBC). Id.

An additional model of pain is the formalin model Like the carrageenan and CFA models, the formalin model involves injection of an irritant intradermally or intraperitoneally into an animal. Injection of formalin, a 37 percent solution of formaldehyde, is the most commonly used agent for intradermal paw injection (the formalin test). Injection of a 0.5 to 15 percent solution of formalin (usually about 3.5%) into the dorsal or plantar surface of the fore- or hindpaw produces a biphasic painful response of increasing and decreasing intensity for about 60 minutes after the injection. Typical responses include the paw being lifted, licked, nibbled, or shaken. These responses are considered nociceptive. The initial phase of the response (also known as the Early Phase), which lasts 3 to 5 minutes, is probably due to direct chemical stimulation of nociceptors. This is followed by 10 to 15 minutes during which animals display little behavior suggestive of nociception. The second phase of this response (also known as the Late Phase) starts about 15 to 20 minutes after the formalin injection and lasts 20 to 40 minutes, initially rising with both number and frequency of nociceptive behaviors, reaching a peak, then falling off. The intensities of these nociceptive behaviors are dependent on the concentration of formalin used. The second phase involves a period of sensitization during which inflammatory phenomena occur. The two phases of responsiveness to formalin injection makes the formalin model an appropriate model for studying mociceptive and acute inflammatory pain. It may also model, in some respects, neuropathic pain.

In addition to any of the foregoing models of chronic pain, compounds that antagonize TRPA1 function can be tested in one or more models of acute pain. Valenzano et al. (2005) Neuropharmacology 48: 658-672. Regardless of whether compounds are tested in models of chronic pain, acute pain, or both, these studies are typically (though not exclusively) conducted, for example, in mice, rats, or guinea pigs. Additionally, compounds can be tested in various cell lines that provide in vitro assays of pain. Wang and Wang (2003).

Many individuals seeking treatment for pain suffer from visceral pain. Animal models of visceral pain include the rat model of inflammatory uterine pain (Wesselmann et al., (1997) Pain 73:309-317), injection of mustard oil into the gastrointestinal tract to mimic irritable bowel syndrome (Kimball et al., (2005) Am J Physiol Gastrointest Liver Physiol, 288(6):G1266-73), injection of mustard oil into the bladder to mimic overactive bladder or bladder cystitis (Riazimand (2004), BJU 94: 158-163). The effectiveness of a TRPA1 compound can be assessed by a decrease in writhing, gastrointestinal inflammation or bladder excitability.

The foregoing animal models are relied upon extensively in the study of pain. The following provide additional exemplary references describing the use of these models in the study of pain: thermal injury model (Jones and Sorkin, 1998, Brain Res 810: 93-99; Nozaki-Taguchi and Yaksh, 1998, Neuroscience Lett 254: 25-28; Jun and Yaksh, 1998, Anesth Analg 86: 348-354), formalin model (Yaksh et al., 2001, J Appl Physiol 90: 2386-2402), carrageenan model (Hargreaves et al., 1988, Pain 32: 77-88), and CFA model (Nagakura et al., 2003, J Pharmacol Exp Ther 306: 490-497).

Inflammation is often an important contributing factor to pain. As such, it is useful to identify compounds that act as anti-inflammatories. Many compounds that reduce neural activity also prevent neurogenic inflammation. To measure inflammation directly, the volume of a rat paw can be assessed using a plethysmometer. After baseline measurement is taken, carrageenan can be injected into the paw and the volume can be monitored over the course of hours in animals that have been treated with vehicle or drug. Drugs that reduce the paw swelling are considered to be anti-inflammatory.

For testing the efficacy of TRPA1 antagonists for the treatment of cough, experiments using the conscious guinea pig model of cough can be readily conducted. Tanaka and Maruyama (2003) Journal Pharmacol Sci 93: 465-470; McLeod et al. (2001) Br J Pharmacol 132: 1175-1178. Briefly, guinea pigs serve as a useful animal model for cough because, unlike other rodents such as mice and rats, guinea pigs actually cough. Furthermore, guinea pig coughing appears to mimic human coughing in terms of the posture, behavior, and appearance of the coughing animal.

To induce cough, conscious guinea pigs are exposed to an inducing agent such as citric acid or capsaicin. The response of the animal is measured by counting the number of coughs. The effectiveness of a cough suppressing agent, for example a compound that inhibits TRPA1, can be measured by administering the agent and assessing the ability of the agent to decrease the number of coughs elicited by exposure to citric acid, capsaicin, or other similar cough-inducing agent. In this way, TRPA1 inhibitors for use in the treatment of cough can be readily evaluated and identified.

Additional models of cough include the unconscious guinea pig model. Rouget et al. (2004) Br J Pharmacol 141: 1077-1083. Either of the foregoing models can be adapted for use with other animals capable of coughing. Exemplary additional animals capable of coughing include cats and dogs.

Numerous rodent models of incontinence exist. These include models of incontinence induced by nerve damage, urethral impingement and inflammation. Models of urethral impingement include the rat bladder outflow obstruction model. (Pandita, R K, and Andersson K E. Effects of intravesical administration of the K+ channel opener, Z.D6169, in conscious rats with and without bladder outflow obstruction. J Urol 162: 943-948, 1999). Inflammatory models include injection of mustard oil into the bladder.

To test the effectiveness of a TRPA1 inhibitor compound in treating incontinence, varying concentrations of compound (e.g., low, medium, and high concentration) can be administered to rats following surgical partial bladder outlet obstruction (BOO). Efficacy of the varying doses of TRPA1 inhibitory compound can be compared to controls administered excipients alone (sham control). Efficacy can further be compared to rats administered a positive control, such as atropine. Atropine is expected to decrease bladder overactivity following partial bladder outlet obstruction in the BOO model. Note that when testing compounds in the BOO model, compounds can be administered directly to the bladder or urethra (e.g., by catheter) or compounds can be administered systemically (e.g., orally, intraveneously, intraperitoneally, etc).

As detailed above, TRPA1 inhibitors can be used to treat the symptoms of pain associated with pancreatitis. The efficacy of TRPA1 inhibitors in pancreatitis pain management may be tested in one or more animal models. Inhibitors may be tested in general animal models of pain, for example models of inflammatory pain or visceral pain. Alternatively or additionally, TRPA1 inhibitors may be tested in animal models that specifically mimic pain accompanying pancreatitis or other pancreatic injury.

Several rat models of pancreatitic pain have recently been described (Lu, 2003, Anesthesiology 98(3): 734-740; Winston et al., 2003, Journal of Pain 4(6): 329-337). Lu et al. induced pancreatitis by systemic delivery of dibutylin dichloride in rats. Rats showed an increase in withdrawal events after von Frey filament stimulation of the abdomen and decreased withdrawal latency after thermal stimulation during a period of 7 days. The pain state induced in these animals was also characterized by increased levels of substance P in spinal cords (Lu, et al., 2003). To test the efficacy of a TRPA1 inhibitor in this model, a TRPA1 inhibitor can be administered following or concurrently with delivery of dibutylin dichloride. Control animals can be administered a carrier or a known pain reliever. Indicia of pain can be measured. Efficacy of a TRPA1 inhibitor can be evaluated by comparing the indicia of pain observed in animals receiving a TRPA1 inhibitor to that of animals that did not receive a TRPA1 inhibitor. Additionally, efficacy of a TRPA1 inhibitor can be compared to that of known pain medicaments.

The efficacy of von Frey filament testing as a means to measure nociceptive behavior was also shown by inducing pancreatitis by systemic L-arginine administration (Winston et al, 2003). The efficacy of a TRPA1 inhibitor can similarly be tested following pancreatitis induced by systemic L-arginine administration.

Lu et al. also described direct behavioral assays for pancreatic pain using acute noxious stimulation of the pancreas via an indwelling ductal canula in awake and freely moving rats. These assays included cage crossing, rearing, and hind limb extension in response to intrapancreatic bradykinin infusion. Intrathecal administration of either D-APV (NMDA receptor antagonist) or morphine alone partially reduced visceral pain behaviors in this model. Combinations of both reduced pain behaviors to baseline. The efficacy of a TRPA1 inhibitor can similarly be tested in this system.

Any of the foregoing animal models may be used to evaluate the efficacy of a TRPA1 inhibitor in treating pain associated with pancreatitis. The efficacy can be compared to a no treatment or placebo control. Additionally or alternatively, efficacy can be evaluated in comparison to one or more known pain relieving medicaments.

Optimizing the Treatment of Pain

TRPA1 inhibitors, according to the present invention, can be used in the treatment of a variety of injuries, diseases, conditions, and disorders. One important therapeutic use for TRPA1 inhibitors is in the treatment of pain. As illustrated by the extensive list of injuries, conditions, and diseases for which pain is a significant and sometimes debilitating symptom, improved methods and compositions for use in the treatment of pain provide substantial benefits for an enormous range of patients. Such methods and compositions have the potential to improve the quality of care and the quality of life for patients afflicted with a diverse range of injuries, diseases, and conditions. The present application contemplates that a compound that inhibits TRPA1 can be used in the treatment of any of the aforementioned injuries, conditions, or diseases.

An important issue with the treatment of pain is how to manage pain while reducing the side effects experienced with many analgesics. For example, although many opiates and other narcotics effectively diminish pain, patients are often unable to drive, work, or concentrate while taking these medications. Thus, while opiates such as morphine or dilaudin may be suitable for short term use or for use during hospitalization, they are not optimal for long term use. Additionally, opiates and other narcotics are habit forming, and patients typically develop a tolerance for these drugs. These characteristics of opioids and other narcotics make them sub-optimal for pain management.

The present invention provides TRPA1 inhibitors for use in vitro and in vivo. The present invention also provides compositions and pharmaceutical compositions comprising particular classes of compounds that inhibit TRPA1 activity. In certain embodiments, the subject TRPA1 inhibitors are selective. In other words, in certain embodiments, the compound inhibits TRPA1 activity preferentially over the activity of other ion channels. In certain embodiments, the compound inhibits TRPA1 activity preferentially over TRPV1, TRPV2, TRPV3, TRPV4, and/or TRPM8 activity. In certain other embodiments, the compound is selected because it cross reacts with one or more other TRP channels involved with pain. For example, in certain embodiments, the compound inhibits the activity of TRPA1 and also inhibits the activity of one or more of TRPV1, TRPV2, TRPV3, TRPV4, and TRPM8.

Combination Therapy

Another aspect of the invention provides a conjoint therapy wherein one or more other therapeutic agents are administered with the TRPA1 modulators. Such conjoint treatment may be achieved by way of the simultaneous, sequential, or separate dosing of the individual components of the treatment.

In certain embodiments, a compound of the invention is conjointly administered with an analgesic. Suitable analgesics include, but are not limited to, opioids, glucocorticosteroids, non-steroidal anti-inflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorpharnol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, mefanamic acid, prednisolone, and dexamethasone. Preferred analgesics are non-steroidal anti-inflammatories and opioids (preferably morphine).

In certain embodiments, a compound of the invention is conjointly administered with a non-steroidal anti-inflammatory. Suitable non-steroidal anti-inflammatory compounds include, but are not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindac, apazone, phenylbutazone, aspirin, celecoxib and rofecoxib.

In certain embodiments, a compound of the invention is conjointly administered with an antiviral agent. Suitable antiviral agents include, but are not limited to, amantadine, acyclovir, cidofovir, desciclovir, deoxyacyclovir, famciclovir, foscamet, ganciclovir, penciclovir, azidouridine, anasmycin, amantadine, bromovinyldeoxusidine, chlorovinyldeoxusidine, cytarbine, didanosine, deoxynojirimycin, dideoxycitidine, dideoxyinosine, dideoxynucleoside, edoxuidine, enviroxime, fiacitabine, foscamet, fialuridine, fluorothymidine, floxuridine, hypericin, interferon, interleukin, isethionate, nevirapine, pentamidine, ribavirin, rimantadine, stavirdine, sargramostin, suramin, trichosanthin, tribromothymidine, trichlorothymidine, vidarabine, zidoviridine, zalcitabine 3-azido-3-deoxythymidine, 2',3'-dideoxyadenosine (ddA), 2',3'-dideoxyguanosine (ddG), 2',3'-dideoxycytidine (ddC), 2',3'-dideoxythymidine (ddT), 2'3'-dideoxy-dideoxythymidine (d4T), 2'-deoxy-3'-thia-cytosine (3TC or lamivudime), 2',3'-dideoxy-2'-fluoroadenosine, 2',3'-dideoxy-2'-fluoroinosine, 2',3'-dideoxy-2'-fluorothymidine, 2',3'-dideoxy-2'-fluorocytosine, 2'3'-dideoxy-2',3'-didehydro-2'-fluorothymidine (Fd4T), 2'3'-dideoxy-2'-beta-fluoroadenosine (F-ddA), 2'3'-dideoxy-2'-beta-fluoroinosine (F-ddI), and 2',3'-dideoxy-2'-beta-fluorocytosine (F-ddC), trisodium phosphomonoformate, trifluorothymidine, 3' azido-3' thymidine (AZT), dideoxyinosine (ddI), and idoxuridine.

In certain embodiments, a compound of the invention is conjointly administered with an antibacterial agent. Suitable antibacterial agents include, but are not limited to, amantadine hydrochloride, amantadine sulfate, amikacin, amikacin sulfate, amoglycosides, amoxicillin, ampicillin, amsamycins, bacitracin, beta-lactams, candicidin, capreomycin, carbenicillin, cephalexin, cephaloridine, cephalothin, cefazolin, cephapirin, cephradine, cephaloglycin, chilomphenicols, chlorhexidine, chloshexidine gluconate, chlorhexidine hydrochloride, chloroxine, chlorquiraldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erhmycin stearate, farnesol, floxacillin, gentamicin, gentamicin sulfate, gramicidin, giseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenine, methenamine hippurate, methenamine mandelate, methicillin, metonidazole, miconazole, miconazole hydrochloride, minocycline, minocycline hydrochloride, mupirocin, nafcillin, neomycin, neomycin sulfate, netimicin, netilmicin sulfate, nitrofurazone, norfloxacin, nystatin, octopirox, oleandomycin, orcephalosporins, oxacillin, oxyteacline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, struptomycin, sulfonamide, tetracyclines, tetracycline, tobramycin, tobramycin sulfate, triclocarbon, triclosan, trimethoprim-sulfamethoxazole, tylosin, vancomycin, and yrothricin.

In certain embodiments, a compound of the invention is conjointly administered with a cough suppressant, decongestant, or expectorant.

Examples of retinoids that be administered with the subject TRPA1 inhibitors, e.g., where the TRPA1 inhibitor can be used to reduce the pain and/or inflammatory effect of the retinoid, include, but are not limited to, compounds such as retinoic acid (both cis and trans), retinol, adapalene, vitamin A and tazarotene. Retinoids are useful in treating acne, psoriasis, rosacea, wrinkles and skin cancers and cancer precursors such as melanoma and actinic keratosis.

Similarly, the subject TRPA1 inhibitors can be used in conjunction with keratolytic agents include benzoyl peroxide, alpha hydroxyacids, fruit acids, glycolic acid, salicylic acid, azelaic acid, trichloroacetic acid, lactic acid and piroctone.

The subject TRPA1 inhibitors can also be administered along with depilatory agents (hair loss).

The subject TRPA1 inhibitors can be used with anti-acne agents, anti-eczema agents and anti-psoratic agents. Compounds particularly useful in treating acne include azelaic acid (an aliphatic diacid with antiacne properties), anthralin (a diphenolic compound with antifungal and antipsoriatic properties), and masoprocol (nordihydroguaiaretic acid, a tetraphenolic compound with antioxidant properties, also useful in the treatment of actinic keratosis) and analogs thereof (such as austrobailignan 6, oxoaustrobailignan 6,4'-O-methyl-7,7'-dioxoaustrobailignan 6, macelignan, demethyldihydroguaiaretic acid, 3,3',4-trihydroxy-4'-methoxylignan, Saururenin, 4-hydroxy-3,3',4'-trimethoxylignan, and isoanwulignan). Anti-eczema agents include pimecrolimus and tacrolimus. Anti-psoriatic active agents suitable for use in the present invention include retinoids (including isomers and derivatives of retinoic acid, as well as other compounds that bind to the retinoic acid receptor, such as retinoic acid, acitretin, 13-cis-retinoic acid (isotretinoin), 9-cis-retinoic acid, tocopheryl-retinoate (tocopherol ester of retinoic acid (trans- or cis-)), etretinate, motretinide, 1-(13-cis-retinoyloxy)-2-propanone, 1-(13-cis-retinoyloxy)-3-decanoyloxy-2-propanone, 1,3-bis-(13-cis-retinoyloxy)-2-propanone, 2-(13-cis-retinoyloxy)-acetophenone, 13-cis-retinoyloxymethyl-2,2-dimethyl propanoate, 2-(13-cis-retinoyloxy)-n-methyl-acetamide, 1-(13-cis-retinoyloxy)-3-hydroxy-2-propanone, 1-(13-cis-retinoyloxy)-2,3-dioleoylpropanone, succinimdyl 13-cis-retinoate, adapalene, and tazarotene), salicylic acid (monoammonium salt), anthralin, 6-azauridine, vitamin D derivatives (including but not limited to Rocaltrol (Roche Laboratories), EB 1089 ($24\alpha,26\alpha,27\alpha$-trihomo-22,24-diene-$1\alpha,25$-$(OH)_2$-$D_3$), KH 1060 (20-epi-22-oxa-$24\alpha,26\alpha,27\alpha$-trihomo-$1\alpha,25$-$(OH)_2$-$D_3$), MC 1288, GS 1558, CB 1093, 1,25-$(OH)_2$-16-ene-$D_3$, 1,25-$(OH)_2$-16-ene-23-yne-$D_3$, and 25-(OH)2-16-ene-23-yne-$D_3$, 22-oxa-calcitriol; $1\alpha$-$(OH)D_5$ (University of Illinois), ZK 161422 and ZK 157202 (Institute of Medical Chemistry-Schering AG), alfacalcidol, calcifediol, calcipotriol (calcipotriene), maxacalcitriol, colecalciferol, doxercalciferol, ergocalciferol, falecalcitriol, lexacalcitol, maxacalcitol, paricalcitol, secalciferol, seocalcitol, tacalcitol, calcipotriene, calcitriol, and other analogs as disclosed in U.S. Pat. No. 5,994,332), pyrogallol, and tacalcitol.

The subject TRPA1 inhibitors can also be administered with vitamins and derivatives thereof including Vitamin A, ascorbic acid (Vitamin C), alpha-tocopherol (Vitamin E), 7-dehydrocholesterol (Vitamin D), Vitamin K, alpha-lipoic acid, lipid soluble anti-oxidants, and the like.

The subject TRPA1 inhibitors can also be used with skin protectants, such allantoin and esculin.

In certain embodiments, two or more compounds of the invention are conjointly administered. When two or more compounds of the invention are conjointly administered, the two or more compounds may have a similar selectivity profile and functional activity, or the two or more compounds may have a different selectivity profile and functional activity. By way of example, the two or more compounds may both be approximately 10, 100, or 1000 fold selective for antagonizing a function of TRPA1 over TRPV1, TRPV5, and TRPV6 (e.g., the two or more compounds have a similar selectivity profile), and further may inhibit a function of TRPA1 with a similar IC50 (e.g., a similar functional activity). Alternatively, the one of the two or more compounds may selectively inhibit TRPA1 while the other of the two or more compounds inhibits both TRPA1 and TRPV1 (e.g., the two or more compounds have differing selectivity profiles). Administration of combinations of two or more compounds of the invention having similar or differing properties are contemplated.

In certain embodiments, a compound of the invention is conjointly administered with one or more additional compounds that antagonize the function of a different channel. By way of example, a compound of the invention may be conjointly administered with one or more compounds that antagonize TRPV1, TRPM8, and/or TRPV3. The compound(s) that antagonize TRPV1, TPRM8, or TRPV3 may be selective for TRPV1, TRPM8 or TRPV3 (e.g., inhibit TRPV1 or TRPV3 10, 100, or 1000 fold more strongly than TRPA1). Alternatively, the compound(s) that antagonize TRPV1 or TRPV3 may cross react with other TRP channels.

In certain other embodiments, a compound of the invention is conjointly administered with one or more additional agents or therapeutic regimens appropriate for the particular injury, disease, condition, or disorder being treated.

Pharmaceutical Compositions

While it is possible for a compound of the present invention to be administered alone, it is preferable to administer the compound as a pharmaceutical formulation (composition). The compounds according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) for inhalation. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect by inhibiting TRPA1 function in at least a sub-population of cells in an animal and thereby blocking the biological consequences of that function in the treated cells, at a reasonable benefit/risk ratio applicable to any medical treatment.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like.

Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as α-, β- and γ-cyclodextrin, dimethyl-β cyclodextrin and 2-hydroxypropyl-β-cyclodextrin.

Formulations of the pharmaceutical compositions of the invention for rectal, vaginal, or urethral administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one are still detectable when the subsequent therapy is administered.

The present invention contemplates formulation of the subject compounds in any of the aforementioned pharmaceutical compositions and preparations. Furthermore, the present invention contemplates administration via any of the foregoing routes of administration. One of skill in the art can select the appropriate formulation and route of administration based on the condition being treated and the overall health, age, and size of the patient being treated.

Nucleic Acid and Amino Acid Compositions

In another aspect, the present invention provides compositions and pharmaceutical compositions comprising, consisting of, or consisting essentially of particular TRPA1 polypeptides and nucleic acids. Such polypeptides and nucleic acids can be used, for example, in drug screening assays or to make primers or probes to study the expression or activity of TRPA1 in cells, tissues, or organisms. As used herein, the term "isolated" when used to refer to nucleic acid and polypeptide compositions refers to nucleic acids or polypeptides existing in a state other than the state in which they exist in nature. In other words, the term is used to denote some level of separation from other proteins and cellular components with which the protein is endogenously found. Isolated, when used in this context, does not necessarily mean that the protein or nucleic acid is provided in a purified form. Additionally, the term "isolated" is not intended to imply that the polypeptide or nucleic acid is isolated from an organism. Rather, the term also includes recombinantly produced nucleic acids and polypeptides.

In certain embodiments, the invention provides an isolated polypeptide comprising, consisting of, or consisting essentially of the amino acid sequence represented in SEQ ID NO: 1. Such polypeptides may include the identical sequence, or may include one, two, or three conservative substitutions, additions, or deletions. In certain other embodiments, the invention provides an isolated polypeptide encoded by a nucleic acid sequence comprising, consisting of, or consisting essentially of a nucleotide sequence represented in SEQ ID NO: 2, or by a nucleotide sequence that varies from SEQ ID NO: 2 due to the degeneracy of the genetic code.

In certain other embodiments, the invention provides an isolated nucleic acid comprising, consisting of, or consisting essentially of a nucleotide sequence represented in SEQ ID NO: 2, or by a nucleotide sequence that varies from SEQ ID NO: 2 due to the degeneracy of the genetic code. In other embodiments, the invention provides an isolated nucleic acid comprising, consisting of, or consisting essentially of a nucleotide sequence which encodes a polypeptide comprising an amino acid sequence represented in SEQ ID No. 1.

In other embodiments, the invention provides an expression vector, which replicates in at least one of a prokaryotic cell and eukaryotic cell. The expression vector comprises any of the foregoing TRPA1 nucleic acids. Similarly provided are cells comprising these expression vectors, which cells express the TRPA1 protein encoded by the expressed nucleic acid. In certain embodiments, the expressed polypeptide retain one or more functions of TRPA1. For example, the cell comprising the expression vector expresses TRPA1 and mediates current and/or ion flux (e.g., a TRPA1-mediated current). Additionally provided are methods of producing a polypeptide. The method includes culturing one of the foregoing cells (e.g., a cell expressing TRPA1 polypeptide) in a suitable cell culture medium to express said polypeptide.

In certain embodiments, the cell is transiently transfected with the expression vector and transiently expresses TRPA1 protein. In certain other embodiments, the cell is stably transfected with the expression vector and a stable cell line expressing TRPA1 is established. In certain embodiments, the cell comprising the expression vector does not endogenously express TRPA1 protein (e.g., the cell does not express appreciable levels of TRPA1 protein in the absence of the expression vector). In other embodiments, the cell comprising the expression vector endogenously expresses TRPA1 protein.

In certain embodiments, cells expressing TRPA1, for example, cells manipulated to comprise a TRPA1 expression vector, can be used in screening assays to identify compounds that modulate a TRPA1 mediated current. Suitable cells include, without limitation, prokaryotic cells and eukaryotic cells. Exemplary eukaryotes include vertebrates and invertebrates. Exemplary eukaryotes include, but are not limited to, humans, mice, rats, cats, dogs, rabbits, sheep, cows, horses, goats, non-human primates, frogs, toads, fish, chicken, flies, worms, and yeast. Exemplary prokaryotes include bacteria. When "a cell" is referred to, it is understood to refer to screening in at least one cell (e.g., a single cell or a culture of cells). Cells may be provided in suspension or grown adherently. Cells of any developmental time and tissue can be used. Exemplary cells include embryonic cells, larval cells, juvenile cells, fetal cells, and adult cells. Exemplary cells and cell line may be derived from any tissue or cell type. In certain embodiments, the cells are sensory neurons or nodose ganglia. Cells include primary cells and transformed cell lines.

In certain embodiments, as noted above, the invention contemplates an expression vector which comprises a coding sequence for a TRPA1 protein, as provided herein. A "vector" is a replicon, such as plasmid, phage or cosmid, to which another DNA segment may be attached. The term "vector" refers to a nucleic acid molecule capable of transporting another nucleic acid to which it has been linked. One type of vector is an episome which is a nucleic acid capable of extra-chromosomal replication. Vectors capable of autonomous replication and/or expression of nucleic acids to which they are linked may also be used. Vectors capable of directing the expression of genes to which they are operatively linked are referred to herein as "expression vectors." In general, expression vectors of utility in recombinant DNA techniques are often in the form of "plasmids" which refer generally to circular double stranded DNA loops which, in their vector form are not bound to the chromosome. However, the invention is intended to include such other forms of expression vectors which serve equivalent functions and which become known in the art subsequently hereto.

A DNA or nucleic acid "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence of the present invention can include, but is not limited to, cDNA from eukaryotic mRNA, genomic DNA sequences from eukaryotic (e.g., mammalian) DNA, and synthetic DNA sequences. A polyadenylation signal and transcription termination sequence may be located 3' of the coding sequence.

Nucleic acid or DNA regulatory sequences or regulatory elements are transcriptional and translational control sequences, such as promoters, enhancers, polyadenylation signals, and terminators, that provide for and/or regulate expression of a coding sequence in a host cell. Regulatory sequences for directing expression of eukaryotic ion channels and detectable markers of certain embodiments are art-recognized and may be selected by a number of well understood criteria. Examples of regulatory sequences are described in Goeddel, Gene Expression Technology: Methods in Enzymology (Academic Press, San Diego, Calif. (1990)). For instance, any of a wide variety of expression control sequences that control the expression of a DNA sequence when operatively linked to it may be used in these vectors to express DNA sequences encoding the ion channels and detectable markers. Such useful expression control sequences, include, for example, the early and late promoters of SV40, beta2 tubulin, adenovirus or cytomegalovirus immediate early promoter, the lac system, the trp system, the TAC or TRC system, T7 promoter whose expression is directed by T7 RNA polymerase, the promoter for 3-phosphoglycerate kinase or other glycolytic enzymes, the promoters of acid phosphatase, e.g., PhoS, and the promoters of the yeast α-mating factors and other sequences known to control the expression of genes of prokaryotic or eukaryotic cells or their viruses, and various combinations thereof. It should be understood that the design of the expression vector may depend on such factors as the choice of the host cell to be transformed. Moreover, the vector's copy number, the ability to control that copy number and the expression of any other protein encoded by the vector, such as antibiotic markers, should also be considered.

The invention contemplates the use of any promoter that can drive the expression of a TRPA1 protein in prokaryotic or eukaryotic cells. As used herein, the term "promoter" means a DNA sequence that regulates expression of a selected DNA sequence operably linked to the promoter, and which effects expression of the selected DNA sequence in cells. A "promoter" generally is a DNA regulatory element capable of binding RNA polymerase in a cell and initiating transcription of a coding sequence. For example, the promoter sequence may be bounded at its 3' terminus by the transcription initiation site and extend upstream (5' direction) to include the minimum number of bases or elements necessary to initiate transcription at levels detectable above background. Within the promoter sequence may be found a transcription initiation site, as well as protein binding domains responsible for the binding of RNA polymerase. Eukaryotic promoters will often, but not always, contain "TATA" boxes and "CAAT" boxes. Various promoters, including inducible promoters, may be used to drive the various vectors of the present invention.

The term "promoter" also encompasses prokaryotic and/or eukaryotic promoters and promoter elements. The term "promoter" as used herein encompasses "cell specific" promoters, i.e. promoters, which effect expression of the selected DNA sequence only in specific cells (e.g., cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e., expression levels can be controlled).

As detailed above and in certain embodiments, the invention contemplates expression vectors comprising a TRPA1 nucleic acid sequence and capable of expressing TRPA1 protein. When expressed in cells, these vectors express TRPA1 protein, preferably functional protein. A functional TRPA1 protein mediates current, and/or ion flux, and/or membrane potential.

Cells expressing a TRPA1 expression vector may be assayed to confirm expression of TRPA1 protein. For example, protein expression may be confirmed using Western blot analysis, immunocytochemistry, or immunohistochemistry. Additionally or alternatively, TRPA1 function can be assessed using, for example, calcium imaging analysis to evaluate ion flux or electrophysiological methods (e.g., patch clamp analysis) to evaluate current.

Synthetic Schemes and Identification of Active Antagonists
Combinatorial Libraries The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential TRPA1 agonist or antagonist lead compounds, as well as to refine the specificity, toxicity, and/or cytotoxic-kinetic profile of a lead compound. For instance, TRPA1 bioactivity assays, such as those disclosed herein, can be used to screen a library of compounds for those having agonist activity or antagonist activity towards TRPA1.

Simply for illustration, a combinatorial library for the purposes of the present invention is a mixture of chemically related compounds that may be screened together for a desired property. The preparation of many related compounds in a single reaction greatly reduces and simplifies the number of screening processes that need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject compounds. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject compounds can be synthesized and screened for particular activity or property.

Many variations on the above and related pathways permit the synthesis of widely diverse libraries of compounds that may be tested as inhibitors or agonists of TRPA1.

EXAMPLES

Example 1: High Thoughput Screening Assay

The assay depended on detection of the rise in intracellular $Ca^{2+}$ concentration ($[Ca^{2+}]_i$) following channel activation in cells inducibly expressing the TRPA1 channel. $Ca^{2+}$ rise was quantified with the use of fluorescent $Ca^{2+}$ indicators that were loaded into cells and thereafter indicated the $[Ca^{2+}]_i$. $Ca^{2+}$ influx followed activation of the TRPA1 channel. Compounds inhibiting the $[Ca^{2+}]_i$ rise were considered hits for further investigation.

The commercially available HEK293/TREx line (Invitrogen) was stably transfected with a TRPA1 construct (specifically a construct encoding a TRPA1 protein with an amino acid sequence depicted in SEQ ID NO: 1) and screened by conventional calcium imaging to find clones with TRPA1 expression following stimulation with 1 μg/ml tetracycline. These cells were maintained in the growth medium recommended by the manufacturer supplemented with 100 μg/ml hygromycin to promote retention of the TRPA1 construct. After growing to near confluency, cells were plated at a density of ~25,000 cells/well in 384 well CellBind plates (Corning) in the presence of 1 μg/ml tetracycline, and allowed to grow for 20-30 hrs. A nearly confluent monolayer resulted. Cells were then loaded with $Ca^{2+}$ dye: Fura-2/AM or Fluo4/AM was added to the wells to a final concentration of 2 μM or 1 μM, respectively, and incubated for 80 min or 60 min, respectively, at room temperature. Supernatant was then removed from the cells by inverting plates with a sharp flick, and 40 μl Hank's Balanced Salt Solution (HBSS; 0.185 g/l D-glucose, 0.9767 g/l $MgSO_4$ (anhydrous), 0.4 g/l KCl, 0.06 g/l $KH_2PO_4$ (anhydrous), 0.35 g/l $NaHCO_3$, 8.0 g/l NaCl, and 0.04788 g/l $Na_2HPO_4$ (anhydrous); pH 7.4) was then added to each well. Following ~1 hour for recovery from loading, cells were assayed using the Hamamatsu FDSS 6000 system, which permitted illumination alternately at 340 nM and 380 nM for Fura-2 experiments, or at 485 nM for Fluo4 experiments. Frames were acquired at a rate of 0.2 Hz. During the assay, the plates were continuously vortexed, with pipette mixing of wells following addition of each reagent. For the screening assay, 13 μl of a diluted stock (at 50 μM) was added to each well for 2 minutes following the collection of a short (4 frame) baseline. 13 μl 37.5 μM AITC (allylisothiocyanate) was then added to each well, achieving a final concentration of 10 μM each compound and 7.5 μM AITC. Data was collected for ~3 minutes following addition of AITC, where the fluorescent intensity (for Fluo4) and the F340/F380 ratio (for Fura-2) were proportional to the $[Ca^{2+}]_i$. Negative controls consisted of HEK293/TREx TRPA1 cells exposed to AITC, but no compound. Positive control cells were usually HEK293/TREx ("parental") cells exposed to AITC but no compound, but sometimes normal HEK/293 TREx TRPA1 cells were also used, but not exposed to AITC or compound. These controls defined a screening window, and "hits" were defined as those compounds inhibiting the fluorescence response by at least 40%. $IC_{50}$ values were determined for compounds defined as "hits." The Fluo4 cell-based fluorescence assay was used to determine the intracellular $Ca^{2+}$ concentration in the presence of varying drug concentration. Concentrations tested were 40 μM, 20 μM, 10 μM, 5 μM, 2.5 μM, 1.25 μM, and 0.625 μM. Compounds were tested in triplicate at all concentrations. Standard software was used to fit $IC_{50}$ curves.

Additionally or alternatively, efficacy can be represented as % inhibition in the presence (of a given concentration of compound) versus the absence of compound or in comparison to a control compound. For example, efficacy can be represented as % inhibition of ion flux in the presence versus the absence of compound.

Example 2: Patch Clamp Experiments

Patch clamp experiments permit the detection of currents through the TRPA1 channel in the cell line described above. To permit recording of current at a stable level and prevent the "rundown" observed by other labs, it is necessary to use the perforated patch technique, which prevents dialysis of the cytoplasm with the pipette solution. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution. In contrast, in the perforated patch mode, an antibiotic, amphotericin, is present in the pipette solution and diffuses into contact with the cell after the seal is achieved, over the course of several minutes. The amphotericin forms ion-permeable pores in the membrane under the pipette, permitting passage of some ions but maintaining most native cytosolic components. A perfusion system permits control of the extracellular solution, including the addition of blockers and activators of the current. The current can be activated by addition of 5 µM AITC to the solution.

TRPA1 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM EGTA, 2.2 mM $CaCl_2$, 2.08 mM $MgCl_2$, and 10 mM HEPES, pH 7.2, with 50 nM calculated free $Ca^{2+}$ and 60 mg/ml amphotericin added immediately prior to experiments. The external solution consisted of 150 mM NaCl, 4.5 mM KCl, 3 mM $MgCl_2$, 10 mM HEPES, 10 mM glutamine, 1 mM EGTA, pH 7.4. Upon addition of AITC, TRPA1 current was induced only in TRPA1-expressing cells and not in parental HEK293 TREx cells. Removal of the AITC stimulus causes most of the current to go away. Potential blockers were tested for ability to block both inward and outward currents in the continued presence of AITC.

$IC_{50}$ of compounds was estimated by testing each compound at 5 µM and 500 nM. When 5 µM compound showed no block, $IC_{50}$ was estimated as >10 µM. When 5 µM compound showed 50% or less block, a rough estimate of $IC_{50}$ in the range of 5-10 µM could be made. $IC_{50}$ for compounds between 500 nM and 5 µM was similarly estimated. Compounds blocking 50% or more at 500 nM are retested at multiple concentrations, and the % block at each is fitted by standard equations to determine $IC_{50}$ accurately using a 5-6 point concentration/response experiment. Except where indicated, the $IC_{50}$ values presented in Tables 1 and 2 were obtained from patch clamp experiments.

Example 3: Other Screening Assays

Although the exemplary TRPA1 inhibitors provided herein were identified using the assays described in Examples 1 and 2, other cell-based assays can be used to identify and/or characterize TRPA1 inhibitors. One such assay is described in U.S. application Ser. No. 11/078,188, filed Mar. 11, 2005, the contents of which are hereby incorporated by reference in their entirety. TRPA1 protein can be expressed in the prokaryotic cell system described in application Ser. No. 11/078,188, and this system can be used to screen for compounds that modulate an activity of the TRPA1 protein. Alternatively, an ion channel other than TRPA1 can be expressed in the prokaryotic cell system, and the system can be used to evaluate the activity profile of an identified TRPA1 inhibitors with respect to other ion channels.

Any assays performed to identify and/or characterize compounds that inhibit an activity of TRPA1 can be performed in a high-throughput fashion, or can be performed on a smaller scale examining individual compounds or small numbers of compounds. Additionally, any of these assays can be performed (i) as a primary assay to identify compounds that inhibit a function of TRPA1; (ii) as a secondary assay to assess the specificity of a compound with respect to its activity against other ion channels; (iii) as an assay used in a medicinal chemistry program to optimize subject compounds.

Example 4: Plasma Levels of a TRPA1 Inhibitor

Compound 200 was stable in rat plasma for >1 hour at 37° C.

Compound 200 plasma levels were determined via HPLC/MS/MS following a single intravenous bolus dose of 0.9 mg/kg, an intraperitoneal dose of 12 mg/kg (suspension), and an oral dose of 12 mg/kg (suspension) in the male Sprague-Dawley rat.

For intravenous administration, Compound 200 solution was formulated in 30% w/v CAPTISOL, at a target concentration of 0.25 mg/mL, was administered as a rapid bolus (2-3 seconds) via the tail vein of conscious rats, at a dose volume of 4 mL/kg.

For intraperitoneal administration, Compound 200 was formulated as a uniform suspension in CMC (carboxymethylcellulose) at a target concentration of 1 mg/mL and administered at a dose volume of 10 mL/kg.

For oral administration, Compound 200 was formulated as a uniform suspension in CMC (carboxymethylcellulose), at a target concentration of 1 mg/mL, administered by gavage, at a dose volume of 10 mL/kg, to the conscious, fasted, male Sprague-Dawley rat.

The estimates of half-life, plasma clearance and volume of distribution were 32 minutes, 27 mL/kg/minute, and 1276 mL/kg, respectively. The estimate of bioavailability in the fasted rat was ~8% following administration of a suspension. The profile of the plasma-concentration-time curve suggested that Compound 200 was absorbed rapidly as highlighted by the observation that Cmax occurred after 45 min.

Plasma levels similar to the $IC_{50}$ against TRPA1 (1000 nM=355 ng/mL) were observed following intraperitoneal administration at 12 mg/kg (15-60 min), and also following oral administration at 12 mg/kg (45 min).

TRPA1 inhibitor was prepared in formulations and administered via several different routes of administration. This indicated that TRPA1 inhibitors could be formulated in any of a number of ways and adapted to most effectively treat particular diseases or injuries. These properties, coupled to the minimal side-effects observed following administration of TRPA1 inhibitors to rats, indicated that TRPA1 inhibitors have characteristics of suitable drugs and drug candidates.

Example 5: Testing of TRPA1 Antagonists in a Model of Incontinence

To test the effectiveness of a TRPA1 inhibitor compound (Compound 200) in treating incontinence, varying concentrations of compound [e.g., low (2.2 micromolar), medium (6.6 micromolar), and high (20 micromolar concentration)] were administered to rats following surgical partial bladder outlet obstruction (BOO). Efficacy of the varying doses of TRPA1 inhibitory compound were compared to controls administered excipients alone (sham control). Efficacy was also compared to rats administered a positive control, such as atropine. Atropine is not a TRPA1 inhibitor but it does decrease bladder over-activity following partial bladder outlet obstruction in the BOO model.

Female Sprague Dawley rats were used in these studies. Rats underwent surgical partial bladder outlet obstruction (BOO) or sham surgery. Five weeks after BOO (or sham) surgery, an intravesical catheter was surgically implanted into the dome of the bladder for conducting urodynamic studies. One week after catheter implantation (6 weeks after BOO or sham), urodynamic studies began. The bladder catheter was connected to one port of a pressure transducer and the other port of the pressure transducer was connected to a syringe pump. An analytic balance beneath the wire-bottom animal cage measured the amount of urine voided during continuous cystometry. A single cystometrogram (CMG) was defined as the simultaneous recording of bladder pressure, infused volume, and void volume during a single filling-voiding cycle.

A TRPA1 inhibitor (Compound 200) was tested in sham obstructed and BOO animals at each concentration. Vehicle administered animals were also tested. An experiment consisted of at least 20 CMG cycles. Briefly, isotonic saline (0.9%) was infused into the bladder at a rate of 175 ul/min (10.5 ml/hr). Following saline infusion, the antagonist compound was infused at 175 ul/min.

For each CMG cycle, the following parameters were assessed: infused volume (the amount of saline or drug infused for each CMG cycle); void volume (the amount of urine voided by the animal for each CMG cycle); minimum pressure (minimum pressure during filling); threshold pressure (pressure prior to micturition when bladder pressure begins to rise steeply); average pressure (average pressure during filling and before threshold); maximum pressure; intermicturition interval (time between two subsequent voiding events); urine flow rate index.

These experiments demonstrated that a TRPA1 inhibitor was well tolerated by bladder obstructed animals. Additionally, these experiments demonstrated that a TRPA1 inhibitor decreased both threshold bladder pressure and maximum bladder pressure in the BOO model of incontinence. These effects were specific and were not observed following administration of vehicle alone.

Example 6: Testing of TRPA1 Antagonists in a Model of Bradykinin Induced Pain

As outlined above, the bradykinin model involves an intraplantar injection of a 5 ng/uL solution of bradykinin. Injection of the bradykinin solution typically causes a rapid sensitization. Sensitization is measured by assessing the thermal escape latency of the injected paw in response to a mild thermal stimulus delivered by a modified Hargreaves apparatus.

FIGS. 1a and 1b summarize data obtained following testing of Compound 200 in the bradykinin model. This study examined the antinociceptive effects of 200 mg/kg, 50 mg/kg, and 12.5 mg/kg intraperitoneal Compound 200 on bradykinin induced tactile allodynia.

Male Holtzmann rats received were administered TRPA1 inhibitor or vehicle (0.5% methycellulose) 30 minutes prior to injection of bradykinin. Inhibitor or vehicle were injected intraperitoneally (IP). Animals receiving TRPA1 inhibitor were administered a dose of at 12.5 mg/kg, 50 mg/kg, or 200 mg/kg. 8 animals were assessed at each concentration of TRPA1 inhibitor delivered, as well as for vehicle. 30 minutes after drug or vehicle administration, bradykinin was delivered at a dose of 30 µg/1000 in the right hind paw.

Throughout the study, general behavioral assessments were made during each period of observation. Observations included tactile allodynia (vocalization/agitation induced by light touch applied to the body surface), spontaneous vocalization, biting and chewing of body surface, loss of hind limb placing and stepping reflex, loss of hind limb weight bearing, and loss of righting reflex. Additionally, mechanical allodynia was assessed and measured. The results provided in FIGS. 1a and 1b are based on assessment of mechanical allodynia.

Bradykinin produced a significant reduction in tactile thresholds required to evoke withdrawal behavior. This allodynia persisted for up to 240 minutes. Pretreatment with a TRPA1 inhibitor delivered IP at doses up to 200 mg/kg showed a dose dependent effect on the mechanical threshold after Bradykinin injection, which lasted for approximately 60 minutes. At the same time, however, no changes in behavioral parameters were noted and only mild sedation was observed in 3 of 8 rats administered the highest dose.

Intraplantar bradykinin in the rat produces a prominent long lasting tactile allodynia. These studies demonstrated that a TRPA1 inhibitor produced a dose dependent decrease of allodynia. Furthermore, the drug decreased this symptom of pain for approximately 60 minutes. These experiments show that a TRPA1 inhibitor is efficacious in decreasing a symptom of pain (e.g., mechanical allodynia) in the bradykinin model of pain.

Example 7: Testing of TRPA1 Antagonists in a Formalin Model of Pain

As outlined above, the formalin model involves injection of a formalin solution intradermally or intraperitoneally. Injection of formalin solution invokes a biphasic response, and thus provides a model for both nociceptive and inflammatory pain. The formalin model can be used to evaluate the effectiveness of an exemplary TRPA1 inhibitor in the treatment of pain.

FIG. 2 summarizes data obtained following testing of Compound 200 in the formalin model. Briefly, the following protocol was followed. Male Holtzmann rats received intraplantar injections of 50 µL of 2% formalin. Paw flinching was detected by an automated sensor detecting movement of a small metal band placed on the injected hind paw. Drug or vehicle was administered approximately 15 minutes prior to the injection of formalin. The animal's response to injection of the irritant was measured by counting flinches per minutes during the Early Phase (the first 5 minutes following injection of formalin), during the Late Phase (approximately 30 minutes after injection of formalin), and during the intervening pain free phase. In FIG. 2, the right most bar for each data set (Early Phase and Late Phase) represents administration of vehicle alone and the left most bar represents administration of gabapentin. The highest concentration of TRPA1 inhibitory compound administered is the bar adjacent to that depicting administration of gabapentin and the lowest concentration of TRPA1 inhibitory compound administered is the bar adjacent to that depicting administration of vehicle.

The results of exemplary experiments are summarized in FIG. 2. Flinches per minute, a measure of the pain and discomfort experienced by the animal, was measured following formalin injection in animals receiving various doses of TRPA1 inhibitor (Compound 200), gabapentin, or a vehicle control. Administration of a TRPA1 inhibitor substantially reduced the flinches per minute during both Early Phase and Late Phase. These results indicated that a TRPA1 inhibitor diminished both phases of pain in the formalin model. The efficacy of the TRPA1 inhibitor in both phases of this model of nociceptive pain and inflammatory pain supports the use of TRPA1 inhibitors in the treatment of severe pain, including chronic and acute pain.

Example 8: Testing of TRPA1 Antagonists in a Carrageenan Model of Acute Inflammatory Pain As outlined above, the carrageenan model is a model of acute inflammatory pain. As such, it may be used to evaluate effectiveness in relieving pain caused by inflammation, for example, pain due to arthritis.

Figure 3:
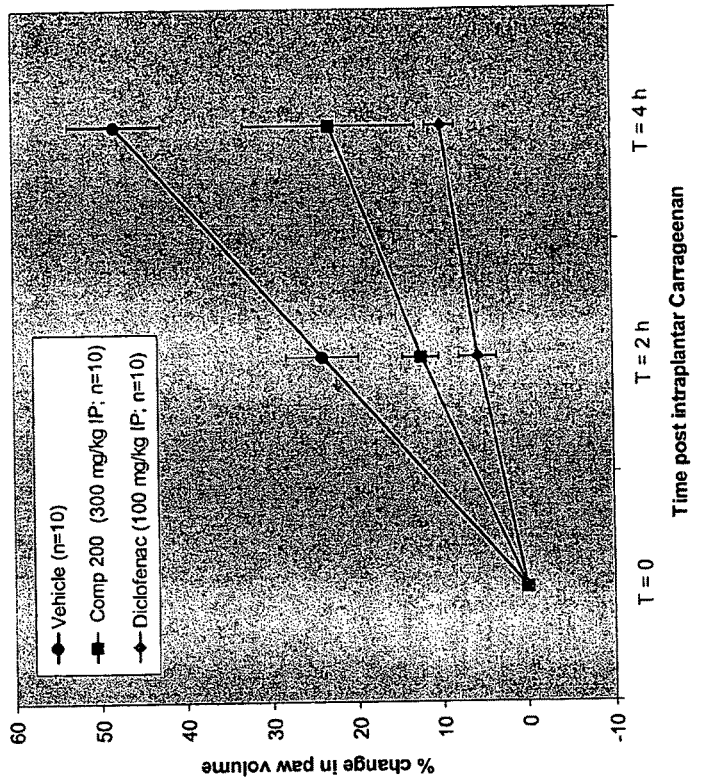

FIG. 3 summarizes data obtained following testing of Compound 200 in the carrageenan model. Briefly, naive rats were pretested for sensitivity to a heat stimulus using the Hargreaves apparatus. The next day, 100 µL of k-carrageenan was injected into the plantar surface of the right hindpaw approximately 4.5 hours before testing. 30-60 minutes before testing the rats were injected intraperitoneally with vehicle or drug (compound 200 or diclofenac to evaluate the efficacy of a TRPA1 inhibitor administered IP).

In this study, the drug administered was either a TRPA1 inhibitor or the non-steroidal anti-inflammatory diclofenac. Following administration of both carrageenan and drug or vehicle control, paw volume was measured and used to assess decreased inflammation.

FIG. 3 summarizes the results of these experiments. For each "drug" (TRPA1 or diclofenac) or vehicle, the dose administered (in mg/kg) and the route of administration (IP) are indicated. The results summarized in FIGS. 3a and 3b show that a TRPA1 inhibitor decreased paw volume (e.g., decreased inflammation). The decrease in inflammation was similar to that observed following administration of diclofenac.

The results summarized in FIG. 3 show that the TRPA1 inhibitor diminished inflammation in the carrageenan model. This decrease in inflammation would be likely be accompanied by a concomitant decrease in pain caused by the inflammation. The efficacy of the TRPA1 inhibitor in this model of inflammatory pain supports the use of TRPA1 inhibitors in the treatment of inflammation and inflammatory pain, for example, due to arthritis.

Note that in this study, change in paw volume was measured. The reduction in volume (e.g., decrease in inflammation) observed following administration of a TRPA1 inhibitor would presumably be accompanied by a corresponding decrease in pain or discomfort associated with the inflammation. Alternatively or additionally, indicia of pain can be directly evaluated. Briefly, the protocol outlined above can be followed and after injection of both carrageenan and drug or vehicle control, the thermal escape latency can be measured. Data is expressed as the recorded Paw Withdrawal Latencies (PWLs) in seconds.

Example 9: Testing of TRPA1 Antagonists in the CFA Model of Inflammatory Pain

As outlined above, the Complete Freund's Adjuvant (CFA) model is a model of inflammatory pain. As such, it may be used to evaluate effectiveness in relieving pain caused by inflammation, for example, pain due to arthritis and other inflammatory conditions.

FIG. 4 summarizes data obtained following testing of Compound 200 in the CFA model. Naive rats were pretested for sensitivity to a heat stimulus in the Hargreaves apparatus. The next day, 100 µL of complete Freund's adjuvant (CFA) was injected into the plantar surface of the right hindpaw. Two days later, in the morning, the rats were again pretested. In the afternoon, rats were injected with either vehicle control or with drug (TRPA1 inhibitor 200 or the non-steroidal anti-inflammatory diclofenac). Drugs or vehicle were injected intraperitoneally, and 45 minutes later rats were tested for hyperalgesia by applying the heat source to the CFA injected and uninjected hindpaw and measuring latency to withdrawal.

FIG. 4 summarizes the results of experiments showing that this TRPA1 inhibitor reduced pain in the CFA model of inflammatory pain. Specifically, the TRPA1 inhibitor reduced thermal hyperalgesia in this model of inflammatory pain. The efficacy of this TRPA1 inhibitor was superior to diclofenac (a non-steroidal anti-inflammatory). Additionally, these experiments indicated that the TRPA1 inhibitor decreased pain in the injured paw without interfering with normal sensation. This is shown by analysis of the control paw (uninflamed) which was not affected.

The efficacy of a TRPA1 inhibitor in this model of inflammatory pain supports the use of TRPA1 inhibitors in the treatment of inflammatory pain, for example, pain due to arthritis. The tested TRPA1 inhibitor appeared to reduce pain without toxicity and without dulling normal sensation. Additionally, the tested TRPA1 inhibitor reduced pain with similar or greater efficacy than a non-steroidal anti-inflammatory. Given the observed side-effects of non-steroidal anti-inflammatory compounds, TRPA1 inhibitors may reduce pain without the side-effects experienced with available analgesics.

Example 10: Testing of TRPA1 Antagonists in a Thermal Injury Model of Pain

The thermal injury model can be used to evaluate the effectiveness of an exemplary TRPA1 inhibitor in the treatment of nociceptive pain.

Briefly, the following protocol may be used. Male Holtzman rats (approximately 300 grams) are tested on thermal escape using a Hargreaves type apparatus. Under light anesthesia, a thermal injury (52° C. for 45 seconds) is applied to one heel. The animals are tested for thermal escape latency of the injured and uninjured paw before and at 30, 60, 80, and 120 minutes after injury. Drug (a TRPA1 inhibitor) or vehicle (0.5% methylcellulose) is administered after the baseline measurement and approximately 15-20 minutes prior to the thermal injury. In addition to the escape latency measurement, behavioral observations are made throughout the experiment.

Example 11: Testing of TRPA1 Antagonists in the Chung Model of Neuropathic Pain

Briefly, male Sprague Dawley rats (approximately 175 grams) are prepared with ligation of the L4/5 nerve roots. After 5-8 days, the animals are tested for tactile allodynia using Von Frey hairs. Thresholds are assessed with the "up-down" method. Drug or vehicle is administered and the animals tested periodically over the next four hours.

Example 12: Synthesis of Compounds of the Invention

2-(1,3-dimethyl-2,6-dioxo-1,2,3,6-tetrahydropurin-7-yl)-N-(4-isopropylphenyl)acetamide (200)

N-[2-(4-Chlorophenyl)-ethyl]-2-(1,3-dimethyl-2,6-dioxo-1,2,3,6-tetrahydro-purin-7-yl)-acetamide (268)

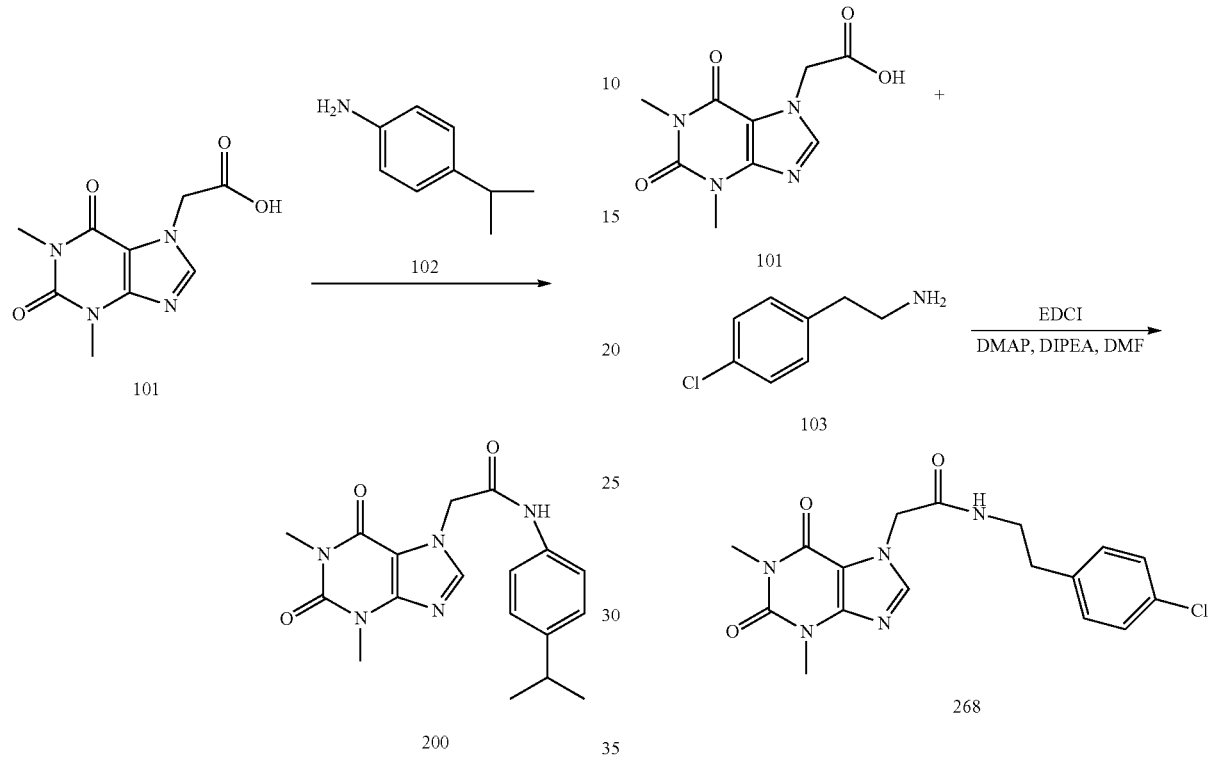

To the suspension of theophylline-7-acetic acid (101, 32.5 g, 0.136 mol) in anhydrous DMF (400 mL), was added DIPEA (54 mL, 0.31 mol) at 0° C. The neat aniline (102, 20.4 mL, 0.143 mol) was added followed by addition of DMAP (19.2 g, 0.16 mol) and EDCI (30.1 g, 0.16 mol). The reaction mixture was warmed to room temperature over 18 h, then stirred at 40-43° C. for 1.5 days. The reaction mixture was diluted with $CH_2Cl_2$ (1.8 L), washed with $H_2O$ (0.7 L), 10% citric acid (0.5 L), $NaHCO_3$ (saturated, 0.6 L), brine, dried over $Na_2SO_4$ and concentrated in vacuo and crystallized from ethyl acetate/hexanes to yield compound 200 (41%, 19.8 g): MS (APCI) m/z: 356.2 $[M+H]^+$. Anal. Calcd. for $C_{18}H_{21}N_5O_3$: C, 60.83; H, 5.96; N, 19.71. Found: C, 60.53; H, 5.97; N, 19.76.

General Procedure A for the Preparation of Amides by Coupling Using EDCI

To a mixture of theophylline-7-acetic acid (2 mmol), DMAP (2 mmol), substituted phenethylamine (2 mmol) and DIPEA (4 mmol) in DMF (20 mL) was added EDCI (2 mmol). The reaction mixture was heated to 40° C. and stirred over night. The solution was concentrated in vacuo and the residue was dissolved in EtOAc (100 mL), washed with $H_2O$, citric acid (10%), $NaHCO_3$ (sat.) and brine, dried over $Na_2SO_4$ and concentrated in vacuo. The crude product was purified by flash chromatography on silica gel eluting with MeOH/EtOAc (1-8%).

Compound 268 (107 mg, 14%) was prepared from 101 (500 mg, 2.1 mmol) and 103 (292 μL, 2.1 mmol) by General Procedure A. MS (APCI): m/z 376 $[M+H]^+$.

2-(1,3-Dimethyl-2,6-dioxo-1,2,3,6-tetrahydro-purin-7-yl)-N-(2-p-tolyl-ethyl)-acetamide (400)

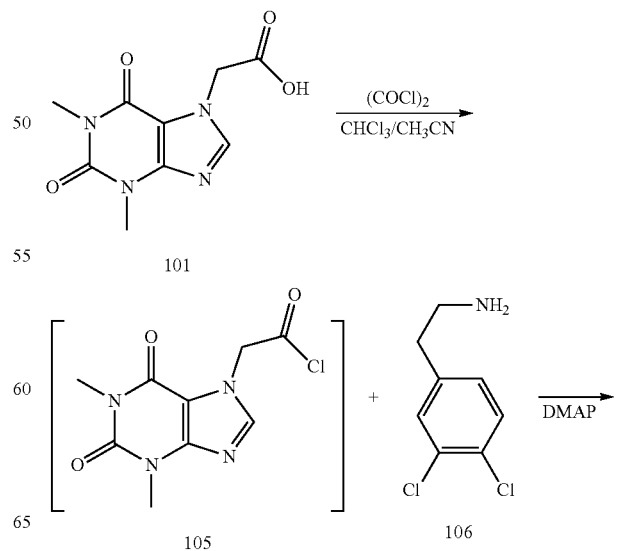

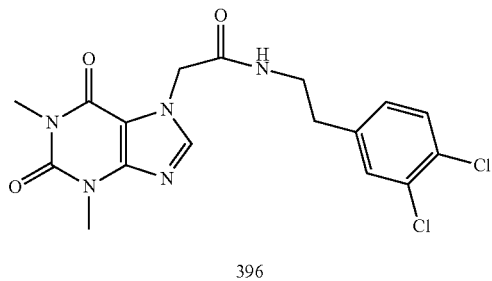

Compound 400 (99 mg, 13%) was prepared from 101 (503 mg, 2.1 mmol) and 104 (308 µL, 2.1 mmol) by General Procedure A. MS (APCI): m/z 356 [M+H]⁺.

General Procedure B for the Preparation of Amides Via Acid Chloride

A suspension of theophylline-7-acetic acid (2 mmol) in CHCl₃ (15 mL) and MeCN (15 mL) was cooled in an ice-water bath. Oxalyl chloride (2.2 mmol) was then added dropwise. Catalytic DMF (~25 µL) was then added. The mixture was stirred at room temperature over night. The solution was then cooled in an ice-water bath, and DMAP (2.5 mmol) was added in one portion. The substituted phenethylamine was added dropwise and the reaction mixture was stirred at room temperature over night. After diluting with CHCl₃ (50 mL), the mixture was washed with H₂O, citric acid (10% in H₂O), NaHCO₃ (sat.), dried over Na₂SO₄ and concentrated in vacuo. The crude product was purified by flash chromatography on silica gel eluting with MeOH/EtOAc (1-8%).

N-[2-(3,4-Dichlorophenyl)-ethyl]-2-(1,3-dimethyl-2,6-dioxo-1,2,3,6-tetrahydro-purin-7-yl)-acetamide (396)

Compound 396 (490 mg, 56%) was prepared from 101 (506 mg, 2.1 mmol) and 106 (320 µL, 2.1 mmol) by General Procedure B. MS (APCI): m/z 410 [M+H]⁺.

N-[2-(4-Dimethylaminophenyl)-ethyl]-2-(1,3-dimethyl-2,6-dioxo-1,2,3,6-tetrahydropurin-7-yl)-acetamide (397)

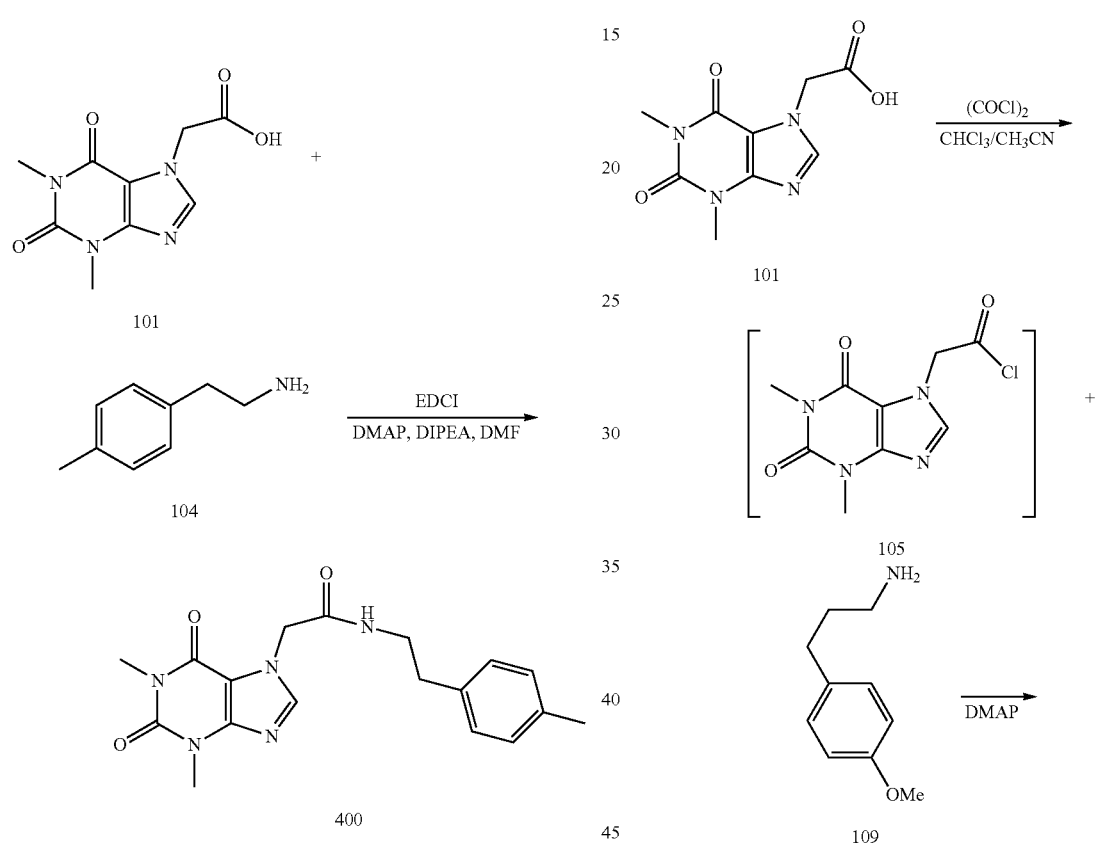

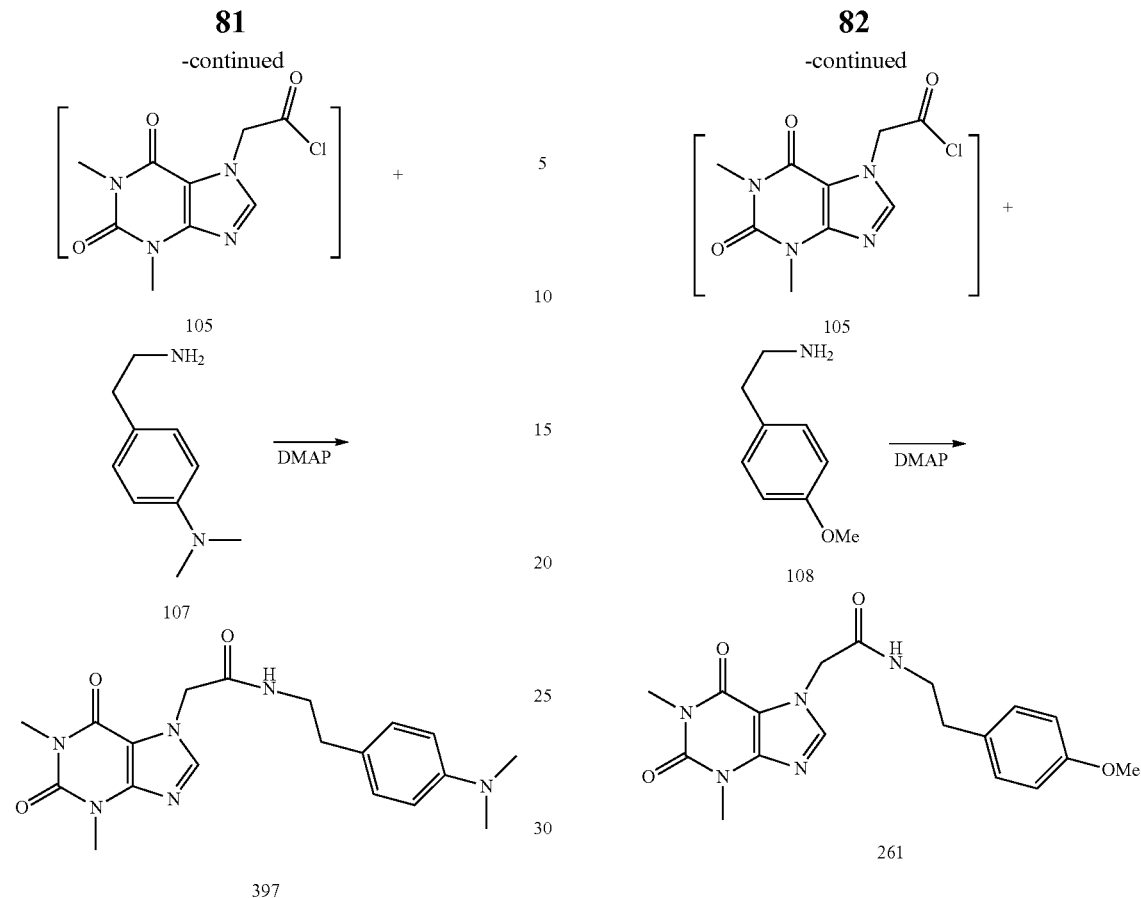

Compound 397 (610 mg, 75%) was prepared from 101 (507 mg, 2.1 mmol) and 107 (350 µL, ~2.2 mmol) by General Procedure B. MS (APCI): m/z 385 [M+H]⁺.

2-(1,3-Dimethyl-2,6-dioxo-1,2,3,6-tetrahydropurin-7-yl)-N-[2-(4-methoxy-phenyl)-ethyl]-acetamide (261)

Compound 261 (820 mg, 52%) was prepared from 101 (1.01 g, 4.2 mmol) and 108 (630 µL, 4.3 mmol) by General Procedure B. MS (APCI): m/z 372 [M+H]⁺.

2-(1,3-Dimethyl-2,6-dioxo-1,2,3,6-tetrahydropurin-7-yl)-N-[3-(4-methoxy-phenyl)-propyl]-acetamide (401)

Compound 401 (495 mg, 60%) was prepared from 101 (506 mg, 2.1 mmol) and 109 (360 µL, ~2.1 mmol) by General Procedure B. MS (APCI): m/z 386 [M+H]⁺. Anal. Calcd. for $C_{19}H_{23}N_5O_4$: C, 59.21; H, 6.01; N, 18.17. Found: C, 59.37; H, 6.06; N, 18.18.

2-(1,3-Dimethyl-2,6-dioxo-1,2,3,6-tetrahydropurin-7-yl)-N-[2-(3-methyl-phenyl)-ethyl]-acetamide (407)

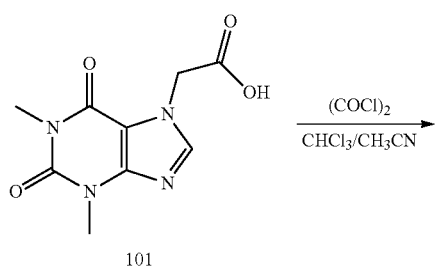

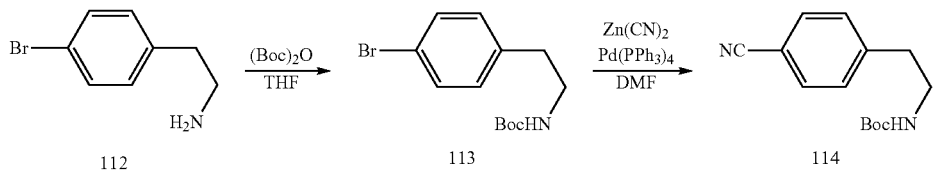

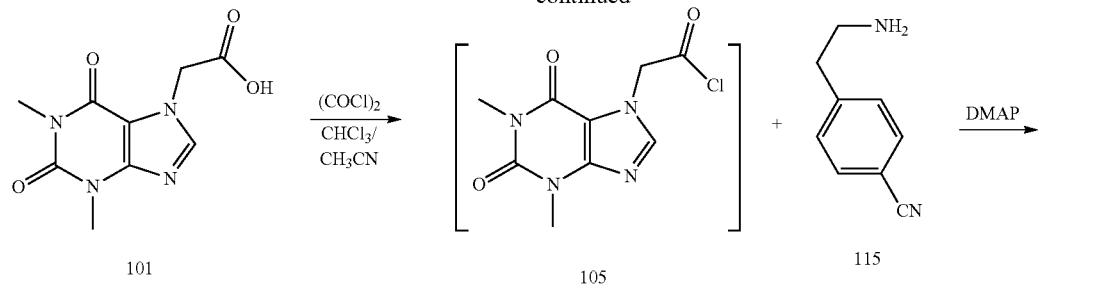
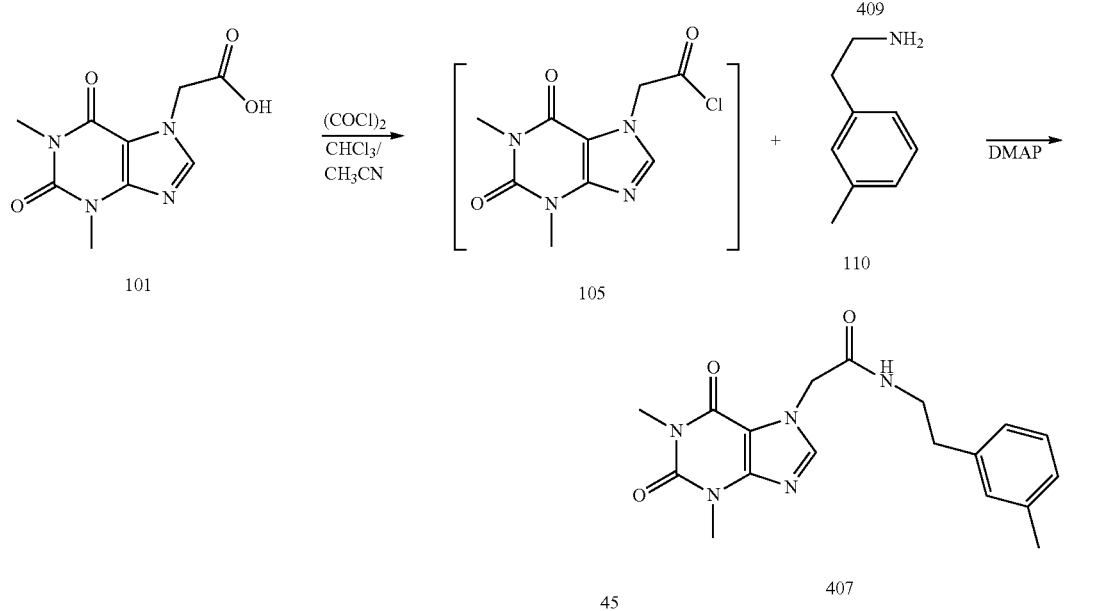
Compound 407 (494 mg, 65%) was prepared from 101 (508 mg, 2.1 mmol) and 110 (290 μL, ~2.1. mmol). MS (APCI): m/z 356 [M+H]$^+$. Anal. Calcd. for $C_{18}H_{21}N_5O_3$: C, 60.83; H, 5.96; N, 19.71. Found: C, 61.09; H, 6.03; N, 19.76.
2-(1,3-Dimethyl-2,6-dioxo-1,2,3,6-tetrahydropurin-7-yl)-N-[2-(3-methoxy-phenyl)-ethyl]acetamide (408)
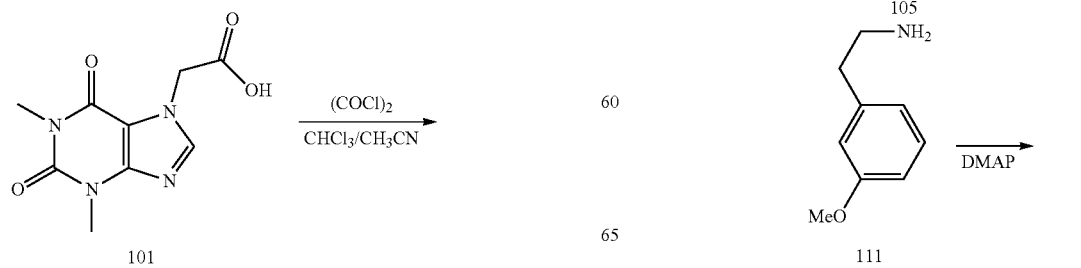

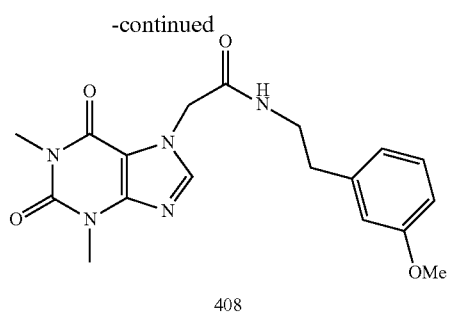

408

Compound 408 (462 mg, 59%) was prepared from 101 (502 g, 2.1 mmol) and 111 (310 μL, 2.1 mmol) via General Procedure B. MS (APCI): m/z 372 [M+H]⁺. Anal. Calcd. for $C_{18}H_{21}N_5O_4$: C, 58.21; H, 5.70; N, 18.86. Found: C, 57.95; H, 5.78; N, 18.61.

N-[2-(4-Cyanophenyl)-ethyl]-2-(1,3-dimethyl-2,6-dioxo-1,2,3,6-tetrahydro-purin-7-yl)-acetamide (409)

t-Butyl 2-(4-bromophenyl)ethylcarbamate (113)

To a pre-cooled 0° C. solution of 112 (2.0 g, 10 mmol) in THF (10 mL) was added (Boc)₂O (2.2 g, 10 mmol) portionwise. The reaction mixture was stirred at room temperature over night. It was concentrated in vacuo to yield 113 (3 g, 100%) as a white solid which was used in the next step without further purification.

t-Butyl 2-(4-cyanophenyl)ethylcarbamate (114)

Compound 113 (530 mg, 1.8 mmol) was dissolved in dry DMF (17 mL) under N₂. Zn(CN)₂ (416 mg, 3.6 mmol) and Pd(PPh₃)₄ (200 mg, 0.18 mmol) was added. The reaction mixture was stirred and heated at 150° C. in a microwave instrument (CEM Discover®) for 20 min and the reaction mixture was then concentrated in vacuo. The residue was purified by flash chromatography on silica gel eluting with EtOAc/hexanes (20-80%) to yield 114 (540 mg, 31%) as a white solid. MS (APCI, negative): m/z 245 [M−H]⁺.

4-Cyanophenethylamine (115)

Compound 114 (308 mg, 1.25 mmol) was dissolved in DCM (4 mL) and the solution was cooled in an ice-water bath. TFA (3.5 mL) was then added and the mixture was stirred at room temperature for 15 min. The reaction mixture was concentrated in vacuo and the residue was dissolved in EtOAc (50 mL). The solution was washed with K₂CO₃ (sat., 3×), brine, dried and concentrated to yield 115 (175 mg, 95%) as a pale yellow oil. MS (APCI): m/z 147 [M+H]⁺.

N-[2-(4-Cyanophenyl)-ethyl]-2-(1,3-dimethyl-2,6-dioxo-1,2,3,6-tetrahydro-purin-7-yl)acetamide (409)

Compound 409 (93 mg, 21%) was prepared from 101 (300 mg, 1.3 mmol) and 115 (175 mg, 1.2 mmol) according to General Procedure B. MS (APCI): m/z 367 [M+H]⁺. Anal. Calcd. for $C_{18}H_{18}N_6O_3 \cdot 0.04$ EtOAc $\cdot 0.1H_2O$: C, 58.68; H, 5.02; N, 22.61. Found: C, 58.75; H, 5.01; N, 22.46.

N-(2-methoxyphenethyl)-2-(1,3-dimethyl-2,6-dioxo-1,2,3,6-tetrahydropurin-7-yl)acetamide (403)

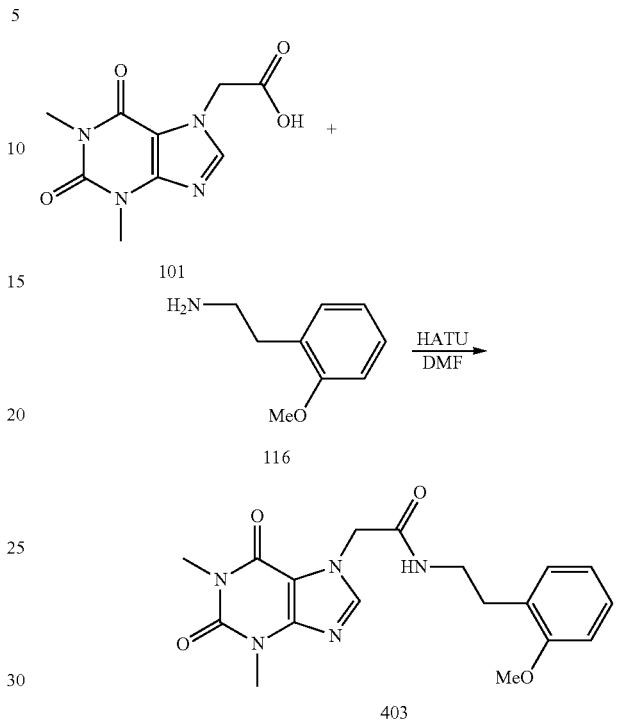

Compound 101 (600 mg, 2.5 mmol) was mixed with HATU (1.14 g, 3.0 mmol) in 20 mL of DMF under N₂ and stirred at room temperature for 20 min. Compound 116 (0.36 mL, 2.5 mmol) was then added. The resulting mixture was stirred overnight and then ethyl acetate (100 mL) was added. The resulting solution was washed with water (3×80 mL) and brine (80 mL) and dried over Na₂SO₄. During drying some solid precipitates appeared, methanol (10 mL) was added to dissolve the precipitates and then the solution was filtered. The filtrate was concentrated in vacuo and the solid residue was purified by flash column chromatography on 40 g of silica gel with EtOAc/hexanes as eluent. The purified product was triturated with ether (25 mL) and filtered to yield 403 as a white solid (224 mg, 24%). MS (APCI): m/z 372 [M+H]⁺. Anal. Calcd for $C_{18}H_{21}N_5O_4$: C, 58.21; H, 5.70; N, 18.86. Found: C, 58.26; H, 5.73; N, 18.74.

N-(2-fluorophenethyl)-2-(1,3-dimethyl-2,6-dioxo-1,2,3,6-tetrahydropurin-7-yl)acetamide (404)

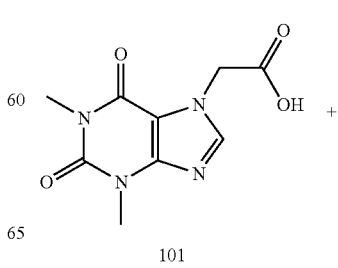

101

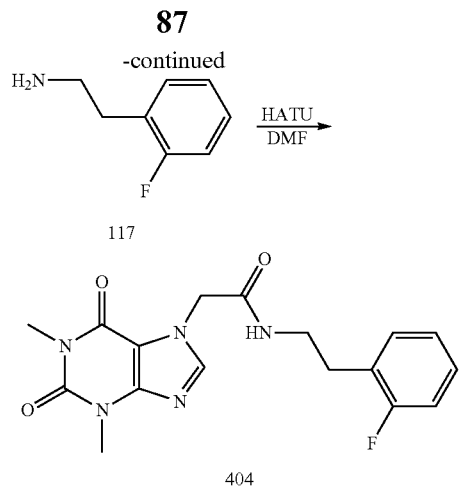

117

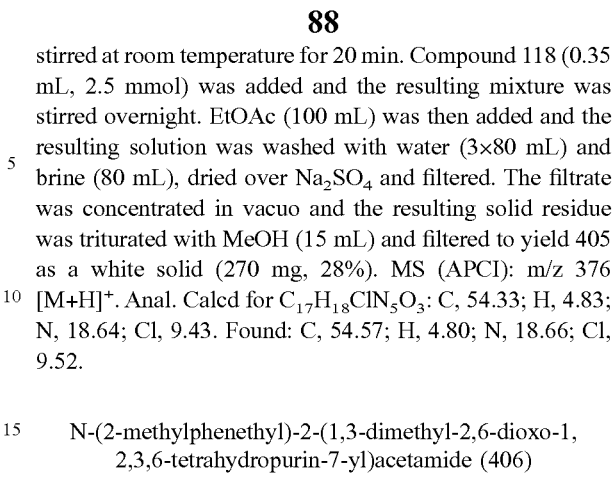

404

Compound 101 (600 mg, 2.5 mmol) was mixed with HATU (1.14 g, 3.0 mmol) in 20 mL of DMF under $N_2$ and stirred at room temperature for 20 min. Compound 117 (0.33 mL, 2.5 mmol) was added. The resulting mixture was stirred overnight. EtOAc (100 mL) was added and the resulting solution was washed with water (3×80 mL) and brine (80 mL), dried over $Na_2SO_4$ and filtered. The filtrate was concentrated in vacuo and the resulting solid residue was purified by flash column chromatography on 40 g of silica gel eluting with EtOAc/hexanes. The purified product was triturated with ether (30 mL) and filtered to yield 404 as a white solid (281 mg, 31%). MS (APCI): m/z 360 [M+H]$^+$. Anal. Calcd for $C_{17}H_{18}FN_5O_3 \cdot 0.3H_2O$: C, 55.98; H, 5.14; N, 19.20. Found: C, 55.87; H, 5.07; N, 19.13.

N-(2-chlorophenethyl)-2-(1,3-dimethyl-2,6-dioxo-1,2,3,6-tetrahydropurin-7-yl)acetamide (405)

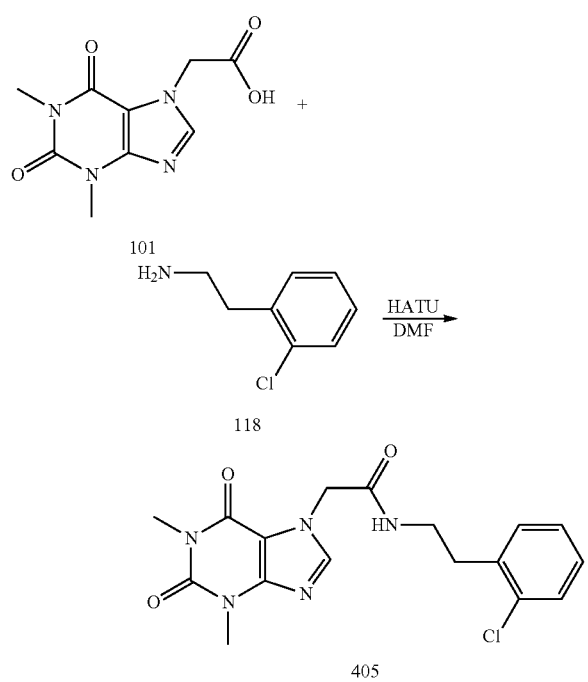

Compound 101 (600 mg, 2.5 mmol) was mixed with HATU (1.14 g, 3.0 mmol) in 20 mL of DMF under $N_2$ and stirred at room temperature for 20 min. Compound 118 (0.35 mL, 2.5 mmol) was added and the resulting mixture was stirred overnight. EtOAc (100 mL) was then added and the resulting solution was washed with water (3×80 mL) and brine (80 mL), dried over $Na_2SO_4$ and filtered. The filtrate was concentrated in vacuo and the resulting solid residue was triturated with MeOH (15 mL) and filtered to yield 405 as a white solid (270 mg, 28%). MS (APCI): m/z 376 [M+H]$^+$. Anal. Calcd for $C_{17}H_{18}ClN_5O_3$: C, 54.33; H, 4.83; N, 18.64; Cl, 9.43. Found: C, 54.57; H, 4.80; N, 18.66; Cl, 9.52.

N-(2-methylphenethyl)-2-(1,3-dimethyl-2,6-dioxo-1,2,3,6-tetrahydropurin-7-yl)acetamide (406)

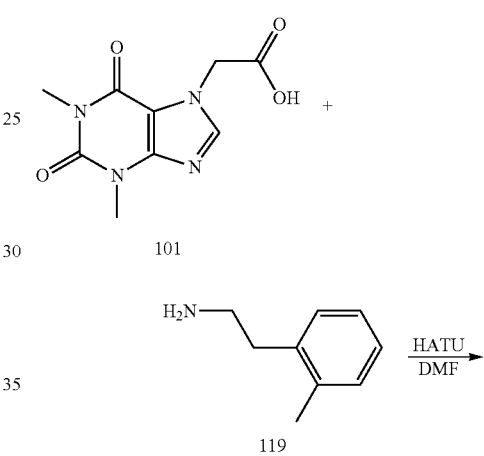

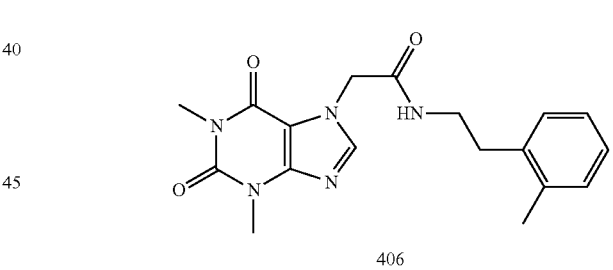

406

Compound 101 (600 mg, 2.5 mmol) was mixed with HATU (1.14 g, 3.0 mmol) in 20 mL of DMF under $N_2$ and stirred at room temperature for 20 min and then compound 119 (338 mg, 2.5 mmol) was added. The resulting mixture was stirred overnight and then ethyl acetate (100 mL) was added. The resulting solution was washed with water (3×80 mL) and brine (80 mL), dried over $Na_2SO_4$ and filtered. The filtrate was concentrated in vacuo and the resulting solid residue was purified by flash column chromatography on 40 g of silica gel eluting with EtOAc/hexanes. The purified product was triturated with ether (30 mL) and filtered to yield 406 as a white solid (290 mg, 32%). MS (APCI): m/z 356 [M+H]$^+$. Anal. Calcd for $C_{18}H_{21}N_5O_3$: C, 60.83; H, 5.96; N, 19.71. Found: C, 60.85; H, 6.01; N, 19.74.

N-(4-isopropylphenyl)-2-(1-methyl-2,6-dioxo-1,2,3,6-tetrahydropurin-7-yl)acetamide (391)

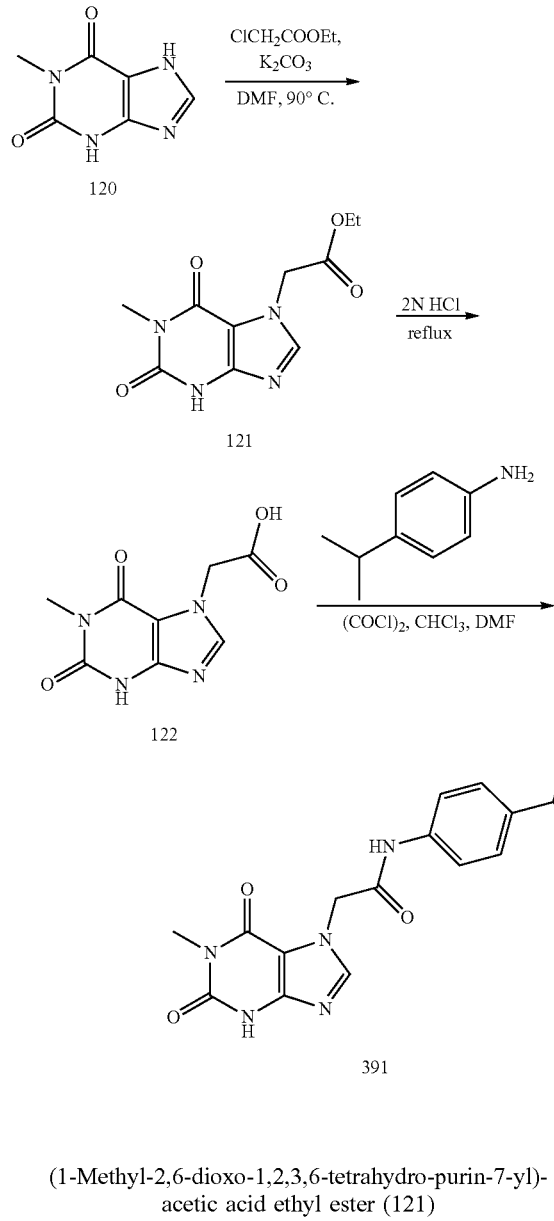

(1-Methyl-2,6-dioxo-1,2,3,6-tetrahydro-purin-7-yl)-acetic acid (122)

Ester 121 (0.6 g, 2.4 mmol) dissolved in 2N HCl (25 mL) and refluxed for 2 h. The reaction mixture was cooled to 0° C. and then warmed to rt. The precipitate was filtered, washed with ether and dried to yield white solid 122 (0.23, 45%). MS (APCI): m/z 224.2 [M+H]$^+$.

N-(4-Isopropyl phenyl)-2-(1-methyl-2,6-dioxo-1,2,3,6-tetrahydro purin-7-yl)acetamide (391)

To a 0° C. solution of acid 122 (0.2 g, 0.89 mmol) in chloroform (35 mL) was added oxalyl chloride (0.67 g, 5.3 mmol) and a catalytic amount of DMF. The reaction was stirred for 2 h at room temperature and then concentrated in vacuo. The resulting material was dissolved in CHCl$_3$ (30 mL), cooled to 0° C., and 4-isopropyl aniline was added and the reaction was stirred overnight warming to rt. The reaction mixture was diluted with CHCl$_3$ (50 mL) and washed with 1 N HCl (50 mL). Combined organic layers were washed with water (75 mL), dried over Na$_2$SO$_4$, concentrated in vacuo and the crude product was purified by flash chromatography on silica gel eluting with EtOAc/hexane and EtOAc/MeOH to yield 391 (0.089 g, 33%) as a white solid. MS (APCI): m/z 342.3 [M+H]$^+$. Anal. Calcd. For C$_{17}$H$_{19}$N$_5$O$_3$ 0.28H$_2$O: C, 58.94; H, 5.69; N, 20.22. Found C, 58.94; H, 5.67; N, 19.78.

2-(1,3-dimethyl-2,6-dioxo-1,2,3,6-tetrahydropurin-7-yl)-N-(4-isopropylphenyl)-2-methylpropanamide (387)

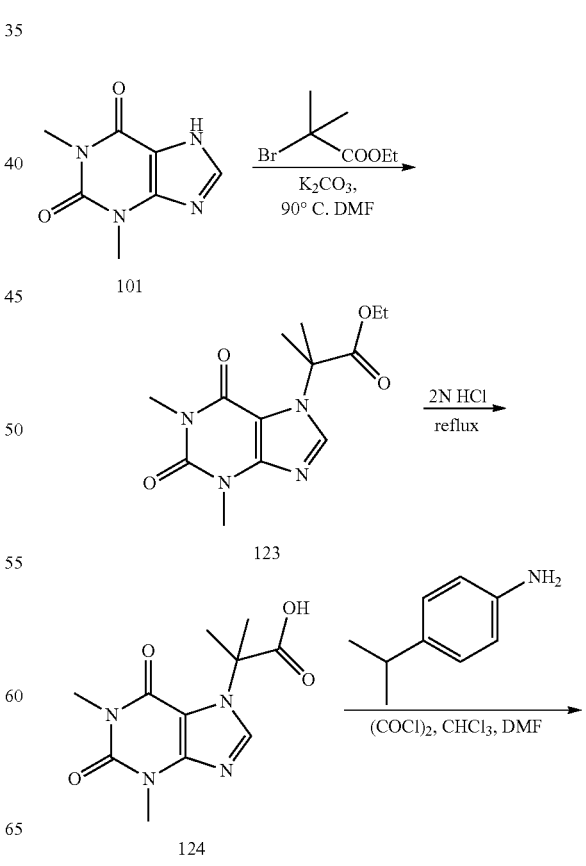

(1-Methyl-2,6-dioxo-1,2,3,6-tetrahydro-purin-7-yl)-acetic acid ethyl ester (121)

To a solution of 1-methyl xanthine (120, 1 g, 6.01 mmol) in DMF, potassium carbonate (0.91 g, 6.6 mmol) was added and the reaction mixture was heated to 90° C. and stirred for 1 h. A solution of ClCH$_2$COOEt (0.36 g, 3.0 mmol) in DMF was then added dropwise to the reaction over 45 min. After stirring an additional 15 min, the reaction was cooled to room temperature and poured into ice cold 1N HCl (50 ml). The reaction was then extracted with chloroform (50×2 ml). The combined organic layers were washed with water (100 mL), dried over Na$_2$SO$_4$ and concentrated in vacuo. To the resulting solid was added 30% dichloromethane in hexanes (400 mL) and the resulting mixture was stirred for 15 min and filtered to yield compound 121 as a yellow solid (0.6 g, 40%). MS (APCI): m/z 253.32 [M+H]$^+$.

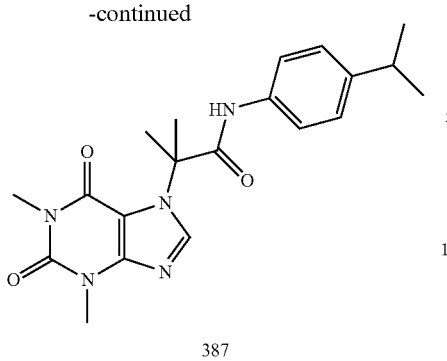

387

2-(1,3-Dimethyl-2,6-dioxo-1,2,36-tetrahydro purin-7-yl)-2-methyl propionic acid ethyl ester (123)

To a solution of theophylline (101, 2 g, 11.10 mmol) in DMF was added potassium carbonate (1.84 g, 13.32 mmol) and the reaction was heated to 90° C. and stirred for 1 h. Then ethyl 2-bromo isobutyrate (2.59 g, 13.32 mmol) in DMF was added dropwise over 10 min. The resulting reaction mixture was stirred for 16 h at 90° C. The reaction was cooled to rt, poured into ice cold 1N HCl (50 ml) and extracted with chloroform (100×2 ml). The combined organic layers were washed with water (100 mL), dried over $Na_2SO_4$ and concentrated in vacuo. Crude 123 was obtained as a light yellow solid (1.1 g, 34%). MS (APCI): m/z 295.5 [M+H]$^+$ and used in the next step without further purification.

2-(1,3-Dimethyl-2,6-dioxo-1,2,3,6-tetrahydro-purin-7-yl)-2-methyl propionic acid (124)

Ester 123 (1 g, 3.39 mmol) dissolved in 2N HCl (25 mL) and the reaction was refluxed for 30 h. The reaction was cooled to 0° C. and then warmed to rt. The resulting precipitate was filtered, washed with ether and dried to yield 124 as a white solid (0.55, 55.5%). MS (APCI): m/z 267.4 [M+H]$^+$.

2-(1,3-Dimethyl-2,6-dioxo-1,2,36-tetrahydro-purin-7-yl)N-(4-isopropyl-phenyl)-isobutyramide (387)

To a solution of acid 124 (0.2 g, 0.75 mmol) in CHCl$_3$ (30 mL) at 0° C. was added oxalyl chloride (0.57 g, 4.5 mmol) and a catalytic amount of DMF. The resulting solution was stirred for 2 h at room temperature and concentrated in vacuo and then re-dissolved in CHCl$_3$. The mixture was cooled to 0° C. and then 4-isopropyl aniline was added and the reaction mixture was stirred overnight warming to rt. The reaction mixture was diluted with CHCl$_3$ (30 mL) and washed with 1 N HCl (50 mL). Combined organic layers were washed with water (75 mL), dried over $Na_2SO_4$ and concentrated in vacuo and the crude product was purified by flash chromatography on silica gel eluting with EtOAc/hexane and EtOAc/MeOH to yield 387 as a white solid (0.19 g, 58.8%). MS (APCI): m/z 384.3 [M+H]$^+$. Anal. Calcd. For $C_{20}H_{25}N_5O_3$: C, 62.65; H, 6.57; N, 18.26. Found C, 62.40; H, 6.51; N, 18.15.

N-(4-isopropylphenyl)-2-(3-methyl-2,6-dioxo-1,2,3,6-tetrahydropurin-7-yl)acetamide (388)

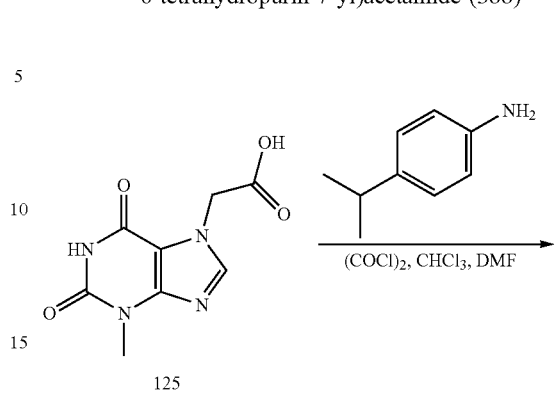

To a solution of acid 125 (0.5 g, 2.23 mmol) in CHCl$_3$ (50 mL) at 0° C. was added oxalyl chloride (1.69 g, 13.3 mmol) and a catalytic amount of DMF. The resulting solution was stirred for 2 h at rt, concentrated in vacuo and re-dissolved in CHCl$_3$. The solution was cooled to 0° C. and 4-isopropyl aniline was added and the reaction was stirred overnight warming to rt. The reaction mixture was then diluted with CHCl$_3$ (30 mL) and washed with 1 N HCl (50 mL). Combined organic layers were washed with water (75 mL), dried over $Na_2SO_4$ and concentrated in vacuo. The product was purified by flash chromatography on silica gel eluting with EtOAc/hexanes and EtOAc/MeOH to yield 388 as a white solid (0.23 g, 31%). MS (APCI): m/z 342.2 [M+H]$^+$. Anal. Calcd. For $C_{17}H_{19}N_5O_3$·0.4H$_2$O: C, 58.58; H, 5.73; N, 20.09. Found C, 58.72; H, 5.63; N, 19.80.

N-(4-cyclopentylphenyl)-2-(3-methyl-2,6-dioxo-1,2,3,6-tetrahydropurin-7-yl)acetamide (394), N-(4-cyclopentylphenyl)-2-(1,3-dimethyl-2,6-dioxo-1,2,3,6-tetrahydropurin-7-yl)acetamide (395) and N-(2-cyclopentylphenyl)-2-(1,3-dimethyl-2,6-dioxo-1,2,3,6-tetrahydropurin-7-yl)acetamide (398)

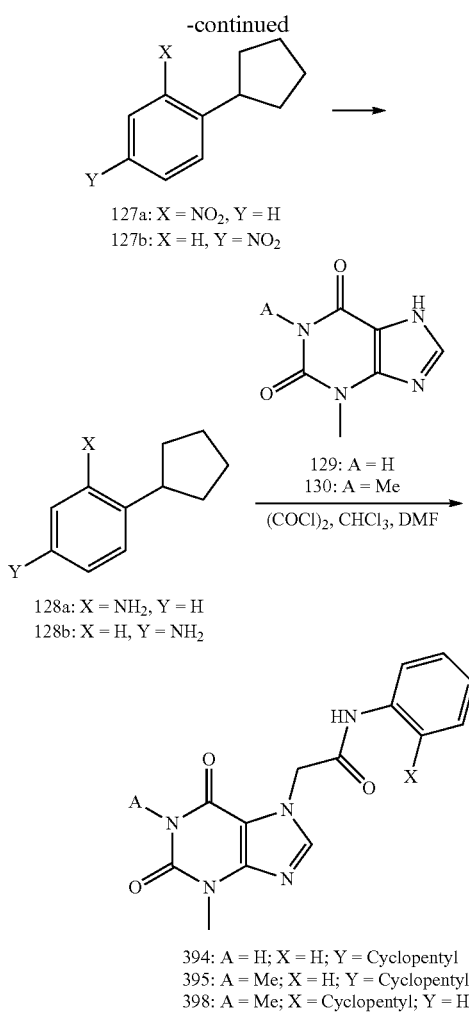

1-Cyclopentyl-2-nitrobenzene (127a) and 1-cyclopentyl-4-nitrobenzene (127b)

To a stirred solution of cyclopentyl benzene 126 (5 g, 34.2) in acetic anhydride (50 mL) at 10° C. was added dropwise 70% nitric acid (2.99 g, 34.2 mmol). The yellow homogeneous mixture was stirred for 1 h at 10° C. The reaction was then poured into water, neutralized with cold, concentrated NaOH and extracted several times with ethyl ether. The ether layers were combined and washed with excess aqueous potassium carbonate (100 mL), dried over $Na_2SO_4$, and concentrated in vacuo to yield a mixture of compounds 127a and 127b (6.4 g). This mixture was used in the subsequent step without further purification.

2-Cyclopentylbenzenamine (128a) and 4-cyclopentylbenzenamine (128b)

To a solution of crude products 127a and 127b (2.5 g) in EtOH (100 mL) was added 10% Pd/C (0.9 g, 3.5 mol %,) and the reaction was stirred under hydrogen balloon for 3 h. The reaction was then filtered through Celite, concentrated in vacuo, and the crude product was purified by flash chromatography on silica gel eluting with EtOAc/hexanes to yield ortho-compound 128a (0.5 g, 23.8%). MS (APCI): m/z 162.3 ([M+H]$^+$) and para-compound 128b (1 g, 47.6%). MS (APCI): m/z 162.3 [M+H]$^+$.

N-(4-cyclopentylphenyl)-2-(3-methyl-2,6-dioxo-1,2,3,6-tetrahydropurin-7-yl)acetamide (394)

To a 0° C. solution of acid 129 (2.1 mmol) in $CHCl_3$ (10 mL) and $CH_3CN$ (10 mL) was added oxalyl chloride (12.6 mmol) and a catalytic amount of DMF. The resulting solution was stirred for 2 h at rt, concentrated in vacuo. The residue was re-dissolved in $CHCl_3$ and cooled to 0° C. To this solution was added cyclopentylamine 128a and the reaction was stirred overnight at rt. The reaction was then diluted with $CHCl_3$ (30 mL) and washed with 1 N HCl (50 mL). The combined organic layers were washed with water (75 mL), dried over $Na_2SO_4$ and concentrated in vacuo. The product was purified by flash chromatography on silica gel eluting with EtOAc/hexanes and EtOAc/MeOH to yield the 394 as a light yellow solid. (22%). mp: 295-300° C. MS (APCI): m/z 368.2 [M+H]$^+$. Anal. Calcd. For $C_{19}H_{21}N_5O_3 \cdot 0.45H_2O$: C, 60.77; H, 5.88; N, 18.65. Found C, 61.07; H, 5.85; N, 18.23.

N-(4-cyclopentylphenyl)-2-(1,3-dimethyl-2,6-dioxo-1,2,3,6-tetrahydropurin-7-yl)acetamide (395) and N-(2-cyclopentylphenyl)-2-(1,3-dimethyl-2,6-dioxo-1,2,3,6-tetrahydropurin-7-yl)acetamide (398)

To a solution of acid 130 (2.1 mmol) in $CHCl_3$ (10 mL) and $CH_3CN$ (10 mL) at 0° C. was added oxalyl chloride (12.6 mmol) and a catalytic amount of DMF. The resulting solution was stirred for 2 h at rt and concentrated in vacuo. The residue was re-dissolved in $CHCl_3$ and cooled to 0° C. To this solution was added cyclopentylamine 128b and the reaction was stirred overnight at rt. The reaction was then diluted with $CHCl_3$ (30 mL) and washed with 1 N HCl (50 mL). The combined organic layers were washed with water (75 mL), dried over $Na_2SO_4$ and concentrated in vacuo and the product was purified by flash chromatography on silica gel eluting with EtOAc/hexanes and EtOAc/MeOH to yield 395 (31%) as a light red solid. Mp: 260-262° C. MS (APCI): m/z 382.2 [M+H]$^+$. Anal. Calcd. For $C_{20}H_{23}N_5O_3 \cdot 0.1H_2O \cdot +0.15$ EtOAc: C, 62.41; H, 6.20; N, 17.67. Found C, 62.47; H, 6.20; N, 17.38 and 398 (63%) as light brown solid. Mp: 201-202° C. MS (APCI): m/z 382.2 [M+H]$^+$. Anal. Calcd. For $C_{20}H_{23}N_5O_3$: C, 62.98; H, 6.08; N, 18.36. Found C, 62.94; H, 6.10; N, 18.33.

N-(4-isopropylphenyl)-N-methyl-2-(1-methyl-2,6-dioxo-1,2,3,6-tetrahydropurin-7-yl)acetamide (392)

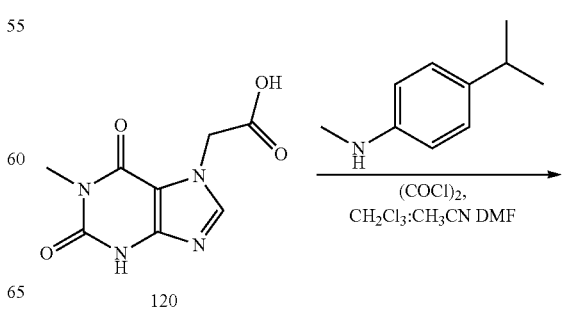

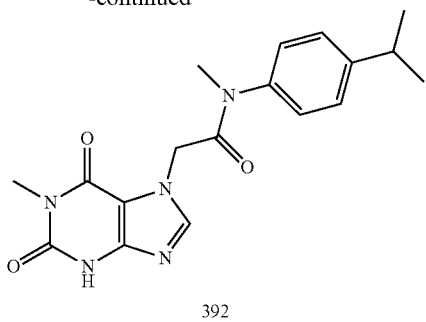

392

To a solution of acid 120 (0.25 g, 1.11 mmol) in CHCl₃ (20 mL) and CH₃CN (20 mL) at 0° C. was added oxalyl chloride (0.84 g, 6.69 mmol) and a catalytic amount of DMF. The resulting solution was stirred for 2 h at rt and concentrated in vacuo. The residue was re-dissolved in CHCl₃ and the resulting solution cooled to 0° C. To this mixture was added N-methyl-4-isopropyl aniline (0.29 g, 2 mmol) and the reaction was stirred overnight warming to rt. The reaction was then diluted with CHCl₃ (30 mL) and washed with 1 N HCl (50 mL). The combined organic layers were washed with water (75 mL), dried over Na₂SO₄ and concentrated in vacuo and the product was purified by chromatography on silica gel eluting with EtOAc/hexanes and EtOAc/MeOH to yield 392 (0.2 g, 51%) as a light brown solid. mp: 271-273° C. MS (APCI): m/z 356.2 [M+H]⁺ Anal. Calcd. For C₁₈H₂₁N₅O₃. 0.35H₂O: C, 59.77; H, 6.05; N, 19.36. Found C, 59.77; H, 6.07; N, 19.29.

2-(1,3-dimethyl-2,6-dioxo-1,2,3,6-tetrahydropurin-7-yl)-N-(4-isopropylphenyl)-N-methylacetamide (393)

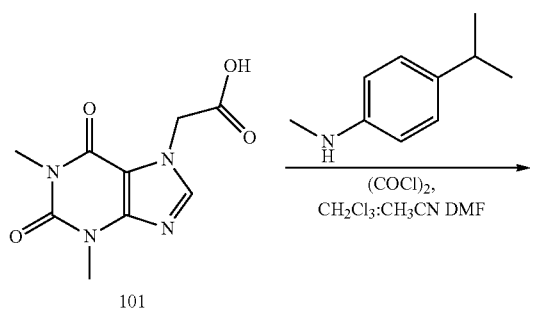

393

To a solution of acid 101 (0.5 g, 2.1 mmol) in CHCl₃ (30 mL) and CH₃CN (30 mL) at 0° C. was added oxalyl chloride (1.59 g, 12.6 mmol) and a catalytic amount of DMF. The resulting solution was stirred for 2 h at rt and concentrated in vacuo. The resulting residue was re-dissolved in CHCl₃ and cooled to 0° C. To this mixture was added N-methyl-4-isopropyl aniline (0.78 g, 5.2 mmol) and the reaction was stirred overnight warming to rt. The reaction mixture was diluted with CHCl₃ (30 mL) and washed with 1 N HCl (50 mL). The combined organic layers were washed with water (75 mL), dried over Na₂SO₄ and concentrated in vacuo. The product was purified by chromatography on silica gel eluting with EtOAc/hexanes and EtOAc/MeOH to yield 393 as a light yellow solid (0.65 g, 84.4%). mp: 231-233° C. MS (APCI): m/z 370.2 [M+H]⁺. Anal. Calcd. For C₁₉H₂₃N₅O₃. 0.1H₂O: C, 61.47; H, 6.30; N, 18.87. Found C, 61.28; H, 6.19; N, 18.57.

2-(2,6-dioxo-1,2,3,6-tetrahydropurin-7-yl)-N-(4-isopropylphenyl)acetamide (399)

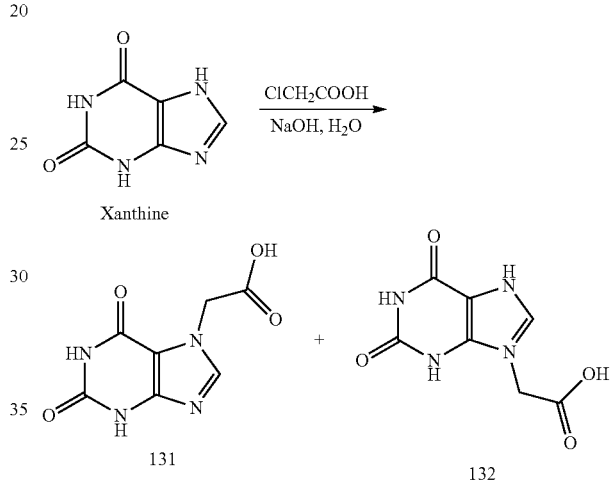

(2,6-Dioxo-1,2,3,6-tetrahydro-purin-7-yl)-acetic acid (131)

Xanthine (4.8 g, 31.5 mmol) was suspended in water and 2 M sodium hydroxide (50 mL) and the resulting suspension was stirred for 30 min. Chloroacetic acid (3 g, 31.5 mmol) was then added. The resulting solution was refluxed for 5 h, cooled to room temperature and stirred overnight. The precipitate was filtered and the aqueous solution was then acidified (pH 3) with 12 M HCl. The resulting precipitate was filtered and then washed with hot EtOH and then hot hexanes to yield a mixture of crude products 131 and 132. Water (65 mL) was added to these crude products and the resulting mixture was refluxed for 30 min. The solution was hot filtered and the precipitate was collected. The precipitate was then washed with hot ethanol and hexanes to yield 131 as a white solid (0.9 g, 13.4%).

2-(2,6-Dioxo-1,2,3,6-tetrahydro-purin-7-yl)-N-(4-isopropyl-phenyl)-acetamide (399)

To a 0° C. solution of acid 131 (0.05 g, 0.23 mmol) in DMF/DMSO (1:1, 10 mL) was added HATU (0.13 g, 0.35 mmol). The reaction mixture was warmed to rt and stirred for an additional 15 min. The reaction was then cooled back to 0° C. and 4-isopropyl amine (0.042 g, 0.31 mmol) was added. The reaction was then stirred overnight at room temperature. The DMF was evaporated and water was added. The resulting precipitate obtained was washed with ethyl acetate and then dissolved in ethanol and refluxed for 20 min. The solution was hot filtered and concentrated in vacuo to yield 399 as a white solid (0.025 g, 32.4%). mp: 320-325° C. MS (APCI): m/z 326.1 [M−H]$^+$ Anal. Calcd. For $C_{16}H_{17}N_5O_3$. 0.4$H_2O$: C, 57.44; H, 5.36; N, 20.93. Found C, 57.43; H, 5.40; N, 20.68.

2-(1,3-dimethyl-2,6-dioxo-1,2,3,6-tetrahydropurin-7-yl)-N-(4-(2-hydroxypropan-2-yl)phenyl)acetamide (402)

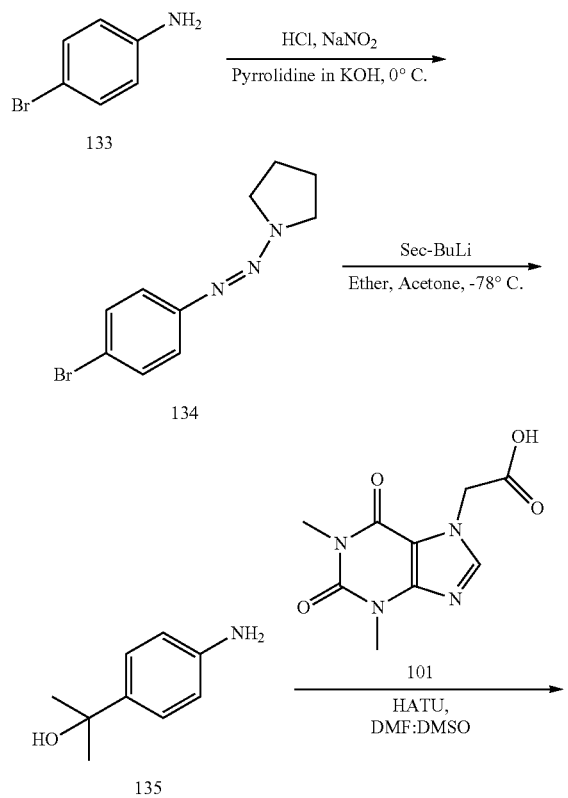

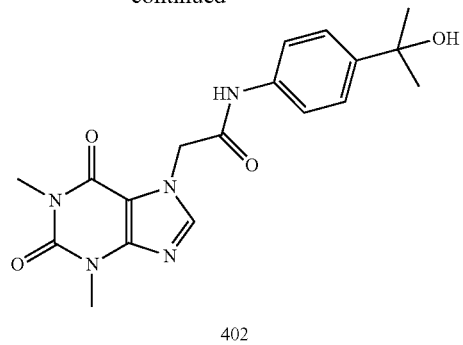

402

(E)-1-((4-Bromophenyl)diazenyl)pyrrolidine (134)

To a 0° C. solution of 4-bromo aniline (133, 10 g, 58.1 mmol) in concentrated HCl (11.7 mL) was added dropwise a solution of $NaNO_2$ (4 g, 57.9 mmol) in $H_2O$ (5 mL). The reaction was then stirred for an additional 10 min. at 0° C. after the addition. The resulting diazonium salt solution was added at once to a solution of pyrrolidine (4.54 g, 63.9 mmol) in 1M KOH (50 mL). The reaction mixture was stirred for 30 min at 0-10° C. The resulting precipitate was then filtered and recrystallized from absolute ethanol (50 mL) to give compound 134 (6.8 g, 46.2%) as light yellow crystals.

2-(4-Aminophenyl)propan-2-ol (135)

To a −78° C. solution of compound 134 (1 g, 3.95 mmol) in ether (20 mL) was added sec-BuLi (1.4 M in hexanes, 0.62 g, 9.67 mmol). The resulting solution was stirred for 30 min at −78° C., followed by addition of acetone (0.91 g, 15.81 mmol) dropwise at −78° C. The reaction mixture was warmed to room temperature overnight. The reaction mixture was partitioned between water and ether and the layers were separated. The aqueous layer was re-extracted with ether. The ether layers were the combined and concentrated in vacuo to yield crude 135 (0.33 g, 55.9%) which was used in the next step without further purification.

2-(1,3-Dimethyl-2,6-dioxo-1,2,3,6-tetrahydro-purin-7-yl)-N-[4-(1-hydroxy-1-methyl-ethyl)-phenyl]-acetamide (402)

To a 0° C. solution of acid 101 (0.32 g, 1.34 mmol) in DMF/DMSO (1:1, 20 mL) was added HATU (0.0.76 g, 2.01 mmol). The reaction was then stirred an additional 15 min at room temperature. The solution was cooled to 0° C. and amine 135 (0.30 g, 2.01 mmol) was added. The reaction was then stirred at rt overnight. The DMF was concentrated in vacuo and water was added to the reaction. The aqueous layer was extracted with EtOAc The ethyl acetate layer was then washed again with water and the organic layer was concentrated in vacuo. The product was purified by flash chromatography on silica gel eluting with EtOAc/hexanes and EtOAc/MeOH to yield 402 as a pure light brown semi solid (0.086 g, 17.5%). MS (APCI): m/z 372.2 [M−H]$^+$ Anal. Calcd. For $C_{18}H_{21}N_5O_4$. 0.35 EtOAc: C, 57.93; H, 5.96; N, 17.41. Found C, 58.36; H, 6.14; N, 16.96.

INCORPORATION BY REFERENCE

All publications and patents mentioned herein, are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

TABLE 1

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| *(structure: 4-chlorophenyl dihydropyrimidinone morpholine amide)* | 335.79 | >10,000 | | | |
| *(structure: 3-fluorophenyl dihydropyrimidinone morpholine amide)* | 319.34 | ≤5,000 | | | |
| *(structure: 4-fluorophenyl dihydropyrimidinone morpholine amide)* | 319.34 | >10,000 | | | |
| *(structure: 3-bromophenyl dihydropyrimidinone morpholine amide)* | 380.24 | >10,000 | | | |
| *(structure: ethyl ester phenyl, 2-bromo-5-hydroxyphenyl dihydropyrimidinethione)* | 433.33 | ≤1,000 | ≤1,000 | ≥20,000 (at least 30-fold selective for TRPA1 over hERG) | ≥30,000 (at least 40-fold selective for TRPA1 over NaV1.2) |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 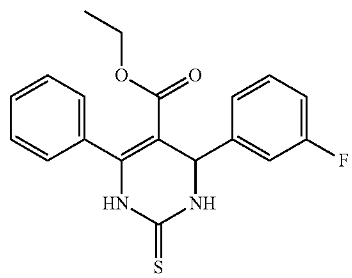 [SMILES: CCOC(=O)C1=C(c2ccccc2)NC(=S)NC1c1cccc(F)c1] | 356.42 | ≤10,000 | >10,000 | | |
| 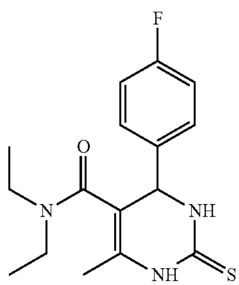 [SMILES: CCN(CC)C(=O)C1=C(C)NC(=S)NC1c1ccc(F)cc1] | 321.42 | | >10,000 | | |
| 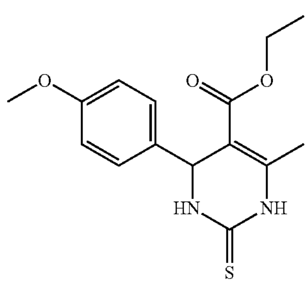 [SMILES: CCOC(=O)C1=C(C)NC(=S)NC1c1ccc(OC)cc1] | 290.31 | | >10,000 | | |
| 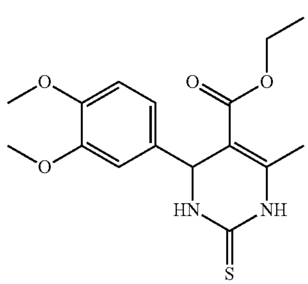 [SMILES: CCOC(=O)C1=C(C)NC(=S)NC1c1ccc(OC)c(OC)c1] | 320.34 | | >10,000 | | |
| 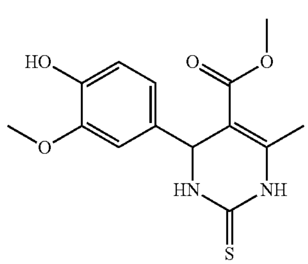 | 308.35 | | ≤10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 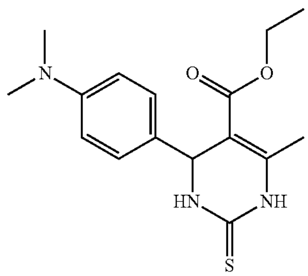 [SMILES: CCOC(=O)C1=C(C)NC(=S)NC1c1ccc(N(C)C)cc1] | 319.42 | | >10,000 | | |
| 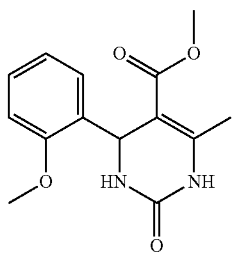 [SMILES: COC(=O)C1=C(C)NC(=O)NC1c1ccccc1OC] | 276.29 | | >10,000 | | |
| 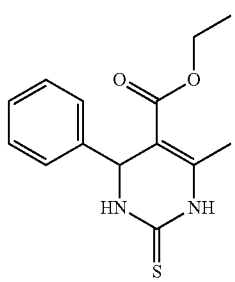 [SMILES: CCOC(=O)C1=C(C)NC(=S)NC1c1ccccc1] | 276.35 | | >10,000 | | |
| 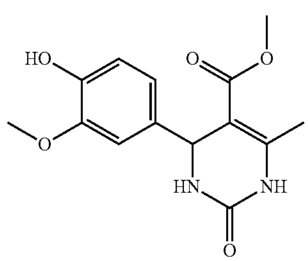 | 292.29 | | >10,000 | | |
| 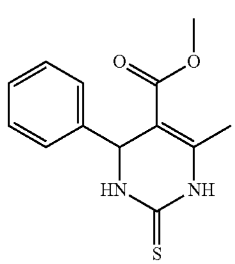 [SMILES: COC(=O)C1=C(C)NC(=S)NC1c1ccccc1] | 262.33 | >10,000 | ≤5,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 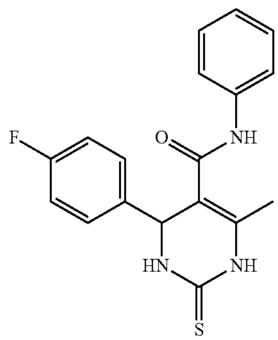 [SMILES: CC1=C(C(=O)Nc2ccccc2)C(c2ccc(F)cc2)NC(=S)N1] | 341.4 | | ≥30,000 | | |
| 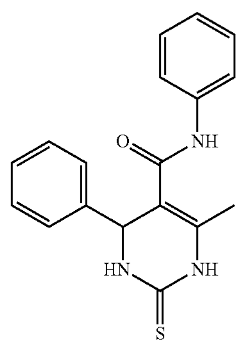 [SMILES: CC1=C(C(=O)Nc2ccccc2)C(c2ccccc2)NC(=S)N1] | 323.41 | | ≥30,000 | | |
| 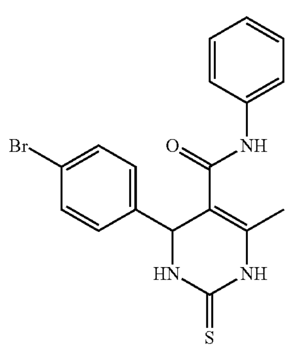 [SMILES: CC1=C(C(=O)Nc2ccccc2)C(c2ccc(Br)cc2)NC(=S)N1] | 402.31 | | >10,000 | | |
| 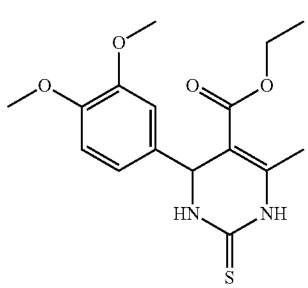 [SMILES: CCOC(=O)C1=C(C)NC(=S)NC1c1ccc(OC)c(OC)c1] | 336.41 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 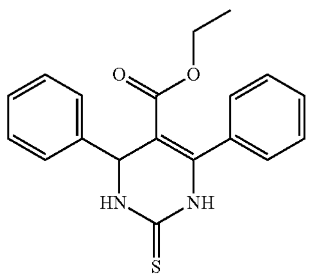 [SMILES: CCOC(=O)C1=C(c2ccccc2)NC(=S)NC1c1ccccc1] | 338.42 | | ≤10,000 | | |
| 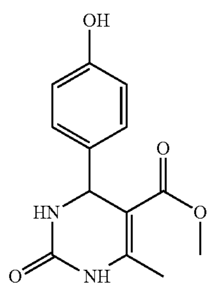 [SMILES: COC(=O)C1=C(C)NC(=O)NC1c1ccc(O)cc1] | 262.26 | | >10,000 | | |
| 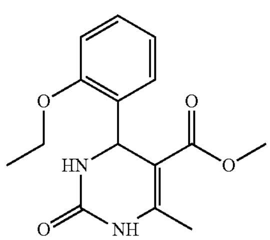 [SMILES: CCOc1ccccc1C1NC(=O)NC(C)=C1C(=O)OC] | 290.31 | | >10,000 | | |
| 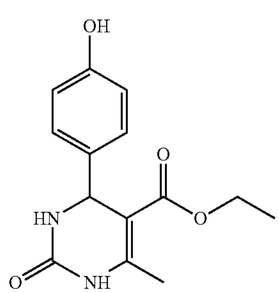 [SMILES: CCOC(=O)C1=C(C)NC(=O)NC1c1ccc(O)cc1] | 276.29 | | >10,000 | | |
| 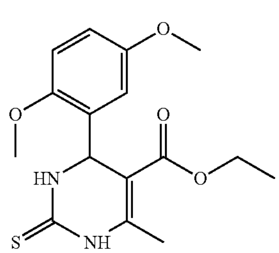 [SMILES: CCOC(=O)C1=C(C)NC(=S)NC1c1cc(OC)ccc1OC] | 336.41 | | >10,000 | | |

TABLE 1-continued
| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 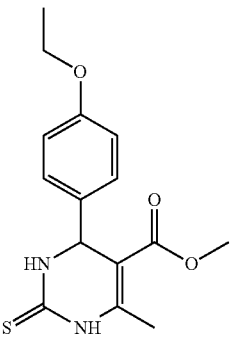 [SMILES: CCOc1ccc(C2NC(=S)NC(C)=C2C(=O)OC)cc1] | 306.38 | ≤10,000 | ≤5,000 | | |
| 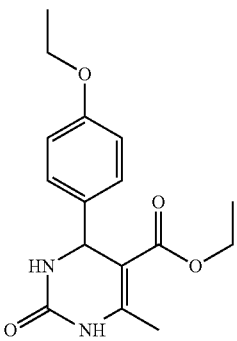 [SMILES: CCOC(=O)C1=C(C)NC(=O)NC1c1ccc(OCC)cc1] | 304.34 | | >10,000 | | |
| 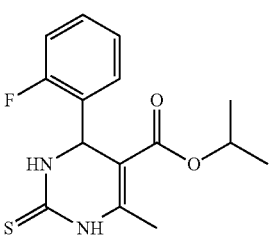 [SMILES: CC1=C(C(=O)OC(C)C)C(c2ccccc2F)NC(=S)N1] | 308.37 | | >10,000 | | |
| 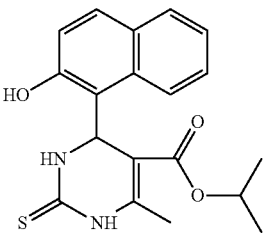 [SMILES: CC1=C(C(=O)OC(C)C)C(c2c(O)ccc3ccccc23)NC(=S)N1] | 356.44 | | >10,000 | | |
| 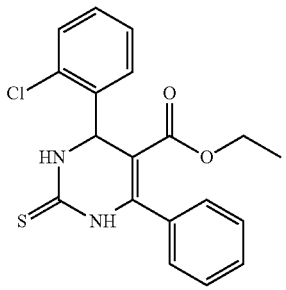 [SMILES: CCOC(=O)C1=C(c2ccccc2)NC(=S)NC1c1ccccc1Cl] | 372.87 | ≤5,000 | >10,000 | ≥20,000 (at least 10-fold selective for TRPA1 over hERG) | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| | 292.35 | | >10,000 | | |
| | 292.35 | >10,000 | ≤10,000 | | |
| 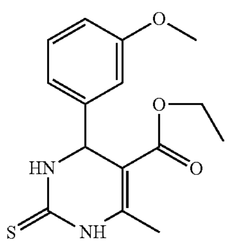 [SMILES: CCOC(=O)C1=C(C)NC(=S)NC1c1cccc(OC)c1] | 306.38 | ≤10,000 | ≤5,000 | | |
| 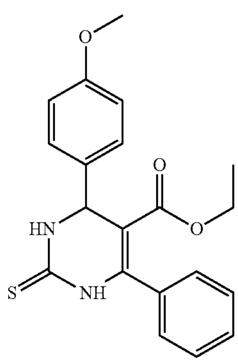 [SMILES: CCOC(=O)C1=C(c2ccccc2)NC(=S)NC1c1ccc(OC)cc1] | 368.45 | >10,000 | >10,000 | | |
| 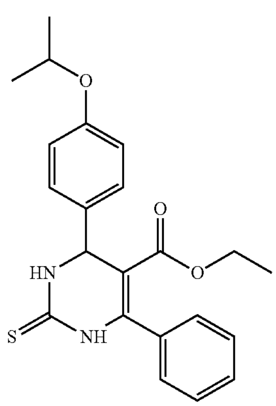 [SMILES: CCOC(=O)C1=C(c2ccccc2)NC(=S)NC1c1ccc(OC(C)C)cc1] | 396.5 | >10,000 | ≥20,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 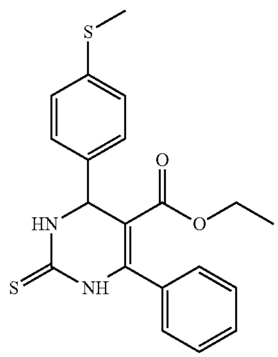 [SMILES: CCOC(=O)C1=C(c2ccccc2)NC(=S)NC1c1ccc(SC)cc1] | 384.52 | | ≤5,000 | | |
| 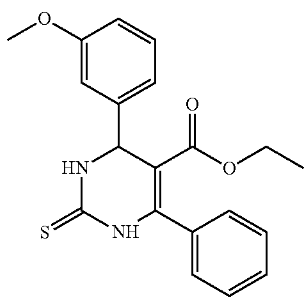 [SMILES: CCOC(=O)C1=C(c2ccccc2)NC(=S)NC1c1cccc(OC)c1] | 368.45 | ≤5,000 | ≤5,000 | | |
| 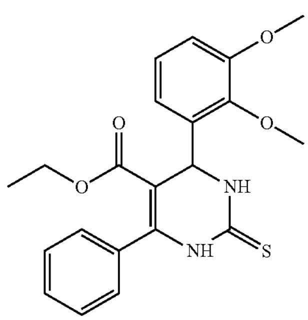 [SMILES: CCOC(=O)C1=C(c2ccccc2)NC(=S)NC1c1cccc(OC)c1OC] | 398.48 | | >10,000 | | |
| 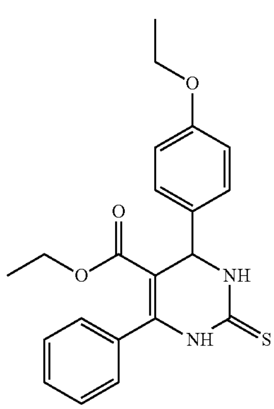 [SMILES: CCOC(=O)C1=C(c2ccccc2)NC(=S)NC1c1ccc(OCC)cc1] | 382.48 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 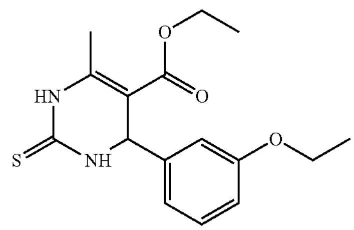 [SMILES: CCOC(=O)C1=C(C)NC(=S)NC1c1cccc(OCC)c1] | 320.41 | ≤1,000 | ≤5,000 | | |
| 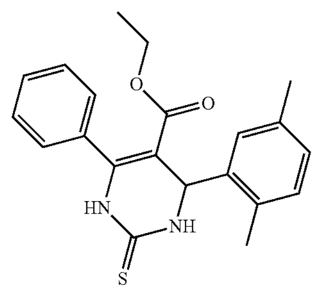 [SMILES: CCOC(=O)C1=C(c2ccccc2)NC(=S)NC1c1cc(C)ccc1C] | 366.48 | >10,000 | >10,000 | | |
| 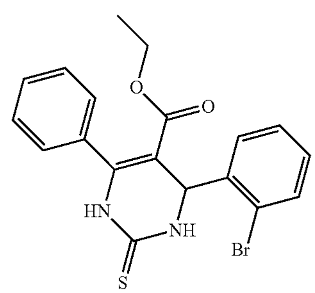 [SMILES: CCOC(=O)C1=C(c2ccccc2)NC(=S)NC1c1ccccc1Br] | 417.32 | ≤5,000 | >10,000 | >10,000 (at least 5-fold selective for TRPA1 over hERG) | |
| 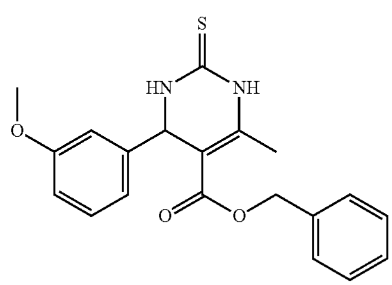 [SMILES: COc1cccc(C2NC(=S)NC(C)=C2C(=O)OCc2ccccc2)c1] | 368.45 | | >10,000 | | |
| 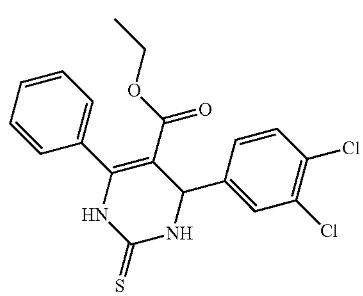 [SMILES: CCOC(=O)C1=C(c2ccccc2)NC(=S)NC1c1ccc(Cl)c(Cl)c1] | 407.31 | >10,000 | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 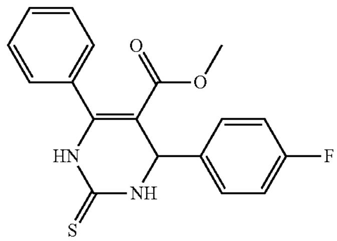 [SMILES: COC(=O)C1=C(c2ccccc2)NC(=S)NC1c1ccc(F)cc1] | 342.39 | >10,000 | >10,000 | | |
| 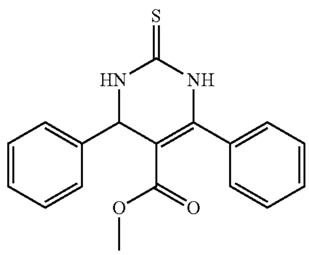 [SMILES: COC(=O)C1=C(c2ccccc2)NC(=S)NC1c1ccccc1] | 324.4 | ≤5,000 | ≤5,000 | | |
| 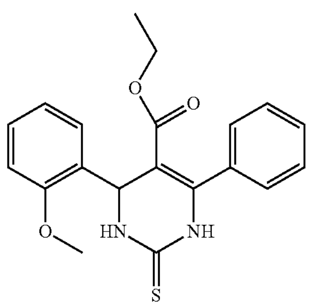 [SMILES: CCOC(=O)C1=C(c2ccccc2)NC(=S)NC1c1ccccc1OC] | 368.45 | | >10,000 | | |
| 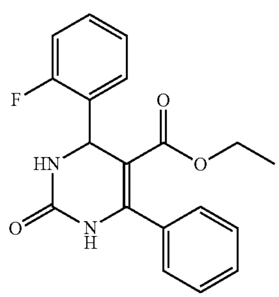 [SMILES: CCOC(=O)C1=C(c2ccccc2)NC(=O)NC1c1ccccc1F] | 340.35 | | >10,000 | | |
| 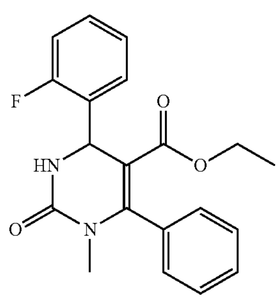 [SMILES: CCOC(=O)C1=C(c2ccccc2)N(C)C(=O)NC1c1ccccc1F] | 354.37 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| *(structure)* | 353.21 | | ≥30,000 | | |
| *(structure)* | 356.8 | | >10,000 | | |
| *(structure)* | 324.83 | | ≤10,000 | | |
| *(structure)* | 356.34 | | ≤5,000 | | |
| *(structure)* | 371.47 | | >10,000 | | |
| *(structure)* | 332.42 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 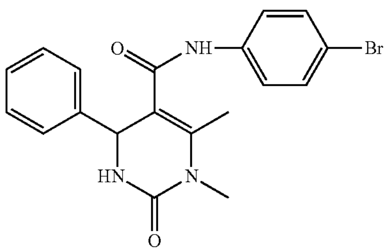 [SMILES: CC1=C(C(=O)Nc2ccc(Br)cc2)C(c2ccccc2)NC(=O)N1C] | 400.27 | | >10,000 | | |
| 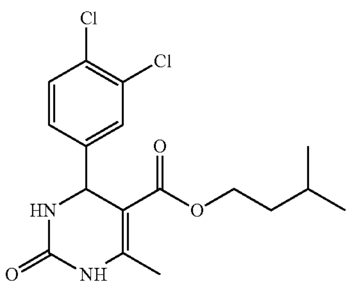 [SMILES: CC1=C(C(=O)OCCC(C)C)C(c2ccc(Cl)c(Cl)c2)NC(=O)N1] | 371.26 | | >10,000 | | |
| 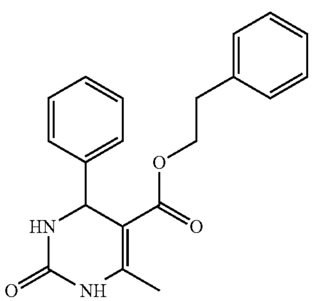 [SMILES: CC1=C(C(=O)OCCc2ccccc2)C(c2ccccc2)NC(=O)N1] | 336.38 | | >10,000 | | |
| 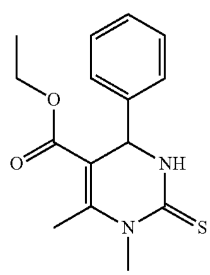 [SMILES: CCOC(=O)C1=C(C)N(C)C(=S)NC1c1ccccc1] | 290.38 | | >10,000 | | |
| 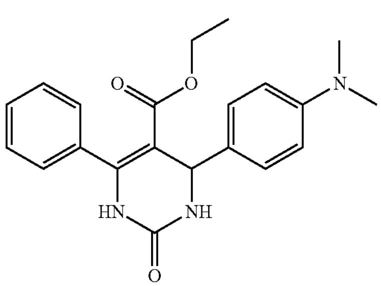 [SMILES: CCOC(=O)C1=C(c2ccccc2)NC(=O)NC1c1ccc(N(C)C)cc1] | 365.43 | | ≤1,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 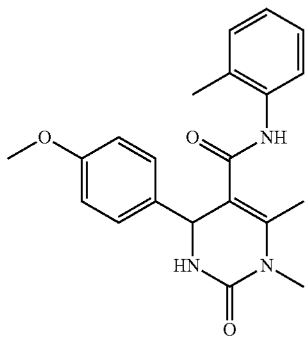 [SMILES: COc1ccc(C2NC(=O)N(C)C(C)=C2C(=O)Nc2ccccc2C)cc1] | 365.43 | | >10,000 | | |
| 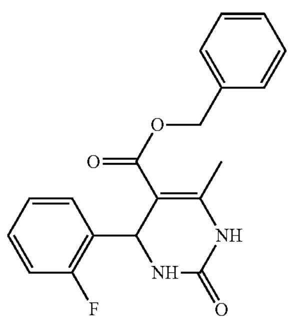 [SMILES: CC1=C(C(=O)OCc2ccccc2)C(c2ccccc2F)NC(=O)N1] | 340.35 | | >10,000 | | |
| 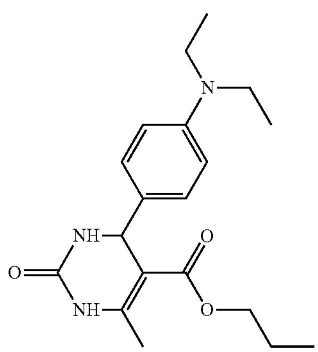 [SMILES: CCCOC(=O)C1=C(C)NC(=O)NC1c1ccc(N(CC)CC)cc1] | 345.44 | | >10,000 | | |
| 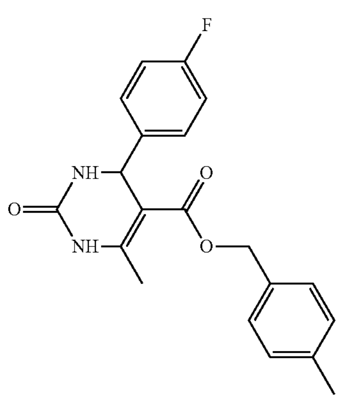 [SMILES: CC1=C(C(=O)OCc2ccc(C)cc2)C(c2ccc(F)cc2)NC(=O)N1] | 354.37 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| *(3-Cl-phenyl dihydropyrimidinone isopropyl ester)* | 308.76 | | >10,000 | | |
| *(4-Cl-phenyl dihydropyrimidinone phenethyl ester)* | 370.83 | | ≤5,000 | | |
| *(4-F-phenyl dihydropyrimidinone cyclohexyl ester)* | 332.37 | | >10,000 | | |
| *(4-F-phenyl dihydropyrimidinone allyl ester)* | 290.29 | | >10,000 | | |
| *(3-Br-phenyl dihydropyrimidinone isopropyl ester)* | 353.21 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| (4-chlorophenyl, isopropyl ester DHPM) | 308.76 | | >10,000 | | |
| (3-bromophenyl, pentyl ester DHPM) | 381.26 | | >10,000 | | |
| (2-chlorophenyl, sec-butyl ester DHPM) | 322.79 | | >10,000 | | |
| (4-diethylaminophenyl, allyl ester DHPM) | 343.42 | | >10,000 | | |
| (4-methylphenyl, allyl ester DHPM) | 286.33 | | ≤5,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 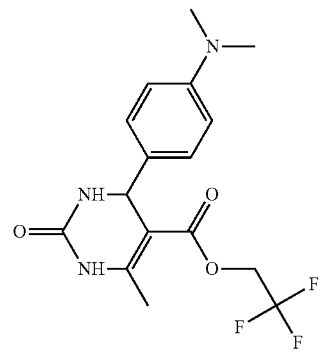 [SMILES: CC1=C(C(=O)OCC(F)(F)F)C(c2ccc(N(C)C)cc2)NC(=O)N1] | 357.33 | | >10,000 | | |
| 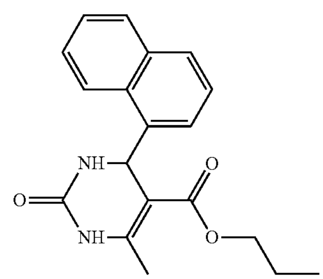 [SMILES: CCCOC(=O)C1=C(C)NC(=O)NC1c1cccc2ccccc12] | 324.37 | | >10,000 | | |
| 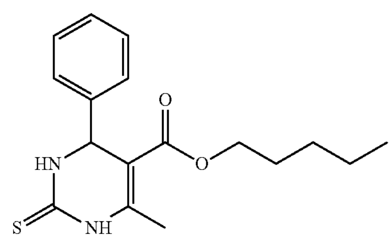 [SMILES: CCCCCOC(=O)C1=C(C)NC(=S)NC1c1ccccc1] | 318.43 | | >10,000 | | |
| 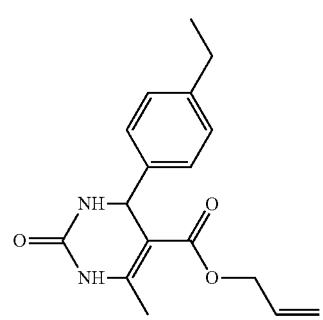 [SMILES: C=CCOC(=O)C1=C(C)NC(=O)NC1c1ccc(CC)cc1] | 300.35 | | >10,000 | | |
| 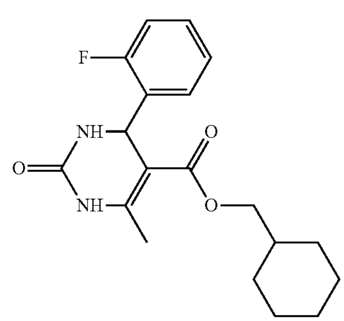 [SMILES: CC1=C(C(=O)OCC2CCCCC2)C(c2ccccc2F)NC(=O)N1] | 346.4 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 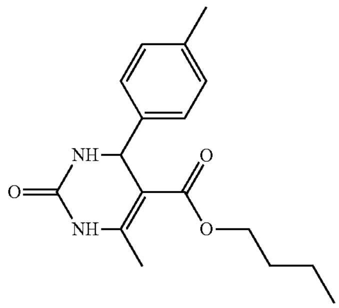 [SMILES: CCCCOC(=O)C1=C(C)NC(=O)NC1c1ccc(C)cc1] | 302.37 | | >10,000 | | |
| 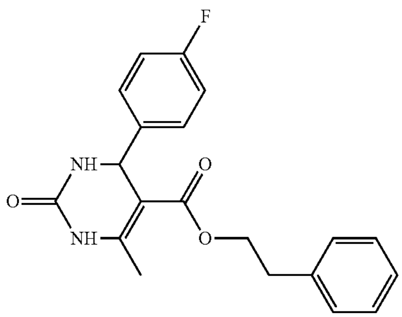 | 354.37 | | >10,000 | | |
| 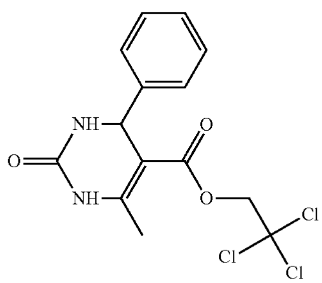 [SMILES: CC1=C(C(=O)OCC(Cl)(Cl)Cl)C(c2ccccc2)NC(=O)N1] | 363.62 | | >10,000 | | |
| 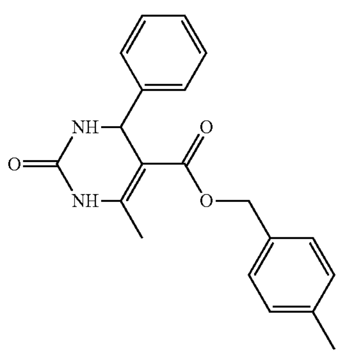 [SMILES: CC1=C(C(=O)OCc2ccc(C)cc2)C(c2ccccc2)NC(=O)N1] | 336.38 | | >10,000 | | |
| 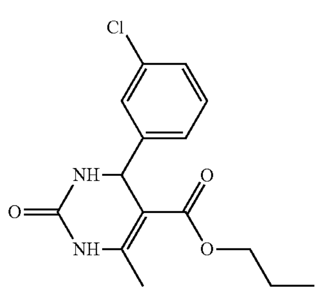 [SMILES: CCCOC(=O)C1=C(C)NC(=O)NC1c1cccc(Cl)c1] | 308.76 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 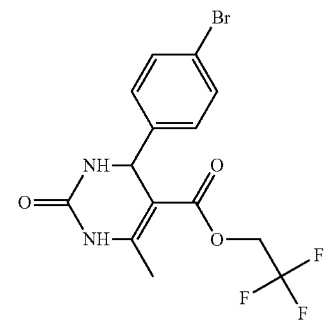 [SMILES: CC1=C(C(=O)OCC(F)(F)F)C(c2ccc(Br)cc2)NC(=O)N1] | 393.16 | | >10,000 | | |
| 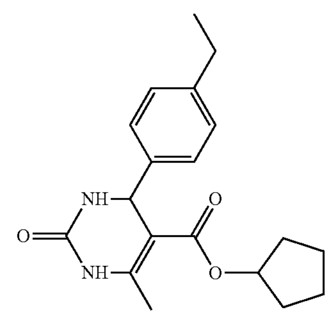 [SMILES: CCc1ccc(C2NC(=O)NC(C)=C2C(=O)OC2CCCC2)cc1] | 328.41 | | >10,000 | | |
| 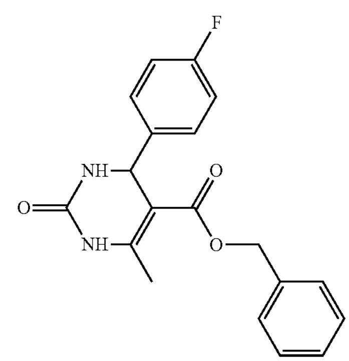 [SMILES: CC1=C(C(=O)OCc2ccccc2)C(c2ccc(F)cc2)NC(=O)N1] | 340.35 | | >10,000 | | |
| 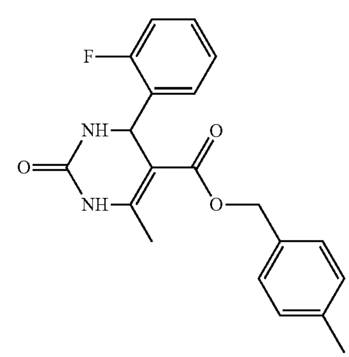 [SMILES: CC1=C(C(=O)OCc2ccc(C)cc2)C(c2ccccc2F)NC(=O)N1] | 354.37 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| [2,3-dichlorophenyl dihydropyrimidinone methyl ester] | 315.15 | | >10,000 | | |
| [3-chlorophenyl dihydropyrimidinone cycloheptyl ester] | 362.85 | | >10,000 | | |
| [3-chlorophenyl dihydropyrimidinone benzyl ester] | 356.8 | | >10,000 | | |
| [4-methylphenyl dihydropyrimidinone isobutyl ester] | 302.37 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 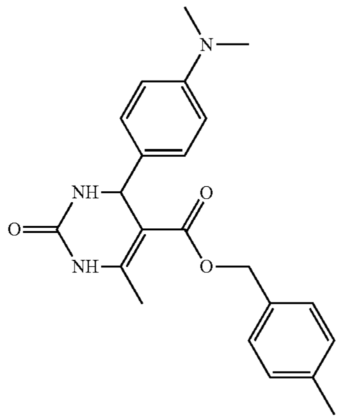 [SMILES: CC1=C(C(=O)OCc2ccc(C)cc2)C(c2ccc(N(C)C)cc2)NC(=O)N1] | 379.45 | | >10,000 | | |
| 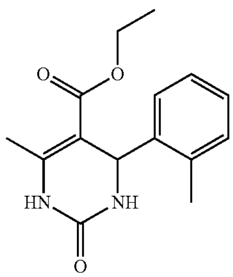 [SMILES: CCOC(=O)C1=C(C)NC(=O)NC1c1ccccc1C] | 274.32 | | >10,000 | | |
| 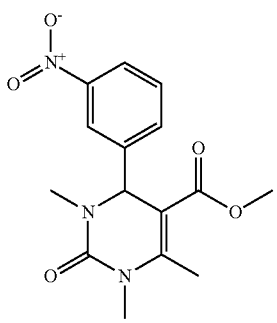 [SMILES: COC(=O)C1=C(C)N(C)C(=O)N(C)C1c1cccc([N+](=O)[O-])c1] | 319.31 | | >10,000 | | |
| 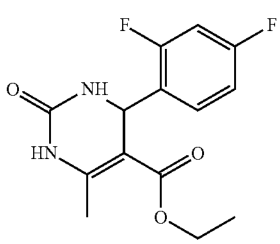 [SMILES: CCOC(=O)C1=C(C)NC(=O)NC1c1ccc(F)cc1F] | 296.27 | | >10,000 | | |
| 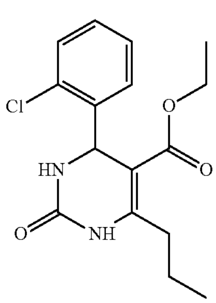 [SMILES: CCCC1=C(C(=O)OCC)C(c2ccccc2Cl)NC(=O)N1] | 322.79 | >10,000 | ≤5,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 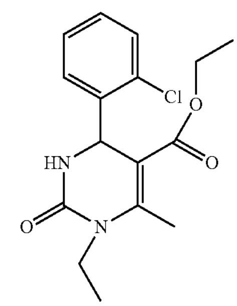 [SMILES: CCOC(=O)C1=C(C)N(CC)C(=O)NC1c1ccccc1Cl] | 322.79 | | ≥20,000 | | |
| 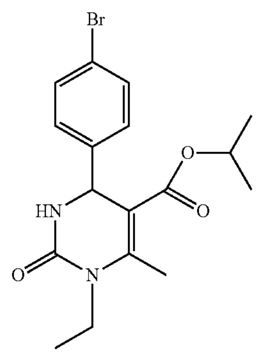 | 381.26 | | ≤5,000 | | |
| 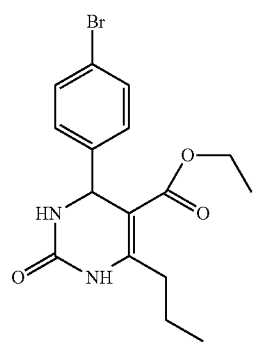 [SMILES: CCCC1=C(C(=O)OCC)C(c2ccc(Br)cc2)NC(=O)N1] | 367.24 | | ≥30,000 | | |
| 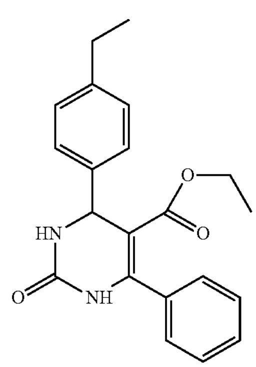 [SMILES: CCOC(=O)C1=C(c2ccccc2)NC(=O)NC1c1ccc(CC)cc1] | 350.41 | | ≤10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 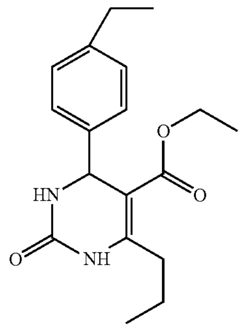 [SMILES: CCCC1=C(C(=O)OCC)C(c2ccc(CC)cc2)NC(=O)N1] | 316.39 | | >10,000 | | |
| 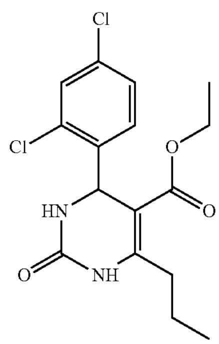 [SMILES: CCCC1=C(C(=O)OCC)C(c2ccc(Cl)cc2Cl)NC(=O)N1] | 357.23 | | >10,000 | | |
| 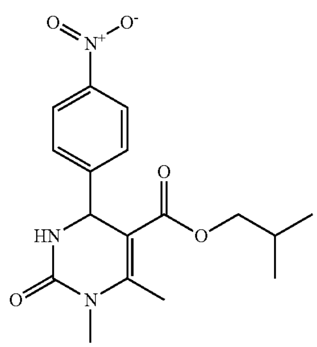 [SMILES: CC1=C(C(=O)OCC(C)C)C(c2ccc([N+](=O)[O-])cc2)NC(=O)N1C] | 347.37 | | ≤5,000 | | |
| 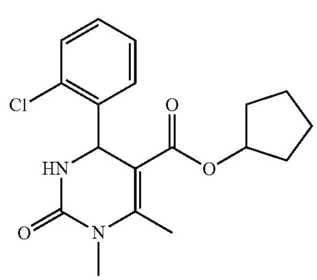 [SMILES: CC1=C(C(=O)OC2CCCC2)C(c2ccccc2Cl)NC(=O)N1C] | 348.82 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
| --- | --- | --- | --- | --- | --- |
| (4-fluorophenyl dihydropyrimidine-thione, 2-methoxyethyl ester) | 324.37 | | ≤5,000 | | |
| (4-bromophenyl dihydropyrimidine-thione, 2-methoxyethyl ester) | 385.28 | | >10,000 | | |
| (3-bromophenyl dihydropyrimidine-thione, 2-methoxyethyl ester) | 385.28 | | >10,000 | | |
| (4-methylthiophenyl dihydropyrimidinone, ethyl ester) | 306.38 | | >10,000 | | |
| (4-methoxyphenyl N-methyl dihydropyrimidine-thione, methyl ester) | 306.38 | | ≥30,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 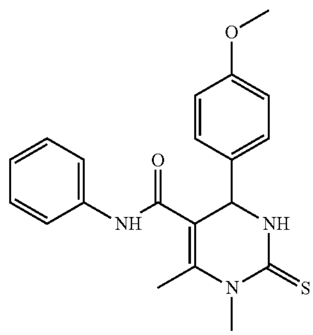 [SMILES: COc1ccc(C2NC(=S)N(C)C(C)=C2C(=O)Nc2ccccc2)cc1] | 367.46 | | >10,000 | | |
| 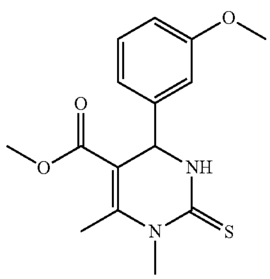 | 306.38 | | ≥20,000 | | |
| 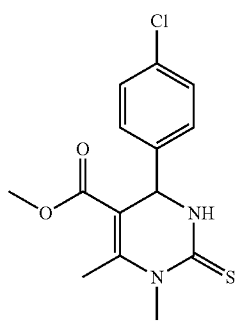 [SMILES: COC(=O)C1=C(C)N(C)C(=S)NC1c1ccc(Cl)cc1] | 310.8 | | ≤10,000 | | |
| 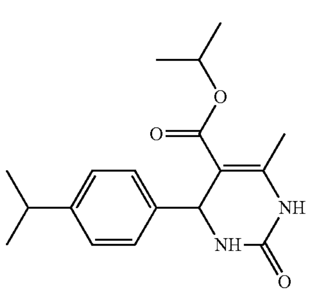 [SMILES: CC1=C(C(=O)OC(C)C)C(c2ccc(C(C)C)cc2)NC(=O)N1] | 316.39 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 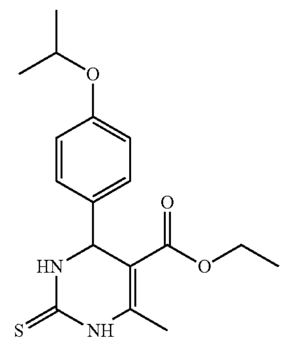 [SMILES: CCOC(=O)C1=C(C)NC(=S)NC1c1ccc(OC(C)C)cc1] | 334.43 | | >10,000 | | |
| 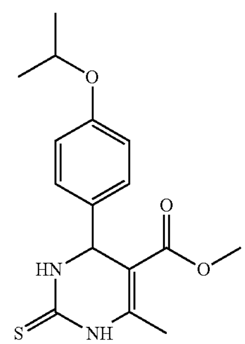 [SMILES: COC(=O)C1=C(C)NC(=S)NC1c1ccc(OC(C)C)cc1] | 320.41 | | >10,000 | | |
| 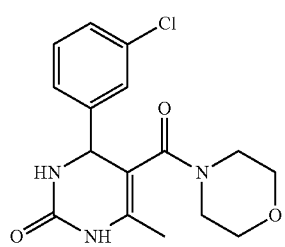 [SMILES: CC1=C(C(=O)N2CCOCC2)C(c2cccc(Cl)c2)NC(=O)N1] | 335.79 | | >10,000 | | |
| 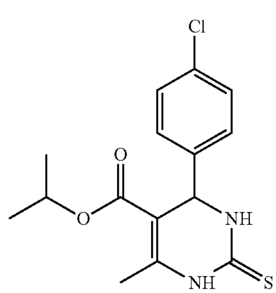 [SMILES: CC1=C(C(=O)OC(C)C)C(c2ccc(Cl)cc2)NC(=S)N1] | 324.83 | | >10,000 | | |
| 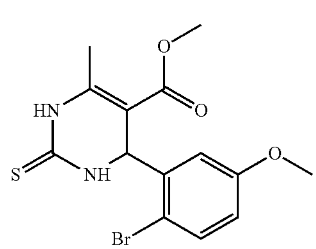 [SMILES: COC(=O)C1=C(C)NC(=S)NC1c1cc(OC)ccc1Br] | 371.25 | | ≤5,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
| --- | --- | --- | --- | --- | --- |
| 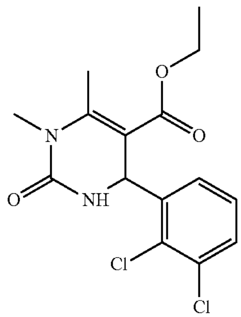 [SMILES: CCOC(=O)C1=C(C)N(C)C(=O)NC1c1cccc(Cl)c1Cl] | 343.21 | | >10,000 | | |
| 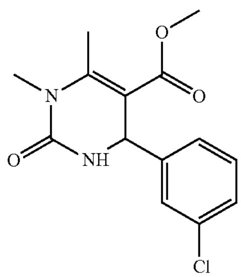 [SMILES: COC(=O)C1=C(C)N(C)C(=O)NC1c1cccc(Cl)c1] | 294.73 | | >10,000 | | |
| 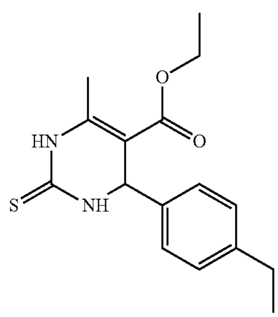 [SMILES: CCOC(=O)C1=C(C)NC(=S)NC1c1ccc(CC)cc1] | 304.41 | | >10,000 | | |
| 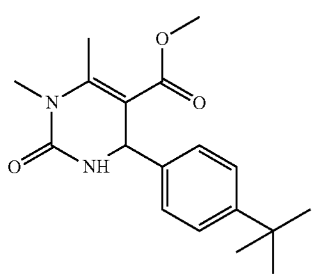 [SMILES: COC(=O)C1=C(C)N(C)C(=O)NC1c1ccc(C(C)(C)C)cc1] | 316.39 | | >10,000 | | |
| 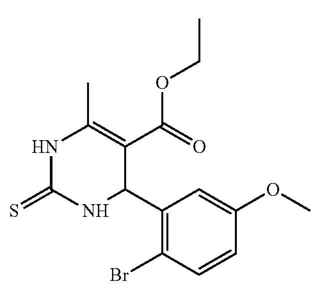 [SMILES: CCOC(=O)C1=C(C)NC(=S)NC1c1cc(OC)ccc1Br] | 385.28 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 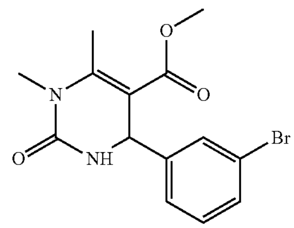 [SMILES: COC(=O)C1=C(C)N(C)C(=O)NC1c1cccc(Br)c1] | 339.18 | >10,000 | ≤5,000 | | |
| 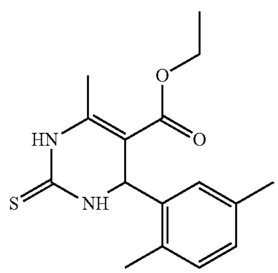 [SMILES: CCOC(=O)C1=C(C)NC(=S)NC1c1cc(C)ccc1C] | 304.41 | | >10,000 | | |
| 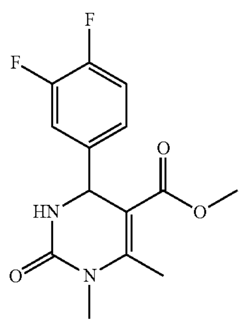 [SMILES: COC(=O)C1=C(C)N(C)C(=O)NC1c1ccc(F)c(F)c1] | 296.27 | ≤1,000 | ≤5,000 | | |
| 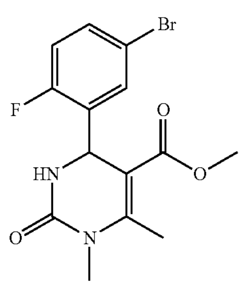 [SMILES: COC(=O)C1=C(C)N(C)C(=O)NC1c1cc(Br)ccc1F] | 357.17 | | >10,000 | | |
| 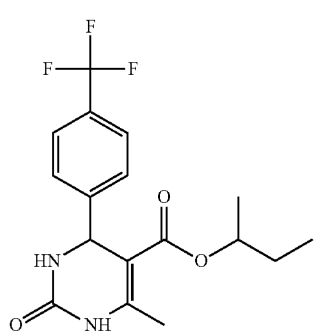 [SMILES: CCC(C)OC(=O)C1=C(C)NC(=O)NC1c1ccc(C(F)(F)F)cc1] | 356.34 | | ≤10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
| --- | --- | --- | --- | --- | --- |
| 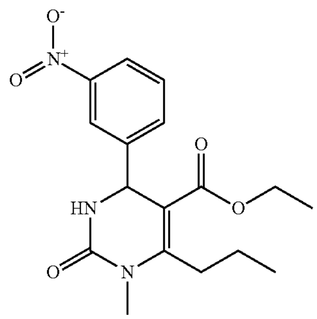 [SMILES: CCCC1=C(C(=O)OCC)C(c2cccc([N+](=O)[O-])c2)NC(=O)N1C] | 347.37 | | >10,000 | | |
| 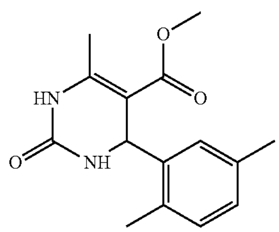 [SMILES: COC(=O)C1=C(C)NC(=O)NC1c1cc(C)ccc1C] | 274.32 | | >10,000 | | |
| 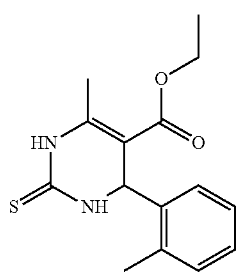 [SMILES: CCOC(=O)C1=C(C)NC(=S)NC1c1ccccc1C] | 290.38 | ≤5,000 | ≤5,000 | | |
| 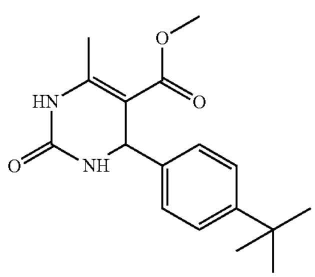 [SMILES: COC(=O)C1=C(C)NC(=O)NC1c1ccc(C(C)(C)C)cc1] | 302.37 | | >10,000 | | |
| 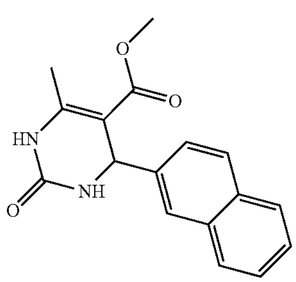 [SMILES: COC(=O)C1=C(C)NC(=O)NC1c1ccc2ccccc2c1] | 296.32 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
| --- | --- | --- | --- | --- | --- |
| | 367.24 | | >10,000 | | |
| | 322.79 | | >10,000 | | |
| | 367.24 | | >10,000 | | |
| | 322.79 | | >10,000 | | |
| 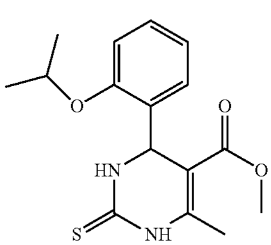 [SMILES: COC(=O)C1=C(C)NC(=S)NC1c1ccccc1OC(C)C] | 320.41 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 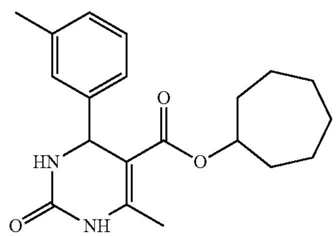 [SMILES: CC1=C(C(=O)OC2CCCCCC2)C(c2cccc(C)c2)NC(=O)N1] | 342.43 | | >10,000 | | |
| 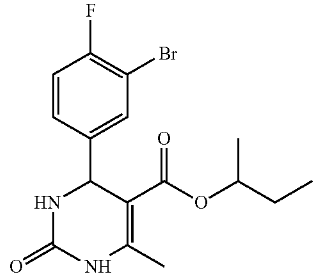 [SMILES: CCC(C)OC(=O)C1=C(C)NC(=O)NC1c1ccc(F)c(Br)c1] | 385.23 | | >10,000 | | |
| 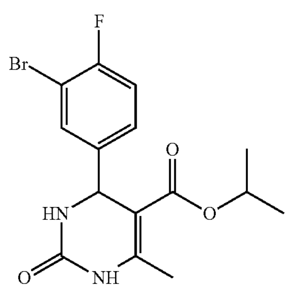 [SMILES: CC1=C(C(=O)OC(C)C)C(c2ccc(F)c(Br)c2)NC(=O)N1] | 371.2 | | >10,000 | | |
| 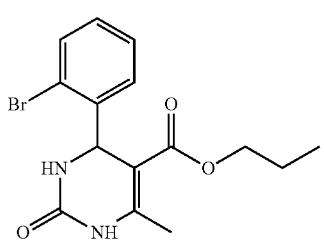 [SMILES: CCCOC(=O)C1=C(C)NC(=O)NC1c1ccccc1Br] | 353.21 | | >10,000 | | |
| 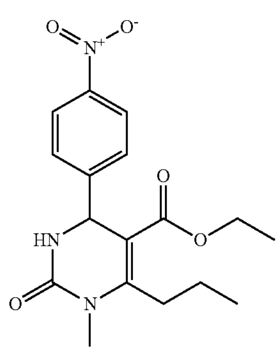 [SMILES: CCCC1=C(C(=O)OCC)C(c2ccc([N+](=O)[O-])cc2)NC(=O)N1C] | 347.37 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 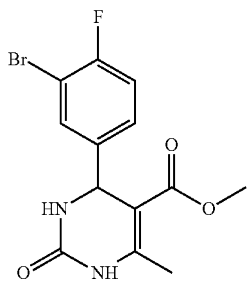 [SMILES: COC(=O)C1=C(C)NC(=O)NC1c1ccc(F)c(Br)c1] | 343.15 | | >10,000 | | |
| 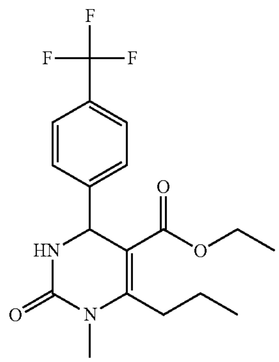 [SMILES: CCCC1=C(C(=O)OCC)C(c2ccc(C(F)(F)F)cc2)NC(=O)N1C] | 370.37 | | >10,000 | | |
| 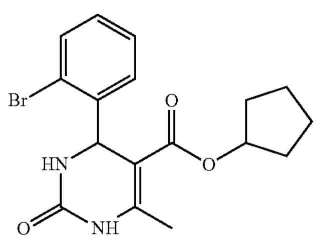 [SMILES: CC1=C(C(=O)OC2CCCC2)C(c2ccccc2Br)NC(=O)N1] | 379.25 | | >10,000 | | |
| 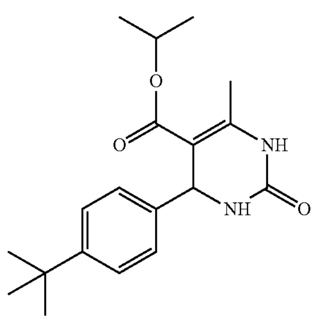 [SMILES: CC1=C(C(=O)OC(C)C)C(c2ccc(C(C)(C)C)cc2)NC(=O)N1] | 330.42 | | >10,000 | | |
| 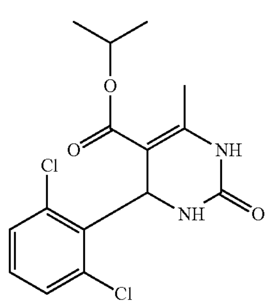 [SMILES: CC1=C(C(=O)OC(C)C)C(c2c(Cl)cccc2Cl)NC(=O)N1] | 343.21 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 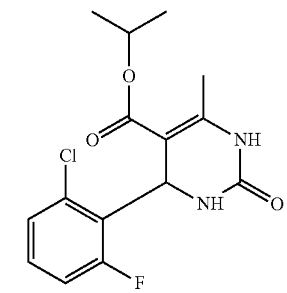 [SMILES: CC1=C(C(=O)OC(C)C)C(c2c(F)cccc2Cl)NC(=O)N1] | 326.75 | >10,000 | | | |
| 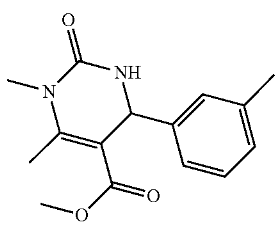 | 274.32 | >10,000 | | | |
| 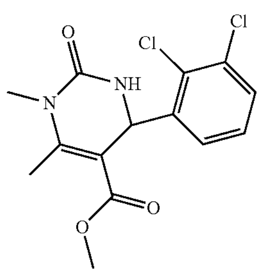 [SMILES: COC(=O)C1=C(C)N(C)C(=O)NC1c1cccc(Cl)c1Cl] | 329.18 | >10,000 | | | |
| 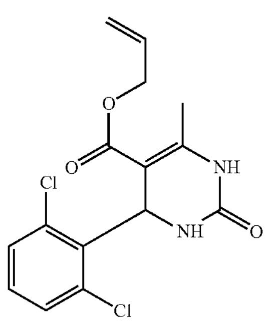 [SMILES: C=CCOC(=O)C1=C(C)NC(=O)NC1c1c(Cl)cccc1Cl] | 341.19 | >10,000 | | | |
| 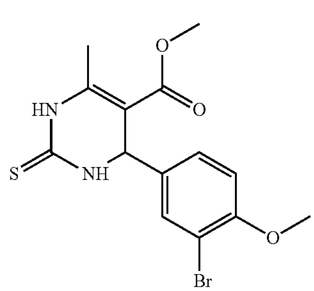 [SMILES: COC(=O)C1=C(C)NC(=S)NC1c1ccc(OC)c(Br)c1] | 371.25 | ≤1,000 | ≤5,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 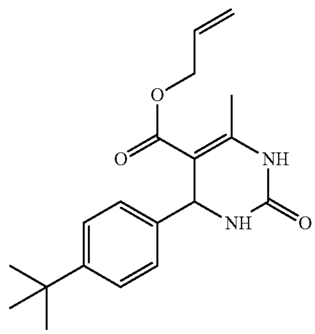 [SMILES: C=CCOC(=O)C1=C(C)NC(=O)NC1c1ccc(C(C)(C)C)cc1] | 328.41 | | >10,000 | | |
| 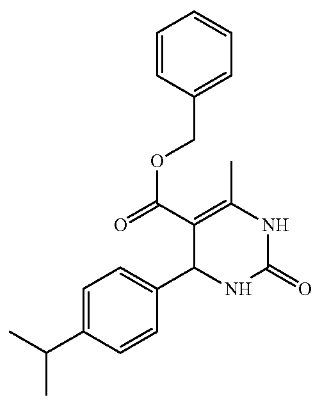 [SMILES: CC1=C(C(=O)OCc2ccccc2)C(c2ccc(C(C)C)cc2)NC(=O)N1] | 364.44 | | >10,000 | | |
| 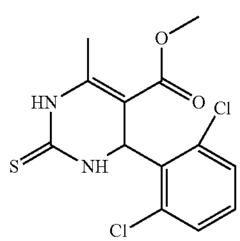 [SMILES: COC(=O)C1=C(C)NC(=S)NC1c1c(Cl)cccc1Cl] | 331.22 | ≤1,000 | ≤5,000 | | |
| 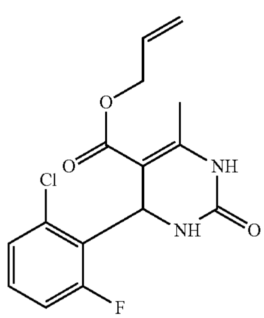 [SMILES: C=CCOC(=O)C1=C(C)NC(=O)NC1c1c(F)cccc1Cl] | 324.73 | | >10,000 | | |
| 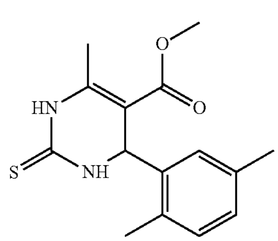 [SMILES: COC(=O)C1=C(C)NC(=S)NC1c1cc(C)ccc1C] | 290.38 | ≤5,000 | ≤5,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 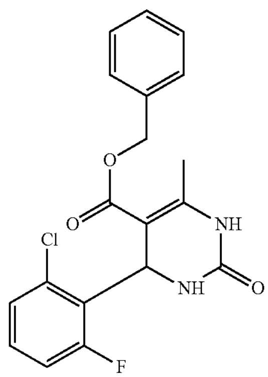 [SMILES: CC1=C(C(=O)OCc2ccccc2)C(c2c(F)cccc2Cl)NC(=O)N1] | 374.79 | | >10,000 | | |
| 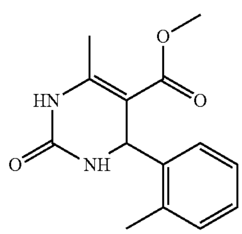 [SMILES: COC(=O)C1=C(C)NC(=O)NC1c1ccccc1C] | 260.29 | | ≥30,000 | | |
| 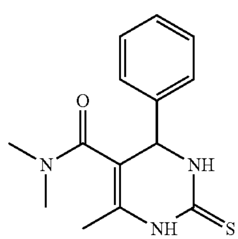 [SMILES: CC1=C(C(=O)N(C)C)C(c2ccccc2)NC(=S)N1] | 275.37 | | >10,000 | | |
| 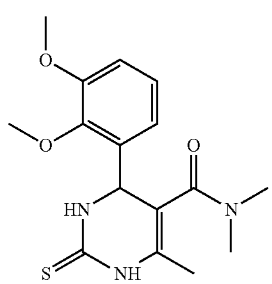 | 335.42 | | >10,000 | | |
| 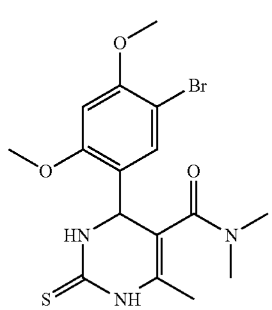 | 414.32 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
| --- | --- | --- | --- | --- | --- |
| 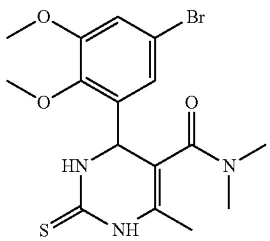 | 414.32 | | >10,000 | | |
| 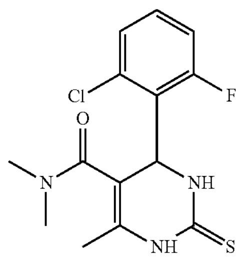 [SMILES: CC1=C(C(=O)N(C)C)C(c2c(F)cccc2Cl)NC(=S)N1] | 327.8 | | >10,000 | | |
| 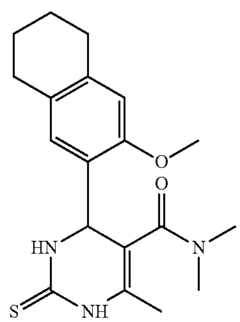 [SMILES: COc1cc2c(cc1C1NC(=S)NC(C)=C1C(=O)N(C)C)CCCC2] | 359.49 | | >10,000 | | |
| 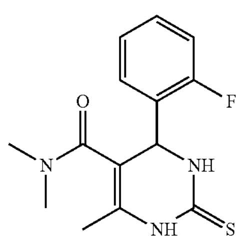 [SMILES: CC1=C(C(=O)N(C)C)C(c2ccccc2F)NC(=S)N1] | 293.36 | | >10,000 | | |
| 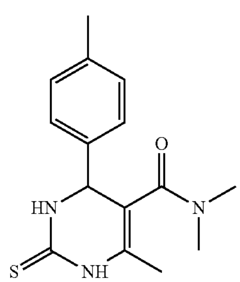 [SMILES: CC1=C(C(=O)N(C)C)C(c2ccc(C)cc2)NC(=S)N1] | 289.4 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| (structure) | 331.22 | ≤1,000 | ≤5,000 | | |
| (structure) | 332.42 | ≤1,000 | ≤5,000 | | |
| (structure) | 354.8 | | ≤10,000 | | |
| (structure) | 348.46 | | >10,000 | | |
| (structure) | 306.38 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 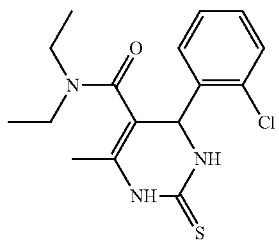 [SMILES: CCN(CC)C(=O)C1=C(C)NC(=S)NC1c1ccccc1Cl] | 337.87 | | >10,000 | | |
| 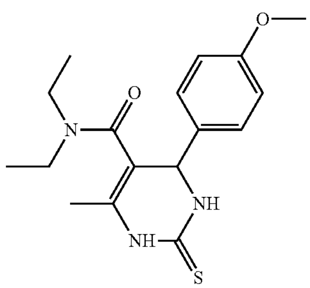 [SMILES: CCN(CC)C(=O)C1=C(C)NC(=S)NC1c1ccc(OC)cc1] | 333.45 | | >10,000 | | |
| 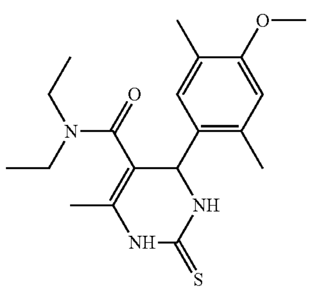 [SMILES: CCN(CC)C(=O)C1=C(C)NC(=S)NC1c1cc(C)c(OC)cc1C] | 361.5 | | >10,000 | | |
| 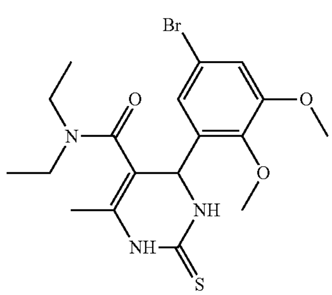 [SMILES: CCN(CC)C(=O)C1=C(C)NC(=S)NC1c1cc(Br)cc(OC)c1OC] | 442.37 | | >10,000 | | |
| 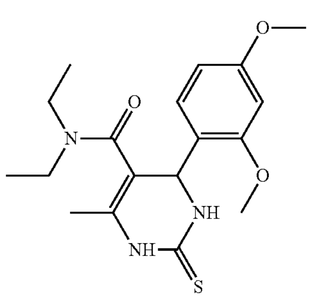 [SMILES: CCN(CC)C(=O)C1=C(C)NC(=S)NC1c1ccc(OC)cc1OC] | 363.47 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 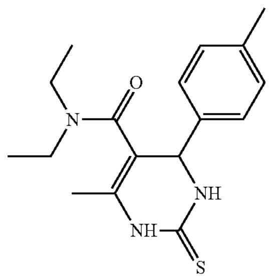 [SMILES: CCN(CC)C(=O)C1=C(C)NC(=S)NC1c1ccc(C)cc1] | 317.45 | | >10,000 | | |
| 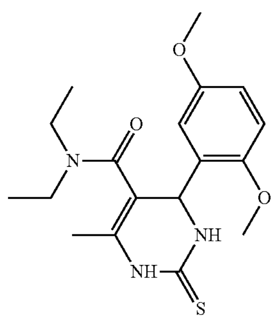 [SMILES: CCN(CC)C(=O)C1=C(C)NC(=S)NC1c1cc(OC)ccc1OC] | 363.47 | | >10,000 | | |
| 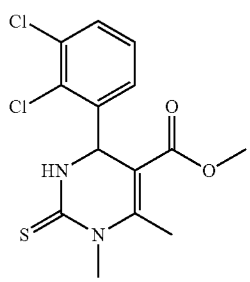 [SMILES: COC(=O)C1=C(C)N(C)C(=S)NC1c1cccc(Cl)c1Cl] | 345.24 | | ≤5,000 | | |
| 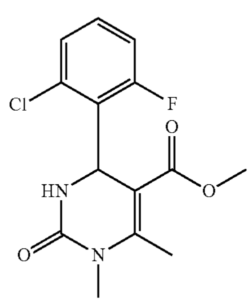 [SMILES: COC(=O)C1=C(C)N(C)C(=O)NC1c1c(F)cccc1Cl] | 312.72 | | >10,000 | | |
| 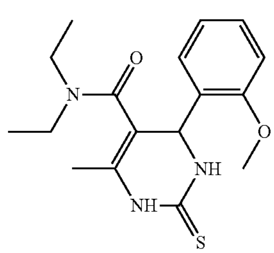 [SMILES: CCN(CC)C(=O)C1=C(C)NC(=S)NC1c1ccccc1OC] | 333.45 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 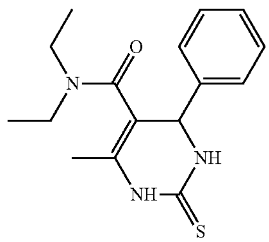 [SMILES: CCN(CC)C(=O)C1=C(C)NC(=S)NC1c1ccccc1] | 303.42 | | >10,000 | | |
| 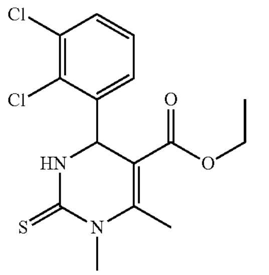 [SMILES: CCOC(=O)C1=C(C)N(C)C(=S)NC1c1cccc(Cl)c1Cl] | 359.27 | | >10,000 | | |
| 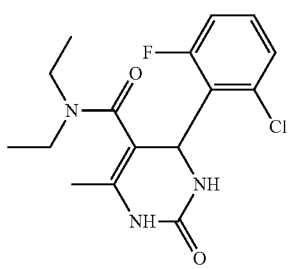 [SMILES: CCN(CC)C(=O)C1=C(C)NC(=O)NC1c1c(F)cccc1Cl] | 339.79 | | >10,000 | | |
| 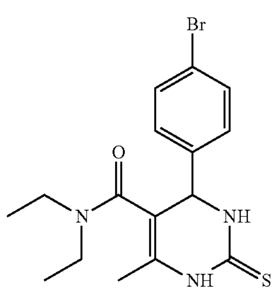 [SMILES: CCN(CC)C(=O)C1=C(C)NC(=S)NC1c1ccc(Br)cc1] | 382.32 | | >10,000 | | |
| 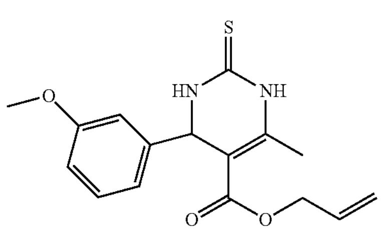 [SMILES: C=CCOC(=O)C1=C(C)NC(=S)NC1c1cccc(OC)c1] | 318.39 | | ≤10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 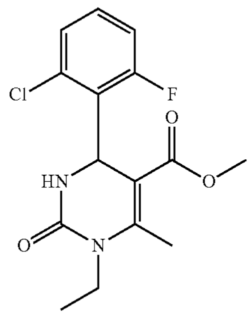 [SMILES: CCN1C(=O)NC(c2c(F)cccc2Cl)C(C(=O)OC)=C1C] | 326.75 | | >10,000 | | |
| 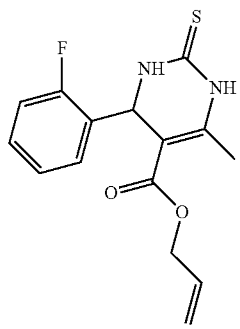 [SMILES: C=CCOC(=O)C1=C(C)NC(=S)NC1c1ccccc1F] | 306.36 | | >10,000 | | |
| 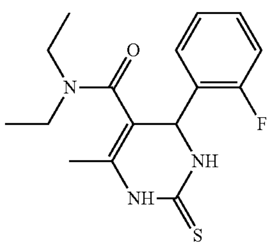 [SMILES: CCN(CC)C(=O)C1=C(C)NC(=S)NC1c1ccccc1F] | 321.41 | | >10,000 | | |
| 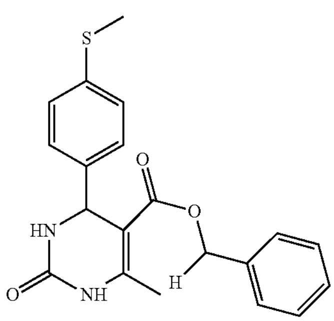 [SMILES: CSc1ccc(C2NC(=O)NC(C)=C2C(=O)OCc2ccccc2)cc1] | 368.45 | | >10,000 | | |
| 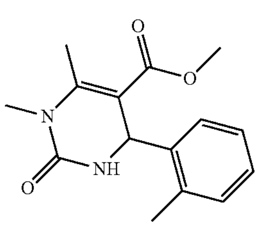 [SMILES: COC(=O)C1=C(C)N(C)C(=O)NC1c1ccccc1C] | 274.32 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 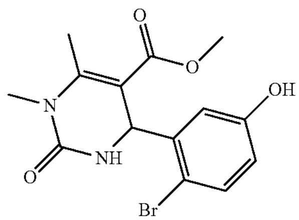 [SMILES: COC(=O)C1=C(C)N(C)C(=O)NC1c1cc(O)ccc1Br] | 355.18 | ≤5,000 | ≤5,000 | | |
| 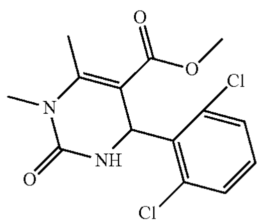 [SMILES: COC(=O)C1=C(C)N(C)C(=O)NC1c1c(Cl)cccc1Cl] | 329.18 | | >10,000 | | |
| 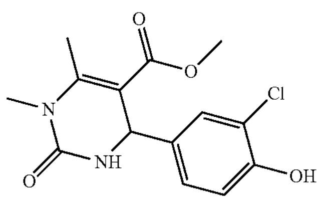 [SMILES: COC(=O)C1=C(C)N(C)C(=O)NC1c1ccc(O)c(Cl)c1] | 310.73 | >10,000 | ≤5,000 | | |
| 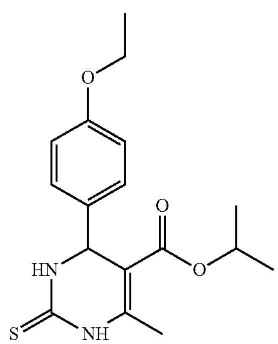 [SMILES: CCOc1ccc(C2NC(=S)NC(C)=C2C(=O)OC(C)C)cc1] | 334.43 | | >10,000 | | |
| 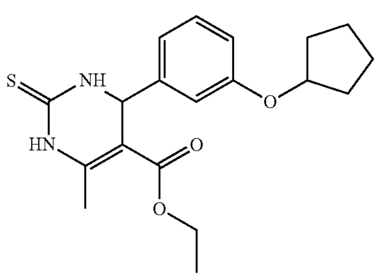 [SMILES: CCOC(=O)C1=C(C)NC(=S)NC1c1cccc(OC2CCCC2)c1] | 360.47 | | ≤5,000 | | |
| 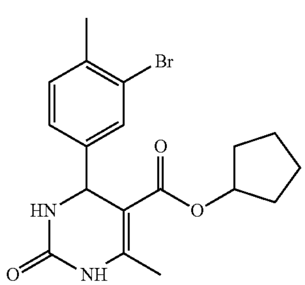 [SMILES: CC1=C(C(=O)OC2CCCC2)C(c2ccc(C)c(Br)c2)NC(=O)N1] | 393.27 | | >10,000 | | |

TABLE 1-continued
| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 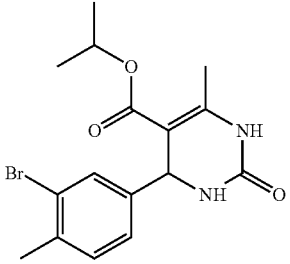 [SMILES: CC1=C(C(=O)OC(C)C)C(c2ccc(C)c(Br)c2)NC(=O)N1] | 367.24 | ≤500 | ≤5,000 | | |
| 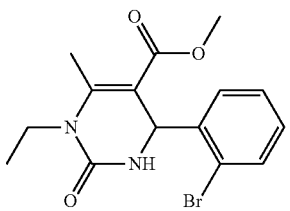 [SMILES: CCN1C(=O)NC(c2ccccc2Br)C(C(=O)OC)=C1C] | 353.21 | | >10,000 | | |
| 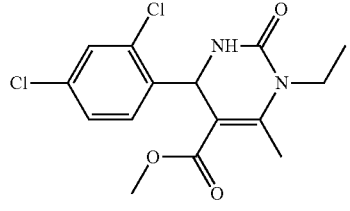 [SMILES: CCN1C(=O)NC(c2ccc(Cl)cc2Cl)C(C(=O)OC)=C1C] | 343.21 | | >10,000 | | |
| 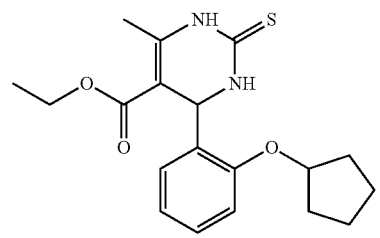 [SMILES: CCOC(=O)C1=C(C)NC(=S)NC1c1ccccc1OC1CCCC1] | 360.47 | | >10,000 | | |
| 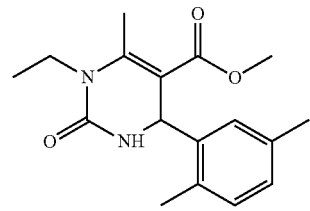 [SMILES: CCN1C(=O)NC(c2cc(C)ccc2C)C(C(=O)OC)=C1C] | 302.37 | | >10,000 | | |
| 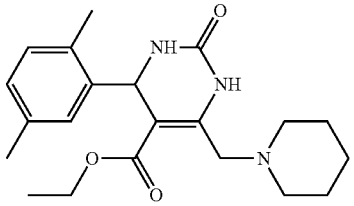 [SMILES: CCOC(=O)C1=C(CN2CCCCC2)NC(=O)NC1c1cc(C)ccc1C] | 371.47 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 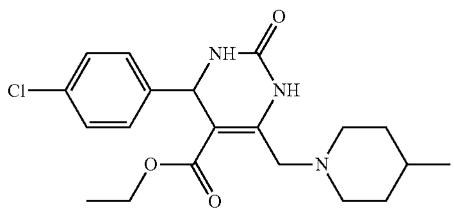 [SMILES: CCOC(=O)C1=C(CN2CCC(C)CC2)NC(=O)NC1c1ccc(Cl)cc1] | 391.89 | | >10,000 | | |
| 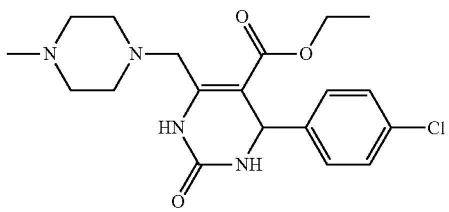 [SMILES: CCOC(=O)C1=C(CN2CCN(C)CC2)NC(=O)NC1c1ccc(Cl)cc1] | 392.88 | | >10,000 | | |
| 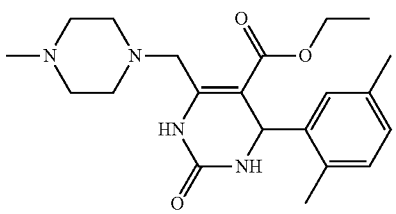 | 386.49 | | >10,000 | | |
| 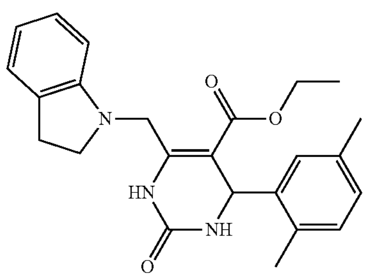 [SMILES: CCOC(=O)C1=C(CN2CCc3ccccc32)NC(=O)NC1c1cc(C)ccc1C] | 405.49 | | >10,000 | | |
| 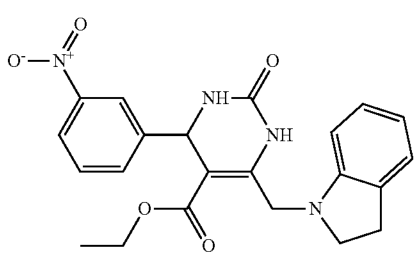 [SMILES: CCOC(=O)C1=C(CN2CCc3ccccc32)NC(=O)NC1c1cccc([N+](=O)[O-])c1] | 422.43 | | >10,000 | | |
| 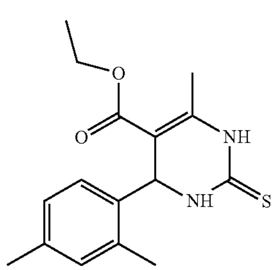 [SMILES: CCOC(=O)C1=C(C)NC(=S)NC1c1ccc(C)cc1C] | 304.41 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 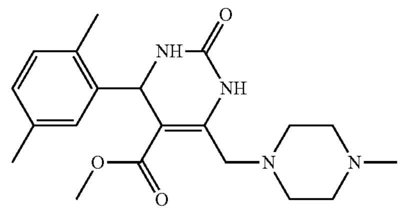 [SMILES: COC(=O)C1=C(CN2CCN(C)CC2)NC(=O)NC1c1cc(C)ccc1C] | 372.46 | | >10,000 | | |
| 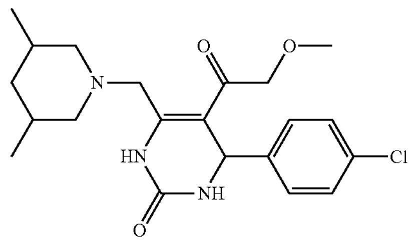 [SMILES: COCC(=O)C1=C(CN2CC(C)CC(C)C2)NC(=O)NC1c1ccc(Cl)cc1] | 405.92 | | >10,000 | | |
| 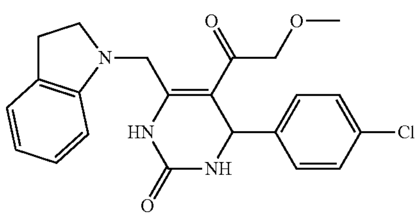 [SMILES: COCC(=O)C1=C(CN2CCc3ccccc32)NC(=O)NC1c1ccc(Cl)cc1] | 411.88 | | ≤10,000 | | |
| 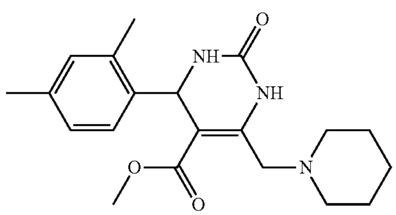 [SMILES: COC(=O)C1=C(CN2CCCCC2)NC(=O)NC1c1ccc(C)cc1C] | 357.45 | | >10,000 | | |
| 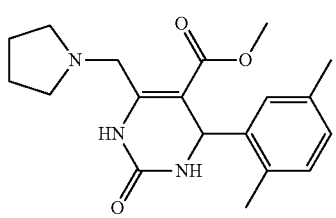 [SMILES: COC(=O)C1=C(CN2CCCC2)NC(=O)NC1c1cc(C)ccc1C] | 343.42 | | >10,000 | | |
| 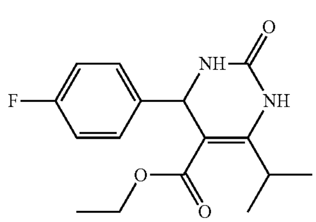 [SMILES: CCOC(=O)C1=C(C(C)C)NC(=O)NC1c1ccc(F)cc1] | 306.33 | | >10,000 | | |
| 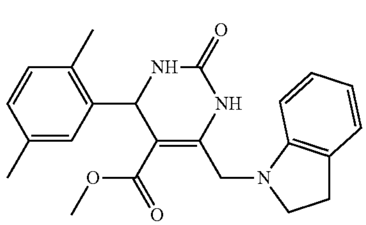 [SMILES: COC(=O)C1=C(CN2CCc3ccccc32)NC(=O)NC1c1cc(C)ccc1C] | 391.46 | | >10,000 | | |

TABLE 1-continued

| Structure | Mol Wt | hTRPA1 Patch IC50 (nM) | hTRPA1 Fluo4 IC50 (nM) | hERG Qpatch IC50 (nM) | hNaV1.2 Qpatch IC50 (nM) |
|---|---|---|---|---|---|
| 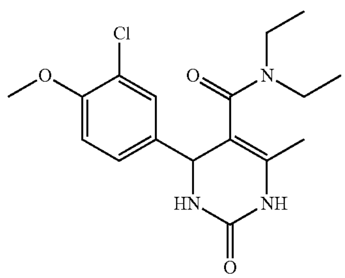 [SMILES: CCN(CC)C(=O)C1=C(C)NC(=O)NC1c1ccc(OC)c(Cl)c1] | 351.83 | | >10,000 | | |
| 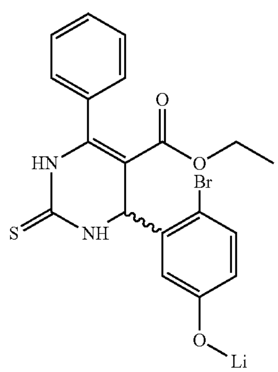 | 439.25 | ≤1,000 | | | |
| 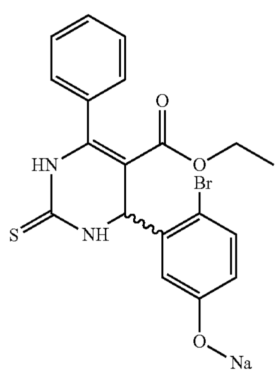 | 455.3 | ≤500 | | | |
| 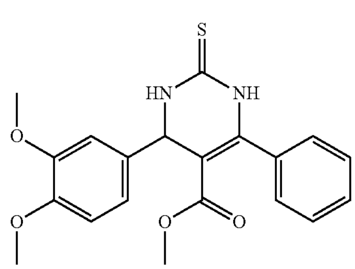 [SMILES: COC(=O)C1=C(c2ccccc2)NC(=S)NC1c1ccc(OC)c(OC)c1] | 384.45 | ≤10,000 | | | |

TABLE 2

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 200 | 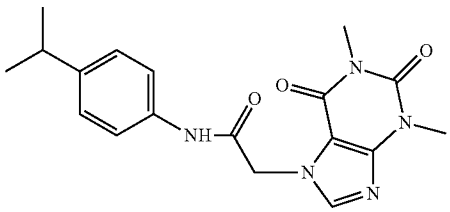 [SMILES: CC(C)c1ccc(NC(=O)Cn2cnc3c2c(=O)n(C)c(=O)n3C)cc1] | 355.4 | ≤5,000 | ≤5,000 | >10,000 (at least 5-fold selective for TRPA1 over TRPV3) | ≥20,000 (at least 20-fold selective for TRPA1 over hERG) | >10,000 (at least 5-fold selective for TRPA1 over TRPV4) | ≥30,000 (at least 25-fold selective for TRPA1 over NaV1.2) |
| 201 | 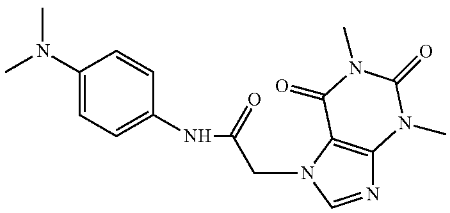 | 356.39 | >10,000 | ≥20,000 | | | | |
| 202 | 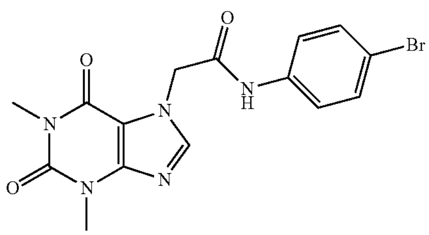 [SMILES: Cn1c(=O)c2c(ncn2CC(=O)Nc2ccc(Br)cc2)n(C)c1=O] | 393.22 | ≤5,000 | ≤5,000 | | >10,000 (at least 5-fold selective for TRPA1 over hERG) | | |
| 203 | 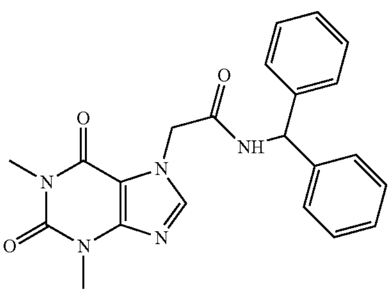 [SMILES: Cn1c(=O)c2c(ncn2CC(=O)NC(c2ccccc2)c2ccccc2)n(C)c1=O] | 403.43 | >10,000 | >10,000 | | | | |
| 204 | 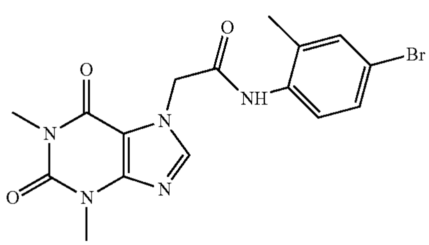 [SMILES: Cc1cc(Br)ccc1NC(=O)Cn1cnc2c1c(=O)n(C)c(=O)n2C] | 406.23 | >10,000 | ≤10,000 | | | | |
| 206 | 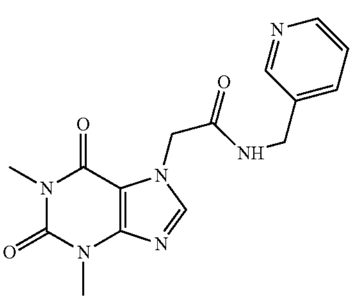 [SMILES: Cn1c(=O)c2c(ncn2CC(=O)NCc2cccnc2)n(C)c1=O] | 328.33 | ≤10,000 | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 207 | 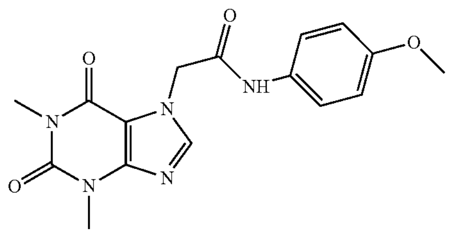 | 343.34 | ≤10,000 | >10,000 | | | | |
| 208 | 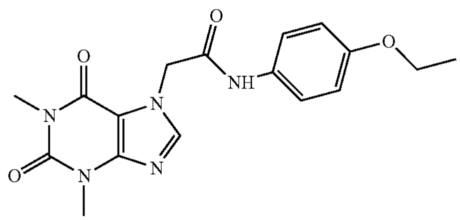 [SMILES: CCOc1ccc(NC(=O)Cn2cnc3c2c(=O)n(C)c(=O)n3C)cc1] | 357.36 | >10,000 | ≤10,000 | | | | |
| 209 | 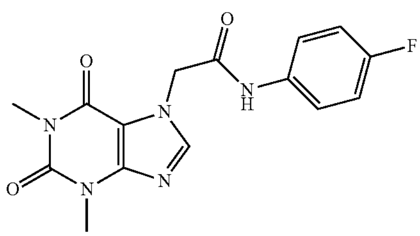 [SMILES: Cn1c(=O)c2c(ncn2CC(=O)Nc2ccc(F)cc2)n(C)c1=O] | 332.31 | >10,000 | ≤10,000 | | | | |
| 210 | 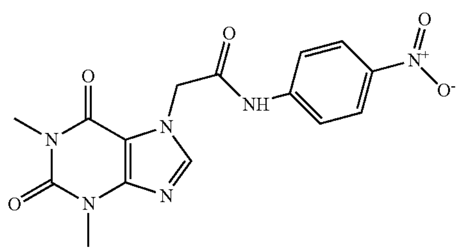 [SMILES: Cn1c(=O)c2c(ncn2CC(=O)Nc2ccc([N+](=O)[O-])cc2)n(C)c1=O] | 358.31 | ≤10,000 | ≥20,000 | | | | |
| 211 | 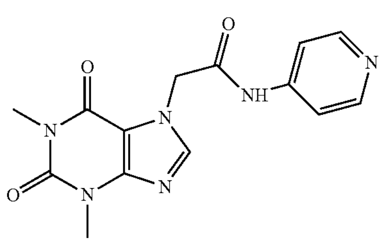 [SMILES: Cn1c(=O)c2c(ncn2CC(=O)Nc2ccncc2)n(C)c1=O] | 314.3 | >10,000 | >10,000 | | | | |
| 212 | 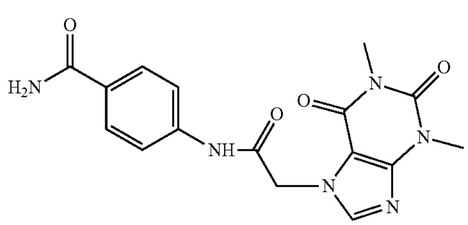 [SMILES: Cn1c(=O)c2c(ncn2CC(=O)Nc2ccc(C(N)=O)cc2)n(C)c1=O] | 356.34 | >10,000 | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 213 | 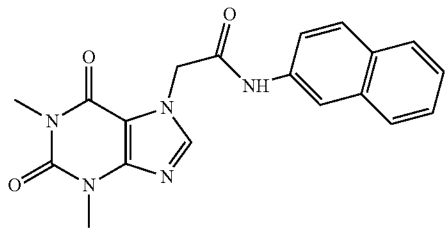 [SMILES: Cn1c(=O)c2c(ncn2CC(=O)Nc2ccc3ccccc3c2)n(C)c1=O] | 363.37 | >10,000 | ≤10,000 | | | | |
| 214 | 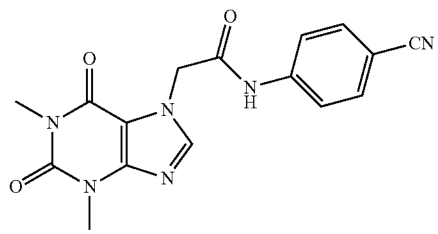 [SMILES: Cn1c(=O)c2c(ncn2CC(=O)Nc2ccc(C#N)cc2)n(C)c1=O] | 339.33 | ≤10,000 | ≤10,000 | | | | |
| 215 | 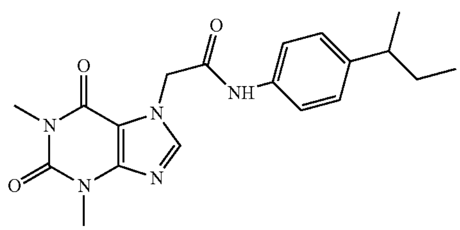 [SMILES: CCC(C)c1ccc(NC(=O)Cn2cnc3c2c(=O)n(C)c(=O)n3C)cc1] | 369.42 | ≤1,000 | ≤5,000 | | ≥10,000 (at least 25-fold selective for TRPA1 over hERG) | | ≥30,000 (at least 55-fold selective for TRPA1 over NaV1.2) |
| 216 | 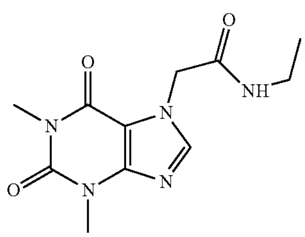 [SMILES: CCNC(=O)Cn1cnc2c1c(=O)n(C)c(=O)n2C] | 265.27 | | >10,000 | | | | |
| 217 | 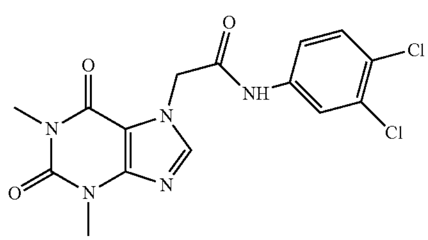 [SMILES: Cn1c(=O)c2c(ncn2CC(=O)Nc2ccc(Cl)c(Cl)c2)n(C)c1=O] | 382.2 | ≤1,000 | ≤10,000 | | ≥20,000 (at least 45-fold selective for TRPA1 over hERG) | | ≥30,000 (at least 50-fold selective for TRPA1 over NaV1.2) |
| 218 | 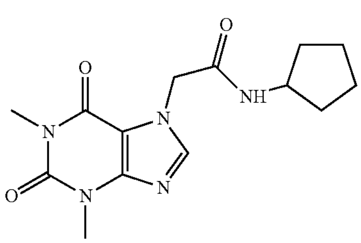 [SMILES: Cn1c(=O)c2c(ncn2CC(=O)NC2CCCC2)n(C)c1=O] | 305.33 | | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 219 | 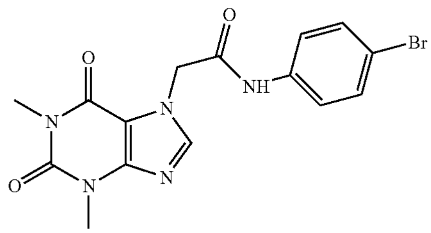 [SMILES: Cn1c(=O)c2c(ncn2CC(=O)Nc2ccc(Br)cc2)n(C)c1=O] | 392.21 | ≤5,000 | ≤5,000 | | ≥20,000 (at least 15-fold selective for TRPA1 over hERG) | | ≥30,000 (at least 25-fold selective for TRPA1 over NaV1.2) |
| 220 | 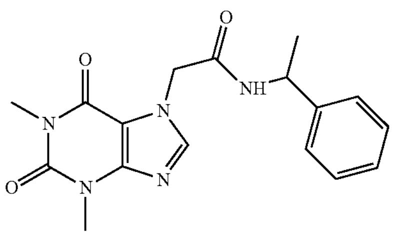 [SMILES: CC(NC(=O)Cn1cnc2c1c(=O)n(C)c(=O)n2C)c1ccccc1] | 341.36 | | >10,000 | | | | |
| 221 | 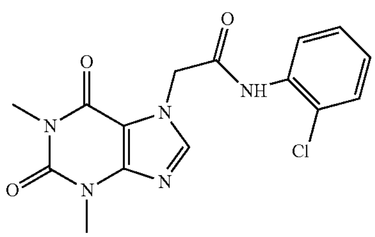 [SMILES: Cn1c(=O)c2c(ncn2CC(=O)Nc2ccccc2Cl)n(C)c1=O] | 347.76 | | >10,000 | | | | |
| 222 | 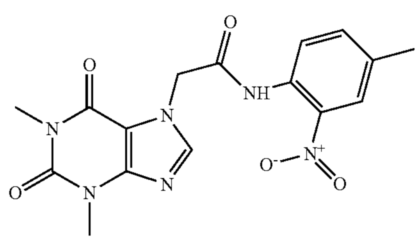 | 372.34 | | >10,000 | | | | |
| 223 | 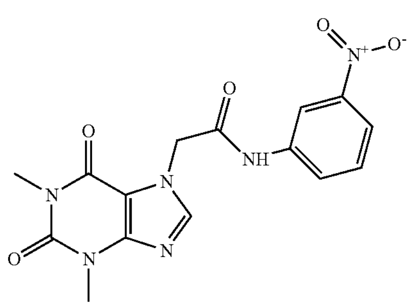 [SMILES: Cn1c(=O)c2c(ncn2CC(=O)Nc2cccc([N+](=O)[O-])c2)n(C)c1=O] | 358.31 | | ≤10,000 | | | | |
| 224 | 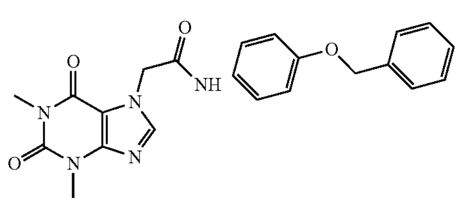 | 419.43 | ≤5,000 | ≤1,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 225 | 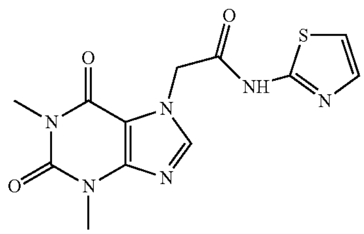 [SMILES: Cn1c(=O)c2c(ncn2CC(=O)Nc2nccs2)n(C)c1=O] | 320.33 | >10,000 | >10,000 | | | | |
| 226 | 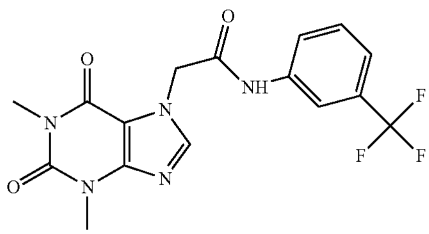 [SMILES: Cn1c(=O)c2c(ncn2CC(=O)Nc2cccc(C(F)(F)F)c2)n(C)c1=O] | 381.31 | ≤10,000 | ≤5,000 | | >10,000 (at least 2-fold selective for TRPA1 over hERG) | | ≥30,000 (at least 5-fold selective for TRPA1 over NaV1.2) |
| 227 | 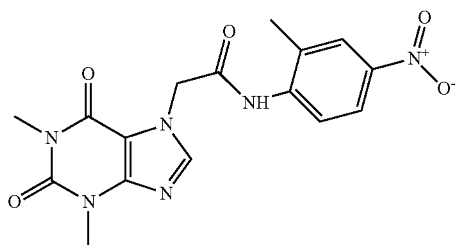 [SMILES: Cc1cc([N+](=O)[O-])ccc1NC(=O)Cn1cnc2c1c(=O)n(C)c(=O)n2C] | 372.34 | | ≥30,000 | | | | |
| 228 | 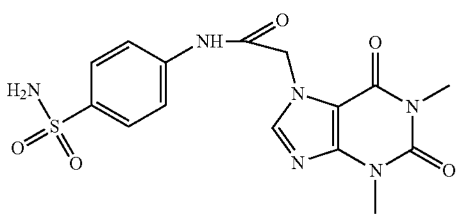 [SMILES: Cn1c(=O)c2c(ncn2CC(=O)Nc2ccc(S(N)(=O)=O)cc2)n(C)c1=O] | 392.39 | >10,000 | >10,000 | | | | |
| 229 | 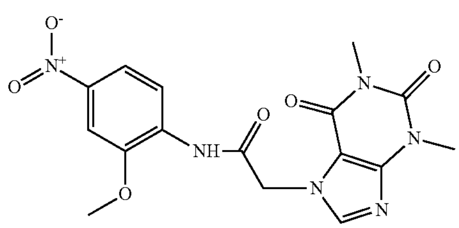 [SMILES: COc1cc([N+](=O)[O-])ccc1NC(=O)Cn1cnc2c1c(=O)n(C)c(=O)n2C] | 388.33 | ≤1,000 | ≤5,000 | | | | |
| 230 | 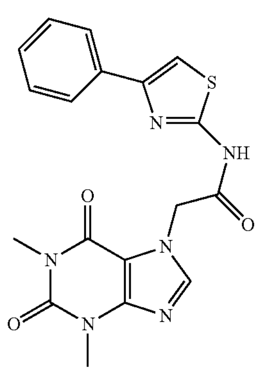 [SMILES: Cn1c(=O)c2c(ncn2CC(=O)Nc2nc(-c3ccccc3)cs2)n(C)c1=O] | 396.42 | ≤10,000 | ≤10,000 | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 231 | 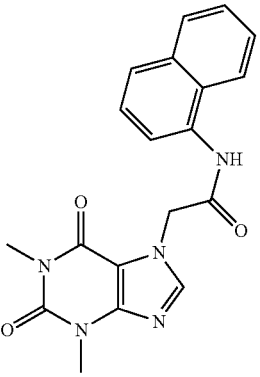 [SMILES: Cn1c(=O)c2c(ncn2CC(=O)Nc2cccc3ccccc23)n(C)c1=O] | 363.37 | >10,000 | | | | | |
| 232 | 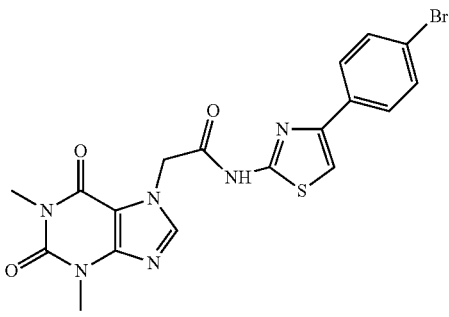 [SMILES: Cn1c(=O)c2c(ncn2CC(=O)Nc2nc(-c3ccc(Br)cc3)cs2)n(C)c1=O] | 475.32 | ≤500 | ≤1,000 | | ≥30,000 (at least 75-fold selective for TRPA1 over hERG) | | ≥30,000 (at least 75-fold selective for TRPA1 over NaV1.2) |
| 233 | 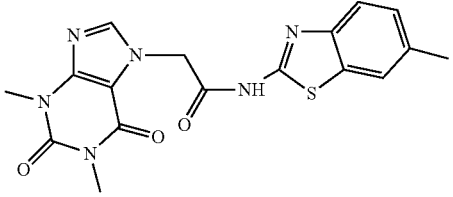 | 384.41 | ≤5,000 | ≤5,000 | | | | |
| 234 | 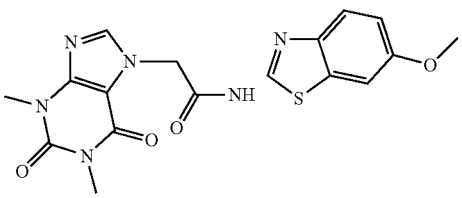 | 400.41 | ≤10,000 | ≤5,000 | | | | |
| 235 | 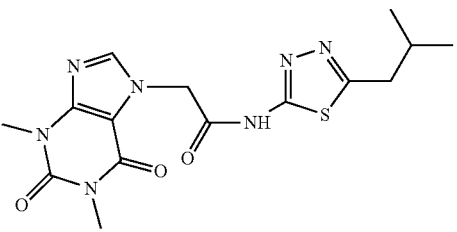 [SMILES: CC(C)Cc1nnc(NC(=O)Cn2cnc3c2c(=O)n(C)c(=O)n3C)s1] | 377.42 | ≤10,000 | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 236 | 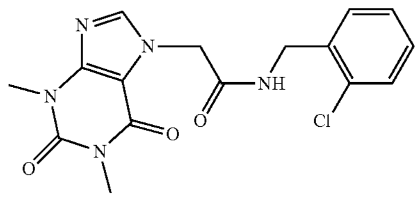 [SMILES: Cn1c(=O)c2c(ncn2CC(=O)NCc2ccccc2Cl)n(C)c1=O] | 361.78 | >10,000 | | | | | |
| 237 | 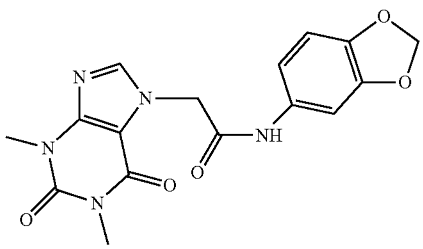 [SMILES: Cn1c(=O)c2c(ncn2CC(=O)Nc2ccc3c(c2)OCO3)n(C)c1=O] | 357.32 | ≤10,000 | >10,000 | | | | |
| 238 | 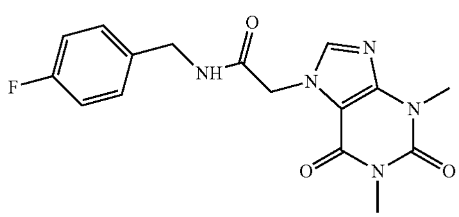 [SMILES: Cn1c(=O)c2c(ncn2CC(=O)NCc2ccc(F)cc2)n(C)c1=O] | 345.33 | | >10,000 | | | | |
| 239 | 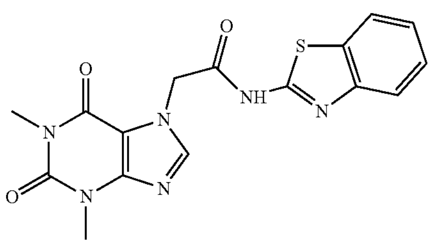 [SMILES: Cn1c(=O)c2c(ncn2CC(=O)Nc2nc3ccccc3s2)n(C)c1=O] | 370.39 | ≤5,000 | ≤5,000 | ≤10,000 (at least 4-fold selective for TRPA1 over TRPV3) | | | |
| 240 | 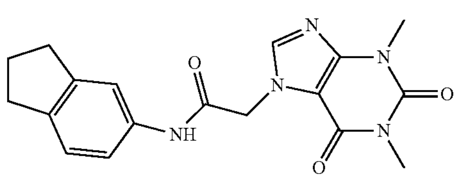 [SMILES: Cn1c(=O)c2c(ncn2CC(=O)Nc2ccc3c(c2)CCC3)n(C)c1=O] | 353.38 | ≤5,000 | | | | | |
| 241 | 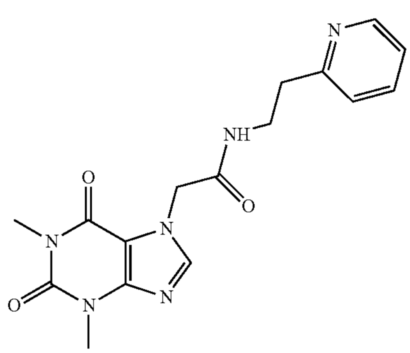 [SMILES: Cn1c(=O)c2c(ncn2CC(=O)NCCc2ccccn2)n(C)c1=O] | 342.35 | | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 242 | 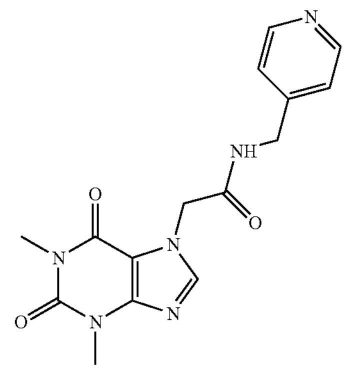 [SMILES: Cn1c(=O)c2c(ncn2CC(=O)NCc2ccncc2)n(C)c1=O] | 328.33 | >10,000 | | | | | |
| 243 | 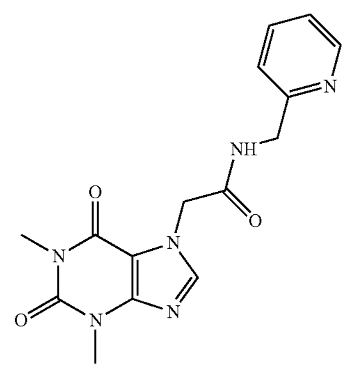 [SMILES: Cn1c(=O)c2c(ncn2CC(=O)NCc2ccccn2)n(C)c1=O] | 328.33 | >10,000 | | | | | |
| 245 | 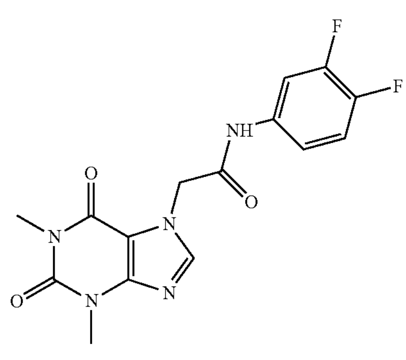 [SMILES: Cn1c(=O)c2c(ncn2CC(=O)Nc2ccc(F)c(F)c2)n(C)c1=O] | 349.29 | ≤10,000 | | | | | |
| 246 | 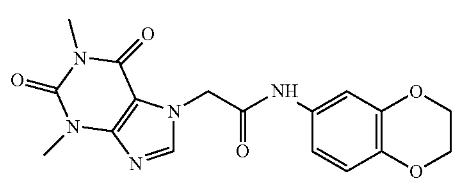 [SMILES: Cn1c(=O)c2c(ncn2CC(=O)Nc2ccc3c(c2)OCCO3)n(C)c1=O] | 371.35 | >10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 247 | 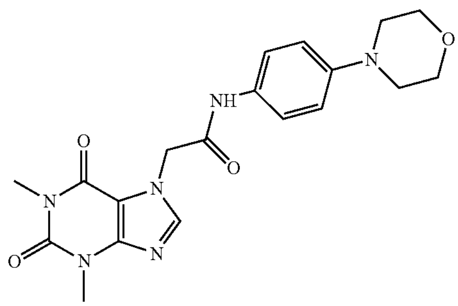 [SMILES: Cn1c(=O)c2c(ncn2CC(=O)Nc2ccc(N3CCOCC3)cc2)n(C)c1=O] | 398.42 | | ≤5,000 | | | | |
| 248 | 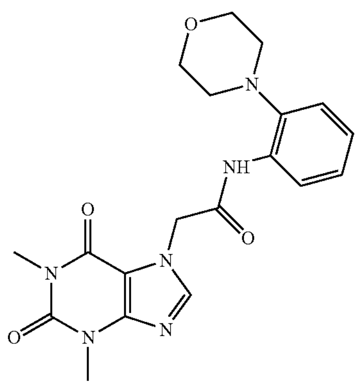 [SMILES: Cn1c(=O)c2c(ncn2CC(=O)Nc2ccccc2N2CCOCC2)n(C)c1=O] | 398.42 | | >10,000 | | | | |
| 249 | 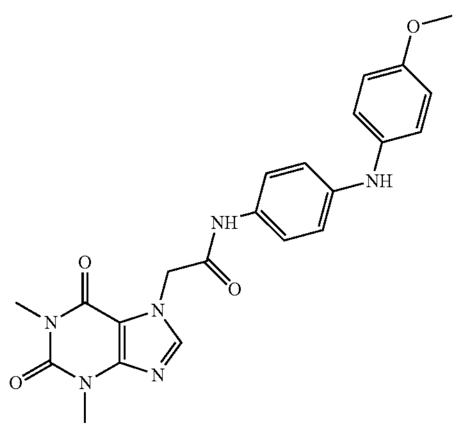 | 434.45 | | ≥20,000 | | | | |
| 250 | 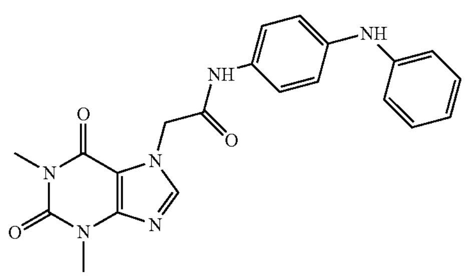 [SMILES: Cn1c(=O)c2c(ncn2CC(=O)Nc2ccc(Nc3ccccc3)cc2)n(C)c1=O] | 404.42 | ≤1,000 | ≤5,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 251 | 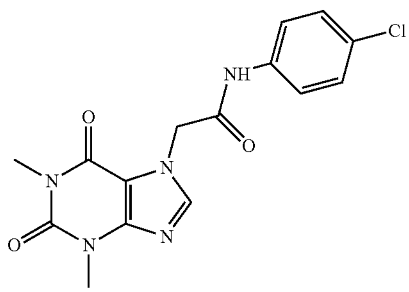 [SMILES: Cn1c(=O)c2c(ncn2CC(=O)Nc2ccc(Cl)cc2)n(C)c1=O] | 347.76 | ≤1,000 | ≤5,000 | | | | |
| 252 | 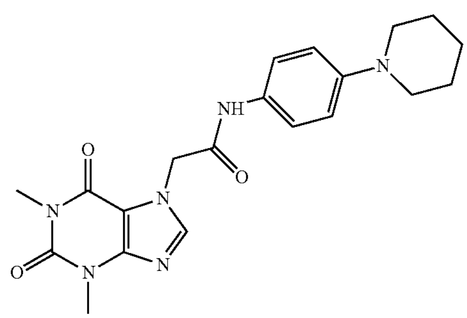 [SMILES: Cn1c(=O)c2c(ncn2CC(=O)Nc2ccc(N3CCCCC3)cc2)n(C)c1=O] | 396.44 | ≤10,000 | ≤5,000 | | | | |
| 253 | 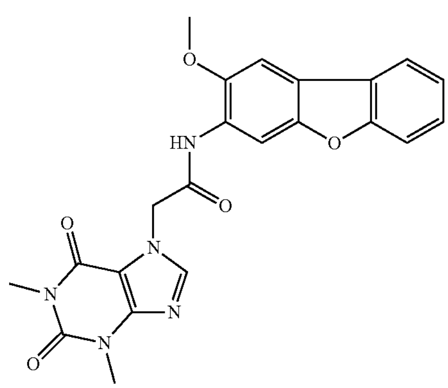 [SMILES: COc1cc2c(cc1NC(=O)Cn1cnc3c1c(=O)n(C)c(=O)n3C)oc1ccccc12] | 433.42 | >10,000 | | | | | |
| 254 | 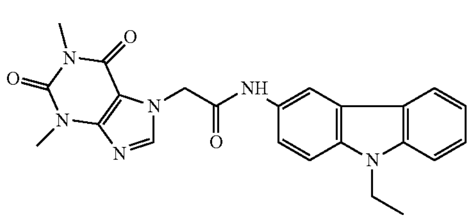 [SMILES: CCn1c2ccccc2c2cc(NC(=O)Cn3cnc4c3c(=O)n(C)c(=O)n4C)ccc21] | 430.46 | >10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 255 | 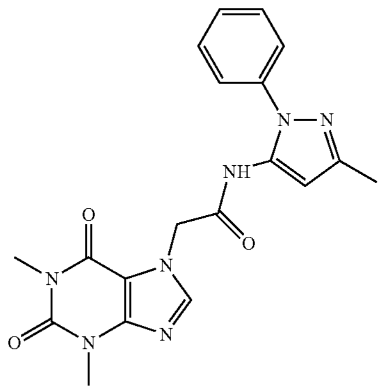 | 393.4 | | ≥20,000 | | | | |
| 256 | 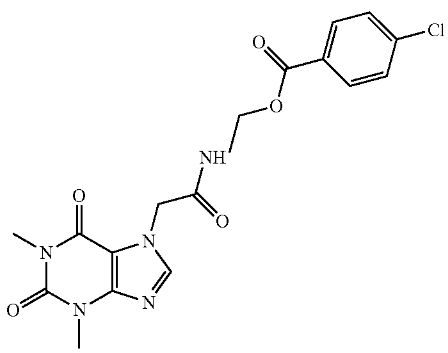 | 419.82 | | >10,000 | | | | |
| 257 | 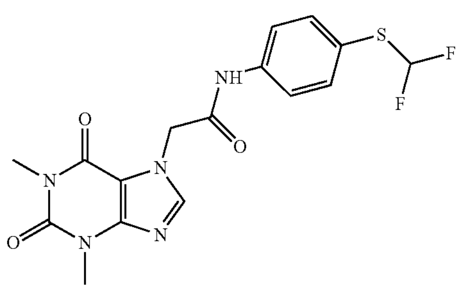 [SMILES: Cn1c(=O)c2c(ncn2CC(=O)Nc2ccc(SC(F)F)cc2)n(C)c1=O] | 395.38 | ≤1,000 | ≤1,000 | | | | |
| 258 | 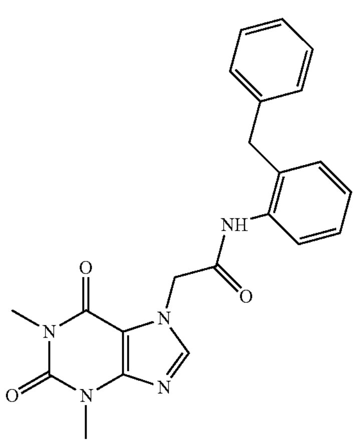 [SMILES: Cn1c(=O)c2c(ncn2CC(=O)Nc2ccccc2Cc2ccccc2)n(C)c1=O] | 403.43 | | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 259 | 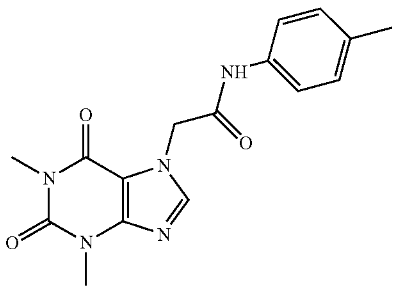 | 327.34 | | >10,000 | | | | |
| 260 | 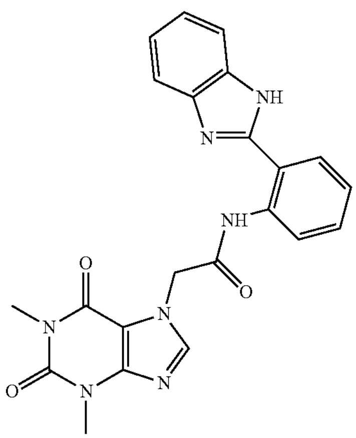 [SMILES: Cn1c(=O)c2c(ncn2CC(=O)Nc2ccccc2-c2nc3ccccc3[nH]2)n(C)c1=O] | 429.43 | | >10,000 | | | | |
| 261 | 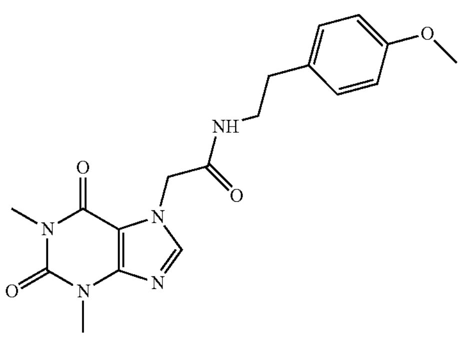 | 371.39 | ≤5,000 | ≤5,000 | | | | |
| 262 | 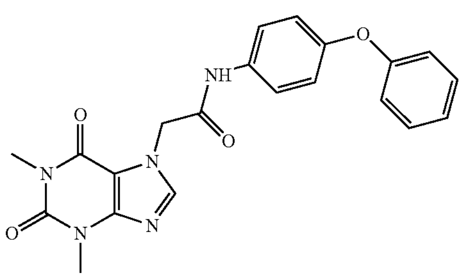 [SMILES: Cn1c(=O)c2c(ncn2CC(=O)Nc2ccc(Oc3ccccc3)cc2)n(C)c1=O] | 405.41 | ≤500 | ≤5,000 | | | | |

TABLE 2-continued

| Cmpd ID | Structure | Mol Wt | hTRPA1 Patch Inwd IC50 (nM) | hTRPA1 Fluor IC50 (nM) | hTRPV3 Pl inward IC50 (nM) | hERG IC50 (nM) | hTRPV4 IC50 (nM) | hNaV1.2 IC50 (nM) |
|---|---|---|---|---|---|---|---|---|
| 263 | 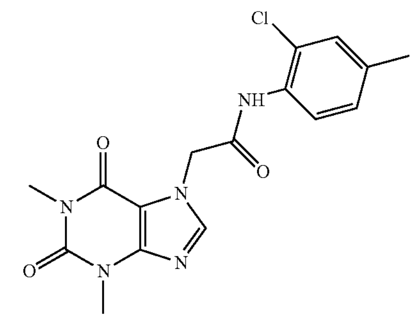 | 361.78 | | >10,000 | | | | |
| 264 | 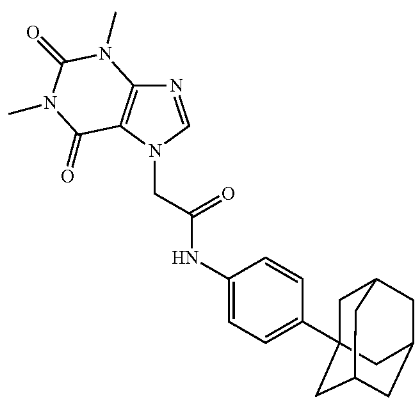 [SMILES: Cn1c(=O)c2c(ncn2CC(=O)Nc2ccc(C34CC5CC(CC(C5)C3)C4)cc2)n(C)c1=O] | 447.53 | ≤500 | ≤5,000 | | | | |
| 265 | 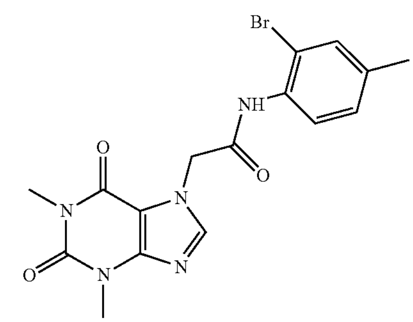 | 406.23 | | ≥20,000 | | | | |
| 266 | 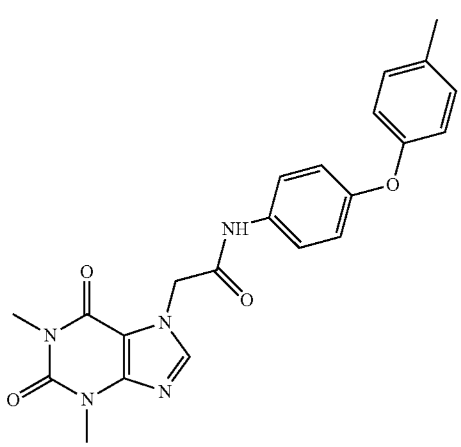 [SMILES: Cc1ccc(Oc2ccc(NC(=O)Cn3cnc4c3c(=O)n(C)c(=O)n4C)cc2)cc1] | 419.43 | ≤500 | ≤5,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 267 | 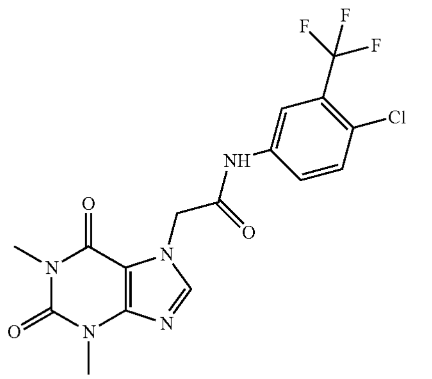 [SMILES: Cn1c(=O)c2c(ncn2CC(=O)Nc2ccc(Cl)c(C(F)(F)F)c2)n(C)c1=O] | 415.75 | ≤1,000 | ≤1,000 | | | | |
| 268 | 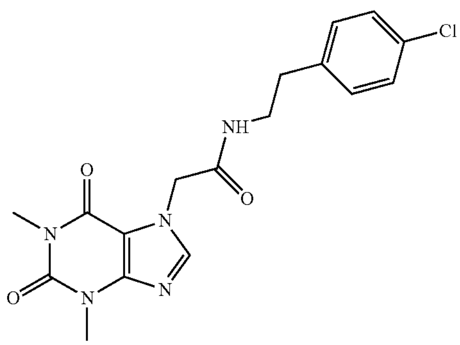 [SMILES: Cn1c(=O)c2c(ncn2CC(=O)NCCc2ccc(Cl)cc2)n(C)c1=O] | 375.81 | ≤1,000 | >10,000 | | | | |
| 269 | 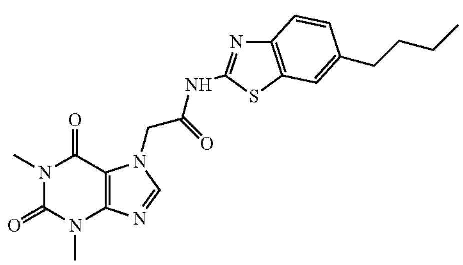 [SMILES: CCCCc1ccc2nc(NC(=O)Cn3cnc4c3c(=O)n(C)c(=O)n4C)sc2c1] | 426.49 | ≤1,000 | ≤5,000 | | | | |
| 270 | 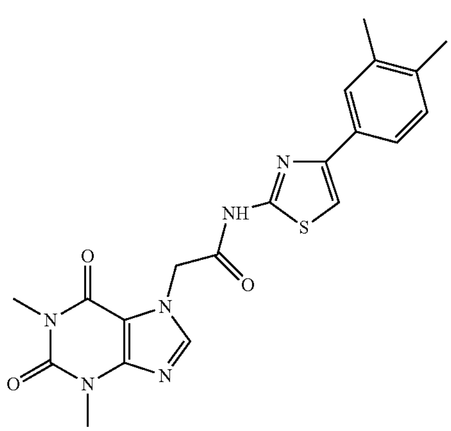 | 424.48 | | >10,000 | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 271 | 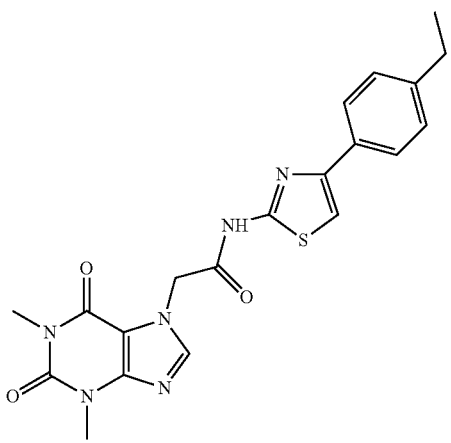 [SMILES: CCc1ccc(-c2csc(NC(=O)Cn3cnc4c3c(=O)n(C)c(=O)n4C)n2)cc1] | 424.48 | ≤500 | ≤5,000 | | ≥30,000 (at least 150-fold selective for TRPA1 over hERG) | | |
| 272 | 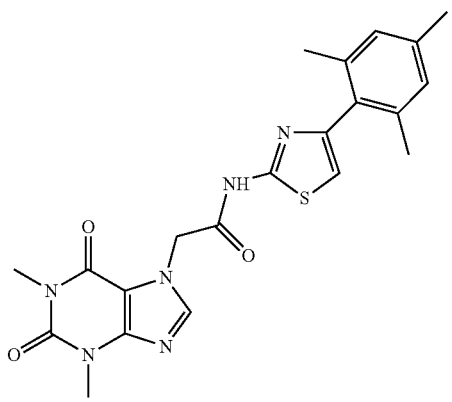 | 438.5 | >10,000 | | | | | |
| 273 | 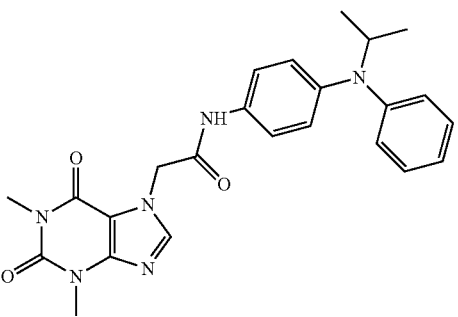 [SMILES: CC(C)N(c1ccccc1)c1ccc(NC(=O)Cn2cnc3c2c(=O)n(C)c(=O)n3C)cc1] | 446.5 | ≤10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 274 | 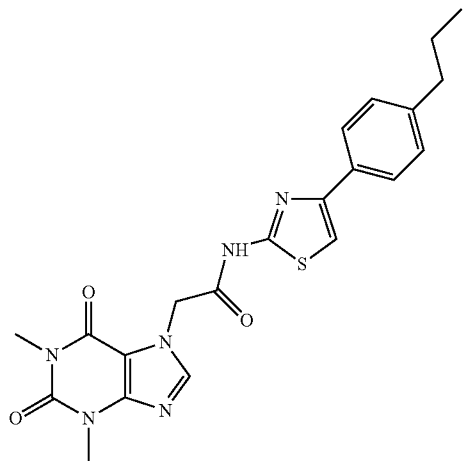 [SMILES: CCCc1ccc(-c2csc(NC(=O)Cn3cnc4c3c(=O)n(C)c(=O)n4C)n2)cc1] | 438.5 | ≤1,000 | ≤5,000 | | | | |
| 275 | 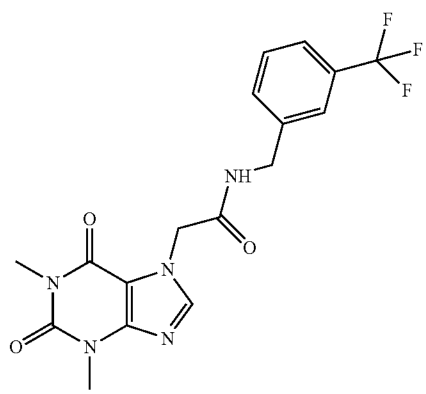 [SMILES: Cn1c(=O)c2c(ncn2CC(=O)NCc2cccc(C(F)(F)F)c2)n(C)c1=O] | 395.34 | | >10,000 | | | | |
| 276 | 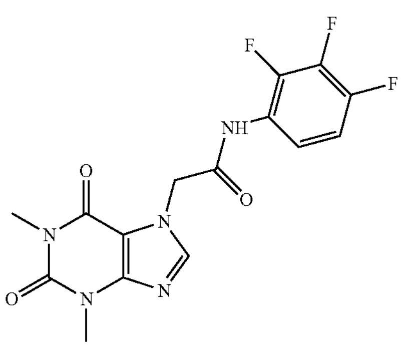 [SMILES: Cn1c(=O)c2c(ncn2CC(=O)Nc2ccc(F)c(F)c2F)n(C)c1=O] | 367.28 | | >10,000 | | | | |
| 277 | 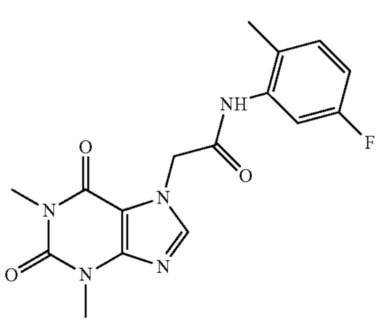 [SMILES: Cc1ccc(F)cc1NC(=O)Cn1cnc2c1c(=O)n(C)c(=O)n2C] | 345.33 | ≤10,000 | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 278 | 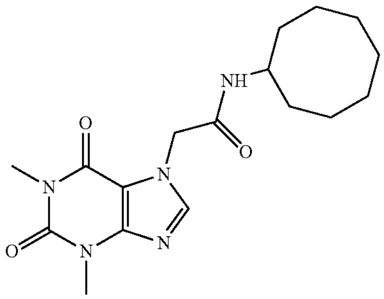 [SMILES: Cn1c(=O)c2c(ncn2CC(=O)NC2CCCCCCC2)n(C)c1=O] | 347.41 | | >10,000 | | | | |
| 279 | 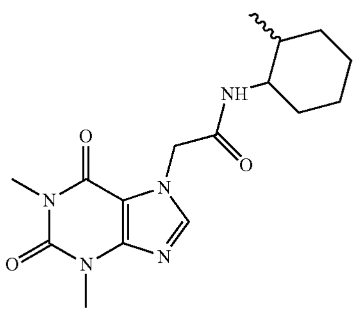 [SMILES: CC1CCCCC1NC(=O)Cn1cnc2c1c(=O)n(C)c(=O)n2C] | 333.39 | | >10,000 | | | | |
| 280 | 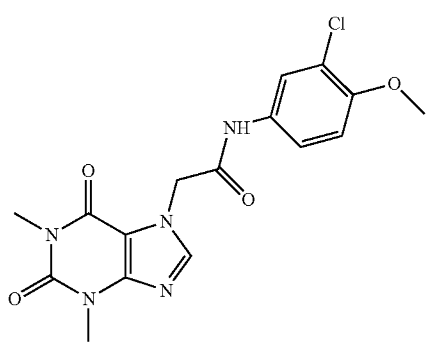 | 377.78 | | ≤10,000 | | | | |
| 281 | 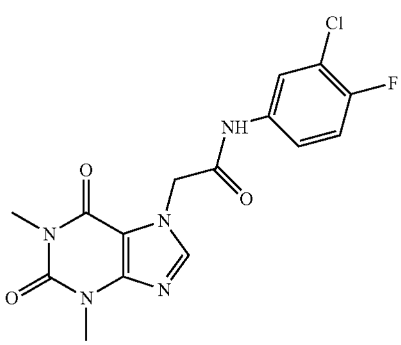 [SMILES: Cn1c(=O)c2c(ncn2CC(=O)Nc2ccc(F)c(Cl)c2)n(C)c1=O] | 365.75 | ≤10,000 | ≤5,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 282 | 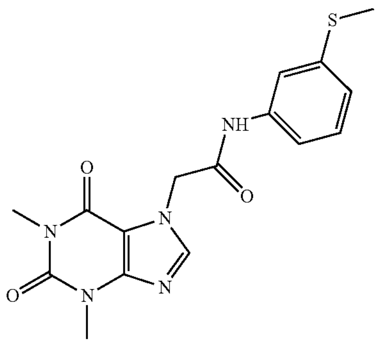 | 359.4 | | ≤10,000 | | | | |
| 283 | 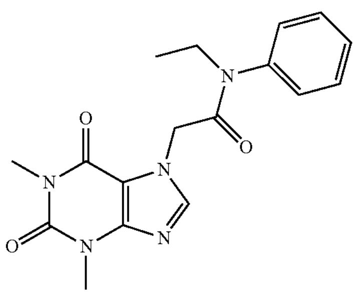 [SMILES: CCN(C(=O)Cn1cnc2c1c(=O)n(C)c(=O)n2C)c1ccccc1] | 341.36 | | >10,000 | | | | |
| 284 | 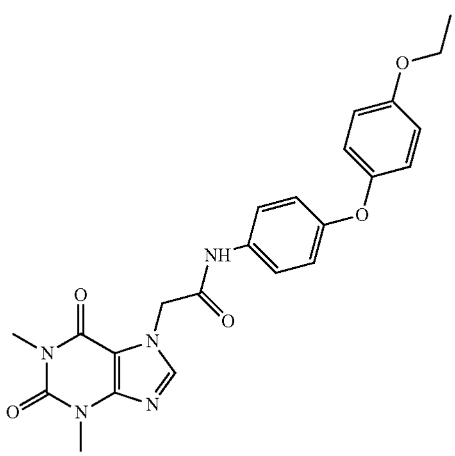 [SMILES: CCOc1ccc(Oc2ccc(NC(=O)Cn3cnc4c3c(=O)n(C)c(=O)n4C)cc2)cc1] | 449.46 | ≤500 | ≤5,000 | | ≤5,000 (at least 10-fold selective for TRPA1 over hERG) | | |
| 285 | 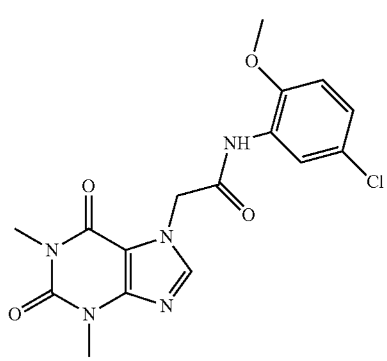 [SMILES: COc1ccc(Cl)cc1NC(=O)Cn1cnc2c1c(=O)n(C)c(=O)n2C] | 377.78 | | ≤5,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 286 | 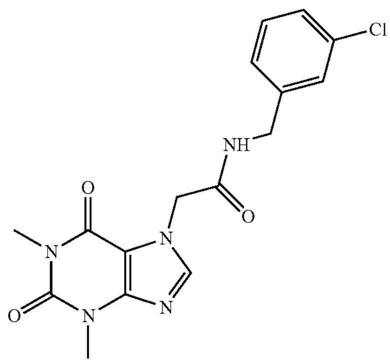 [SMILES: Cn1c(=O)c2c(ncn2CC(=O)NCc2cccc(Cl)c2)n(C)c1=O] | 361.78 | >10,000 | | | | | |
| 287 | 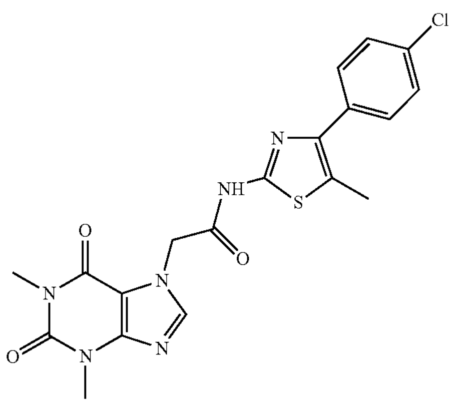 [SMILES: Cc1sc(NC(=O)Cn2cnc3c2c(=O)n(C)c(=O)n3C)nc1-c1ccc(Cl)cc1] | 444.89 | ≤10,000 | | | | | |
| 288 | 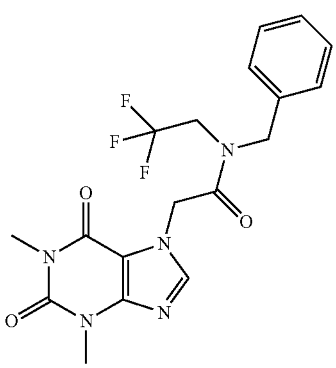 [SMILES: Cn1c(=O)c2c(ncn2CC(=O)N(Cc2ccccc2)CC(F)(F)F)n(C)c1=O] | 409.36 | >10,000 | | | | | |
| 289 | 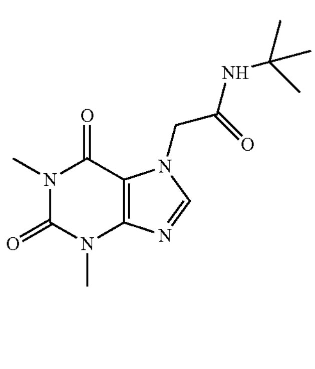 [SMILES: Cn1c(=O)c2c(ncn2CC(=O)NC(C)(C)C)n(C)c1=O] | 293.32 | >10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 290 | 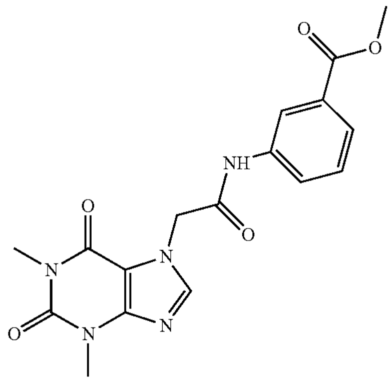 | 371.35 | ≤10,000 | | | | | |
| 291 | 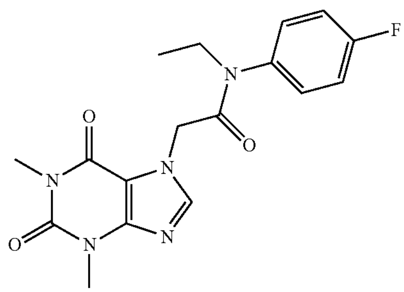 [SMILES: CCN(C(=O)Cn1cnc2c1c(=O)n(C)c(=O)n2C)c1ccc(F)cc1] | 359.35 | ≤5,000 | | | | | |
| 292 | 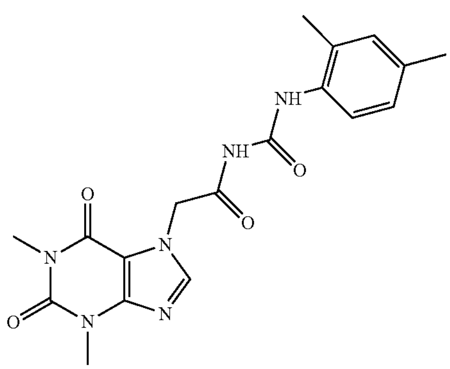 | 384.39 | >10,000 | | | | | |
| 293 | 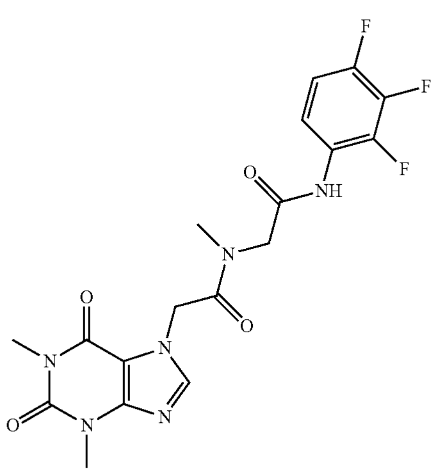 [SMILES: CN(CC(=O)Nc1ccc(F)c(F)c1F)C(=O)Cn1cnc2c1c(=O)n(C)c(=O)n2C] | 438.36 | >10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 294 | 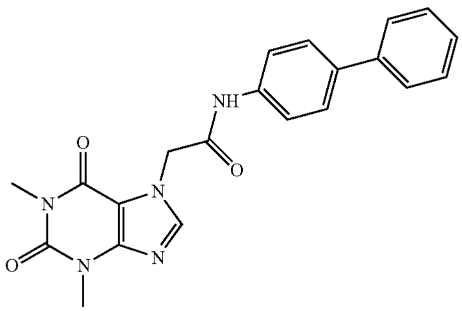 [SMILES: Cn1c(=O)c2c(ncn2CC(=O)Nc2ccc(-c3ccccc3)cc2)n(C)c1=O] | 389.41 | ≤1,000 | ≤5,000 | | | | |
| 295 | 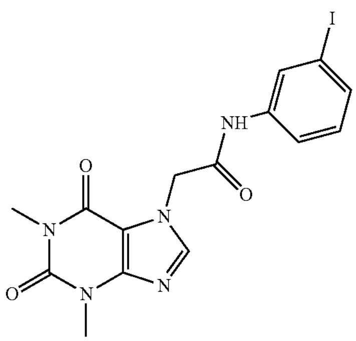 [SMILES: Cn1c(=O)c2c(ncn2CC(=O)Nc2cccc(I)c2)n(C)c1=O] | 439.21 | ≤1,000 | ≤5,000 | | | | |
| 296 | 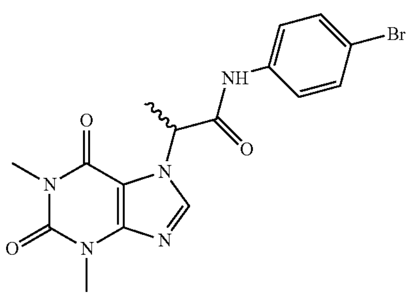 [SMILES: CC(C(=O)Nc1ccc(Br)cc1)n1cnc2c1c(=O)n(C)c(=O)n2C] | 406.23 | ≤10,000 | ≤5,000 | | | | |
| 297 | 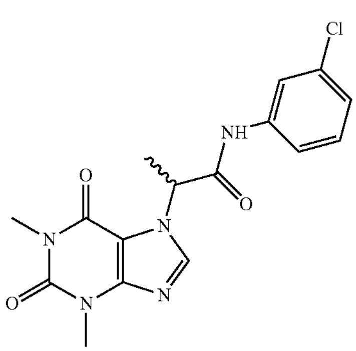 [SMILES: CC(C(=O)Nc1cccc(Cl)c1)n1cnc2c1c(=O)n(C)c(=O)n2C] | 361.78 | >10,000 | | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 298 | 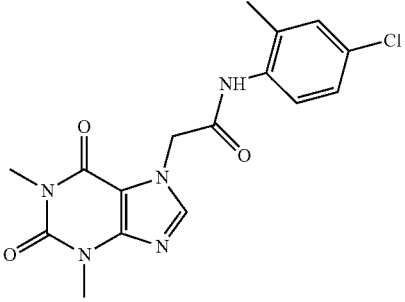 [SMILES: Cc1cc(Cl)ccc1NC(=O)Cn1cnc2c1c(=O)n(C)c(=O)n2C] | 361.78 | | >10,000 | | | | |
| 299 | 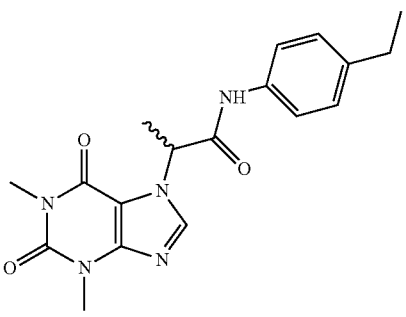 [SMILES: CCc1ccc(NC(=O)C(C)n2cnc3c2c(=O)n(C)c(=O)n3C)cc1] | 355.39 | ≤10,000 | ≤5,000 | | | | |
| 300 | 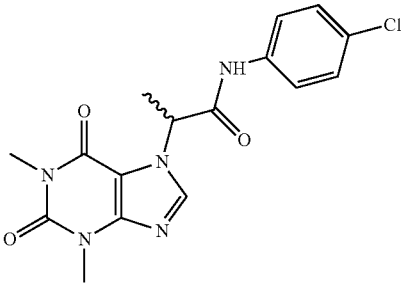 [SMILES: CC(C(=O)Nc1ccc(Cl)cc1)n1cnc2c1c(=O)n(C)c(=O)n2C] | 361.78 | ≤1,000 | ≤5,000 | | | | |
| 301 | 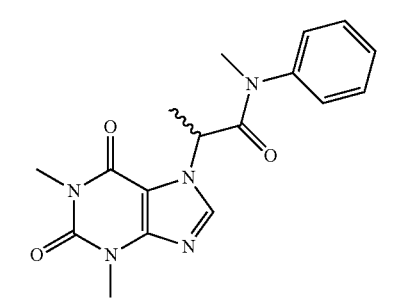 [SMILES: CC(C(=O)N(C)c1ccccc1)n1cnc2c1c(=O)n(C)c(=O)n2C] | 341.36 | | >10,000 | | | | |
| 302 | 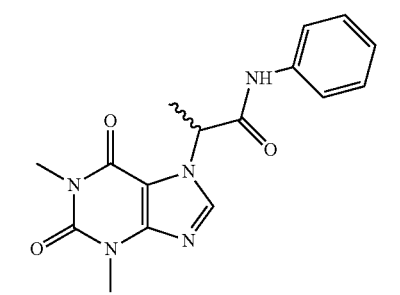 [SMILES: CC(C(=O)Nc1ccccc1)n1cnc2c1c(=O)n(C)c(=O)n2C] | 327.34 | | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 303 | 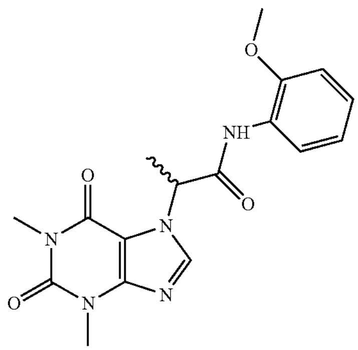 [SMILES: COc1ccccc1NC(=O)C(C)n1cnc2c1c(=O)n(C)c(=O)n2C] | 357.36 | >10,000 | | | | | |
| 304 | 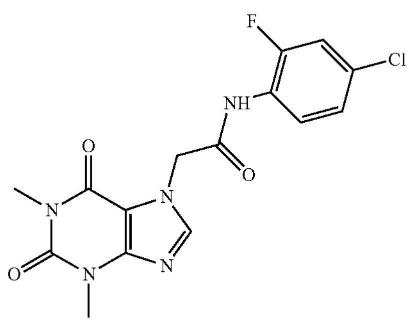 [SMILES: Cn1c(=O)c2c(ncn2CC(=O)Nc2ccc(Cl)cc2F)n(C)c1=O] | 365.75 | ≤5,000 | | | | | |
| 305 | 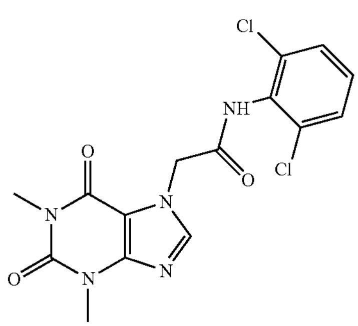 [SMILES: Cn1c(=O)c2c(ncn2CC(=O)Nc2c(Cl)cccc2Cl)n(C)c1=O] | 382.2 | ≤10,000 | >10,000 | | | | |
| 306 | 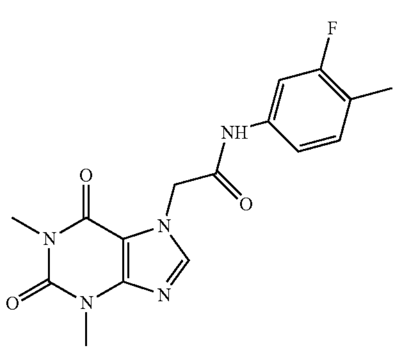 | 345.33 | >10,000 | | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 308 | 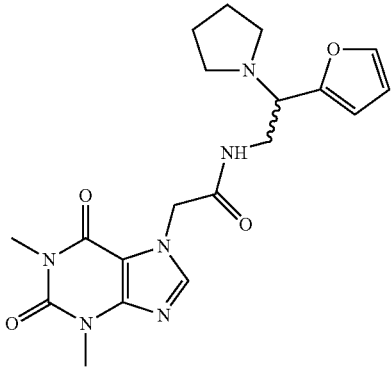 | 400.43 | >10,000 | | | | | |
| 309 | 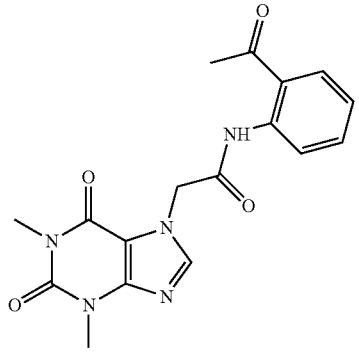 [SMILES: CC(=O)c1ccccc1NC(=O)Cn1cnc2c1c(=O)n(C)c(=O)n2C] | 355.35 | >10,000 | | | | | |
| 310 | 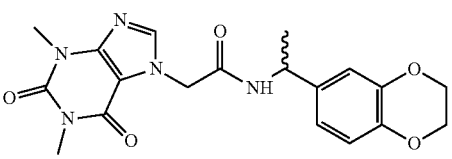 [SMILES: CC(NC(=O)Cn1cnc2c1c(=O)n(C)c(=O)n2C)c1ccc2c(c1)OCCO2] | 399.4 | >10,000 | | | | | |
| 311 | 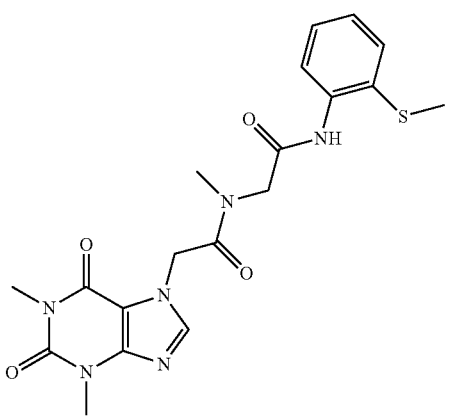 | 430.48 | >10,000 | | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 312 | 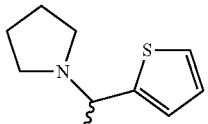 | 416.5 | | >10,000 | | | | |
| 313 | 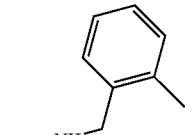 | 341.36 | ≤10,000 | >10,000 | | | | |
| 314 | 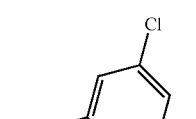 | 369.23 | | ≤10,000 | | | | |
| 315 | 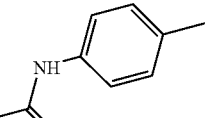 | 341.36 | ≤1,000 | >10,000 | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 316 | 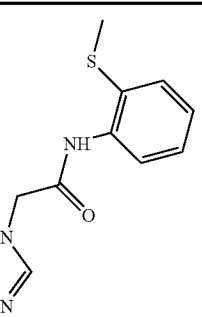 | 359.4 | | >10,000 | | | | |
| 317 | 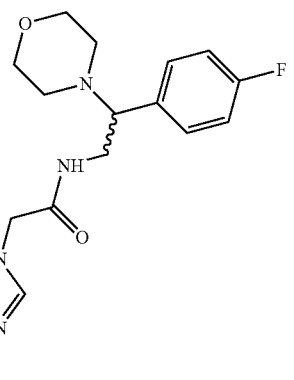 | 444.46 | | >10,000 | | | | |
| 318 | 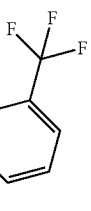 | 395.34 | | >10,000 | | | | |
| 319 | 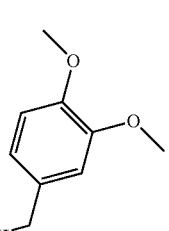 | 387.39 | | >10,000 | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 320 | 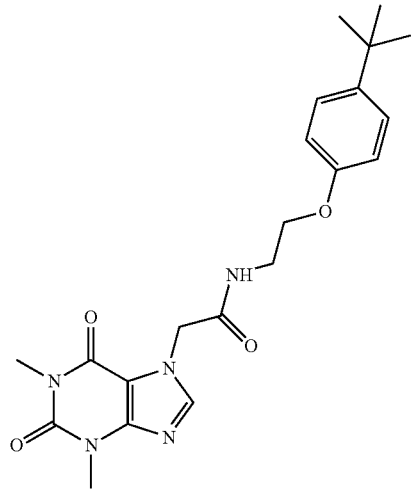 [SMILES: Cn1c(=O)c2c(ncn2CC(=O)NCCOc2ccc(C(C)(C)C)cc2)n(C)c1=O] | 413.47 | ≤10,000 | | | | | |
| 321 | 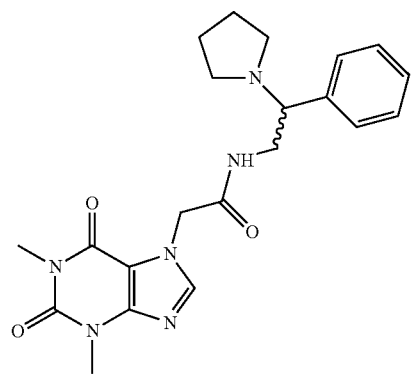 [SMILES: Cn1c(=O)c2c(ncn2CC(=O)NCC(c2ccccc2)N2CCCC2)n(C)c1=O] | 410.47 | >10,000 | | | | | |
| 322 | 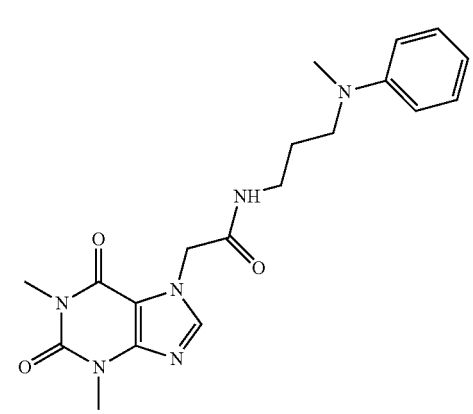 [SMILES: CN(CCCNC(=O)Cn1cnc2c1c(=O)n(C)c(=O)n2C)c1ccccc1] | 384.43 | >10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 323 | 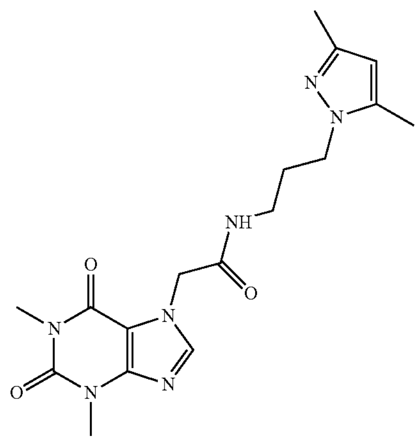 | 373.41 | >10,000 | | | | | |
| 324 | 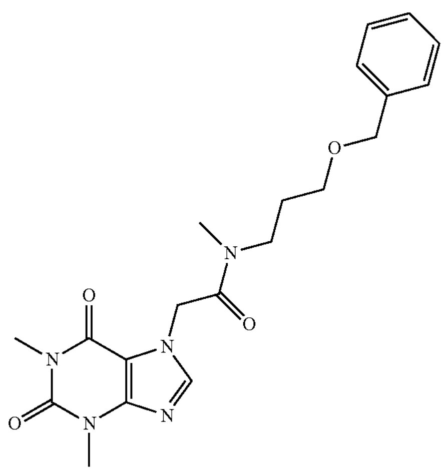 [SMILES: CN(CCCOCc1ccccc1)C(=O)Cn1cnc2c1c(=O)n(C)c(=O)n2C] | 371.39 | ≥20,000 | | | | | |
| 325 | 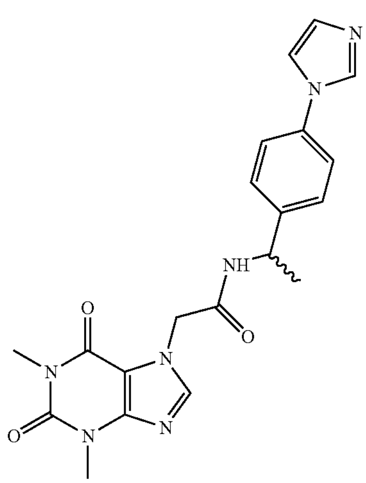 [SMILES: CC(NC(=O)Cn1cnc2c1c(=O)n(C)c(=O)n2C)c1ccc(-n2ccnc2)cc1] | 407.43 | ≥20,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 326 | 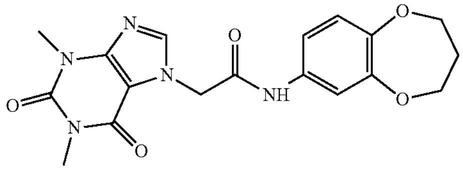 [SMILES: Cn1c(=O)c2c(ncn2CC(=O)Nc2ccc3c(c2)OCCCO3)n(C)c1=O] | 385.37 | ≤10,000 | | | | | |
| 327 | 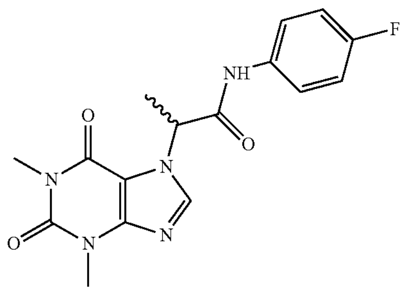 [SMILES: CC(C(=O)Nc1ccc(F)cc1)n1cnc2c1c(=O)n(C)c(=O)n2C] | 345.33 | >10,000 | | | | | |
| 328 | 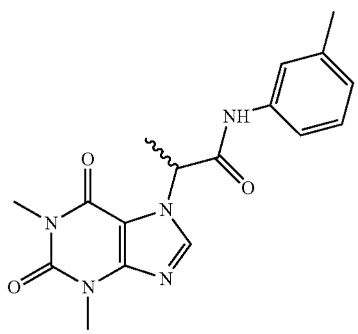 [SMILES: Cc1cccc(NC(=O)C(C)n2cnc3c2c(=O)n(C)c(=O)n3C)c1] | 341.36 | ≥30,000 | | | | | |
| 329 | 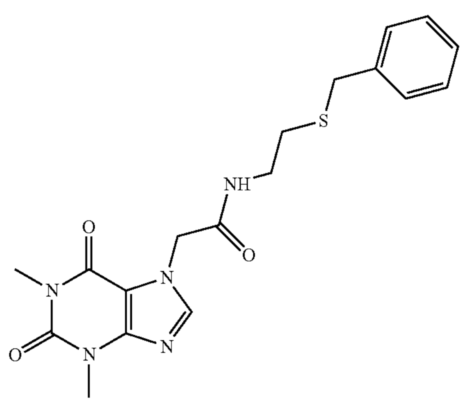 [SMILES: Cn1c(=O)c2c(ncn2CC(=O)NCCSCc2ccccc2)n(C)c1=O] | 387.46 | ≤10,000 | ≤10,000 | | | | |
| 330 | 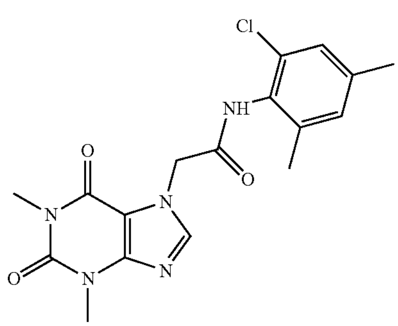 | 375.81 | >10,000 | | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 331 | 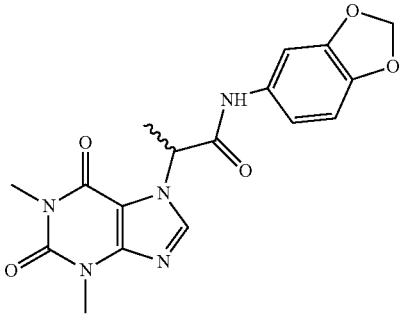 [SMILES: CC(C(=O)Nc1ccc2c(c1)OCO2)n1cnc2c1c(=O)n(C)c(=O)n2C] | 371.35 | >10,000 | | | | | |
| 332 | 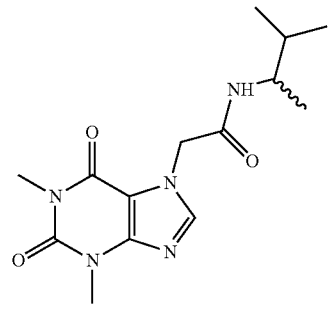 [SMILES: CC(C)C(C)NC(=O)Cn1cnc2c1c(=O)n(C)c(=O)n2C] | 307.35 | >10,000 | | | | | |
| 333 | 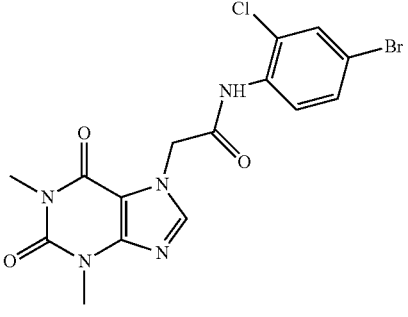 [SMILES: Cn1c(=O)c2c(ncn2CC(=O)Nc2ccc(Br)cc2Cl)n(C)c1=O] | 426.65 | ≤1,000 | ≤5,000 | | | | |
| 334 | 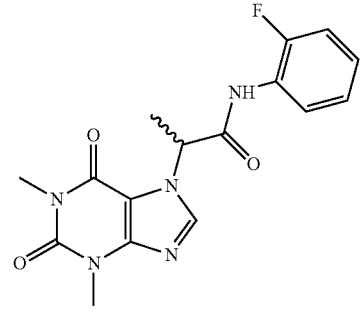 [SMILES: CC(C(=O)Nc1ccccc1F)n1cnc2c1c(=O)n(C)c(=O)n2C] | 345.33 | >10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 335 | 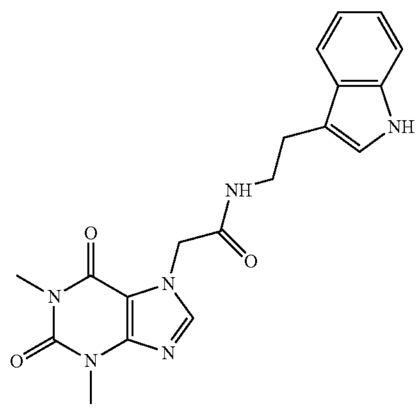 [SMILES: Cn1c(=O)c2c(ncn2CC(=O)NCCc2c[nH]c3ccccc23)n(C)c1=O] | 380.4 | | >10,000 | | | | |
| 336 | 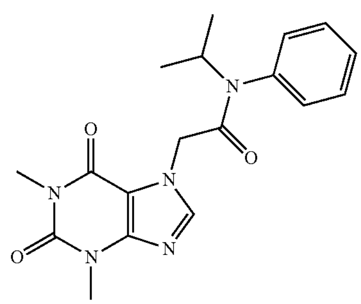 [SMILES: CC(C)N(C(=O)Cn1cnc2c1c(=O)n(C)c(=O)n2C)c1ccccc1] | 355.39 | | >10,000 | | | | |
| 337 | 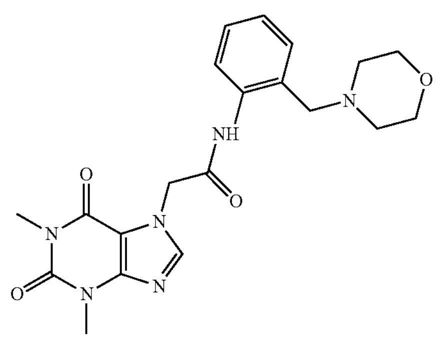 [SMILES: Cn1c(=O)c2c(ncn2CC(=O)Nc2ccccc2CN2CCOCC2)n(C)c1=O] | 426.47 | | >10,000 | | | | |
| 338 | 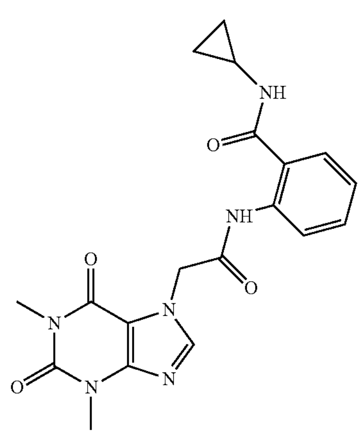 [SMILES: Cn1c(=O)c2c(ncn2CC(=O)Nc2ccccc2C(=O)NC2CC2)n(C)c1=O] | 396.4 | | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 339 | 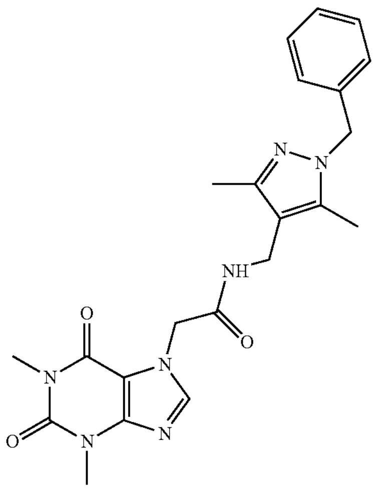 [SMILES: Cc1nn(Cc2ccccc2)c(C)c1CNC(=O)Cn1cnc2c1c(=O)n(C)c(=O)n2C] | 435.48 | >10,000 | | | | | |
| 340 | 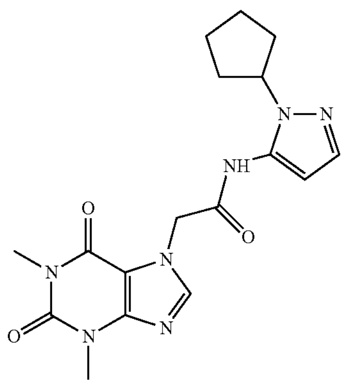 [SMILES: Cn1c(=O)c2c(ncn2CC(=O)Nc2ccnn2C2CCCC2)n(C)c1=O] | 371.39 | >10,000 | | | | | |
| 341 | 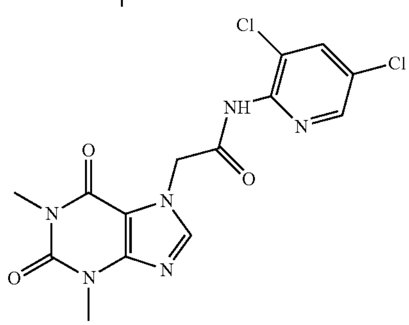 | 383.19 | >10,000 | | | | | |
| 342 | 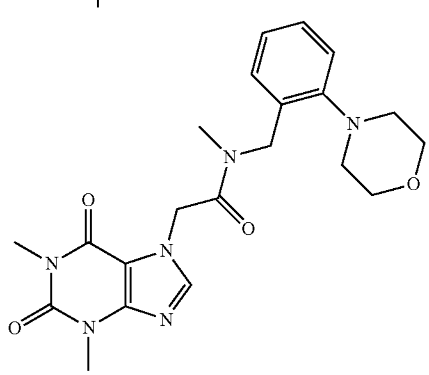 | 426.47 | >10,000 | | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 343 | 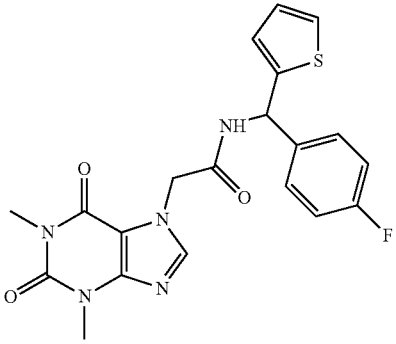 [SMILES: Cn1c(=O)c2c(ncn2CC(=O)NC(c2ccc(F)cc2)c2cccs2)n(C)c1=O] | 427.45 | | >10,000 | | | | |
| 344 | 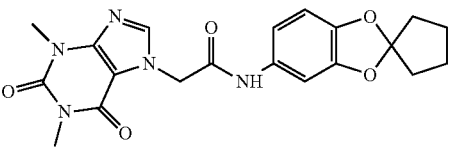 [SMILES: Cn1c(=O)c2c(ncn2CC(=O)Nc2ccc3c(c2)OC2(CCCC2)O3)n(C)c1=O] | 411.41 | ≤5,000 | ≤5,000 | | | | |
| 345 | 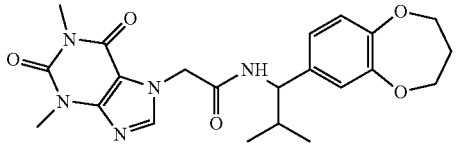 [SMILES: CC(C)C(NC(=O)Cn1cnc2c1c(=O)n(C)c(=O)n2C)c1ccc2c(c1)OCCCO2] | 441.48 | | >10,000 | | | | |
| 346 | 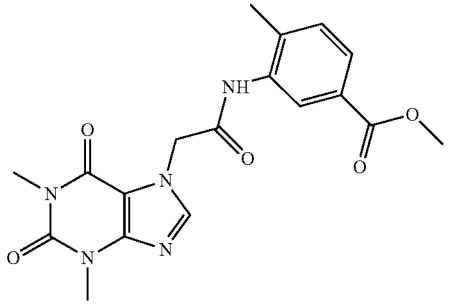 | 385.37 | | ≥30,000 | | | | |
| 347 | 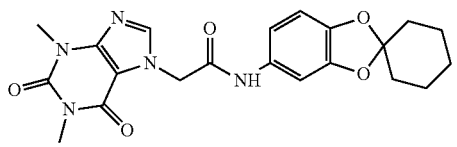 [SMILES: Cn1c(=O)c2c(ncn2CC(=O)Nc2ccc3c(c2)OC2(CCCCC2)O3)n(C)c1=O] | 425.44 | ≤1,000 | ≤1,000 | | ≥20,000 (at least 45-fold selective for TRPA1 over hERG) | >10,000 (at least 15-fold selective for TRPA1 over TRPV4) | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 348 | 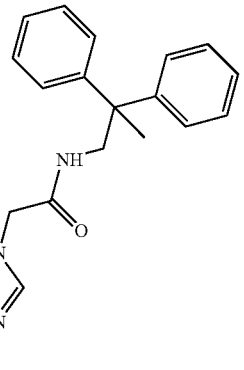 | 431.49 | >10,000 | ≤5,000 | | | | |
| 349 | 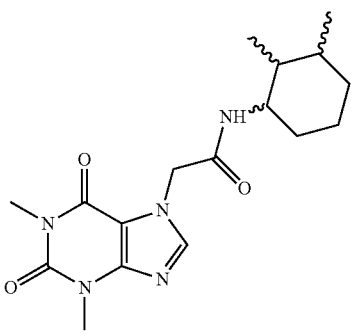 | 347.41 | | >10,000 | | | | |
| 350 | 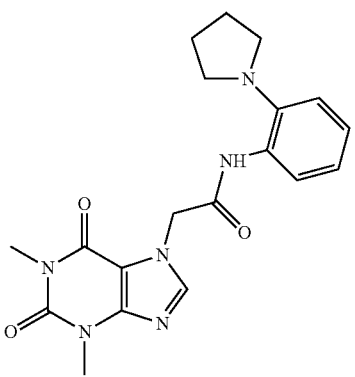 | 382.42 | >10,000 | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 351 | 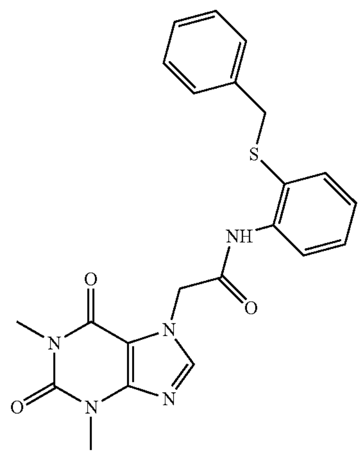 [SMILES: Cn1c(=O)c2c(ncn2CC(=O)Nc2ccccc2SCc2ccccc2)n(C)c1=O] | 435.5 | >10,000 | | | | | |
| 352 | 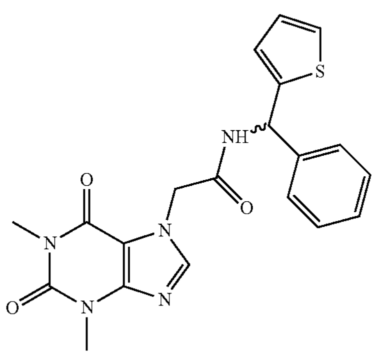 [SMILES: Cn1c(=O)c2c(ncn2CC(=O)NC(c2ccccc2)c2cccs2)n(C)c1=O] | 409.46 | >10,000 | | | | | |
| 353 | 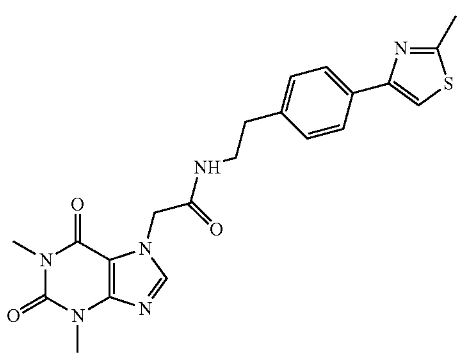 | 438.5 | ≤5,000 | | | | | |
| 354 | 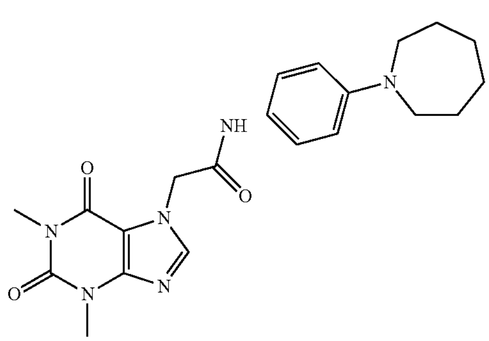 | 410.47 | ≤5,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 355 | 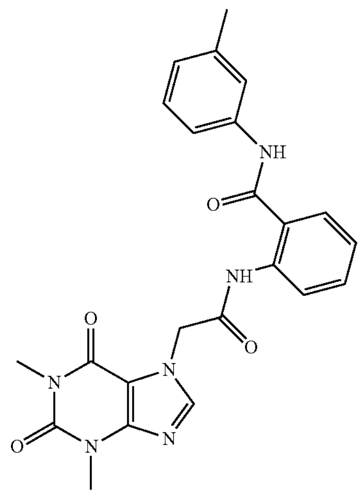 [SMILES: Cc1cccc(NC(=O)c2ccccc2NC(=O)Cn2cnc3c2c(=O)n(C)c(=O)n3C)c1] | 446.46 | | ≥20,000 | | | | |
| 356 | 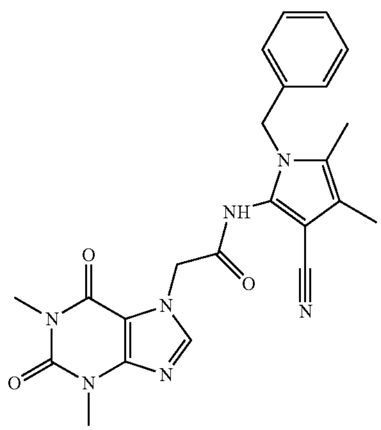 | 445.47 | | >10,000 | | | | |
| 357 | 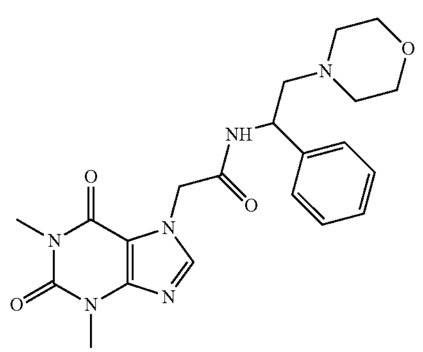 [SMILES: Cn1c(=O)c2c(ncn2CC(=O)NC(CN2CCOCC2)c2ccccc2)n(C)c1=O] | 426.47 | | >10,000 | | | | |
| 358 | 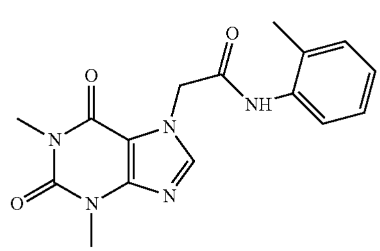 [SMILES: Cc1ccccc1NC(=O)Cn1cnc2c1c(=O)n(C)c(=O)n2C] | 327.34 | | >10,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 359 | 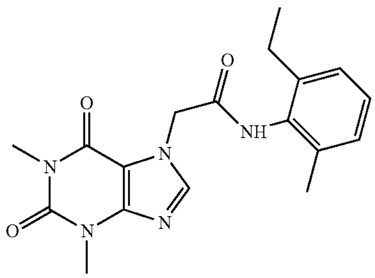 [SMILES: CCc1cccc(C)c1NC(=O)Cn1cnc2c1c(=O)n(C)c(=O)n2C] | 355.39 | >10,000 | | | | | |
| 360 | 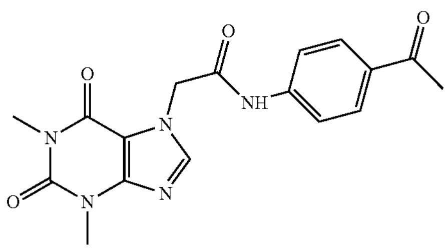 [SMILES: CC(=O)c1ccc(NC(=O)Cn2cnc3c2c(=O)n(C)c(=O)n3C)cc1] | 355.35 | ≤10,000 | | | | | |
| 361 | 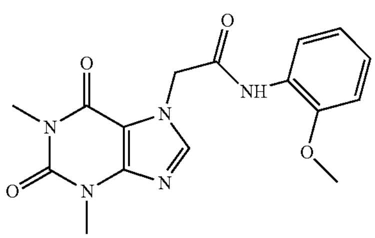 [SMILES: COc1ccccc1NC(=O)Cn1cnc2c1c(=O)n(C)c(=O)n2C] | 343.34 | >10,000 | | | | | |
| 362 | 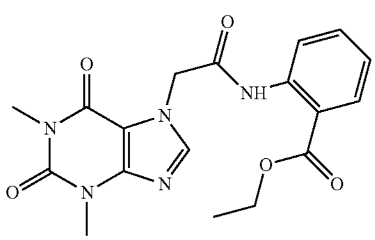 [SMILES: CCOC(=O)c1ccccc1NC(=O)Cn1cnc2c1c(=O)n(C)c(=O)n2C] | 385.37 | >10,000 | | | | | |
| 363 | 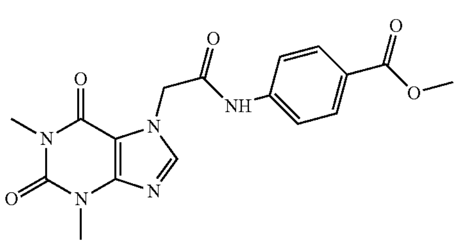 | 371.35 | ≤10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 364 | 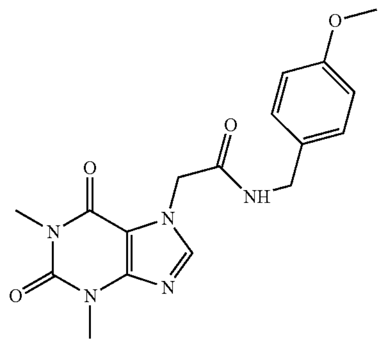 | 357.36 | >10,000 | | | | | |
| 365 | 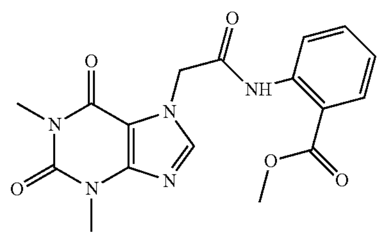 [SMILES: COC(=O)c1ccccc1NC(=O)Cn1cnc2c1c(=O)n(C)c(=O)n2C] | 371.35 | >10,000 | | | | | |
| 366 | 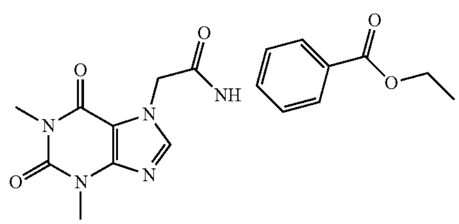 | 385.37 | ≤5,000 | | | | | |
| 367 | 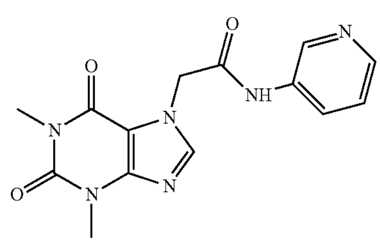 [SMILES: Cn1c(=O)c2c(ncn2CC(=O)Nc2cccnc2)n(C)c1=O] | 314.3 | >10,000 | | | | | |
| 368 | 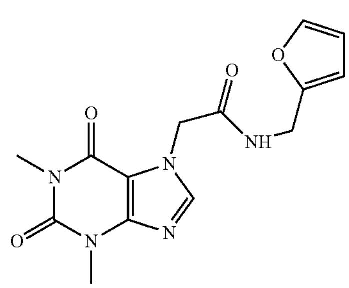 [SMILES: Cn1c(=O)c2c(ncn2CC(=O)NCc2ccco2)n(C)c1=O] | 317.3 | >10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 369 | 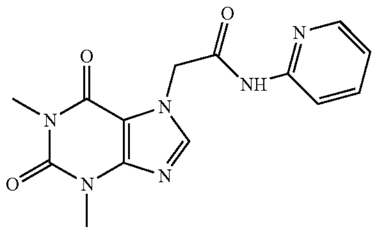 [SMILES: Cn1c(=O)c2c(ncn2CC(=O)Nc2ccccn2)n(C)c1=O] | 314.3 | | >10,000 | | | | |
| 370 | 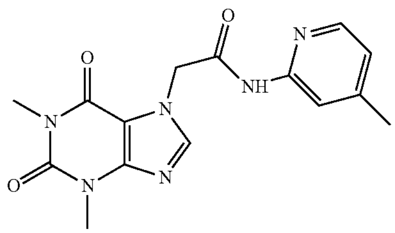 | 328.33 | | >10,000 | | | | |
| 371 | 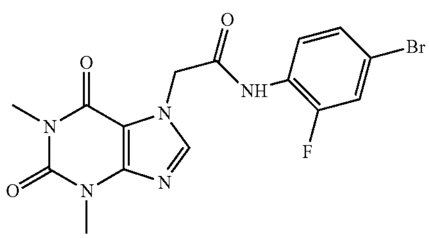 [SMILES: Cn1c(=O)c2c(ncn2CC(=O)Nc2ccc(Br)cc2F)n(C)c1=O] | 410.2 | ≤5,000 | ≤5,000 | | | | |
| 372 | 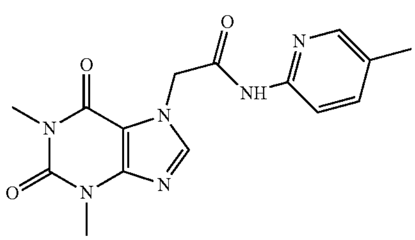 | 328.33 | | ≥30,000 | | | | |
| 373 | 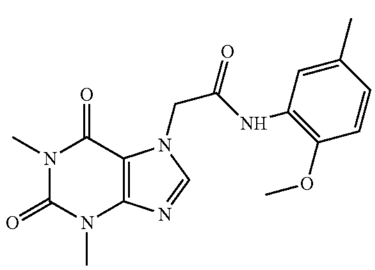 [SMILES: COc1ccc(C)cc1NC(=O)Cn1cnc2c1c(=O)n(C)c(=O)n2C] | 357.36 | | >10,000 | | | | |
| 374 | 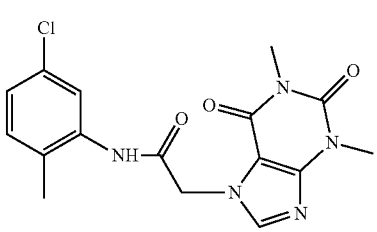 [SMILES: Cc1ccc(Cl)cc1NC(=O)Cn1cnc2c1c(=O)n(C)c(=O)n2C] | 361.78 | | ≥20,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 375 | 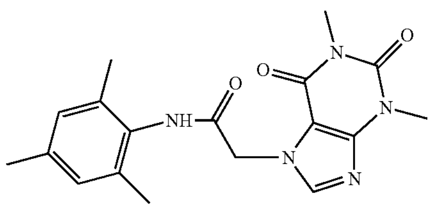 | 355.39 | >10,000 | | | | | |
| 376 | 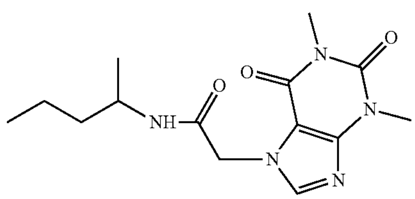 [SMILES: CCCC(C)NC(=O)Cn1cnc2c1c(=O)n(C)c(=O)n2C] | 307.35 | >10,000 | | | | | |
| 377 | 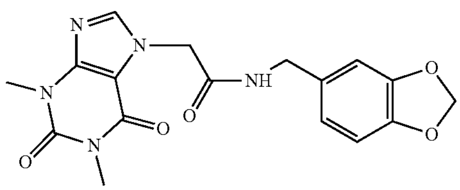 [SMILES: Cn1c(=O)c2c(ncn2CC(=O)NCc2ccc3c(c2)OCO3)n(C)c1=O] | 371.35 | >10,000 | | | | | |
| 378 | 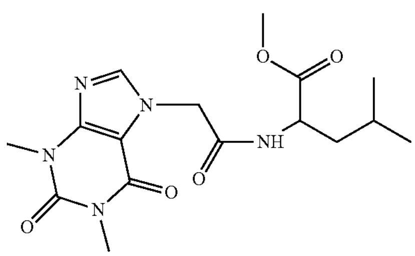 [SMILES: COC(=O)C(CC(C)C)NC(=O)Cn1cnc2c1c(=O)n(C)c(=O)n2C] | 365.38 | >10,000 | | | | | |
| 379 | 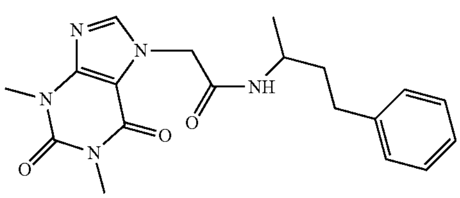 [SMILES: CC(CCc1ccccc1)NC(=O)Cn1cnc2c1c(=O)n(C)c(=O)n2C] | 369.42 | >10,000 | | | | | |
| 380 | 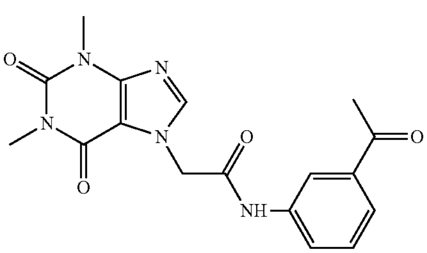 [SMILES: CC(=O)c1cccc(NC(=O)Cn2cnc3c2c(=O)n(C)c(=O)n3C)c1] | 355.35 | >10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 381 | 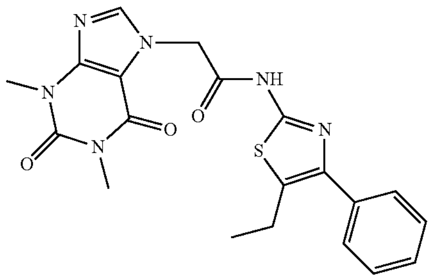 [SMILES: CCc1sc(NC(=O)Cn2cnc3c2c(=O)n(C)c(=O)n3C)nc1-c1ccccc1] | 424.48 | | ≤10,000 | | | | |
| 382 | 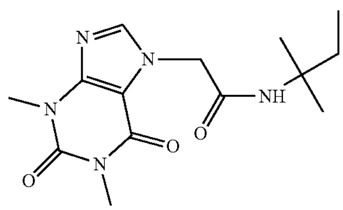 [SMILES: CCC(C)(C)NC(=O)Cn1cnc2c1c(=O)n(C)c(=O)n2C] | 307.35 | | >10,000 | | | | |
| 383 | 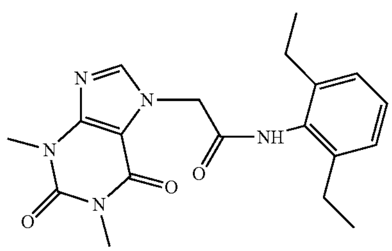 [SMILES: CCc1cccc(CC)c1NC(=O)Cn1cnc2c1c(=O)n(C)c(=O)n2C] | 369.42 | | >10,000 | | | | |
| 384 | 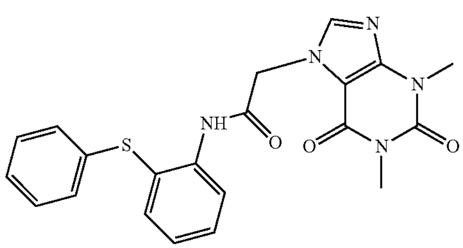 [SMILES: Cn1c(=O)c2c(ncn2CC(=O)Nc2ccccc2Sc2ccccc2)n(C)c1=O] | 421.47 | | ≤10,000 | | | | |
| 385 | 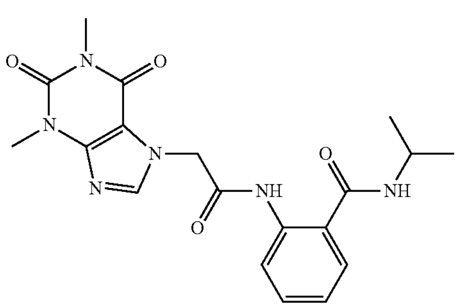 [SMILES: CC(C)NC(=O)c1ccccc1NC(=O)Cn1cnc2c1c(=O)n(C)c(=O)n2C] | 398.42 | | >10,000 | | | | |
| 386 | 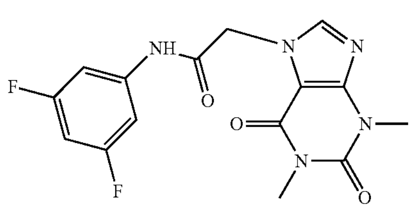 [SMILES: Cn1c(=O)c2c(ncn2CC(=O)Nc2cc(F)cc(F)c2)n(C)c1=O] | 349.29 | | ≤5,000 | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 387 | 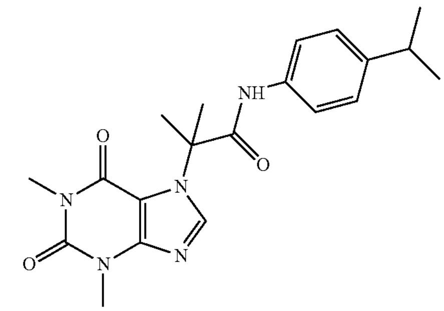 [SMILES: CC(C)c1ccc(NC(=O)C(C)(C)n2cnc3c2c(=O)n(C)c(=O)n3C)cc1] | 383.44 | >10,000 | | | | | |
| 388 | 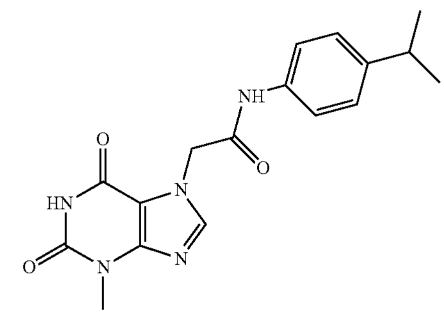 [SMILES: CC(C)c1ccc(NC(=O)Cn2cnc3c2c(=O)[nH]c(=O)n3C)cc1] | 341.36 | >10,000 | | | | | |
| 389 | 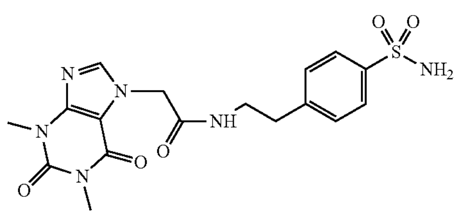 [SMILES: Cn1c(=O)c2c(ncn2CC(=O)NCCc2ccc(S(N)(=O)=O)cc2)n(C)c1=O] | 420.44 | >10,000 | | | | | |
| 390 | 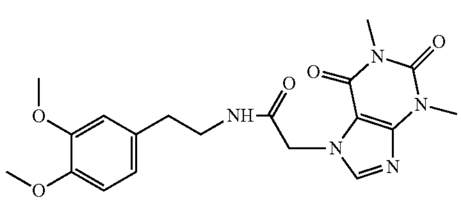 | 401.42 | ≤10,000 | | | | | |
| 391 | 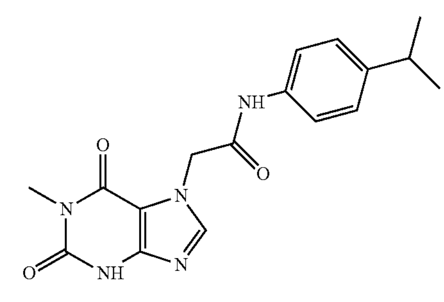 [SMILES: CC(C)c1ccc(NC(=O)Cn2cnc3[nH]c(=O)n(C)c(=O)c32)cc1] | 341.36 | ≤10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 392 | 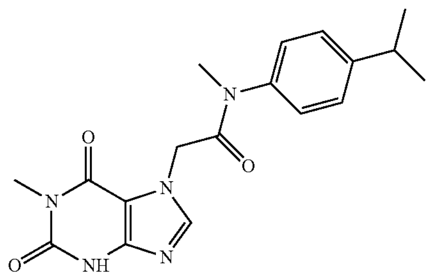 [SMILES: CC(C)c1ccc(N(C)C(=O)Cn2cnc3[nH]c(=O)n(C)c(=O)c32)cc1] | 355.39 | >10,000 | | | | | |
| 393 | 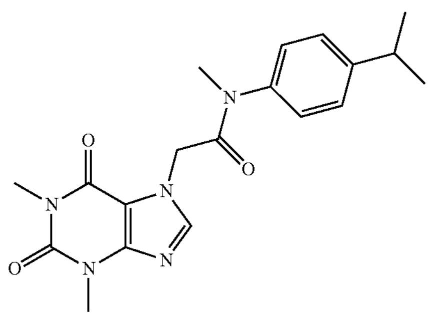 [SMILES: CC(C)c1ccc(N(C)C(=O)Cn2cnc3c2c(=O)n(C)c(=O)n3C)cc1] | 369.42 | >10,000 | | | | | |
| 394 | 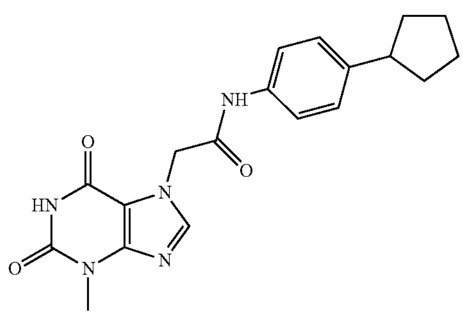 [SMILES: Cn1c(=O)[nH]c(=O)c2c1ncn2CC(=O)Nc1ccc(C2CCCC2)cc1] | 367.4 | ≤5,000 | | | | | |
| 395 | 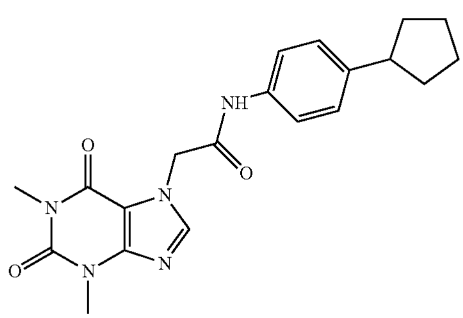 [SMILES: Cn1c(=O)c2c(ncn2CC(=O)Nc2ccc(C3CCCC3)cc2)n(C)c1=O] | 381.43 | ≤500 | | | | | |

TABLE 2-continued
| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 396 | 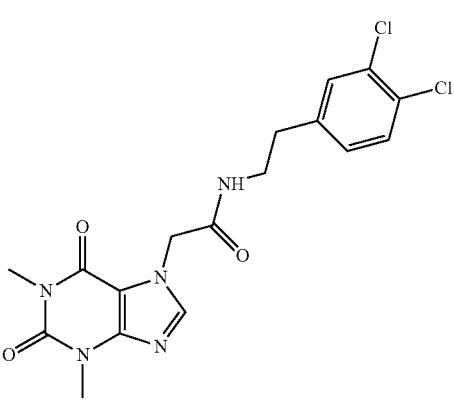 [SMILES: Cn1c(=O)c2c(ncn2CC(=O)NCCc2ccc(Cl)c(Cl)c2)n(C)c1=O] | 410.25 | ≤1,000 | | | | | |
| 397 | 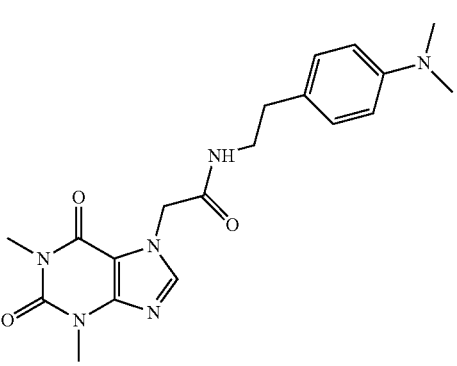 | 384.43 | ≤5,000 | | | | | |
| 398 | 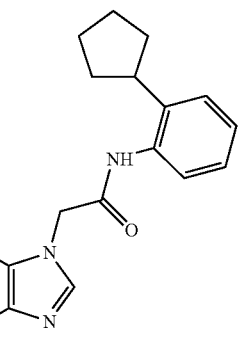 | 381.43 | ≤10,000 | | | | | |
| 399 | 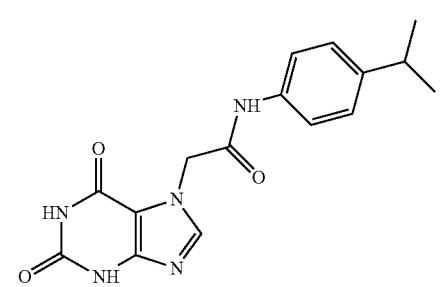 [SMILES: CC(C)c1ccc(NC(=O)Cn2cnc3[nH]c(=O)[nH]c(=O)c32)cc1] | 327.34 | ≤10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 400 | 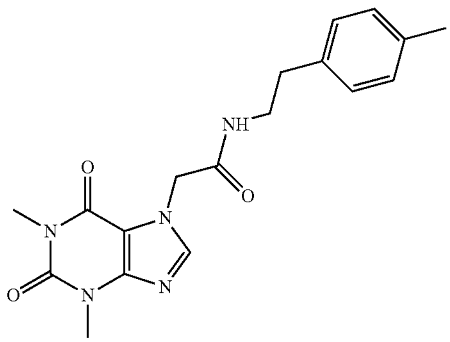 | 355.39 | ≤1,000 | | | | | |
| 401 | 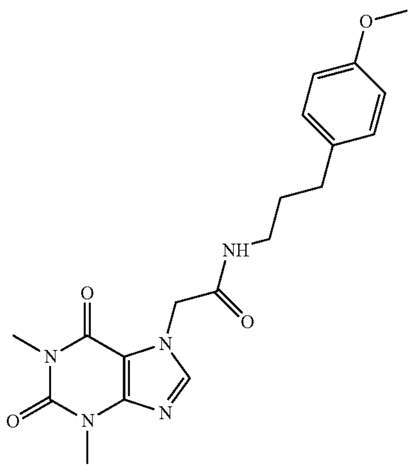 | 385.42 | ≤5,000 | | | | | |
| 402 | 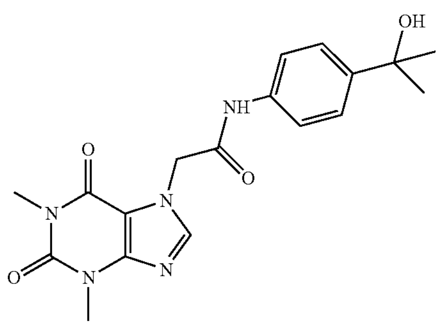 [SMILES: Cn1c(=O)c2c(ncn2CC(=O)Nc2ccc(C(C)(C)O)cc2)n(C)c1=O] | 371.39 | ≤5,000 | | | | | |
| 403 | 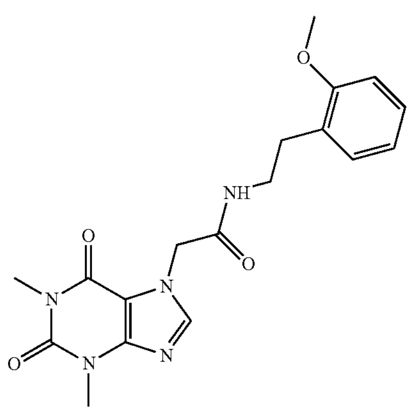 [SMILES: COc1ccccc1CCNC(=O)Cn1cnc2c1c(=O)n(C)c(=O)n2C] | 371.39 | >10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 404 | 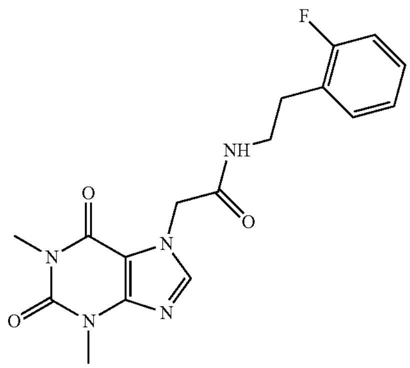 | 359.35 | ≤1,000 | | | | | |
| 405 | 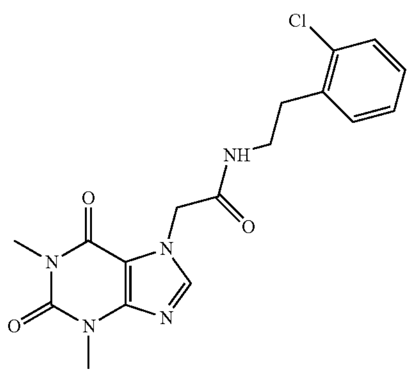 [SMILES: Cn1c(=O)c2c(ncn2CC(=O)NCCc2ccccc2Cl)n(C)c1=O] | 375.81 | ≤10,000 | | | | | |
| 406 | 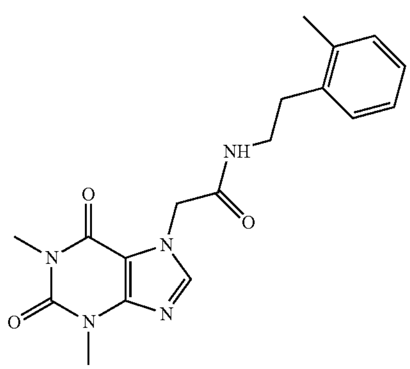 [SMILES: Cc1ccccc1CCNC(=O)Cn1cnc2c1c(=O)n(C)c(=O)n2C] | 355.39 | ≤10,000 | | | | | |
| 407 | 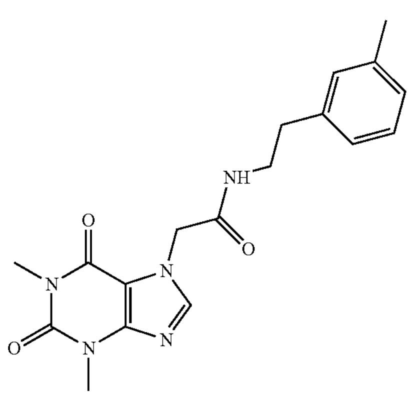 [SMILES: Cc1cccc(CCNC(=O)Cn2cnc3c2c(=O)n(C)c(=O)n3C)c1] | 355.39 | ≤10,000 | | | | | |

TABLE 2-continued

| Cmpd ID | Structure | Mol Wt | hTRPA1 Patch Inwd IC50 (nM) | hTRPA1 Fluor IC50 (nM) | hTRPV3 P1 inward IC50 (nM) | hERG IC50 (nM) | hTRPV4 IC50 (nM) | hNaV1.2 IC50 (nM) |
|---|---|---|---|---|---|---|---|---|
| 408 | 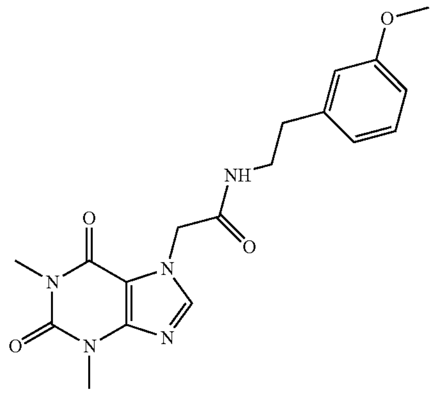 | 371.39 | ≤5,000 | | | | | |
| 409 | 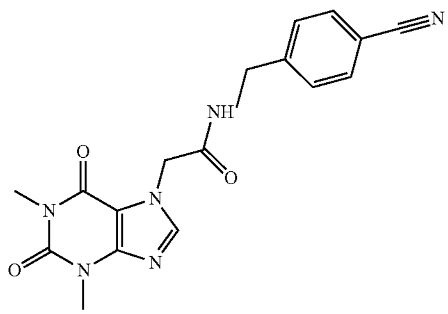 | 366.37 | ≤10,000 | | | | | |

We claim:

1. A method for treating a condition involving activation of TRPA1 or for which reduced TRPA1 activity can reduce the severity, comprising administering an effective amount of a compound of Formula II or a salt thereof, or a solvate, hydrate, oxidative metabolite or prodrug of the compound or its salt:

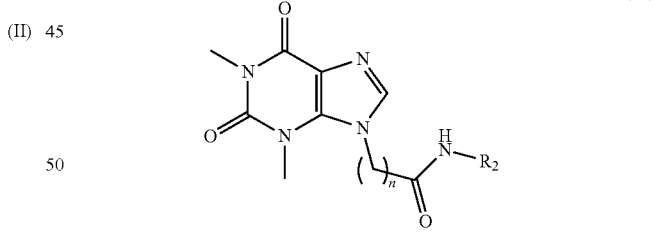

(II)

wherein
n is an integer from 1 to 3; and
R₂ represents substituted heteroaryl and
wherein said compound inhibits a TRPA1 mediated current with an with an IC₅₀ less than 10 micromolar, and the condition is selected from diabetic neuropathy, psoriasis, eczema, dermatitis, post-herpetic neuralgia (shingles), migraine, incontinence, fever, hot flashes, osteoarthritis, pancreatitis, chronic regional pain syndrome, rheumatoid arthritis, cough, pain, sensitivity to touch, bladder cystitis, irritable bowel syndrome, and inflammatory pain.

2. A method for treating a condition involving activation of TRPA1 or for which reduced TRPA1 activity can reduce the severity, comprising administering an effective amount of a compound of Formula III or a salt thereof, or a solvate, hydrate, oxidative metabolite or prodrug of the compound or its salt:

(III)

wherein
n is an integer from 1 to 3; and
R₂ represents a substituent; and
wherein said compound inhibits a TRPA1 mediated current with an with an IC₅₀ less than 10 micromolar, and the condition is selected from diabetic neuropathy, psoriasis, eczema, dermatitis, post-herpetic neuralgia (shingles), migraine, incontinence, fever, hot flashes, osteoarthritis, pancreatitis, chronic regional pain syndrome, rheumatoid arthritis, cough, pain, sensitivity to touch, bladder cystitis, irritable bowel syndrome, and inflammatory pain.

3. The method of claim 1, used to treat or alleviate symptoms of pain or sensitivity to touch.

4. The method of claim 2, used to treat or alleviate symptoms of pain or sensitivity to touch.

5. The method of claim 2, wherein $R_2$ represents optionally substituted alkyl, optionally substituted aryl, optionally substituted heteroaryl, optionally substituted aralkyl, optionally substituted cycloalkyl, optionally substituted heterocyclyl, or optionally substituted heteroaralkyl.

6. The method of claim 1, wherein $R_2$ is substituted with optionally substituted aryl, optionally substituted heteroaryl, optionally substituted aralkyl, optionally substituted cycloalkyl, optionally substituted heterocyclyl, or optionally substituted heteroaralkyl.

7. The method of claim 1, wherein the condition is selected from psoriasis, eczema, dermatitis, and post-herpetic neuralgia (shingles).

8. The method of claim 2, wherein the condition is selected from psoriasis, eczema, dermatitis, and post-herpetic neuralgia (shingles).

\* \* \* \* \*